US008809501B2

(12) United States Patent
Siekmann et al.

(10) Patent No.: US 8,809,501 B2
(45) **Date of Patent: *Aug. 19, 2014**

(54) NUCLEOPHILIC CATALYSTS FOR OXIME LINKAGE

(75) Inventors: Juergen Siekmann, Vienna (AT); Stefan Haider, Prinzerdorf (AT); Hanspeter Rottensteiner, Vienna (AT); Peter Turecek, Klosterneuburg (AT)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/488,043

(22) Filed: Jun. 4, 2012

(65) Prior Publication Data

US 2013/0011900 A1 Jan. 10, 2013

Related U.S. Application Data

(63) Continuation-in-part of application No. 13/194,038, filed on Jul. 29, 2011, which is a continuation-in-part of application No. 12/843,542, filed on Jul. 26, 2010.

(60) Provisional application No. 61/369,186, filed on Jul. 30, 2010, provisional application No. 61/228,828, filed on Jul. 27, 2009, provisional application No. 61/347,136, filed on May 21, 2010.

(51) Int. Cl.

| | |
|---|---|
| ***C07K 14/62*** | (2006.01) |
| ***C07K 14/48*** | (2006.01) |
| ***C07K 14/475*** | (2006.01) |
| ***C07K 16/00*** | (2006.01) |

(52) U.S. Cl.
USPC ........... 530/380; 530/351; 530/303; 530/381; 530/383; 530/391.1; 530/395; 530/397; 530/399

(58) Field of Classification Search
None
See application file for complete search history.

(56) References Cited

U.S. PATENT DOCUMENTS

| | | | |
|---|---|---|---|
| 4,179,337 | A | 12/1979 | Davis et al. |
| 4,757,006 | A | 7/1988 | Toole, Jr. et al. |
| 4,966,999 | A | 10/1990 | Coughlin et al. |
| 4,970,300 | A | 11/1990 | Fulton et al. |
| 5,153,265 | A | 10/1992 | Shadle et al. |
| 5,198,349 | A | 3/1993 | Kaufman |
| 5,198,493 | A | 3/1993 | Holmberg et al. |
| 5,250,421 | A | 10/1993 | Kaufman et al. |
| 5,492,821 | A | 2/1996 | Callstrom et al. |
| 5,621,039 | A | 4/1997 | Hallahan et al. |
| 5,733,873 | A | 3/1998 | Osterberg et al. |
| 5,919,766 | A | 7/1999 | Osterberg et al. |
| 5,969,040 | A | 10/1999 | Hallahan et al. |
| 6,037,452 | A | 3/2000 | Minamino et al. |
| 6,048,720 | A | 4/2000 | Dalborg et al. |
| 6,183,738 | B1 | 2/2001 | Clark |
| 6,586,398 | B1 | 7/2003 | Kinstler et al. |
| 6,692,931 | B1 | 2/2004 | Reutter et al. |
| 6,743,908 | B2 | 6/2004 | Filpula et al. |
| 6,806,063 | B2 | 10/2004 | Pedersen et al. |
| 6,872,393 | B2 | 3/2005 | Whitlow et al. |
| 6,913,915 | B2 | 7/2005 | Ensor et al. |
| 7,118,737 | B2 | 10/2006 | Kochendoerfer et al. |
| 7,230,081 | B1 | 6/2007 | Jensen et al. |
| 7,338,788 | B2 | 3/2008 | Pedersen et al. |
| 2002/0110535 | A1 | 8/2002 | Jones |
| 2003/0143596 | A1 | 7/2003 | Bentley et al. |
| 2004/0063911 | A1 | 4/2004 | DeFrees et al. |
| 2004/0137557 | A1 | 7/2004 | DeFrees et al. |
| 2004/0235734 | A1 | 11/2004 | Bossard et al. |
| 2005/0106658 | A1 | 5/2005 | DeFrees et al. |
| 2006/0019877 | A1 | 1/2006 | Conradt et al. |
| 2006/0088906 | A1 | 4/2006 | DeFrees et al. |
| 2006/0286634 | A1 | 12/2006 | Kingsman et al. |
| 2007/0244301 | A1 | 10/2007 | Siekmann et al. |
| 2008/0146771 | A1 | 6/2008 | Kozlowski et al. |
| 2008/0260755 | A1 | 10/2008 | Metzner et al. |
| 2009/0076237 | A1 | 3/2009 | Turecek et al. |

FOREIGN PATENT DOCUMENTS

| | | | |
|---|---|---|---|
| CA | 2647314 | A1 | 11/2007 |
| EP | 0306968 | A2 | 3/1989 |
| EP | 0605963 | | 7/1994 |
| EP | 1258497 | A2 | 11/2002 |
| EP | 1260582 | A1 | 11/2002 |
| WO | WO-91/09122 | A1 | 6/1991 |
| WO | WO-92/16555 | A1 | 10/1992 |

(Continued)

OTHER PUBLICATIONS

Abuchowski et al., Cancer therapy with chemically modified enzymes. I. Antitumor properties of polyethylene glycol-asparaginase conjugates. *Cancer Biochem. Biophys.* 7: 175-86 (1984).

(Continued)

*Primary Examiner* — Lisa J Hobbs

(74) *Attorney, Agent, or Firm* — Marshall, Gerstein & Borun LLP

(57) ABSTRACT

The invention relates to materials and methods of conjugating a water soluble polymer to an oxidized carbohydrate moiety of a therapeutic protein comprising contacting the oxidized carbohydrate moiety with an activated water soluble polymer under conditions that allow conjugation. More specifically, the present invention relates to the aforementioned materials and methods wherein the water soluble polymer contains an active aminooxy group and wherein an oxime or hydrazone linkage is formed between the oxidized carbohydrate moiety and the active aminooxy group on the water soluble polymer, and wherein the conjugation is carried out in the presence of a nucleophilic catalyst.

34 Claims, 6 Drawing Sheets

(56) References Cited

FOREIGN PATENT DOCUMENTS

| | | | |
|---|---|---|---|
| WO | WO-94/05332 | A2 | 3/1994 |
| WO | WO-94/15625 | A | 7/1994 |
| WO | WO-94/28024 | A1 | 12/1994 |
| WO | WO-94/29370 | A1 | 12/1994 |
| WO | WO-95/01804 | A1 | 1/1995 |
| WO | WO-96/40731 | A1 | 12/1996 |
| WO | WO-96/41813 | A2 | 12/1996 |
| WO | WO-97/11957 | A1 | 4/1997 |
| WO | WO-99/28455 | A1 | 6/1999 |
| WO | WO-99/32134 | A1 | 7/1999 |
| WO | WO-00/12587 | A2 | 3/2000 |
| WO | WO-00/23114 | A2 | 4/2000 |
| WO | WO-00/48635 | A1 | 8/2000 |
| WO | WO-01/82943 | A2 | 11/2001 |
| WO | WO-01/83725 | A1 | 11/2001 |
| WO | WO-02/02764 | A2 | 1/2002 |
| WO | WO-02/22776 | A2 | 3/2002 |
| WO | WO-02/29025 | A2 | 4/2002 |
| WO | WO-02/077218 | A1 | 10/2002 |
| WO | WO-03/031464 | A2 | 4/2003 |
| WO | WO-03/045980 | A2 | 6/2003 |
| WO | WO-03/046150 | A2 | 6/2003 |
| WO | WO-2004/000366 | | 12/2003 |
| WO | WO-2004/014424 | A1 | 2/2004 |
| WO | WO-2004/030617 | A2 | 4/2004 |
| WO | WO-2004/060965 | | 7/2004 |
| WO | WO-2004/075923 | A2 | 9/2004 |
| WO | WO-2004/089280 | A2 | 10/2004 |
| WO | WO-2004/108070 | A2 | 12/2004 |
| WO | WO-2005/014024 | A2 | 2/2005 |
| WO | WO-2005/014035 | A2 | 2/2005 |
| WO | WO-2005/055950 | A2 | 6/2005 |
| WO | WO-2005/070138 | A2 | 8/2005 |
| WO | WO-2006/013202 | A2 | 2/2006 |
| WO | WO-2006/020372 | A2 | 2/2006 |
| WO | WO-2006/016168 | A3 | 5/2006 |
| WO | WO-2006/053299 | A2 | 5/2006 |
| WO | WO-2006/071801 | A2 | 7/2006 |
| WO | WO-2006/074279 | A1 | 7/2006 |
| WO | WO-2006/127896 | A2 | 11/2006 |
| WO | WO-2006/134173 | A2 | 12/2006 |
| WO | WO-2007/022784 | A2 | 3/2007 |
| WO | WO-2007/076062 | A2 | 7/2007 |
| WO | WO-2007/140282 | A1 | 12/2007 |
| WO | WO-2008/012540 | A1 | 1/2008 |
| WO | WO-2008/025856 | A2 | 3/2008 |
| WO | WO-2008/035373 | A2 | 3/2008 |
| WO | WO-2008/057683 | A2 | 5/2008 |
| WO | WO-2008/074032 | A1 | 6/2008 |
| WO | WO-2008/081024 | A1 | 7/2008 |
| WO | WO-2008/119815 | A1 | 10/2008 |
| WO | WO-2009/000522 | A1 | 12/2008 |
| WO | WO-2009/006620 | A1 | 1/2009 |
| WO | WO-2009/047500 | A1 | 4/2009 |
| WO | WO-2009/089396 | A2 | 7/2009 |
| WO | WO-2009/108806 | A1 | 9/2009 |
| WO | WO-2009/130602 | A2 | 10/2009 |
| WO | WO-2009/141418 | A1 | 11/2009 |
| WO | WO-2009/141433 | A1 | 11/2009 |
| WO | WO-2009/149303 | A1 | 12/2009 |
| WO | WO-2010/010324 | A1 | 1/2010 |
| WO | WO-2010/062768 | A1 | 6/2010 |
| WO | WO-2010/083536 | A1 | 7/2010 |
| WO | WO-2010/100430 | A1 | 9/2010 |
| WO | WO-2010/102886 | A1 | 9/2010 |
| WO | WO-2010/120365 | A2 | 10/2010 |
| WO | WO-2010/131015 | A1 | 11/2010 |
| WO | WO-2011/012850 | A2 | 2/2011 |
| WO | WO-2011/014890 | A1 | 2/2011 |
| WO | WO-2011/017055 | A2 | 2/2011 |
| WO | WO-2011/018496 | A2 | 2/2011 |
| WO | WO-2011/037896 | A2 | 3/2011 |
| WO | WO-2011/064247 | A1 | 6/2011 |
| WO | WO-2011/101242 | A1 | 8/2011 |
| WO | WO-2011/101267 | A1 | 8/2011 |
| WO | WO-2011/135307 | A1 | 11/2011 |
| WO | WO-2011/135308 | A1 | 11/2011 |
| WO | WO-2012/068134 | A1 | 5/2012 |
| WO | WO-2013/009627 | A2 | 1/2013 |

OTHER PUBLICATIONS

Baxter announces collaborations to develop longer acting forms of blood clotting factors. *Baxter News* (*online*), Sep. 29, 2005.
Bi et al., Target disruption of the mouse factor VIII gene produces a model of Haemophilia A. *Nat. Genet.* 10: 119-21 (1995).
Caliceti et al., Pharmacokinetics of pegylated interferons: What is misleading? *Digest. Liver Dis.* 36(Suppl. 3): S334-9 (2004).
Cordes et al., Nucleophilic catalysis of semicarbazone formation by anilines. *J. Am. Chem. Soc.*, 84: 826-31 (1962).
Dirksen et al., Nucleophilic catalysis of hydrazone formation and transimination: Implications for dynamic covalent chemistry. *J. Am. Chem. Soc.*, 128: 15602-3 (2006).
Dirksen et al., Nucleophilic catalysis of oxime ligation. *Ange. Chem. Int. Ed.*, 45(45): 7581-4 (2006).
Dirksen et al., Rapid oxime and hydrazone ligations with aromatic aldehyres for biomolecular labeling. *Bioconj. Chem.*, 19(12): 2543-8 (2008).
Gregoriadis et al., Improving the therapeutic efficacy of peptides and proteins: A role for polysialic acids. *Int. J. Pharmaceut.*, 300(1-2): 125-30 (2005).
Harris et al., Effect of pegylation on pharmaceuticals. *Nat. Rev. Drug Discovery.* 2: 214-21 (2003).
Jain et al., Polysialylation: The natural way to improve the stability and pharmacokinestics of protein and peptide drugs <<http://www.lipoxen.co.uk/media/48760/dds%20and%20s%20pp3-9.pdf>>, *dds&s*, 4(1): 3-9 (2004).
Jiang et al., Chemistry for pegylation of protein and peptide molecules, *Chin. J. Organ. Chem.*, 23(12): 1340-7 (2003).—English Abstract.
Kohler, Aniline: A catalyst for sialic acid detection. *ChemBioChem*, 10: 2147-50 (2009).
Kozlowski et al., Development of pegylated interferons for the treatment of chronic Hepatitis C. *BioDrugs.* 15(7): 419-29 (2001).
Lees et al., Versatile and efficient synthesis of protein-polysaccharide conjugate vaccines using aminooxy reagents and oxime chemistry. *Vaccine*, 24(6): 716-29 (2006).
Nektar Advanced PEGylation Catalog 2005-2006, p. 30 (2005).
Nektar Advanced PEGylation Price List 2005-2006, p. 11 (2005).
NOF Corporation DDS Catalogue, p. 58 (2005).
Roberts et a., Chemistry for peptide and protein pegylation *Adv. Drug Del. Rev.* 54: 459-76 (2002).
Rosen et al., Assay of factor VIII: C with a chromogenic substrate. *Scand J. Haematol.* 33(Suppl. 40): 139-45 (1984).
Rostin et al., B-domain deleted recombinant coagulation factor VIII modified with monomethoxy polyethylene glycol. *Bioconjugate Chem.* 11: 387-96 (2000).
Saenko et al., Strategies towards a longer acting factor VIII. *Haemophilia.* 12: 42-51 (2006).
Sakuragawa et al., Studies on the stability of factor VIII modified by polyethylene glycol. *Acta Med. Biol.* 36: 1-5 (1988).
Seffernick et al., Melamine deaminase and atrazine chlorohydrolase: 98% identical but functionally different. *J. Bacteriology.* 2405-10 (2001).
Severs et al., Characterization of PEGylated factor VIII molecules. *Blood.* 108: 11-12 (2006). Abstract.
Study shows molecular size and structure of PEG interferon molecules, as used in pegintron(R), affect antiviral activity in vitro. *Hispanic PR Wire*, Oct. 28, 2003.
Thygesen et al., Nucleophilic catalysis of carbohydrate oxime formation by anilines. *J. Org. Chem.*, 75: 1752-5 (2010).
Tsubery et al., Prolonging the action of protein and peptide drugs by a novel approach of reversible polyethylene glycol modification. *J. Biol. Chem.* 279(37): 38118-24 (2004).
Tsutsumi et al., Site-specific chemical modification with polyethylene glycol of recombinant immunotoxin anti-Tac(Fv)-PE38 (LMB-

(56) References Cited

OTHER PUBLICATIONS 2) improves antitumor activity and reduces animal toxicity and immunogenicity. *Proc. Natl. Acad. Sci. USA*. 97: 8548-53 (2000).

Urrutigoity et al., Biocatalysis in organic solvents with a polymer-bound horseradish peroxidase. *Biocatalysis*. 2: 145-9 (1989).

Veronese et al., Bioconjugation in pharmaceutical chemistry. *IL Farmaco*. 54: 497-516 (1999).

Wells et al., Additivity of mutational effects in proteins. *Biochemistry*. 29(37): 8509-17 (1990).

Wilchek et al., Labeling glycoconjugates with hydrazide reagents. *Methods Enzymol*. 138: 429-42 (1987).

Zalipsky et al., Hydrazide derivatives of poly(ethylene glycol) and their bioconjugates. Poly(ethylene glycol) Chemistry and Biological Applications. Chapter 21, pp. 318-341 (1997).

Zeng et al., High-efficency labeling of sialylated glycoproteins on living cells. *Nat. Methods*, 6(3): 207-9 (2009).

Great Britain Search Report and Written Opinion, GB-1012482.4, dated Nov. 24, 2010.

International Search Report and Written Opinion of the International Searching Authority, PCT/US2007/007560, European Patent Office, dated Sep. 18, 2007.

International Preliminary Report on Patentability, PCT/US2007/007560, dated Sep. 30, 2008.

International Search Report and Written Opinion of the International Searching Authority, PCT/US2009/052103, European Patent Office, dated Feb. 12, 2010.

International Preliminary Report on Patentability, PCT/US2009/052103, dated Feb. 1, 2011.

International Search Report and Written Opinion, PCT/US2010/043242, dated Feb. 10, 2011.

International Preliminary Report on Patentability, PCT/US2010/043242, dated Jan. 31, 2012.

International Search Report and Written Opinion of the International Searching Authority, PCT/GB2010/001422, European Patent Office, dated Feb. 4, 2011.

International Preliminary Report on Patentability, PCT/GB2010/001422, dated Jan. 31, 2012.

International Search Report and Written Opinion of the International Searching Authority, PCT/US2011/045873, European Patent Office, dated Nov. 24, 2011.

International Preliminary Report on Patentability, PCT/US2011/045873, dated Feb. 5, 2013.

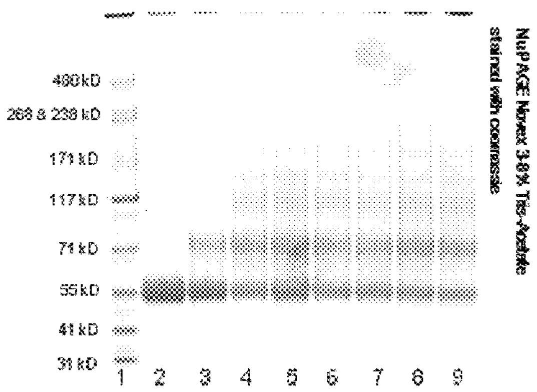

Lane 1: HiMark MW Standard
Lane 2: rFIX Standard
Lane 3: rFIX +100μM NaIO4, 0mM catalyst, 5X PSA
Lane 4: rFIX +100μM NaIO4, 2.5mM aniline, 5X PSA
Lane 5: rFIX +100μM NaIO4, 5mM aniline, 5X PSA
Lane 6: rFIX +100μM NaIO4, 10mM aniline, 5X PSA
Lane 7: rFIX +100μM NaIO4, 2.5mM m-toluidine, 5X PSA
Lane 8: rFIX +100μM NaIO4, 5mM m-toluidine, 5X PSA
Lane 9: rFIX +100μM NaIO4, 10mM m-toluidine, 5X PSA

B

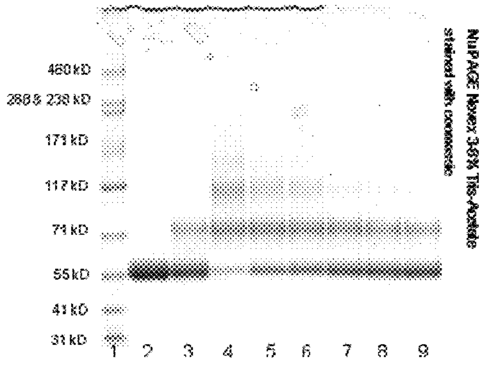

Lane 1: HiMark MW Standard
Lane 2: rFIX Standard
Lane 3: rFIX +100μM NaIO4, 0mM catalyst, 5X PSA
Lane 4: rFIX +100μM NaIO4, 10mM aniline, 5X PSA
Lane 5: rFIX +100μM NaIO4, 10mM o-aminobenzoic acid, 5X PSA
Lane 6: rFIX +100μM NaIO4, 10mM m-aminobenzoic acid, 5X PSA
Lane 7: rFIX +100μM NaIO4, 10mM p-aminobenzoic acid, 5X PSA
Lane 8: rFIX +100μM NaIO4, 10mM p-aminobenzamide, 5X PSA
Lane 9: rFIX +100μM NaIO4, 10mM sulfanilic acid, 5X PSA

C

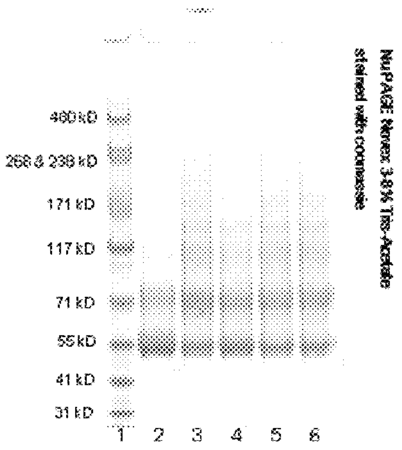

Lane 1: HiMark MW Standard
Lane 2: rFIX +100μM NaIO4, 0mM catalyst, 5X PSA
Lane 3: rFIX +100μM NaIO4, 10mM aniline, 5X PSA
Lane 4: rFIX +100μM NaIO4, 10mM o-anisidine, 5X PSA
Lane 5: rFIX +100μM NaIO4, 10mM m-anisidine, 5X PSA
Lane 6: rFIX +100μM NaIO4, 10mM m-toluidine, 5X PSA

SEQUENCE LISTING

```
<160> NUMBER OF SEQ ID NOS: 1

<210> SEQ ID NO 1
<211> LENGTH: 422
<212> TYPE: PRT
<213> ORGANISM: Homo sapiens

<400> SEQUENCE: 1

Leu Asn Arg Pro Lys Arg Tyr Asn Ser Gly Lys Leu Glu Glu Phe Val
1               5                   10                  15

Gln Gly Asn Leu Glu Arg Glu Cys Met Glu Glu Lys Cys Ser Phe Glu
            20                  25                  30

Glu Pro Arg Glu Val Phe Glu Asn Thr Glu Lys Thr Thr Glu Phe Trp
        35                  40                  45

Lys Gln Tyr Val Asp Gly Asp Gln Cys Glu Ser Asn Pro Cys Leu Asn
    50                  55                  60

Gly Gly Ser Cys Lys Asp Asp Ile Asn Ser Tyr Glu Cys Trp Cys Pro
65                  70                  75                  80

Phe Gly Phe Glu Gly Lys Asn Cys Glu Leu Asp Val Thr Cys Asn Ile
                85                  90                  95

Lys Asn Gly Arg Cys Glu Gln Phe Cys Lys Asn Ser Ala Asp Asn Lys
            100                 105                 110

Val Val Cys Ser Cys Thr Glu Gly Tyr Arg Leu Ala Glu Asn Gln Lys
        115                 120                 125

Ser Cys Glu Pro Ala Val Pro Phe Pro Cys Gly Arg Val Ser Val Ser
    130                 135                 140

Gln Thr Ser Lys Leu Thr Arg Ala Glu Ala Val Phe Pro Asp Val Asp
145                 150                 155                 160

Tyr Val Asn Pro Thr Glu Ala Glu Thr Ile Leu Asp Asn Ile Thr Gln
                165                 170                 175
```

-continued

```
Gly Thr Gln Ser Phe Asn Asp Phe Thr Arg Val Val Gly Gly Glu Asp
            180                 185                 190

Ala Lys Pro Gly Gln Phe Pro Trp Gln Val Val Leu Asn Gly Lys Val
        195                 200                 205

Asp Ala Phe Cys Gly Gly Ser Ile Val Asn Glu Lys Trp Ile Val Thr
    210                 215                 220

Ala Ala His Cys Val Glu Thr Gly Val Lys Ile Thr Val Val Ala Gly
225                 230                 235                 240

Glu His Asn Ile Glu Glu Thr Glu His Thr Glu Gln Lys Arg Asn Val
                245                 250                 255

Ile Arg Ala Ile Ile Pro His His Asn Tyr Asn Ala Ala Ile Asn Lys
            260                 265                 270

Tyr Asn His Asp Ile Ala Leu Leu Glu Leu Asp Glu Pro Leu Val Leu
        275                 280                 285

Asn Ser Tyr Val Thr Pro Ile Cys Ile Ala Asp Lys Glu Tyr Thr Asn
    290                 295                 300

Ile Phe Leu Lys Phe Gly Ser Gly Tyr Val Ser Gly Trp Ala Arg Val
305                 310                 315                 320

Phe His Lys Gly Arg Ser Ala Leu Val Leu Gln Tyr Leu Arg Val Pro
                325                 330                 335

Leu Val Asp Arg Ala Thr Cys Leu Arg Ser Thr Lys Phe Thr Ile Tyr
            340                 345                 350

Asn Asn Met Phe Cys Ala Gly Phe His Glu Gly Gly Arg Asp Ser Cys
        355                 360                 365

Gln Gly Asp Ser Gly Gly Pro His Val Thr Glu Val Glu Gly Thr Ser
    370                 375                 380

Phe Leu Thr Gly Ile Ile Ser Trp Gly Glu Glu Cys Ala Met Lys Gly
385                 390                 395                 400

Lys Tyr Gly Ile Tyr Thr Lys Val Ser Arg Tyr Val Asn Trp Ile Lys
                405                 410                 415

Glu Lys Thr Lys Leu Thr
            420
```

NUCLEOPHILIC CATALYSTS FOR OXIME LINKAGE

FIELD OF THE INVENTION

The present invention relates to materials and methods for conjugating a water soluble polymer to a protein.

BACKGROUND OF THE INVENTION

The preparation of conjugates by forming a covalent linkage between the water soluble polymer and the therapeutic protein can be carried out by a variety of chemical methods. PEGylation of polypeptide drugs protects them in circulation and improves their pharmacodynamic and pharmacokinetic profiles (Harris and Chess, Nat Rev Drug Discov. 2003; 2:214-21). The PEGylation process attaches repeating units of ethylene glycol (polyethylene glycol (PEG)) to a polypeptide drug. PEG molecules have a large hydrodynamic volume (5-10 times the size of globular proteins), are highly water soluble and hydrated, non-toxic, non-immunogenic and rapidly cleared from the body. PEGylation of molecules can lead to increased resistance of drugs to enzymatic degradation, increased half-life in vivo, reduced dosing frequency, decreased immunogenicity, increased physical and thermal stability, increased solubility, increased liquid stability, and reduced aggregation. The first PEGylated drugs were approved by the FDA in the early 1990s. Since then, the FDA has approved several PEGylated drugs for oral, injectable, and topical administration.

Polysialic acid (PSA), also referred to as colominic acid (CA), is a naturally occurring polysaccharide. It is a homopolymer of N-acetylneuraminic acid with $\alpha(2\rightarrow8)$ ketosidic linkage and contains vicinal diol groups at its non-reducing end. It is negatively charged and a natural constituent of the human body. It can easily be produced from bacteria in large quantities and with pre-determined physical characteristics (U.S. Pat. No. 5,846,951). Because the bacterially-produced PSA is chemically and immunologically identical to PSA produced in the human body, bacterial PSA is non-immunogenic, even when coupled to proteins. Unlike some polymers, PSA acid is biodegradable. Covalent coupling of colominic acid to catalase and asparaginase has been shown to increase enzyme stability in the presence of proteolytic enzymes or blood plasma. Comparative studies in vivo with polysialylated and unmodified asparaginase revealed that polysialylation increased the half-life of the enzyme (Fernandes and Gregoriadis, Int J Pharm. 2001; 217:215-24).

Coupling of PEG-derivatives to peptides or proteins is reviewed by Roberts et al. (Adv Drug Deliv Rev 2002; 54:459-76). One approach for coupling water soluble polymers to therapeutic proteins is the conjugation of the polymers via the carbohydrate moieties of the protein. Vicinal hydroxyl (OH) groups of carbohydrates in proteins can be easily oxidized with sodium periodate ($NaIO_4$) to form active aldehyde groups (Rothfus et Smith, J Biol Chem 1963; 238: 1402-10; van Lenten et Ashwell, J Biol Chem 1971; 246: 1889-94). Subsequently the polymer can be coupled to the aldehyde groups of the carbohydrate by use of reagents containing, for example, an active hydrazide group (Wilchek M and Bayer E A, Methods Enzymol 1987; 138:429-42). A more recent technology is the use of reagents containing aminooxy groups which react with aldehydes to form oxime linkages (WO 96/40662, WO2008/025856).

Additional examples describing conjugation of a water soluble polymer to a therapeutic protein are described in WO 06/071801 which teaches the oxidation of carbohydrate moieties in Von Willebrand factor and subsequent coupling to PEG using hydrazide chemistry; US Publication No. 2009/0076237 which teaches the oxidation of rFVIII and subsequent coupling to PEG and other water soluble polymers (e.g. PSA, HES, dextran) using hydrazide chemistry; WO 2008/025856 which teaches oxidation of different coagulation factors, e.g. rFIX, FVIII and FVIIa and subsequent coupling to e.g., PEG, using aminooxy chemistry by forming an oxime linkage; and U.S. Pat. No. 5,621,039 which teaches the oxidation of FIX and subsequent coupling to PEG using hydrazide chemistry.

Recently, an improved method was described comprising mild periodate oxidation of sialic acids to generate aldehydes followed by reaction with an aminooxy group containing reagent in the presence of catalytic amounts of aniline (Dirksen A., and Dawson P E, Bioconjugate Chem. 2008; 19, 2543-8; and Zeng Y et al., Nature Methods 2009; 6:207-9). The aniline catalysis dramatically accelerates the oxime ligation, allowing the use of very low concentrations of the reagent. The use of nucleophilic catalysts are also described in Dirksen, A., et al., J Am Chem. Soc., 128:15602-3 (2006); Dirksen, A., et al., Angew chem. Int Ed., 45:7581-4 (2006); Kohler, J. J., ChemBioChem., 10:2147-50 (2009); Giuseppone, N., et al., J Am Chem. Soc., 127:5528-39 (2005); and Thygesen, M. B., et al., J Org. Chem., 75:1752-5 (2010).

Although aniline catalysis can accelerate the oxime ligation allowing short reaction times and the use of low concentrations of the aminooxy reagent, aniline has toxic properties that must be considered when, for example, the conjugated therapeutic protein to form the basis of a pharmaceutical. For example, aniline has been shown to induce methemoglobinemia (Harrison, J. H., and Jollow, D. J., Molecular Pharmacology, 32(3) 423-431, 1987). Long-term dietary treatment of rats has been shown to induce tumors in the spleen (Goodman, D G., et al., J Natl Cancer Inst., 73(1):265-73, 1984). In vitro studies have also shown that aniline has the potential to induce chromosome mutations and has the potentially genotoxic activity (Bombhard E. M. et Herbold B, Critical Reviews in Toxicology 35,783-835, 2005).

There remains a need to develop materials and methods for conjugating water soluble polymers to proteins that improves the protein's pharmacodynamic and/or pharmacokinetic properties while minimizing the costs associated with the various reagents and minimizing the health risks to the patient recipient.

SUMMARY OF THE INVENTION

The present invention provides materials and methods for conjugating polymers to proteins that improves the protein's pharmacodynamic and/or pharmacokinetic properties while minimizing the costs associated with the various reagents and the health risks to the patient recipients when the conjugation reaction is catalyzed by a nucleophilic catalyst. In various embodiments of the invention, alternative catalysts to substitute for aniline are provided.

The present disclosure also provides an optimized procedure for preparation of various water-soluble polymer-aminooxy linker reagents that can be used to conjugate therapeutic proteins as described herein. Recent NMR studies showed that side reactions at the reducing end of PSA can occur if the preparation of the PSA-aminooxy reagent is performed at room temperature. Thus, in various embodiments of the present disclosure, the new process is carried out at a temperature between 2-8° C. In one embodiment, the PSA-aminooxy reagent is prepared at 4° C. according to the process described herein. In addition, purification of the reagent using a chromatographic purification step (e.g., IEX) at a temperature between 2-8° C. is also contemplated by the present disclosure. Unwanted side reactions at the reducing end of the PSA are substantially reduced when the entire process (chemical reaction and purification of the conjugate by IEX) is performed at a temperature between 2-8° C.

In one embodiment according to the present disclosure, a method of conjugating a water soluble polymer to an oxidized carbohydrate moiety of a therapeutic protein is provided comprising contacting the oxidized carbohydrate moiety with an activated water soluble polymer under conditions that allow conjugation; said water soluble polymer containing an active aminooxy group and is selected from the group consisting of polyethylene glycol (PEG), branched PEG, PolyPEG® (Warwick Effect Polymers; Coventry, UK), polysialic acid (PSA), starch, hydroxyalkyl starch (HAS), hydroxylethyl starch (HES), carbohydrate, polysaccharides, pullulane, chitosan, hyaluronic acid, chondroitin sulfate, dermatan sulfate, starch, dextran, carboxymethyl-dextran, polyalkylene oxide (PAO), polyalkylene glycol (PAG), polypropylene glycol (PPG), polyoxazoline, polyacryloylmorpholine, polyvinyl alcohol (PVA), polycarboxylate, polyvinylpyrrolidone, polyphosphazene, polyoxazoline, polyethylene-co-maleic acid anhydride, polystyrene-co-maleic acid anhydride, poly(1-hydroxymethylethylene hydroxymethylformal) (PHF), 2-methacryloyloxy-2'-ethyltrimethylammoniumphosphate (MPC); wherein the water soluble polymer containing an active aminooxy group is prepared by a method comprising: a) incubating a solution comprising an oxidized water-soluble polymer with an aminooxy linker comprising an active aminooxy group under conditions that allow the formation of a stable oxime linkage between the oxidized water-soluble polymer and the activated aminooxy linker, said conditions comprising a time period between about 1 minute and about 24 hours; a temperature between about 2° C. and about 8° C.; in the presence or absence of light, and with or without stirring; thereby forming a water-soluble polymer containing an active aminooxy group; and b) purifying the water soluble polymer containing an active aminooxy group by a method selected from the group consisting of chromatography, filtration, dialysis, and precipitation, at a temperature between about 2° C. and about 8° C.; said carbohydrate moiety oxidized by incubation with a buffer comprising an oxidizing agent selected from the group consisting of sodium periodate ($NaIO_4$), lead tetraacetate ($Pb(OAc)_4$) and potassium perruthenate (KRuO4); wherein an oxime linkage is formed between the oxidized carbohydrate moiety and the active aminooxy group on the water soluble polymer; and wherein said oxime linkage formation is catalyzed by a nucleophilic catalyst selected from the group consisting of o-amino benzoic acid, m-amino benzoic acid, p-amino benzoic acid, sulfanilic acid, o-aminobenzamide, o-toluidine, m-toluidine, p-toluidine, o-anisidine, m-anisidine, and p-anisidine.

In another embodiment, the aforementioned method is provided wherein the solution comprising the oxidized water-soluble polymer and the aminooxy linker comprising an active aminooxy group is incubated at 4° C. for 1 h in the absence of light with stirring. In another embodiment, the aforementioned method is provided wherein the water soluble polymer containing an active aminooxy group is purified by anion exchange chromatography at a temperature of 4° C. In another embodiment, an aforementioned method is provided wherein the oxidized water soluble polymer is PSA and is oxidized by incubation with $NaIO_4$.

In another embodiment of the present disclosure, a method of conjugating a water soluble polymer to an oxidized carbohydrate moiety of a therapeutic protein is provided comprising contacting the oxidized carbohydrate moiety with an activated water soluble polymer under conditions that allow conjugation; said water soluble polymer containing an active aminooxy group and is selected from the group consisting of polyethylene glycol (PEG), branched PEG, PolyPEG® (Warwick Effect Polymers; Coventry, UK), polysialic acid (PSA), starch, hydroxyalkyl starch (HAS), hydroxylethyl starch (HES), carbohydrate, polysaccharides, pullulane, chitosan, hyaluronic acid, chondroitin sulfate, dermatan sulfate, starch, dextran, carboxymethyl-dextran, polyalkylene oxide (PAO), polyalkylene glycol (PAG), polypropylene glycol (PPG), polyoxazoline, polyacryloylmorpholine, polyvinyl alcohol (PVA), polycarboxylate, polyvinylpyrrolidone, polyphosphazene, polyoxazoline, polyethylene-co-maleic acid anhydride, polystyrene-co-maleic acid anhydride, poly(1-hydroxymethylethylene hydroxymethylformal) (PHF), 2-methacryloyloxy-2'-ethyltrimethylammoniumphosphate (MPC); wherein the water soluble polymer containing an active aminooxy group is prepared by a method comprising: a) incubating a solution comprising a water-soluble polymer with an aminooxy linker comprising an active aminooxy group under conditions that allow the formation of a stable oxime linkage between the water-soluble polymer and the activated aminooxy linker, said conditions comprising a time period between about 1 minute and about 24 hours; a temperature between about 22° C. and about 37° C.; in the presence or absence of light, and with or without stirring; thereby forming a water-soluble polymer containing an active aminooxy group; and b) purifying the water soluble polymer containing an active aminooxy group by a method selected from the group consisting of chromatography, filtration, dialysis, and precipitation; said carbohydrate moiety oxidized by incubation with a buffer comprising an oxidizing agent selected from the group consisting of sodium periodate ($NaIO_4$), lead tetraacetate ($Pb(OAc)_4$) and potassium perruthenate (KRuO4); wherein an oxime linkage is formed between the oxidized carbohydrate moiety and the active aminooxy group on the water soluble polymer; and wherein said oxime linkage formation is catalyzed by a nucleophilic catalyst selected from the group consisting of, o-amino benzoic acid, m-amino benzoic acid, p-amino benzoic acid, sulfanilic acid, o-aminobenzamide, o-toluidine, m-toluidine, p-toluidine, o-anisidine, m-anisidine, and p-anisidine.

In another embodiment, the aforementioned method is provided wherein the solution comprising the water-soluble polymer and the aminooxy linker comprising an active aminooxy group is incubated at 22° C. for 2 h in the absence of light with stirring. In another embodiment, the aforementioned method is provided wherein the solution comprising the water-soluble polymer and the aminooxy linker comprising an active aminooxy group is incubated at 22° C. for 2 h in the absence of light with stirring; said method further comprising the step of increasing the temperature of the solution to a temperature between about 32° C. and about 37° C. and incubating for an additional 12-24 hours. In another embodiment, the aforementioned method is provided comprising the additional step of adding an additional amount of aminooxy linker comprising an active aminooxy group immediately prior to increasing the temperature. In another embodiment, the aforementioned method is provided wherein the water soluble polymer containing an active aminooxy group is purified by a method selected from the group consisting of dialysis, ultrafiltration/diafiltration (UF/DF), and chromatography at a temperature of 22° C. In another embodiment, the aforementioned method is provided further comprising the step of purifying the water soluble polymer containing an active aminooxy group by a method selected from the group consisting of dialysis, UF/DF or chromatography at 4° C.

In various embodiments of the present disclosure, an aforementioned method is provided wherein the therapeutic protein selected from the group consisting of Factor IX (FIX), Factor VIII (FVIII), Factor VIIa (FVIIa), Von Willebrand Factor (VWF), Factor FV (FV), Factor X (FX), Factor XI (FXI), Factor XII (FXII), thrombin (FII), protein C, protein S, tPA, PAI-1, tissue factor (TF), ADAMTS 13 protease, IL-1 alpha, IL-1 beta, IL-2, IL-3, IL-4, IL-5, IL-6, IL-11, colony stimulating factor-1 (CSF-1), M-CSF, SCF, GM-CSF, granulocyte colony stimulating factor (G-CSF), EPO, interferon-alpha (IFN-alpha), consensus interferon, IFN-beta, IFN-gamma, IFN-omega, IL-7, IL-8, IL-9, IL-10, IL-12, IL-13, IL-14, IL-15, IL-16, IL-17, IL-18, IL-19, IL-20, IL-21, IL-22, IL-23, IL-24, IL-31, IL-32 alpha, IL-33, thrombopoietin (TPO), Ang-1, Ang-2, Ang-4, Ang-Y, angiopoietin-like polypeptide 1 (ANGPTL1), angiopoietin-like polypeptide 2 (ANGPTL2), angiopoietin-like polypeptide 3 (ANGPTL3), angiopoietin-like polypeptide 4 (ANGPTL4), angiopoietin-like polypeptide 5 (ANGPTL5), angiopoietin-like polypeptide 6 (ANGPTL6), angiopoietin-like polypeptide 7 (ANGPTL7), vitronectin, vascular endothelial growth factor (VEGF), angiogenin, activin A, activin B, activin C, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, bone morphogenic protein receptor II, brain derived neurotrophic factor, cardiotrophin-1, ciliary neutrophic factor, ciliary neutrophic factor receptor, cripto, cryptic, cytokine-induced neutrophil chemotactic factor 1, cytokine-induced neutrophil, chemotactic factor 2α, cytokine-induced neutrophil chemotactic factor 2β, β endothelial cell growth factor, endothelin 1, epidermal growth factor, epigen, epiregulin, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor 11, fibroblast growth factor 12, fibroblast growth factor 13, fibroblast growth factor 16, fibroblast growth factor 17, fibroblast growth factor 19, fibroblast growth factor 20, fibroblast growth factor 21, fibroblast growth factor acidic, fibroblast growth factor basic, glial cell line-derived neutrophic factor receptor α1, glial cell line-derived neutrophic factor receptor α2, growth related protein, growth related protein α, growth related protein β, growth related protein γ, heparin binding epidermal growth factor, hepatocyte growth factor, hepatocyte growth factor receptor, hepatoma-derived growth factor, insulin-like growth factor I, insulin-like growth factor receptor, insulin-like growth factor II, insulin-like growth factor binding protein, keratinocyte growth factor, leukemia inhibitory factor, leukemia inhibitory factor receptor α, nerve growth factor nerve growth factor receptor, neuropoietin, neurotrophin-3, neurotrophin-4, oncostatin M (OSM), placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor α, platelet derived growth factor receptor β, pre-B cell growth stimulating factor, stem cell factor (SCF), stem cell factor receptor, TNF, TNF0, TNF1, TNF2, transforming growth factor α, transforming growth factor β, transforming growth factor β1, transforming growth factor β1.2, transforming growth factor β2, transforming growth factor β3, transforming growth factor β5, latent transforming growth factor β1, transforming growth factor β binding protein I, transforming growth factor β binding protein II, transforming growth factor β binding protein III, thymic stromal lymphopoietin (TSLP), tumor necrosis factor receptor type I, tumor necrosis factor receptor type II, urokinase-type plasminogen activator receptor, phospholipase-activating protein (PUP), insulin, lectin ricin, prolactin, chorionic gonadotropin, follicle-stimulating hormone, thyroid-stimulating hormone, tissue plasminogen activator, IgG, IgE, IgM, IgA, and IgD, α-galactosidase, β-galactosidase, DNAse, fetuin, leutinizing hormone, estrogen, insulin, albumin, lipoproteins, fetoprotein, transferrin, thrombopoietin, urokinase, integrin, thrombin, leptin, Humira (adalimumab), Prolia (denosumab), Enbrel (etanercept), a protein in Table 1, or a biologically active fragment, derivative or variant thereof.

In still another embodiment, the aforementioned method is provided wherein a solution comprising an initial concentration of the therapeutic protein between about 0.3 mg/ml and about 3.0 mg/ml is adjusted to a pH value between about 5.0 and about 8.0 prior to contacting with the activated water soluble polymer. In one embodiment, the initial concentration of the therapeutic protein is about 1.0 mg/ml and the pH is about 6.0.

In another embodiment, the aforementioned method is provided wherein the therapeutic protein is contacted by a desired excess concentration of activated water soluble polymer, wherein the excess concentration is between about 1-molar and about 300-molar excess. In one embodiment, the excess concentration is about 50-fold molar excess.

In another embodiment, the aforementioned method is provided wherein the therapeutic protein is incubated with the activated water soluble polymer under conditions comprising a time period between about 0.5 hours and about 24 hours; a temperature between about 2° C. and about 37° C.; in the presence or absence of light; and with or without stirring. In one embodiment, the conditions comprise a time period of about 120 minutes, a temperature of about 22° C., the absence of light; and with stirring.

In yet another embodiment, an aforementioned method is provided wherein the nucleophilic catalyst is added in an amount to result in a final concentration between about 1.0 mM and about 50 mM nucleophilic catalyst, under conditions comprising a time period between about 0.1 minutes and about 30 minutes; a temperature between about 2° C. and about 37° C.; in the presence or absence of light; and with or without stirring. In one embodiment, the final concentration of the nucleophilic catalyst is about 10 mM, and the conditions comprise a time period of up to about 15 minutes, a temperature of about 22° C., the absence of light; and with stirring.

In yet another embodiment, the aforementioned method is provided wherein the oxidizing agent is added in an amount to result in a final concentration between about 50 μM and about 1000 μM oxidizing agent, under conditions comprising a time period between about 0.1 minutes and 120 minutes; a temperature between about 2° C. and about 37° C.; in the presence or absence of light; and with or without stirring. In one embodiment, the final concentration of oxidizing agent is about 400 μM, and the conditions comprise a time period of about 10 minutes, a temperature of about 22° C., the absence of light and with stirring.

In still another embodiment, the aforementioned method is provided wherein the conjugating the water soluble polymer to the oxidized carbohydrate moiety of the therapeutic protein is stopped by the addition of a quenching agent selected from the group consisting of L-cysteine, methionine, glutathione, glycerol, sodium meta bisulfite ($Na_2S_2O_5$), tryptophane, tyrosine, histidine or derivatives thereof, kresol, imidazol, and combinations thereof; wherein the quenching agent is added in an amount to result in a final concentration between about 1 mM and about 100 mM quenching agent, under conditions comprising a time period between about 5 minutes and about 120 minutes; a temperature between about 2° C. and about 37° C.; in the presence or absence of light; and with or without stirring. In one embodiment the quenching agent is L-cysteine. In still another embodiment, the L-cysteine is added to result in a final concentration of about 10 mM and the conditions comprise a time period of about 60 minutes, a temperature of about 22° C., the absence of light and with stirring.

In another embodiment, an aforementioned method is provided comprising: a) a first step comprising adjusting the pH value of a solution comprising the therapeutic protein to a pH value between about 5.0 and about 8.0, wherein the therapeutic protein concentration is between about 0.3 mg/ml and about 3.0 mg/ml; b) a second step comprising oxidizing one or more carbohydrates on the therapeutic protein, wherein the oxidizing agent is added to the solution in the first step to result in a final concentration between about 50 μM and about 1000 μM, under conditions comprising a time period between about 0.1 minutes and about 120 minutes; a temperature between about 2° C. and about 37° C.; in the presence or absence of light, and with or without stirring; c) a third step comprising contacting the therapeutic protein with a desired excess concentration of activated water soluble polymer, wherein the excess concentration is between about 1-molar excess and about 300-molar excess, under conditions comprising a time period between about 0.5 hours and about 24 hours, a temperature between about 2° C. and about 37° C.; in the presence or absence of light; and with or without stirring; d) a fourth step comprising adding a nucleophilic catalyst to the solution of the third step, wherein the nucleophilic catalyst is added to result in a final concentration between about 1 mM and about 50 mM, under conditions comprising a time period between about 0.1 minutes and about 30 minutes; a temperature between about 2° C. and about 37° C.; in the presence or absence of light, and with or without stirring; e) a fifth step wherein the therapeutic protein is incubated with the activated water soluble polymer and nucleophilic catalyst under conditions that allow conjugation of the activated water-soluble polymer to one or more oxidized carbohydrates on the therapeutic protein, said conditions comprising a time period between about 0.5 hours and about 24 hours, a temperature between about 2° C. and about 37° C.; in the presence or absence of light, and with or without stirring; and f) a sixth step wherein the conjugating the water soluble polymer to the one or more oxidized carbohydrates of the therapeutic protein in the fifth step is stopped by the addition of a quenching agent selected from the group consisting of L-cysteine, methionine, glutathione, glycerol, $Na_2S_2O_5$ (sodium meta bisulfite), tryptophane, tyrosine, histidine or derivatives thereof, kresol, imidazol, and combinations thereof; wherein the quenching agent is added to result in a final concentration of about 1 mM and about 100 mM, under conditions comprising a time period between about 5 minutes and about 120 minutes; a temperature between about 2° C. and about 37° C.; in the presence or absence of light, and with or without stirring. In another embodiment, the initial concentration of the therapeutic protein in the first step is about 1 mg/ml and the pH is about 6.0; wherein the final concentration of oxidizing agent in the second step is about 400 μM, and the conditions in the fifth step comprise a time period of about 10 minutes, a temperature of about 22° C., the absence of light and with stirring; wherein the excess concentration in the third step is about 50 molar excess; wherein the conditions in the third step comprise a time period of about 15 minutes, a temperature of about 22° C., the absence of light and with stirring; wherein the final concentration of the nucleophilic catalyst in the fourth step is about 10 mM, and the conditions in the fourth step comprise a time period of about 15 minutes, a temperature of about 22° C., the absence of light and with stirring; wherein the conditions of incubating the therapeutic protein with the activated water soluble polymer and nucleophilic catalyst in the fifth step comprise a time period of about 2 hours; a temperature of about 22° C.; the absence of light; and with stirring; and wherein the quenching agent in the sixth step is L-cysteine; and wherein the L-cysteine is added to result in a final concentration of about 10 mM and the conditions in the sixth step comprise a time period of about 60 minutes, a temperature of about 22° C., the absence of light and with stirring. In still another embodiment, the water soluble polymer is PSA. In one embodiment, the water soluble polymer is PEG. In another embodiment, the water soluble polymer is HES. In yet another embodiment, the water soluble polymer is HAS. In another embodiment the PSA is comprised of about 10-300 sialic acid units. In still another embodiment, the therapeutic protein is FIX. In another embodiment, the therapeutic protein is FVIIa. In yet another embodiment, the therapeutic protein is FVIII.

In another embodiment, an aforementioned method is provided wherein the oxidizing agent is sodium periodate ($NaIO_4$).

In another embodiment, the aforementioned method is provided wherein the oxidized carbohydrate moiety of the therapeutic protein is located in the activation peptide of the blood coagulation protein.

In another embodiment, the aforementioned method is provided wherein the PSA comprises an activated aminooxy linker selected from the group consisting of: a) a 3-oxa-pentane-1,5-dioxyamine linker of the formula:

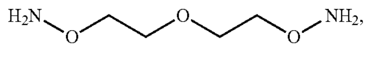

b) a 3,6,9-trioxa-undecane-1,11-dioxyamine linker of the formula:

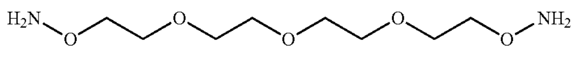 [SMILES: NOCCOCCOCCOCCON]

and c) a 3,6,9,12,15-penatoxa-heptadecane-1,17-dioxyamine linker of the formula:

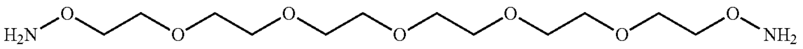

wherein the PSA is oxidized by incubation with an oxidizing agent to form a terminal aldehyde group at the non-reducing end of the PSA.

In another embodiment, the aminooxy linker is 3-oxa-pentane-1,5-dioxyamine.

In another embodiment, the aforementioned method is provided wherein the nucleophilic catalyst is provided at a concentration between about 1 mM and about 50 mM. In another embodiment, the nucleophilic catalyst is m-toluidine. In still another embodiment, the m-toluidine is present in the conjugation reaction at a concentration of about 10 mM.

In another embodiment, the aforementioned method is provided further comprising the step of purifying the conjugated therapeutic protein. In one embodiment, the conjugated therapeutic protein is purified by a method selected from the group consisting of chromatography, filtration and precipitation. In still another embodiment, the chromatography is selected from the group consisting of Hydrophobic Interaction Chromatography (HIC), Ion Exchange chromatography (IEC), Size exclusion chromatography (SEC), Affinity chromatography, and Reversed-phase chromatography. In one embodiment, an anti-chaotropic salt is used in a chromatography loading step and in a chromatography washing step. In still another embodiment, the chromatography takes place in a column. In one embodiment, the column comprises a chromatography resin selected from the group consisting of Phenyl-Sepharose FF and Butyl-Sepharose FF. In yet another embodiment, the resin is present in the column at a bed height of between about 5 cm and about 20 cm.

In still another embodiment, the bed height is about 10 cm. In another embodiment, an aforementioned method is provided wherein comprising one or more washing steps wherein flow direction is set to up-flow and wherein the flow rate is between about 0.2 cm/min and about 6.7 cm/min. In one embodiment, the flow rate is about 2 cm/min. In another embodiment, the aforementioned method is provided comprising one or more elution steps wherein flow direction is set to down-flow and wherein the flow rate is between about 0.1 cm/min and about 6.7 cm/min. In one embodiment, the flow rate is about 1 cm/min.

In yet another embodiment, the aforementioned method is provided further comprising concentrating the conjugated therapeutic protein by ultra-/diafiltration (UF/DF). In another embodiment, the aforementioned method is provided wherein the final concentration of therapeutic protein is between about 0.5 and about 3 mg/ml. In another embodiment, the aforementioned method is provided wherein the therapeutic protein comprises between about 5 and about 11 water soluble polymer moieties.

In still another embodiment, the aforementioned method is provided wherein the conjugated therapeutic protein is purified using chromatography; wherein an anti-chaotropic salt is used for a loading step and for a washing step; the method comprising one or more washing steps wherein flow direction is set to up-flow and wherein the flow rate is between about 0.2 cm/min and about 6.7 cm/min and one or more elution steps wherein flow direction is set to down-flow and wherein the flow rate is between about 0.2 cm/min and about 6.7 cm/min; further comprising concentrating the conjugated therapeutic protein by ultra-/diafiltration (UF/DF).

In another embodiment, the aforementioned method is provided wherein the chromatography is hydrophobic interaction chromatography (HIC); wherein the one or more washing steps flow rate is about 2 cm/min; and wherein the one or more elution steps flow rate is about 1 cm/min.

A modified therapeutic protein produced by an aforementioned method is also provided by the present disclosure.

In one embodiment of the present disclosure, a method of preparing a water-soluble polymer containing an active aminooxy group is provided comprising: a) incubating a solution comprising an oxidized water-soluble polymer with an aminooxy linker comprising an active aminooxy group under conditions that allow the formation of a stable oxime linkage between the oxidized water-soluble polymer and the activated aminooxy linker, said conditions comprising a time period between about 1 minute and about 24 hours; a temperature between about 2° C. and about 8° C.; in the presence or absence of light, and with or without stirring; thereby forming a water-soluble polymer containing an active aminooxy group; and b) purifying the water soluble polymer containing an active aminooxy group by a method selected from the group consisting of chromatography, filtration, dialysis, and precipitation, at a temperature between about 2° C. and about 8° C.; said water soluble polymer is selected from the group consisting of polyethylene glycol (PEG), branched PEG, PolyPEG® (Warwick Effect Polymers; Coventry, UK), polysialic acid (PSA), starch, hydroxyalkyl starch (HAS), hydroxylethyl starch (HES), carbohydrate, polysaccharides, pullulane, chitosan, hyaluronic acid, chondroitin sulfate, dermatan sulfate, starch, dextran, carboxymethyl-dextran, polyalkylene oxide (PAO), polyalkylene glycol (PAG), polypropylene glycol (PPG), polyoxazoline, poly-acryloylmorpholine, polyvinyl alcohol (PVA), polycarboxylate, polyvinylpyrrolidone, polyphosphazene, polyoxazoline, polyethylene-co-maleic acid anhydride, polystyrene-co-maleic acid anhydride, poly(1-hydroxymethylethylene hydroxymethylformal) (PHF), 2-methacryloyloxy-2'-ethyltrimethylammoniumphosphate (MPC); thereby forming an oxime linkage between the water-soluble polymer and the aminooxy linker.

In another embodiment, the aforementioned method is provided wherein the oxime linkage formation is catalyzed by a nucleophilic catalyst selected from the group consisting of o-amino benzoic acid, m-amino benzoic acid, p-amino benzoic acid, sulfanilic acid, o-aminobenzamide, o-toluidine, m-toluidine, p-toluidine, o-anisidine, m-anisidine, and p-anisidine.

In another embodiment, the aforementioned method is provided wherein the water soluble polymer is PSA In another embodiment, the aforementioned method is provided wherein the water-soluble polymer is PEG. In another embodiment, the aforementioned method is provided wherein the solution comprising the oxidized water-soluble polymer and the aminooxy linker comprising an active aminooxy group is incubated at 4° C. for 1 h in the absence of light with stirring. In another embodiment, the aforementioned method is provided wherein the water soluble polymer containing an active aminooxy group is purified by anion exchange chromatography at a temperature of 4° C.

In yet another embodiment of the present disclosure, a method of preparing a water soluble polymer containing an active aminooxy group is provided comprising: a) incubating a solution comprising a water-soluble polymer with an aminooxy linker comprising an active aminooxy group under conditions that allow the formation of a stable oxime linkage between the water-soluble polymer and the activated aminooxy linker, said conditions comprising a time period between about 1 minute and about 24 hours; a temperature between about 22° C. and about 37° C.; in the presence or absence of light, and with or without stirring; thereby forming a water-soluble polymer containing an active aminooxy group; and b) purifying the water soluble polymer containing an active aminooxy group by a method selected from the group consisting of chromatography, filtration, dialysis, and precipitation; thereby forming an oxime linkage between the water-soluble polymer and aminooxy linker.

In another embodiment, the aforementioned method is provided wherein said oxime linkage formation is catalyzed by a nucleophilic catalyst selected from the group consisting of o-amino benzoic acid, m-amino benzoic acid, p-amino benzoic acid, sulfanilic acid, o-aminobenzamide, o-toluidine, m-toluidine, p-toluidine, o-anisidine, m-anisidine, and p-anisidine.

In another embodiment, the aforementioned method is provided wherein the solution comprising the water-soluble polymer and the aminooxy linker comprising an active aminooxy group is incubated at 22° C. for 2 h in the absence of light with stirring. In another embodiment, the aforementioned method is provided wherein the solution comprising the water-soluble polymer and the aminooxy linker comprising an active aminooxy group is incubated at 22° C. for 2 h in the absence of light with stirring; said method further comprising the step of increasing the temperature of the solution to a temperature between about 32° C. and about 37° C. and incubating for an additional 12-24 hours. In another embodiment, the aforementioned method is provided comprising the additional step of adding an additional amount of aminooxy linker comprising an active aminooxy group immediately prior to increasing the temperature.

In another embodiment, the aforementioned method is provided wherein the water soluble polymer containing an active aminooxy group is purified by a method selected from the group consisting of dialysis, ultrafiltration/diafiltration (UF/DF), and chromatography at a temperature of 22° C. In another embodiment, the aforementioned method is provided further comprising the step of purifying the water soluble polymer containing an active aminooxy group by a method selected from the group consisting of dialysis, UF/DF or chromatography at 4° C.

In still another embodiment of the present disclosure, a method of preparing a PSA-aminooxy reagent aminooxy group is provided comprising: a) incubating a solution comprising an oxidized PSA with an aminooxy linker comprising an active aminooxy group under conditions that allow the formation of a stable oxime linkage between the oxidized PSA and the activated aminooxy linker, said conditions comprising a time period 1 hour; a temperature of 4° C.; in the absence of light, and with stirring; thereby forming a PSA containing an active aminooxy group; and b) purifying the PSA containing an active aminooxy group by anion exchange chromatography, a temperature of 4° C.; said activated aminooxy linker is 3-oxa-pentane-1,5-dioxyamine linker of the formula:

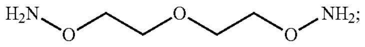

thereby forming an oxime linkage between the PSA and the aminooxy linker.

In yet another embodiment of the present disclosure, a method of preparing a PSA-aminooxy reagent aminooxy group is provided comprising: a) incubating a solution comprising a non-oxidized PSA with an aminooxy linker comprising an active aminooxy group under conditions that allow the formation of a stable oxime linkage between the non-oxidized PSA and the activated aminooxy linker, said conditions comprising a time period 2 hours; a temperature of 22° C.; in the absence of light, and with stirring; thereby forming a PSA containing an active aminooxy group; and b) purifying the PSA containing an active aminooxy group by dialysis at a temperature of 22° C.; said activated aminooxy linker is 3-oxa-pentane-1,5-dioxyamine linker of the formula:

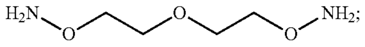

thereby forming an oxime linkage between the non-oxidized PSA and the aminooxy linker.

In still another embodiment of the present disclosure, a method of conjugating a water soluble polymer to an oxidized carbohydrate moiety of a blood coagulation protein is provided comprising contacting the oxidized carbohydrate moiety with an activated water soluble polymer under conditions that allow conjugation; said blood coagulation protein selected from the group consisting of Factor IX (FIX), Factor VIII (FVIII), Factor VIIa (FVIIa), Von Willebrand Factor (VWF), Factor FV (FV), Factor X (FX), Factor XI (FXI), Factor XII (FXII), thrombin (FII), protein C, protein S, tPA, PAI-1, tissue factor (TF) and ADAMTS 13 protease or a biologically active fragment, derivative or variant thereof; said water soluble polymer containing an active aminooxy group and is selected from the group consisting of polyethylene glycol (PEG), branched PEG, polysialic acid (PSA), carbohydrate, polysaccharides, pullulane, chitosan, hyaluronic acid, chondroitin sulfate, dermatan sulfate, starch, dextran, carboxymethyl-dextran, polyalkylene oxide (PAO), polyalkylene glycol (PAG), polypropylene glycol (PPG), polyoxazoline, polyacryloylmorpholine, polyvinyl alcohol (PVA), polycarboxylate, polyvinylpyrrolidone, polyphosphazene, polyoxazoline, polyethylene-co-maleic acid anhydride, polystyrene-co-maleic acid anhydride, poly(1-hydroxymethylethylene hydroxymethylformal) (PHF), 2-methacryloyloxy-2'-ethyltrimethylammoniumphosphate (MPC); and said carbohydrate moiety oxidized by incubation with a buffer comprising an oxidizing agent selected from the group consisting of sodium periodate ($NaIO_4$), lead tetraacetate ($Pb(OAc)_4$) and potassium perruthenate (KRuO4); wherein an oxime linkage is formed between the oxidized carbohydrate moiety and the active aminooxy group on the water soluble polymer.

FIGURES

FIG. 5 shows the visualization of PSA-FIX conjugates prepared in the presence of different catalysts by SDS PAGE. a) Comparison of aniline with m-toluidine using different concentrations; b) Comparison of aniline with o-aminobenzoic acid, m-aminobenzoic acid, p-aminobenzoic acid, p-aminobenzamide and sulfanilic acid; c) Comparison of aniline and m-toluidine with o-anisidine and m-anisidine.

DETAILED DESCRIPTION OF THE INVENTION

Figure 1:
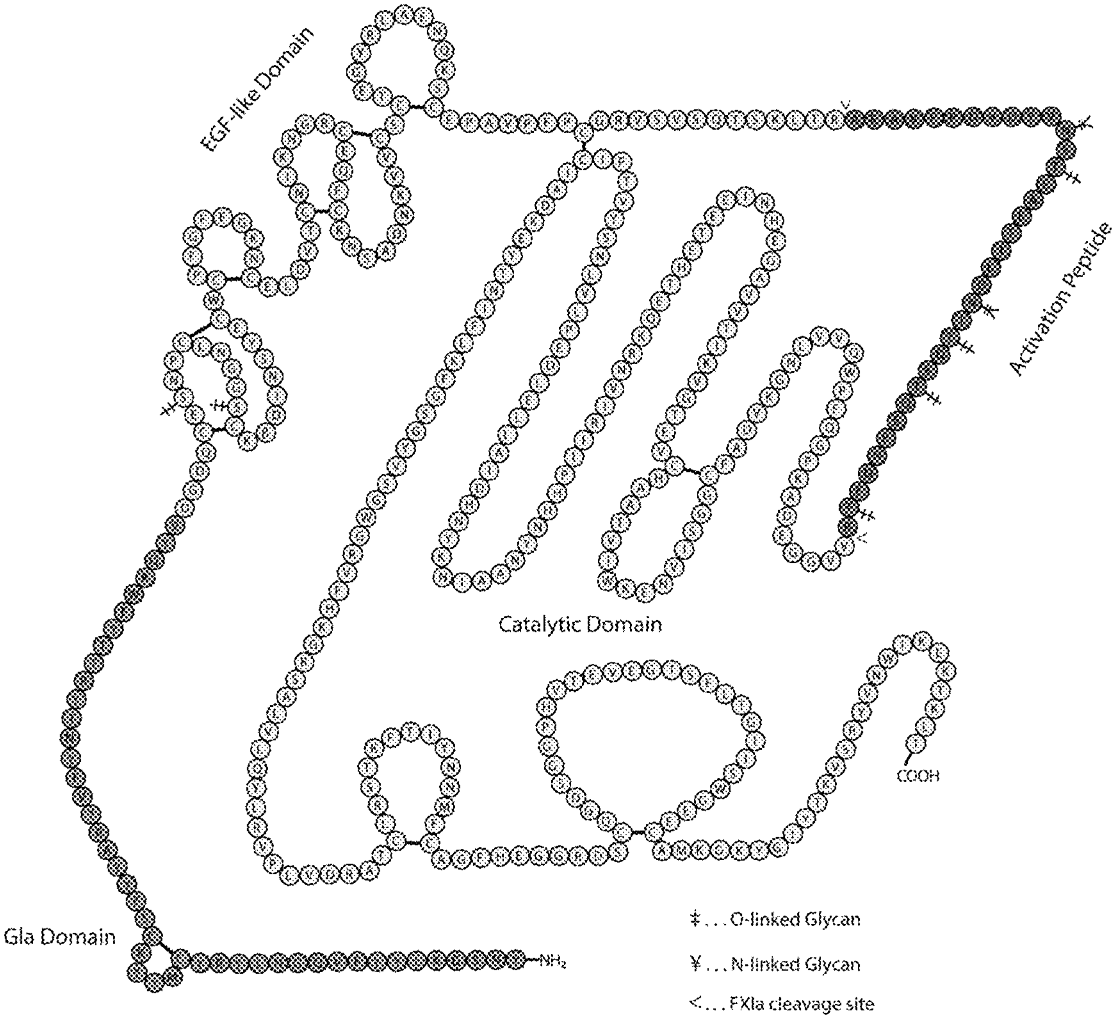
FIG. 1 shows the primary structure of coagulation Factor IX (SEQ ID NO: 1).

The pharmacological and immunological properties of therapeutic proteins can be improved by chemical modification and conjugation with polymeric compounds such as polyethylene glycol (PEG), branched PEG, polysialic acid (PSA), hydroxyalkyl starch (HAS), hydroxylethyl starch (HES), carbohydrate, polysaccharides, pullulane, chitosan, hyaluronic acid, chondroitin sulfate, dermatan sulfate, starch, dextran, carboxymethyl-dextran, polyalkylene oxide (PAO), polyalkylene glycol (PAG), polypropylene glycol (PPG), polyoxazoline, polyacryloylmorpholine, polyvinyl alcohol (PVA), polycarboxylate, polyvinylpyrrolidone, polyphosphazene, polyoxazoline, polyethylene-co-maleic acid anhydride, polystyrene-co-maleic acid anhydride, poly(1-hydroxymethylethylene hydroxymethylformal) (PHF), 2-methacryloyloxy-2'-ethyltrimethylammoniumphosphate (MPC). The properties of the resulting conjugates generally strongly depend on the structure and the size of the polymer. Thus, polymers with a defined and narrow size distribution are usually preferred in the art. Synthetic polymers like PEG can be manufactured easily with a narrow size distribution, while PSA can be purified in such a manner that results in a final PSA preparation with a narrow size distribution. In addition PEGylation reagents with defined polymer chains and narrow size distribution are on the market and commercially available for a reasonable price.

The addition of a soluble polymer, such as through polysialylation, is one approach to improve the properties of therapeutic proteins such as the blood coagulation protein FIX, as well as other coagulation proteins (e.g., VWF, FVIIa (see, e.g., US 2008/0221032A1, incorporated herein by reference) and FVIII).

Therapeutic Proteins

In certain embodiments of the invention, the aforementioned polypeptides and polynucleotides are exemplified by the following therapeutic proteins: enzymes, antigens, antibodies, receptors, blood coagulation proteins, growth factors, hormones, and ligands. In certain embodiments, the therapeutic protein is a blood coagulation protein such as Factor IX (FIX), Factor VIII (FVIII), Factor VIIa (FVIIa), Von Willebrand Factor (VWF), Factor FV (FV), Factor X (FX), Factor XI (FXI), Factor XII (FXII), thrombin (FII), protein C, protein S, tPA, PAI-1, tissue factor (TF) or ADAMTS 13 protease. In one embodiment, a therapeutic protein according to the invention is a glycoprotein or, in various embodiments, a protein that is not naturally glycosylated in vivo (i.e., a protein that does not contain a natural glycosylation site or a protein that is not glycosylated in a host cell prior to purification).

In certain embodiments, the therapeutic protein is immunoglobulins, cytokines such IL-1 alpha, IL-1 beta, IL-2, IL-3, IL-4, IL-5, IL-6, IL-11, colony stimulating factor-1 (CSF-1), M-CSF, SCF, GM-CSF, granulocyte colony stimulating factor (G-CSF), EPO, interferon-alpha (IFN-alpha), consensus interferon, IFN-beta, IFN-gamma, IFN-omega, IL-7, IL-8, IL-9, IL-10, IL-12, IL-13, IL-14, IL-15, IL-16, IL-17, IL-18, IL-19, IL-20, IL-21, IL-22, IL-23, IL-24, IL-31, IL-32 alpha, IL-33, thrombopoietin (TPO), angiopoietins, for example Ang-1, Ang-2, Ang-4, Ang-Y, the human angiopoietin-like polypeptides ANGPTL1 through 7, vitronectin, vascular endothelial growth factor (VEGF), angiogenin, activin A, activin B, activin C, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, bone morphogenic protein receptor II, brain derived neurotrophic factor, cardiotrophin-1, ciliary neutrophic factor, ciliary neutrophic factor receptor, cripto, cryptic, cytokine-induced neutrophil chemotactic factor 1, cytokine-induced neutrophil, chemotactic factor 2α, cytokine-induced neutrophil chemotactic factor 2β, β endothelial cell growth factor, endothelin 1, epidermal growth factor, epigen, epiregulin, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor 11, fibroblast growth factor 12, fibroblast growth factor 13, fibroblast growth factor 16, fibroblast growth factor 17, fibroblast growth factor 19, fibroblast growth factor 20, fibroblast growth factor 21, fibroblast growth factor acidic, fibroblast growth factor basic, glial cell line-derived neutrophic factor receptor α1, glial cell line-derived neutrophic factor receptor α2, growth related protein, growth related protein α, growth related protein β, growth related protein γ, heparin binding epidermal growth factor, hepatocyte growth factor, hepatocyte growth factor receptor, hepatoma-derived growth factor, insulin-like growth factor I, insulin-like growth factor receptor, insulin-like growth factor II, insulin-like growth factor binding protein, keratinocyte growth factor, leukemia inhibitory factor, leukemia inhibitory factor receptor α, nerve growth factor nerve growth factor receptor, neuropoietin, neurotrophin-3, neurotrophin-4, oncostatin M (OSM), placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor α, platelet derived growth factor receptor β, pre-B cell growth stimulating factor, stem cell factor (SCF), stem cell factor receptor, TNF, including TNF0, TNF1, TNF2, transforming growth factor α, transforming growth factor β, transforming growth factor β1, transforming growth factor β1.2, transforming growth factor β2, transforming growth factor β3, transforming growth factor β5, latent transforming growth factor β1, transforming growth factor β binding protein I, transforming growth factor β binding protein II, transforming growth factor β binding protein III, thymic stromal lymphopoietin (TSLP), tumor necrosis factor receptor type I, tumor necrosis factor receptor type II, urokinase-type plasminogen activator receptor, vascular endothelial growth factor, and chimeric proteins and biologically or immunologically active fragments thereof.

In certain embodiments, the therapeutic protein is alpha-, beta-, and gamma-interferons, colony stimulating factors including granulocyte colony stimulating factors, fibroblast growth factors, platelet derived growth factors, phospholipase-activating protein (PUP), insulin, plant proteins such as lectins and ricins, tumor necrosis factors and related alleles, soluble forms of tumor necrosis factor receptors, interleukin receptors and soluble forms of interleukin receptors, growth factors such as tissue growth factors, such as TGFαs or TGFβs and epidermal growth factors, hormones, somatomedins, pigmentary hormones, hypothalamic releasing factors, antidiuretic hormones, prolactin, chorionic gonadotropin, follicle-stimulating hormone, thyroid-stimulating hormone, tissue plasminogen activator, and immunoglobulins such as IgG, IgE, IgM, IgA, and IgD, a galactosidase, α-galactosidase, β-galactosidase, DNAse, fetuin, leutinizing hormone, estrogen, corticosteroids, insulin, albumin, lipoproteins, fetoprotein, transferrin, thrombopoietin, urokinase, DNase, integrins, thrombin, hematopoietic growth actors, leptin, glycosidases, Humira (adalimumab), Prolia (denosumab), Enbrel (etanercept), and fragments thereof, or any fusion proteins comprising any of the above mentioned proteins or fragments thereof. In addition to the aforementioned proteins, the following Table 1 provides therapeutic proteins contemplated by the present invention:

TABLE 1

| | | | |
|---|---|---|---|
| Follicular dendritic cell secreted peptide | Angiotensin-converting enzyme | Interleukin-1 family member 6 | Herstatin |
| Dermokine | Antithrombin-III | Prostate and testis expressed protein 2 | Leucine-rich repeat-containing protein 28 |
| Secreted frizzled-related protein 1 | Apolipoprotein B-100 | Group XIIA secretory phospholipase A2 | LRRN4 C-terminal-like protein |
| Ectodysplasin-A | Apolipoprotein D | Collagen alpha-3(V) chain | Ly6/PLAUR domain-containing protein 2 |
| Secreted frizzled-related protein 2 | Apolipoprotein E | Alpha-2-macroglobulin-like protein 1 | Transmembrane protein 81 |
| Resistin | Beta-1,4-galactosyltransferase 1 | Dermatopontin | Myelin protein zero-like protein 3 |
| Osteopontin | Bone morphogenetic protein 7 | Cartilage-associated protein | Protein notum homolog |
| Secreted frizzled-related protein 5 | Complement C1q subcomponent subunit B | Desert hedgehog protein | UDP-glucuronosyltransferase 3A2 |
| Secreted frizzled-related protein 4 | C4b-binding protein alpha chain | Extracellular matrix protein 2 | Protocadherin alpha-1 |
| Secreted phosphoprotein 24 | Calreticulin | Gastric intrinsic factor | Phospholipase D4 |
| Glypican-6 | Corticosteroid-binding globulin | Interleukin-33 | Retinol dehydrogenase 10 |
| Secreted frizzled-related protein 3 | Carboxypeptidase A1 | Bone morphogenetic protein 2 | Sialic acid-binding Ig-like lectin 14 |
| C-C motif chemokine 4 | Carboxypeptidase A2 | Bone morphogenetic protein 6 | Transmembrane protein 161A |
| Melanocyte protein Pmel 17 | Eotaxin | Uncharacterized protein KIAA0564 | Transmembrane protein 161B |
| Secreted Ly-6/uPAR-related protein 1 | C-C motif chemokine 13 | Cerberus | Transmembrane protein 182 |
| Beta-microseminoprotein | C-C motif chemokine 18 | Carbohydrate sulfotransferase 8 | Protein FAM24B |
| Glypican-4 | C-C motif chemokine 20 | Contactin-associated protein-like 3 | Transmembrane protein 52 |
| Tumor necrosis factor ligand superfamily member 15 | Triggering receptor expressed on myeloid cells 2 | Group XIIB secretory phospholipase A2-like protein | Major facilitator superfamily domain-containing protein 4 |
| Resistin-like beta | C-C motif chemokine 2 | Corticoliberin | UDP-glucuronosyltransferase 2A3 |
| Tumor necrosis factor ligand superfamily member 12 | Transforming growth factor-beta-induced protein ig-h3 | A disintegrin and metalloproteinase with thrombospondin motifs 19 | Odontogenic ameloblast-associated protein |
| SPARC | CD40 ligand | UPF0556 protein C19orf10 | Neurosecretory protein VGF |
| Glypican-5 | Corneodesmosin | C-X-C motif chemokine 3 | Secreted phosphoprotein 2, 24 kDa |
| Anterior gradient protein 2 homolog | Complement factor D | Cystatin-M | Protein FAM150B |
| Protein canopy homolog 2 | Chromogranin-A | Defensin-5 | Growth/differentiation factor 9 |
| Glypican-1 | Collagen alpha-1(I) chain | Defensin-6 | Clusterin-like protein 1 |
| von Willebrand factor A domain-containing protein 2 | Disintegrin and metalloproteinase domain-containing protein 18 | A disintegrin and metalloproteinase with thrombospondin motifs 18 | Transmembrane and immunoglobulin domain-containing protein 2 |
| WNT1-inducible-signaling pathway protein 1 | Cysteine-rich secretory protein LCCL domain-containing 1 | A disintegrin and metalloproteinase with thrombospondin motifs 3 | C-type lectin domain-containing protein UNQ5810/PRO19627 |
| C-C motif chemokine 1 | Collagen alpha-4(IV) chain | Dickkopf-related protein 4 | Epididymal-specific lipocalin-10 |
| SPARC-related modular calcium-binding protein 2 | Keratinocyte differentiation-associated protein | A disintegrin and metalloproteinase with thrombospondin motifs 5 | A disintegrin and metalloproteinase with thrombospondin motifs 8 |
| C-type lectin domain family 11 member A | Complement C4-B | Mammalian ependymin-related protein 1 | Epididymal-specific lipocalin-8 |
| Secreted Ly-6/uPAR-related protein 2 | Collagen alpha-2(V) chain | Fibrillin-3 | Basic proline-rich peptide P-E |
| Glypican-3 | Complement C5 | Fetuin-B | Putative uncharacterized protein C10orf99 |
| Secreted and transmembrane protein 1 | Collagen alpha-1(VII) chain | Fibroblast growth factor 6 | Uncharacterized protein C17orf77 |
| Testis-expressed sequence 264 protein | Complement component C7 | Keratinocyte growth factor | Arylacetamide deacetylase-like 2 |
| Glypican-2 | Complement component C8 beta chain | Growth/differentiation factor 8 | Epididymal-specific lipocalin-12 |
| Serine protease 23 | Complement component C8 gamma chain | Gastric inhibitory polypeptide | B melanoma antigen 2 |
| 39S ribosomal protein L55, mitochondrial | Collagen alpha-1(XV) chain | Glycoprotein hormone beta-5 | B melanoma antigen 3 |
| Protein NipSnap homolog 3A | Collagen alpha-1(XVI) chain | Granzyme M | Bovine seminal plasma protein homolog 1 |
| Fibronectin | Collagen alpha-1(XVIII) chain | Gastrin-releasing peptide | Complement C1q-like protein 3 |
| Neudesin | Collagen alpha-1(XIX) chain | Serine protease HTRA1 | UPF0565 protein C2orf69 |
| Fibroblast growth factor receptor 2 | Cartilage oligomeric matrix protein | Interferon alpha-4 | UPF0669 protein C6orf120 |
| Carbonic anhydrase 6 | C-reactive protein | Interferon alpha-5 | Colipase-like protein C6orf127 |
| Deleted in malignant brain tumors 1 protein | Granulocyte colony-stimulating factor | Interferon alpha-7 | Uncharacterized protein C7orf69 |
| SPARC-related modular calcium-binding protein 1 | Granulocyte-macrophage colony-stimulating factor | A disintegrin and metalloproteinase with thrombospondin motifs 7 | Platelet-derived growth factor receptor-like protein |
| Amyloid beta A4 protein | Protein CYR61 | Immunoglobulin superfamily member 10 | Chondroadherin-like protein |

TABLE 1-continued

| | | | |
|---|---|---|---|
| Tumor necrosis factor receptor superfamily member 6 | Complement component receptor 1-like protein | Protease-associated domain-containing protein of 21 kDa | Putative uncharacterized protein UNQ6490/PRO21339 |
| Gamma-aminobutyric acid type B receptor subunit 1 | Stem cell growth factor; lymphocyte secreted C-type lectin | Abhydrolase domain-containing protein FAM108A1 | Putative uncharacterized protein UNQ6493/PRO21345 |
| Pro-neuregulin-1, membrane-bound isoform | CMP-N-acetylneuraminate-beta-galactosamide-alpha-2,3-sialyltransferase | A disintegrin and metalloproteinase with thrombospondin motifs 9 | Putative uncharacterized protein UNQ5815/PRO19632 |
| Glycoprotein hormone alpha-2 | Dipeptidyl peptidase 4 | Interleukin-9 receptor | Cystatin-A |
| Membrane metallo-endopeptidase-like 1 | Dentin sialophosphoprotein | Interleukin-9 | Peptidase inhibitor R3HDML |
| Fc receptor-like A | Endothelin-1 | Inhibin beta B chain | Cystatin-9 |
| C-C motif chemokine 4-like | Ephrin-B1 | Serine protease inhibitor Kazal-type 2 | DAN domain family member 5 |
| Epithelial discoidin domain-containing receptor 1 | Epidermis-specific serine protease-like protein | BMP-binding endothelial regulator protein | Insulin-like growth factor-binding protein-like 1 |
| Mucin-1 | EMILIN-1 | Keratinocyte-associated protein 2 | Epididymal sperm-binding protein 1 |
| Vascular endothelial growth factor A | Endoplasmin | Laminin subunit alpha-1 | Elafin |
| Fibulin-1 | Ephrin type-A receptor 3 | Leukocyte cell-derived chemotaxin-2 | Protein FAM55A |
| Prolactin receptor | Ephrin type-B receptor 6 | Gastric triacylglycerol lipase | Growth/differentiation factor 6 |
| Proprotein convertase subtilisin/kexin type 6 | Glycosyltransferase 1 domain-containing protein 1 | Leucine-rich repeat and calponin homology domain-containing protein 3 | Glucose-fructose oxidoreductase domain-containing protein 1 |
| CD209 antigen | Coagulation factor X | Pancreatic lipase-related protein 2 | Erythropoietin |
| Collagen alpha-2(XI) chain | Coagulation factor VIII | Epididymis-specific alpha-mannosidase | Glutathione peroxidase 6 |
| Granulocyte-macrophage colony-stimulating factor receptor subunit alpha | Complement C1q tumor necrosis factor-related protein 7 | Fibronectin type III domain-containing protein 7 | Uncharacterized protein UNQ511/PRO1026 |
| Elastin | Fibrillin-2 | Microfibrillar-associated protein 5 | Beta-defensin 128 |
| Interleukin-15 receptor subunit alpha | Alpha-2-HS-glycoprotein | Muellerian-inhibiting factor | Interleukin-31 |
| Midkine | Fibroblast growth factor 10 | Matrix metalloproteinase-21 | Interleukin-34 |
| Integrin alpha-7 | Fibrinogen alpha chain | Matrix metalloproteinase-17 | Plasma kallikrein-like protein 4 |
| Mucin-4 | Fibrinogen beta chain | Matrix metalloproteinase-20 | Epididymal-specific lipocalin-9 |
| Peptidyl-glycine alpha-amidating monooxygenase | Long palate, lung and nasal epithelium carcinoma-associated protein 1 | N-acetylglucosamine-1-phosphotransferase subunit gamma | cDNA FLJ60957, highly similar to Secreted frizzled-related protein 4 |
| Apolipoprotein A-I | Gastrin | Multimerin-2 | Lipase member M |
| Proteoglycan 4 | Glycoprotein hormones alpha chain | Promotilin | CLECSF12 |
| Tumor necrosis factor receptor superfamily member 25 | N-acetylglucosamine-1-phosphotransferase subunits alpha/beta | FRAS1-related extracellular matrix protein 3 | Putative inactive group IIC secretory phospholipase A2 |
| Attractin | Granzyme A | Protein kinase C-binding protein NELL1 | Serine protease MPN2 |
| Prostate-associated microseminoprotein | Hepatocyte growth factor-like protein | Protein kinase C-binding protein NELL2 | Netrin-5 |
| Alpha-amylase 1 | Insulin-like growth factor-binding protein 1 | Neurotrypsin | NHL repeat-containing protein 3 |
| Brain-derived neurotrophic factor | Insulin-like growth factor-binding protein 2 | Neuroserpin | Olfactomedin-like protein 2B |
| C-type lectin domain family 4 member M | Insulin-like growth factor-binding protein 4 | Nidogen-2 | Ovochymase-2 |
| Granulocyte colony-stimulating factor receptor | Tumor necrosis factor receptor superfamily member 10D | Abhydrolase domain-containing protein FAM108B1 | Putative uncharacterized protein UNQ3029/PRO9830 |
| Insulin-like growth factor II | Interferon alpha-1/13 | Neurotrophin-4 | Ovochymase-1 |
| Carcinoembryonic antigen-related cell adhesion molecule 1 | Interferon-induced helicase C domain-containing protein 1 | Epididymal secretory glutathione peroxidase | Putative pregnancy-specific beta-1-glycoprotein 7 |
| C-type lectin domain family 7 member A | Interferon alpha-2 | Group 10 secretory phospholipase A2 | Ovostatin homolog 2 |
| CMRF35-like molecule 1 | Interferon beta | Group IID secretory phospholipase A2 | Orexigenic neuropeptide QRFP |
| Choline transporter-like protein 4 | Interferon gamma | Lactoperoxidase | Lymphocyte antigen 6K |
| Pulmonary surfactant-associated protein A1 | Insulin-like growth factor IB | p53 apoptosis effector related to PMP-22 | Prostate and testis expressed protein 1 |
| Spermine oxidase | Indian hedgehog protein | Placenta-specific protein 1 | Putative phospholipase B-like 1 |
| CMP-N-acetylneuraminate-beta-1,4-galactoside alpha-2,3-sialyltransferase | Neural cell adhesion molecule L1-like protein | Tuberoinfundibular peptide of 39 residues | Putative uncharacterized protein FLJ42147 |
| Kallikrein-8 | Interleukin-13 | Prolargin | Otogelin |
| Tissue-type plasminogen activator | Interleukin-2 | Secretogranin-2 | Ribonuclease 8 |
| Peroxisomal N(1)-acetyl- | Chymotrypsin-like elastase family | Endonuclease domain-containing 1 | Nuclear pore complex-interacting protein- |

TABLE 1-continued spermine/spermidine oxidase
Probable palmitoyltransferase ZDHHC4
Cholesteryl ester transfer protein
HLA class I histocompatibility antigen, A-2 alpha chain
Collagen alpha-1(II) chain
Pro-interleukin-16
Leptin receptor
Decorin
Stromal cell-derived factor 1
Tenascin
Disintegrin and metalloproteinase domain-containing protein 12
A disintegrin and metalloproteinase with thrombospondin motifs 13
T-cell surface glycoprotein CD3 alpha chain
EGFR-coamplified and overexpressed protein
Autophagy-related protein 16-1
Breast cancer anti-estrogen resistance protein 3
Cadherin-23
Macrophage colony-stimulating factor 1
Folate receptor alpha
Low-density lipoprotein receptor-related protein 8
E3 ubiquitin-protein ligase LRSAM1
Neural cell adhesion molecule 1
Neuroligin-4, X-linked
Netrin-G1
GPI transamidase component PIG-T
Kit ligand
Seizure 6-like protein
SLAM family member 7
Tumor necrosis factor
Uromodulin
Tumor necrosis factor ligand superfamily member 13
Protein CREG1
EGF-like domain-containing protein 8
Aminoacyl tRNA synthetase complex-interacting multifunctional protein 1
ADAMTS-like protein 4
Coagulation factor XI
Interleukin-22 receptor subunit alpha-2
Deformed epidermal autoregulatory factor 1 homolog
Prostaglandin-H2 D-isomerase
Alpha-1-antitrypsin
Alpha-1-antichymotrypsin
Acyl-CoA-binding protein
Complement factor B
Choriogonadotropin subunit beta
member 2A
Inhibin beta A chain
Pancreatic secretory trypsin inhibitor
Tumor necrosis factor receptor superfamily member 21
Inter-alpha-trypsin inhibitor heavy chain H1
Inter-alpha-trypsin inhibitor heavy chain H2
Inter-alpha-trypsin inhibitor heavy chain H3
Prostate-specific antigen
Kallikrein-4
Plasma kallikrein
Calcium-activated chloride channel regulator 4
Bactericidal/permeability-increasing protein-like 1
Leptin
A disintegrin and metalloproteinase with thrombospondin motifs 4
Hepatic triacylglycerol lipase
Lymphocyte antigen 6 complex locus protein G6c
Eosinophil lysophospholipase
Lutropin subunit beta
Microfibrillar-associated protein 1
Mesencephalic astrocyte-derived neurotrophic factor
Matrix Gla protein
72 kDa type IV collagenase
Stromelysin-1
Neutrophil collagenase
Mesothelin
Mucin-5AC
Mucin-6
Norrin
Oxytocin-neurophysin 1
Beta-nerve growth factor
Tumor necrosis factor ligand superfamily member 18
Neurotrophin-3
Platelet-derived growth factor subunit A
Phosphopantothenoylcysteine decarboxylase
Plasminogen activator inhibitor 1
Plasminogen activator inhibitor 2
Procollagen C-endopeptidase enhancer 1
Transmembrane and ubiquitin-like domain-containing protein 2
Protein disulfide-isomerase
Pigment epithelium-derived factor
Pepsin A
Gastricsin
Sonic hedgehog protein
Peptidoglycan recognition protein I-alpha
protein
Semaphorin-3B
Somatostatin
Dehydrogenase/reductase SDR family member 4-like 2
Transcobalamin-1
Trefoil factor 2
Testican-1
Serum paraoxonase/lactonase 3
Tolloid-like protein 2
Trypsin-2
RING finger and SPRY domain-containing protein 1
Calcium-binding and coiled-coil domain-containing protein 1
Protein Wnt-2
Ectonucleoside triphosphate diphosphohydrolase 8
Protein Wnt-8b
UDP-GlcNAc: betaGal beta-1,3-N-acetylglucosaminyltransferase 4
EMI domain-containing protein 1
Uncharacterized protein C6orf15
Collectin-10
Long-chain-fatty-acid--CoA ligase ACSBG2
Oncoprotein-induced transcript 3 protein
Peptidase inhibitor 15
Proline-rich acidic protein 1
Urocortin
Trypsin-X3 (EC 3.4.21.4)
HHIP-like protein 2
Fractalkine
Protein Wnt-11
Protein Wnt-7a
FCH and double SH3 domains protein 1
Hepatoma-derived growth factor-related protein 2
Interleukin-12 subunit alpha
UPF0577 protein KIAA1324
Complement C1q tumor necrosis factor-related protein 9
Mucin-17
Lysosomal protein NCU-G1
Prolyl 4-hydroxylase subunit alpha-3
Peptidyl-prolyl cis-trans isomerase SDCCAG10
Peptidase inhibitor 16
Poliovirus receptor-related protein 4
Solute carrier family 22 member 15
GPI inositol-deacylase
Transmembrane protein 43
Angiopoietin-related protein 2
like 2
Proactivator polypeptide-like 1
Protein spinster homolog 2
von Willebrand factor C domain-containing protein 2-like
Urotensin-2B
Tetraspanin-18
UPF0514 membrane protein FAM159A
Latherin
Methyltransferase-like protein 7B
Protein TEX261
Alkylated DNA repair protein alkB homolog 7
Transmembrane emp24 domain-containing protein 6
XK-related protein 5
Putative V-set and immunoglobulin domain-containing protein 7
Insulin growth factor-like family member 3
Nuclear pore complex-interacting protein-like 1
Secreted phosphoprotein 1
Collagen alpha-5(VI) chain
B melanoma antigen 5
WAP four-disulfide core domain protein 10A
UPF0369 protein C6orf57
Putative uncharacterized protein C10orf31
Putative uncharacterized protein C11orf45
Uncharacterized protein C12orf28
Uncharacterized protein C17orf67
Beta-defensin 121
Beta-defensin 130
Histidine triad nucleotide-binding protein 2
Apelin
Placenta-specific protein 9
Hepatocellular carcinoma-associated protein TD26
Persephin
Regulated endocrine-specific protein 18
Complement C1q tumor necrosis factor-related protein 8
Bone morphogenetic protein 8A
Protein WFDC13
Protein Wnt-8a
Ig-like domain-containing protein ENSP00000270642
Abhydrolase domain-containing protein 15
Ribonuclease-like protein 9
Uncharacterized protein C2orf66
Uncharacterized protein C17orf99
Protein FAM150A
Placenta-specific 1-like protein TABLE 1-continued

| | | | |
|---|---|---|---|
| Versican core protein | Biglycan | Angiopoietin-related protein 6 | Uncharacterized protein C18orf20 |
| Epidermal growth factor receptor | Prolactin-inducible protein | Arylsulfatase K | Beta-defensin 110 |
| Ecto-NOX disulfide-thiol exchanger 2 | Platelet factor 4 | Augurin | Neuritin-like protein |
| Hyaluronidase-1 | Plasminogen | Brain-specific serine protease 4 | Histidine-rich carboxyl terminus protein 1 |
| Interleukin-1 receptor antagonist protein | Serum paraoxonase/arylesterase 1 | DBH-like monooxygenase protein 1 | C-type lectin domain family 2 member A |
| Interleukin-6 receptor subunit beta | Alkaline phosphatase, placental type | Uncharacterized protein C1orf56 | Leucine-rich repeat-containing protein 70 |
| Interleukin-1 receptor-like 1 | Peptidyl-prolyl cis-trans isomerase B | Cerebellin-3 | Serpin A13 |
| Insulin | Bone marrow proteoglycan | Cerebellin-4 | BTB/POZ domain-containing protein 17 |
| Glycodelin | Basic salivary proline-rich protein 1 | Colipase-like protein C6orf126 | Uncharacterized protein C12orf53 |
| Parathyroid hormone-related protein | Pulmonary surfactant-associated protein C | Uncharacterized protein C11orf83 | C-type lectin domain family 9 member A |
| Nurim | Parathyroid hormone | Uncharacterized protein C16orf89 | Complement C1q-like protein 4 |
| Prolyl 4-hydroxylase subunit alpha-2 | Serum amyloid P-component | Carboxypeptidase-like protein X2 | CMRF35-like molecule 4 |
| CD276 antigen | Secretogranin-1 | Cystatin-9-like | Protein FAM151B |
| Cysteine-rich with EGF-like domain protein 1 | Basement membrane-specific heparan sulfate proteoglycan core protein | Dehydrogenase/reductase SDR family member 13 | Abhydrolase domain-containing protein FAM108A2/A3 |
| CUB and sushi domain-containing protein 1 | Antileukoproteinase | Beta-defensin 123 | Osteocrin |
| Ficolin-2 | Stabilin-1 | Beta-defensin 132 | Transmembrane protease, serine 11E2 |
| Fc receptor-like protein 5 | Extracellular superoxide dismutase [Cu—Zn] | Cytokine-like protein 1 | Transmembrane protein 14E |
| Protein GPR89 | Somatotropin | Dickkopf-related protein 2 | Transmembrane protein 207 |
| Junctional adhesion molecule A | Serpin B5 | Dickkopf-like protein 1 | TOMM20-like protein 1 |
| Leucine-rich repeat-containing protein 8A | Spondin-1 | Epididymal secretory protein E3-beta | Uncharacterized protein C3orf41 |
| Multiple inositol polyphosphate phosphatase 1 | Structural maintenance of chromosomes protein 3 | EGF-like repeat and discoidin I-like domain-containing protein 3 | Submaxillary gland androgen-regulated protein 3A |
| Neuropilin-1 | Syntaxin-1A | Protein FAM55D | B melanoma antigen 1 |
| Plexin-A4 | Tetranectin | Fibroblast growth factor 17 | Inactive carboxylesterase 4 |
| Plexin-B1 | Transforming growth factor beta-1 | Fibroblast growth factor 22 | Four-jointed box protein 1 |
| Periostin | Thyroglobulin | Fibroblast growth factor-binding protein 2 | Protein HSN2 |
| Protein RIC-3 | Metalloproteinase inhibitor 1 | Growth/differentiation factor 3 | Humanin |
| SLIT and NTRK-like protein 2 | Metalloproteinase inhibitor 2 | GLIPR1-like protein 1 | Kielin/chordin-like protein |
| Sulfatase-modifying factor 1 | Metalloproteinase inhibitor 3 | Serine protease inhibitor Kazal-type 6 | UPF0624 protein C6orf186 |
| Sulfatase-modifying factor 2 | Urokinase-type plasminogen activator | Interleukin-17B | Putative neurofibromin 1-like protein 4/6 |
| Transmembrane protease, serine 6 | Lactotransferrin | Interleukin-17C | Peroxidasin-like protein |
| Lymphotoxin-alpha | Trypsin-1 | Interleukin-17D | SCO-spondin |
| Tumor necrosis factor receptor superfamily member 10B | Submaxillary gland androgen-regulated protein 3B | Hyaluronan and proteoglycan link protein 3 | Putative uncharacterized protein UNQ9165/PRO28630 |
| Urokinase plasminogen activator surface receptor | Tumor necrosis factor receptor superfamily member 1A | Vitelline membrane outer layer protein 1 homolog | Calcium-activated chloride channel regulator family member 3 |
| V-set domain-containing T-cell activation inhibitor 1 | Vascular endothelial growth factor receptor 1 | Choriogonadotropin subunit beta variant 1 | Probable serine protease UNQ9391/PRO34284 |
| Glucagon | Vitamin D-binding protein | Lysozyme-like protein 1 | Uncharacterized protein C4orf26 |
| N-acetylmuramoyl-L-alanine amidase | Vitronectin | Matrix metalloproteinase-28 | Uncharacterized protein C4orf40 |
| Sulfhydryl oxidase 1 | von Willebrand factor | Nephronectin | Uncharacterized protein C5orf55 |
| Dehydrogenase/reductase SDR family member 4 | Lymphocyte antigen 6 complex locus protein G5c | WAP four-disulfide core domain protein 12 | Putative macrophage-stimulating protein MSTP9 |
| Interleukin-18-binding protein | Zinc-alpha-2-glycoprotein | Olfactomedin-like protein 1 | Uncharacterized protein C15orf61 |
| Kin of IRRE-like protein 2 | Uncharacterized protein C14orf93 | Olfactomedin-like protein 2A | Chymotrypsinogen B2 |
| Myeloid-associated differentiation marker | Retinoschisin | Serine protease 27 | Beta-defensin 108A |
| Chordin | Alpha-1,3-mannosyltransferase ALG2 | Secretoglobin family 3A member 2 | Beta-defensin 111 |
| 1-acyl-sn-glycerol-3-phosphate acyltransferase gamma | C-type lectin domain family 11, member A, isoform CRA_b | A disintegrin and metalloproteinase with thrombospondin motifs 2 | Putative V-set and immunoglobulin domain-containing protein 6 |
| Advanced glycosylation end product-specific receptor | Major facilitator superfamily domain-containing protein 7 | Disintegrin and metalloproteinase domain-containing protein 28 | Serine protease inhibitor Kazal-type 5-like 3 |
| NLR family CARD domain-containing | Leucine-rich repeat transmembrane | Bactericidal/permeability-increasing | Putative serine protease inhibitor Kazal- |

TABLE 1-continued

| | | | |
|---|---|---|---|
| protein 4 | neuronal protein 1 | protein-like 2 | type 5-like 2 |
| Pro-neuregulin-2, membrane-bound | NADH dehydrogenase [ubiquinone] 1 beta | Acid sphingomyelinase-like | Dehydrogenase/reductase SDR family |
| isoform | subcomplex subunit 11, mitochondrial | phosphodiesterase 3b | member 7C |
| Sperm-associated antigen 11A | UPF0546 membrane protein C1orf91 | Serine protease inhibitor Kazal-type 7 | Beta-defensin 131 |
| Oocyte-secreted protein 1 homolog | Carbonic anhydrase-related protein 10 | Neurexophilin-4 | Beta-defensin 134 |
| Serum albumin | Cholecystokinin | Protein Wnt-9b | Beta-defensin 136 |
| Cochlin | Codanin-1 | Zymogen granule protein 16 homolog B | Beta-defensin 116 |
| Plasma protease C1 inhibitor | Uncharacterized protein C6orf89 | Semaphorin-3D | Protein FAM132A |
| Interleukin-7 receptor subunit alpha | Chondroitin sulfate glucuronyltransferase | Apolipoprotein L4 | Protein FAM132B |
| Inter-alpha-trypsin inhibitor heavy chain H5 | Chitinase domain-containing protein 1 | Transmembrane protease, serine 11D | Beta-defensin 115 |
| Platelet-derived growth factor D | Transmembrane protein C9orf7 | Scrapie-responsive protein 1 | Beta-defensin 114 |
| Protein S100-A7 | CMRF35-like molecule 9 | Putative annexin A2-like protein | Serine protease inhibitor Kazal-type 9 |
| Sialic acid-binding Ig-like lectin 10 | Cytochrome P450 2S1 | Bone morphogenetic protein 10 | Lipase member N |
| Tubulointerstitial nephritis antigen-like | Crumbs protein homolog 3 | Secretogranin-3 | Pancreatic lipase-related protein 3 |
| Tumor necrosis factor ligand superfamily | Dehydrogenase/reductase SDR family | Complement C1q tumor necrosis factor- | Testis, prostate and placenta-expressed |
| member 13B | member 7 | related protein 4 | protein |
| Long-chain-fatty-acid--CoA ligase 5 | Protein ENED | Uncharacterized protein C1orf54 | Neuromedin-S |
| Claudin-14 | Complement factor H-related protein 4 | Carboxypeptidase A6 | Neuropeptide S |
| Leucine-rich repeat-containing protein 20 | Leucine-rich repeat LGI family member 3 | C-C motif chemokine 19 | Neuronal pentraxin-like protein C16orf38 |
| Interleukin-1 family member 7 | Gliomedin | C-C motif chemokine 25 | Otolin-1 |
| Lymphocyte antigen 6 complex locus | Glycerophosphodiester phosphodiesterase | Chymotrypsin-like elastase family | Iron/zinc purple acid phosphatase-like |
| protein G5b | domain-containing protein 5 | member 2B | protein |
| Acetylcholinesterase | Probable G-protein coupled receptor 113 | Protein CEI | Ovostatin homolog 1 |
| Amelogenin, X isoform | Probable G-protein coupled receptor 114 | Uncharacterized protein C6orf1 | Plasminogen-related protein A |
| Angiogenin | Glycerol-3-phosphate acyltransferase 4 | Uncharacterized protein C7orf34 | Polyserase-3 |
| Anthrax toxin receptor 2 | Gremlin-1 | Keratinocyte-associated protein 3 | Putative peptide YY-2 |
| Annexin A2 | Potassium channel subfamily K member 17 | Uncharacterized protein C9orf47 | Putative peptide YY-3 |
| Apolipoprotein C-III | KDEL motif-containing protein 2 | Collagen alpha-1(VIII) chain | Ribonuclease-like protein 10 |
| Apolipoprotein L1 | Layilin | Uncharacterized protein C18orf54 | Ribonuclease-like protein 12 |
| Complement C1q subcomponent subunit A | Leucine-rich repeat-containing protein 8B | Cystatin-like 1 | Ribonuclease-like protein 13 |
| Complement C1q subcomponent subunit C | Leucine-rich repeat-containing protein 8D | C2 domain-containing protein 2 | Serpin A11 |
| Calcitonin | Sialic acid-binding Ig-like lectin 6 | DDRGK domain-containing protein 1 | Kunitz-type protease inhibitor 4 |
| Soluble calcium-activated nucleotidase 1 | Pregnancy-specific beta-1-glycoprotein 2 | Protein FAM55C | Meteorin-like protein |
| C-C motif chemokine 15 | Ly6/PLAUR domain-containing protein 1 | Collagen alpha-1(XXVI) chain | Putative testis serine protease 2 |
| CD97 antigen ( | Ly6/PLAUR domain-containing protein 5 | Protein FAM19A2 | Beta-defensin 112 |
| Contactin-4 | MLN64 N-terminal domain homolog | Protein FAM5B | Uncharacterized protein FLJ37543 |
| Complement C2 | Macrophage migration inhibitory factor | Fibroblast growth factor 5 | Protein FAM24A |
| Collagen alpha-6(IV) chain | 2-acylglycerol O-acyltransferase 3 | Probable serine protease HTRA3 | Secreted frizzled-related protein 4 |
| Collagen alpha-2(VI) chain | Mitochondrial carrier homolog 1 | Interleukin-1 family member 8 | Complement C1q-like protein 2 |
| Collagen alpha-1(XI) chain | Apolipoprotein L6 | Serine protease inhibitor Kazal-type 4 | Putative uncharacterized protein C17orf69 |
| Crumbs homolog 1 | Protocadherin alpha-6 | Otospiralin | Putative cystatin-13 |
| Cystatin-C | Protocadherin gamma-A12 | Liver-expressed antimicrobial peptide 2 | Beta-defensin 109 |
| Neutrophil defensin 1 | Voltage-gated hydrogen channel 1 | Lysyl oxidase homolog 1 | Beta-defensin 113 |
| Endothelin-3 | All-trans-retinol 13,14-reductase | Lysyl oxidase homolog 2 | Beta-defensin 135 |
| Low affinity immunoglobulin epsilon | Regulator of microtubule dynamics | Long palate, lung and nasal epithelium | Peptidase S1 domain-containing protein |
| Fc receptor | protein 2 | carcinoma-associated protein 4 | LOC136242 |
| Fibroblast growth factor receptor 3 | R-spondin-4 | Lysozyme g-like protein 2 | Growth/differentiation factor 7 |
| Fibroblast growth factor receptor 4 | Long-chain fatty acid transport protein 3 | Endomucin | IgA-inducing protein homolog |
| Growth arrest-specific protein 6 | Vesicle-trafficking protein SEC22c | Neuropeptide B | Putative lipocalin 1-like protein 1 |
| Growth hormone receptor | Claudin-1 | Kinesin-like protein KIF7 | Putative serine protease 29 |
| Bifunctional UDP-N-acetylglucosamine 2- | Leucine-rich repeats and immunoglobulin- | Leukocyte-associated immunoglobulin- | Putative scavenger receptor cysteine-rich |
| epimerase/N-acetylmannosamine kinase | like domains protein 3 | like receptor 2 | domain-containing protein LOC619207 |
| Immunoglobulin superfamily member 8 | SLAM family member 9 | Calcium-dependent phospholipase A2 | Secretoglobin-like protein |

TABLE 1-continued

| | | | |
|---|---|---|---|
| Interleukin-4 receptor alpha chain | Transthyretin | Proapoptotic caspase adapter protein | Putative stereocilin-like protein |
| Kallikrein-14 | Serine/threonine-protein kinase 32B | Integrin beta-like protein 1 | Insulin growth factor-like family member 2 |
| Kallikrein-6 | Platelet-derived growth factor subunit B | Tolloid-like protein 1 | KIR2DL4 |
| Laminin subunit beta-3 | Noggin | Kunitz-type protease inhibitor 3 | Putative zinc-alpha-2-glycoprotein-like 1 |
| Leucyl-cystinyl aminopeptidase | Tryptase alpha-1 | Protein TMEM155 | Insulin growth factor-like family member 4 |
| Mannan-binding lectin serine protease 1 | Tetratricopeptide repeat protein 14 | Prosalusin | Uncharacterized protein C2orf72 |
| Mannan-binding lectin serine protease 2 | XTP3-transactivated gene B protein | Protein amnionless | Replication initiation-like protein |
| Neutrophil gelatinase-associated lipocalin | Palmitoyltransferase ZDHHC15 | Protein WFDC10B | Prostate and testis expressed protein 3 |
| Neuropeptide Y | Zona pellucida sperm-binding protein 3 | WAP four-disulfide core domain protein 8 | B melanoma antigen 4 |
| Aggrecan core protein | Leucine-rich repeat-containing protein 39 | Protein Wnt-5b | Putative uncharacterized protein C1orf191 |
| Pulmonary surfactant-associated protein B | Pancreatic triacylglycerol lipase | Protein Wnt-7b | Beta-defensin 108B-like |
| Poliovirus receptor-related protein 1 | Transmembrane protein 139 | Zona pellucida-binding protein 2 | Uncharacterized protein FLJ90687 |
| Renin | Leukemia inhibitory factor | SH3 domain-binding protein 5-like | Secreted frizzled-related protein 2 |
| Ribonuclease pancreatic | Galectin-1 | Adipocyte adhesion molecule | Basic proline-rich peptide IB-1 |
| Semenogelin-1 | C-C motif chemokine 21 | Uncharacterized protein C12orf59 | Fibroblast growth factor 16 |
| Signaling lymphocytic activation molecule | CD5 antigen-like | Apolipoprotein A-I-binding protein | Serine protease inhibitor Kazal-type 8 |
| Tissue factor pathway inhibitor | Carbohydrate sulfotransferase 9 | Claudin-17 | Uncharacterized protein KIAA0495 |
| Usherin | Lipopolysaccharide-binding protein | Inactive caspase-12 | Platelet basic protein-like 2 |
| Fibroblast growth factor 23 | Cysteine-rich motor neuron 1 protein | Uncharacterized protein C7orf58 | Serpin E3 |
| Interleukin-23 subunit alpha | Connective tissue growth factor | Collagen alpha-1(XXVIII) chain | CR1 receptor |
| Epididymal secretory protein E1 | Protein eyes shut homolog | Dentin matrix protein 4 | Secreted phosphoprotein 1 |
| ADAMTS-like protein 1 | Mucin-like protein 1 | Uncharacterized protein C16orf48 | Stress induced secreted protein 1 |
| Chemokine-like factor | Fibroblast growth factor 19 | Carboxylesterase 3 | Protein Wnt |
| EGF-like domain-containing protein 7 | Follistatin-related protein 3 | Protein FAM20B | Protein Wnt (Fragment) |
| Tectonic-1 | Hedgehog-interacting protein | GPN-loop GTPase 3 | Putative serine protease LOC138652 |
| Transmembrane protein 25 | Interleukin-17 receptor B | GRAM domain-containing protein 1B | TOM1 |
| UDP-GalNAc: beta-1,3-N-acetylgalactosaminyltransferase 1 | FXYD domain-containing ion transport regulator 5 | Phosphatidylinositol glycan anchor biosynthesis class U protein | Putative uncharacterized protein FLJ46089 |
| Interleukin-15 (IL-15) | Endothelial lipase | Interleukin-27 subunit alpha | Putative uncharacterized protein C1orf134 |
| Multiple epidermal growth factor-like domains 11 | EGF-containing fibulin-like extracellular matrix protein 2 | Pro-neuregulin-4, membrane-bound isoform | UDP-GlcNAc: betaGal beta-1,3-N-acetylglucosaminyltransferase 9 |
| Mucin and cadherin-like protein | Otoraplin | Leucine-rich repeat neuronal protein 3 | Uncharacterized protein C11orf44 |
| Ribonuclease 4 | Group 3 secretory phospholipase A2 | NMDA receptor-regulated protein 2 | Uncharacterized protein C12orf73 |
| SH2 domain-containing protein 3C | Group XV phospholipase A2 | NADH-cytochrome b5 reductase 1 | Putative cystatin-9-like 2 |
| CMP-N-acetylneuraminate-beta-galactosamide-alpha-2,3-sialyltransferase | Tumor necrosis factor ligand superfamily member 14 | Parkinson disease 7 domain-containing protein 1 | Putative abhydrolase domain-containing protein FAM108A5 |
| Transmembrane protein 9 | Plexin-A2 | FK506-binding protein 11 | Beta-defensin 133 |
| WAP four-disulfide core domain protein 2 | Papilin | C-type lectin domain family 12 member B | Fibrosin-1 |
| Adenosine A3 receptor | Prokineticin-1 | Solute carrier family 35 member F5 | Probable folate receptor delta |
| Gamma-secretase subunit APH-1A | Ribonuclease 7 | Sialic acid-binding Ig-like lectin 12 | RPE-spondin |
| Basigin | Kunitz-type protease inhibitor 1 | Protein FAM19A3 | NPIP-like protein ENSP00000346774 |
| Baculoviral IAP repeat-containing protein 7 | Spondin-2 | WD repeat-containing protein 82 | Putative testis-specific prion protein |
| Calumenin | Testican-2 | Adipocyte enhancer-binding protein 1 | Proline-rich protein 1 |
| Alpha-S1-casein | Inactive serine protease PAMR1 | ADAMTS-like protein 3 | Putative uncharacterized protein FP248 |
| Cyclin-L1 | Torsin-2A | Coiled-coil domain-containing protein 80 | UPF0670 protein C8orf55 |
| Complement factor H | Vasohibin-1 | Ecto-NOX disulfide-thiol exchanger 1 | Putative zinc-alpha-2-glycoprotein-like 2 |
| Chorionic somatomammotropin hormone | Vasorin | Neuronal growth regulator 1 | SPARC protein |
| Coxsackievirus and adenovirus receptor | Xylosyltransferase 1 | Interphotoreceptor matrix proteoglycan 1 | Otopetrin-1 |
| Ectonucleotide pyrophosphatase/phosphodiesterase family member 2 | Ectonucleotide pyrophosphatase/phosphodiesterase family member 6 | cDNA FLJ36603 fis, clone TRACH2015180, highly similar to Secreted frizzled-related protein 2 | cDNA FLJ55667, highly similar to Secreted protein acidic and rich in cysteine |
| ERO1-like protein alpha | Oncostatin-M | Lipase member H | Lipase member K |
| Coagulation factor IX | Derlin-1 | Mucin-19 (MUC-19) | C-type lectin domain family 18 member C |

TABLE 1-continued

| | | | |
|---|---|---|---|
| Low affinity immunoglobulin gamma Fc region receptor III-B | HERV-FRD_6p24.1 provirus ancestral Env polyprotein | Psoriasis susceptibility 1 candidate gene 2 protein | Putative uncharacterized protein UNQ6125/PRO20090 |
| Ficolin-3 | Prostasin | Integral membrane protein 2A | Complement C3 |
| Fc receptor-like protein 2 | Transmembrane protease, serine 11E | Vesicle transport protein SFT2B | Collagen alpha-2(IV) chain |
| Leucine-rich repeat transmembrane protein FLRT3 | HLA class I histocompatibility antigen, Cw-16 alpha chain | von Willebrand factor A domain-containing protein 3A | Uncharacterized protein UNQ6126/PRO20091 |
| Gelsolin | Wnt inhibitory factor 1 | Protein shisa-2 homolog | Serpin-like protein HMSD |
| Granulysin | C-type natriuretic peptide | Signal peptidase complex subunit 3 | Prostate and testis expressed protein 4 |
| Transmembrane glycoprotein NMB | Angiopoietin-2 | CD164 sialomucin-like 2 protein | Collagen alpha-1(XXII) chain |
| Granulins | Deoxyribonuclease gamma | Cadherin-16 | Putative uncharacterized protein C13orf28 |
| Heparanase | Carboxypeptidase A5 | Cadherin-19 | Cystatin-S |
| Ig mu chain C region | C-C motif chemokine 14 | Cerebellin-2 | R-spondin-1 |
| Interleukin-1 alpha | Interleukin-5 | Transmembrane protein C3orf1 | C8orf2 |
| Interleukin-31 receptor A | Interleukin-10 | Sperm equatorial segment protein 1 | Odorant-binding protein 2a |
| Junctional adhesion molecule B | C-X-C motif chemokine 2 | Uncharacterized protein C6orf72 | Opiorphin |
| Lipocalin-1 | C-X-C motif chemokine 5 | Uncharacterized protein C11orf24 | Kidney androgen-regulated protein |
| Leucine-rich repeat-containing G-protein coupled receptor 6 | A disintegrin and metalloproteinase with thrombospondin motifs 6 | Acyl-CoA synthetase family member 2, mitochondrial | Putative uncharacterized protein UNQ5830/PRO19650/PRO19816 |
| Latent-transforming growth factor beta-binding protein 1 | Polypeptide N-acetylgalactosaminyltransferase 1 | Probable UDP-sugar transporter protein SLC35A5 | Putative uncharacterized protein UNQ6975/PRO21958 |
| Matrilin-3 | Fibulin-2 | C-type lectin domain family 1 member A | Tachykinin-3 |
| Myelin protein zero-like protein 1 | Ficolin-1 | C-type lectin domain family 3 member A | Secreted phosphoprotein 1 |
| Neurobeachin-like protein 2 | SL cytokine | C-type lectin domain family 4 member E | Sclerostin |
| Nicastrin | Follistatin | C-type lectin domain family 4 member G | ADAMTS-like protein 2 |
| ADP-ribose pyrophosphatase, mitochondrial | FRAS1-related extracellular matrix protein 1 | Probable cation-transporting ATPase 13A4 | Scavenger receptor cysteine-rich domain-containing protein LOC284297 |
| Protocadherin-15 | Enamelin | UPF0480 protein C15orf24 | Tryptase beta-1 |
| Placenta growth factor | Hyaluronan and proteoglycan link protein 1 | Zona pellucida sperm-binding protein 4 | Tryptase delta |
| Protein O-linked-mannose beta-1,2-N-acetylglucosaminyltransferase 1 | Leukocyte immunoglobulin-like receptor subfamily A member 3 | Endoplasmic reticulum resident protein ERp27 | Putative cat eye syndrome critical region protein 9 |
| Probable hydrolase PNKD | Interleukin-17F | Transmembrane protein C16orf54 | Plexin domain-containing protein 1 |
| Pleiotrophin | Interleukin-1 receptor accessory protein | Cytochrome P450 4F12 | MC51L-53L-54L homolog (Fragment) |
| Poliovirus receptor | Serine protease inhibitor Kazal-type 5 | Cytochrome P450 4X1 | COBW-like placental protein (Fragment) |
| Reticulon-4 receptor | Kallikrein-15 | Cytochrome P450 4Z1 | Cytokine receptor-like factor 2 |
| Serum amyloid A protein | Interferon alpha-14 | Protein CREG2 | Beta-defensin 103 |
| Sex hormone-binding globulin | Pregnancy-specific beta-1-glycoprotein 4 | DnaJ homolog subfamily B member 9 | Beta-defensin 106 |
| SLAM family member 6 | Collagenase 3 | Dipeptidase 3 | Hyaluronidase-3 |
| Sarcolemmal membrane-associated protein | Matrix metalloproteinase-16 | Membrane protein FAM174A | Interleukin-28 receptor alpha chain |
| Sushi, von Willebrand factor type A, EGF and pentraxin domain-containing protein 1 | Pituitary adenylate cyclase-activating polypeptide | Thioredoxin domain-containing protein 15 | Glycosyltransferase 54 domain-containing protein |
| Thyroxine-binding globulin | Prokineticin-2 | Protein FAM19A4 | Chordin-like protein 1 |
| Transmembrane and coiled-coil domain-containing protein 1 | Latent-transforming growth factor beta-binding protein 3 | Adenosine monophosphate-protein transferase FICD | Putative uncharacterized protein UNQ9370/PRO34162 |
| Transmembrane protease, serine 3 | Somatoliberin | Prenylcysteine oxidase-like | Netrin receptor UNC5B |
| Tumor necrosis factor receptor superfamily member 10C | Thrombospondin type-1 domain-containing protein 1 | Phytanoyl-CoA hydroxylase-interacting protein-like | Fibroblast growth factor receptor FGFR-1 secreted form protein (Fragment) |
| Tumor necrosis factor receptor superfamily member 11B | Angiogenic factor with G patch and FHA domains 1 | FXYD domain-containing ion transport regulator 4 | Uncharacterized protein ENSP00000244321 |
| Serotransferrin | TGF-beta receptor type III | Growth/differentiation factor 11 | ECE2 |
| Tryptase beta-2 | Thyrotropin subunit beta | Cerebral dopamine neurotrophic factor | EPA6 |
| Protein YIPF5 | Uncharacterized protein C19orf36 | GPN-loop GTPase 2 | Putative soluble interleukin 18 receptor 1 |
| Vesicle-associated membrane protein-associated protein B/C | Complement C1q tumor necrosis factor-related protein 2 | Growth hormone-inducible transmembrane protein | Putative abhydrolase domain-containing protein FAM108A6 |

TABLE 1-continued

| | | | |
|---|---|---|---|
| cDNA, FLJ96669, highly similar to *Homo sapiens* secreted protein, acidic, cysteine-rich (osteonectin)(SPARC), mRNA | Ectonucleotide pyrophosphatase/phosphodiesterase family member 5 | Glycerophosphodiester phosphodiesterase domain-containing protein 2 | Putative V-set and immunoglobulin domain-containing-like protein ENSP00000303034 |
| cDNA FLJ77519, highly similar to *Homo sapiens* secreted frizzled related protein mRNA | Polypeptide N-acetylgalactosaminyltransferase-like protein 2 | WAP, kazal, immunoglobulin, kunitz and NTR domain-containing protein 1 | B cell maturation antigen transcript variant 4 (Tumor necrosis factor receptor superfamily member 17) |
| T-cell differentiation antigen CD6 | Slit homolog 1 protein | KDEL motif-containing protein 1 | UPF0672 protein C3orf58 |
| Pikachurin | Growth hormone variant | Adipophilin | Methylthioribose-1-phosphate isomerase |
| Fibrinogen-like protein 1 | Angiopoietin-related protein 3 | Lactase-like protein | 17-beta hydroxysteroid dehydrogenase 13 |
| Interleukin-32 | Angiopoietin-related protein 7 | Chondromodulin-1 | Aminopeptidase B |
| Matrilin-4 | Ecto-ADP-ribosyltransferase 5 | Collagen alpha-6(VI) chain | Dermcidin |
| Sperm-associated antigen 11B | Carbonic anhydrase-related protein 11 | Leucine-rich repeat-containing protein 33 | Meteorin |
| Coagulation factor XII | Probable ribonuclease 11 | MANSC domain-containing protein 1 | Methyltransferase-like protein 7A |
| Hepcidin | Probable carboxypeptidase X1 | Lipocalin-15 | NL3 |
| Klotho | Protein FAM3D | Arylsulfatase I | N-acetyltransferase 15 |
| Serglycin | C-X-C motif chemokine 14 | Mesoderm development candidate 2 | Ephrin-A4 |
| Tomoregulin-2 | Beta-defensin 127 | Dickkopf-related protein 1 | Protein Plunc |
| Chordin-like protein 2 | Beta-defensin 129 | Podocan | Kallikrein-11 |
| Tumor necrosis factor receptor superfamily member 6B | Cysteine-rich secretory protein LCCL domain-containing 2 | Fibronectin type III domain-containing protein 1 | WNT1 induced secreted protein 1 splice variant x (Fragment) |
| UPF0414 transmembrane protein C20orf30 | Fibroblast growth factor 21 | Neurotrimin | Interleukin-1 family member 10 |
| C-type lectin domain family 4 member C | Plasma alpha-L-fucosidase | Olfactory receptor 10W1 | PLA2G2D |
| UPF0317 protein C14orf159, mitochondrial | Gastrokine-1 | Protein PARM-1 | Proteoglycan 3 |
| Netrin-G2 | Gastrokine-2 | PDZ domain-containing protein 2 | Insulin-like peptide INSL5 |
| Metalloreductase STEAP2 | Glutathione peroxidase 7 | Proepiregulin | Olfactomedin-like protein 3 |
| Sushi domain-containing protein 4 | HHIP-like protein 1 | Polycystic kidney disease protein 1-like 1 | Extracellular glycoprotein lacritin |
| Protein YIF1B | Interferon kappa | WLPL514 | Retinol dehydrogenase 13 |
| Apolipoprotein M | Apolipoprotein C-I | Matrix metalloproteinase-26 | Neutrophil defensin 3 |
| C4b-binding protein beta chain | Procollagen C-endopeptidase enhancer 2 | RELT-like protein 2 | GLGQ5807 |
| T-cell surface glycoprotein CD8 beta chain | Left-right determination factor 1 | Solute carrier family 35 member E3 | TUFT1 |
| C-C motif chemokine 3-like 1 | Leucine-rich repeat LGI family member 4 | Zinc transporter ZIP9 | DRLV8200 |
| Fibroblast growth factor 8 | BRCA1-A complex subunit Abraxas | Noelin-2 | IDLW5808 |
| Sialomucin core protein 24 | Leucine zipper protein 2 | Seizure 6-like protein 2 | UBAP2 |
| Programmed cell death 1 ligand 2 | Neurexophilin-3 | Semaphorin-3A | C1q/TNF-related protein 8 |
| Secreted and transmembrane 1 | Osteomodulin | Semaphorin-4C | KIR2DL4 (Fragment) |
| Complement C1q tumor necrosis factor-related protein 6 | Kazal-type serine protease inhibitor domain-containing protein 1 | Abhydrolase domain-containing protein 14A | Chemokine-like factor super family 2 transcript variant 2 |
| EGF-like module-containing mucin-like hormone receptor-like 3 | Sperm acrosome membrane-associated protein 3 | Ankyrin repeat domain-containing protein 36 | Keratinocytes associated transmembrane protein 1 |
| Noelin-3 | Secretoglobin family 3A member 1 | Protein shisa-4 | GKGM353 |
| Odorant-binding protein 2b | Tsukushin | Neuromedin-U | MATL2963 |
| Urotensin-2 | Claudin-2 (SP82) | Nodal homolog | NINP6167 |
| Vitrin | Complement factor H-related protein 2 | Synaptogyrin-2 | POM121-like |
| WNT1-inducible-signaling pathway protein 3 | Immunoglobulin superfamily containing leucine-rich repeat protein | Brain-specific angiogenesis inhibitor 1-associated protein 2-like protein 2 | RTFV9368 (SLE-dependent upregulation 1) |
| cDNA FLJ75759, highly similar to *Homo sapiens* follistatin-like 3 (secreted glycoprotein) (FSTL3), mRNA | Leucine-rich repeat and immunoglobulin-like domain-containing nogo receptor-interacting protein 1 | Coiled-coil domain-containing protein 104 | Leucine-rich repeat and immunoglobulin-like domain-containing nogo receptor-interacting protein 4 |
| Angiotensin-converting enzyme 2 | Kin of IRRE-like protein 3 | Transmembrane 4 L6 family member 20 | KCNQ2 |
| Adiponectin | Hematopoietic cell signal transducer | Transmembrane protein 107 | ELCV5929 |
| Angiopoietin-related protein 4 | Follitropin subunit beta | Transmembrane protein 143 | KVVM3106 |
| Apolipoprotein A-V | Melanoma inhibitory activity protein 3 | Transmembrane protein 178 | ISPF6484 |
| Asporin | Leucine-rich repeat-containing protein 4 | Transmembrane protein 205 | LKHP9428 |

TABLE 1-continued

| | | | |
|---|---|---|---|
| Bactericidal permeability-increasing protein | Zinc transporter 5 | Transmembrane protein 41A | VNFT9373 |
| CUB domain-containing protein 1 | Leucine-rich repeat neuronal protein 1 | Transmembrane protein 50A | ACAH3104 |
| Cartilage intermediate layer protein 1 | Apical endosomal glycoprotein | Transmembrane protein 50B | RVLA1944 |
| Beta-Ala-His dipeptidase | Serum amyloid A-4 protein | Interleukin-28B | Wpep3002 |
| Collagen alpha-1(V) chain | Probetacellulin | Neuronal pentraxin-2 | ZDHHC11 |
| Collagen alpha-1(XXV) chain | Beta-1,4-galactosyltransferase 7 | Collectrin | AGLW2560 |
| Estradiol 17-beta-dehydrogenase 11 | 3-hydroxybutyrate dehydrogenase type 2 | Transmembrane protein 92 | TSSP3028 |
| DnaJ homolog subfamily C member 10 | C1GALT1-specific chaperone 1 | Transmembrane protein 95 | RFVG5814 |
| EGF-like domain-containing protein 6 | Beta-casein | Transmembrane protein 9B | SHSS3124 |
| Coagulation factor XIII A chain | Kappa-casein | Probable carboxypeptidase PM20D1 | MMP19 |
| Glucose-6-phosphate isomerase | Transmembrane protein C2orf18 | Tetraspanin-12 | GSQS6193 |
| Appetite-regulating hormone | Carboxypeptidase N catalytic chain | Tetraspanin-13 | VGPW2523 |
| Interleukin-12 subunit beta | CD320 antigen | Tetraspanin-15 | LMNE6487 |
| Interleukin-22 | Chondroitin sulfate synthase 1 | UPF0513 transmembrane protein | ALLA2487 |
| Intelectin-1 | Chondroitin sulfate synthase 2 | Mitochondrial uncoupling protein 4 | GALI1870 |
| Leucine-rich glioma-inactivated protein 1 | CMRF35-like molecule 7 | Polyserase-2 | FRSS1829 |
| Lymphocyte antigen 96 | Protein canopy homolog 3 | Probable palmitoyltransferase ZDHHC24 | MRSS6228 |
| Matrilysin | Short-chain dehydrogenase/reductase 3 | Zona pellucida sperm-binding protein 1 | GRPR5811 |
| Mucin-20 | Delta-like protein 4 | Zona pellucida sperm-binding protein 2 | AVLL5809 |
| Proprotein convertase subtilisin/kexin type 9 | Delta and Notch-like epidermal growth factor-related receptor | Conserved oligomeric Golgi complex subunit 7 | CR1 C3b/C4b receptor SCR9 (or 16) C-term. exon SCR = short consensus repeat |
| Peptidoglycan recognition protein | Dolichol kinase | Adiponectin receptor protein 2 | PIKR2786 |
| Interferon-induced 17 kDa protein | Endothelin-converting enzyme-like 1 | Inhibin beta C chain | S100 calcium binding protein A7-like 3 |
| Protein Wnt-4 | Integral membrane protein 2B | Brorin | GTWW5826 (LP5085 protein) |
| Allograft inflammatory factor 1-like | Insulin-like growth factor-binding protein 5 | Semaphorin-3C | KTIS8219 (HCG2020043) |
| Armadillo repeat-containing X-linked protein 3 | Endothelial cell-selective adhesion molecule | Heparan sulfate glucosamine 3-O-sulfotransferase 2 | Hyaluronan and proteoglycan link protein 4 |
| Chondroitin sulfate N-acetylgalactosaminyltransferase 1 | Signal peptide, CUB and EGF-like domain-containing protein 1 | Leptin receptor overlapping transcript-like 1 | Micronovel |
| Chitotriosidase-1 | Complement factor H-related protein 3 | SPARC-like protein 1 | SAMK3000 |
| Claudin domain-containing protein 1 | Prorelaxin H1 | Fibulin-7 | VFLL3057 |
| Erlin-2 | Follistatin-related protein 1 | Protein HEG homolog 1 | CVWG5837 |
| Glycosyltransferase 8 domain-containing protein 1 | Globoside alpha-1,3-N-acetylgalactosaminyltransferase 1 | Fibrinogen C domain-containing protein 1 | VGSA5840 |
| Golgi membrane protein 1 | Gamma-glutamyl hydrolase | Phospholipase A1 member A | GHPS3125 |
| Probable G-protein coupled receptor 125 | Cadherin-24 | Basic salivary proline-rich protein 2 | GRTR3118 |
| Interleukin-20 receptor alpha chain | Glycerol-3-phosphate acyltransferase 3 | Spermatogenesis-associated protein 6 | PAMP6501 |
| Galectin-7 | G-protein coupled receptor 56 | Sushi repeat-containing protein SRPX2 | LTLL9335 |
| NKG2D ligand 4 | Hyaluronan-binding protein 2 | Twisted gastrulation protein homolog 1 | VCEW9374 |
| L-amino-acid oxidase | Proheparin-binding EGF-like growth factor | Torsin-1B | AHPA9419 |
| Prolyl 3-hydroxylase 1 | Histidine-rich glycoprotein | Protein Wnt-5a | MDHV1887 |
| GPI ethanolamine phosphate transferase 2 | Carbohydrate sulfotransferase 14 | Acrosin-binding protein | HSAL5836 |
| GPI ethanolamine phosphate transferase 3 | Interleukin-20 receptor beta chain | C-type lectin domain family 18 member B | LHLC1946 |
| Calcium-binding mitochondrial carrier protein SCaMC-2 (Small calcium-binding mitochondrial carrier protein 2) | Ectonucleotide pyrophosphatase/phosphodiesterase family member 3 | Lysosomal-associated transmembrane protein 4A | Long palate, lung and nasal epithelium carcinoma-associated protein 3 (Ligand-binding protein RYA3) |
| Pulmonary surfactant-associated protein A2 | Insulin-like growth factor-binding protein 7 | Semaphorin-3E | LPPA601 |
| Splicing factor, arginine/serine-rich 16 | Kallistatin | Ameloblastin | PINK1 |
| Alpha-N-acetylgalactosaminide alpha-2,6-sialyltransferase 6 | Fibronectin type III domain-containing protein 3B | Major facilitator superfamily domain-containing protein 5 | SERH2790 |
| Single Ig IL-1-related receptor | Leukemia inhibitory factor receptor | Angiopoietin-1 | FLFF9364 |
| Tectonic-3 | Lin-7 homolog B | Angiopoietin-4 | APELIN |
| Tumor necrosis factor ligand superfamily | Thioredoxin-related transmembrane | Multiple epidermal growth factor-like | GLSH6409 |

TABLE 1-continued

| | | | |
|---|---|---|---|
| member 11 | protein 1 | domains 9 | |
| Tumor necrosis factor receptor superfamily member 19 | Disintegrin and metalloproteinase domain-containing protein 32 | Acid sphingomyelinase-like phosphodiesterase 3a | SFVP2550 |
| Palmitoyltransferase ZDHHC9 | Ly6/PLAUR domain-containing protein 3 | ADAMTS-like protein 5 | RRLF9220 |
| Fibulin-5 | C-type lectin domain family 14 member A | Spexin | PTML5838 |
| Protein Z-dependent protease inhibitor | Protein cornichon homolog | Putative trypsin-6 | VLGN1945 |
| Alpha-2-macroglobulin | Protein FAM151A | Proto-oncogene protein Wnt-1 | AVPC1948 |
| Agouti-related protein | FK506-binding protein 14 | Bone morphogenetic protein 3b | AWQG2491 |
| Pancreatic alpha-amylase | Neuropilin and tolloid-like protein 2 | Bone morphogenetic protein 5 | PSVL6168 |
| Natriuretic peptides B | Protocadherin beta-13 | Bone morphogenetic protein 8B | LCII3035 |
| Atrial natriuretic factor | Prenylcysteine oxidase 1 | Protein FAM26D | PPRR6495 |
| Neutral ceramidase | Peflin | C1q-related factor | RLSC6348 |
| Beta-2-microglobulin | Peptidyl-prolyl cis-trans isomerase-like 1 | WAP four-disulfide core domain protein 1 | CSRP2BP |
| Bone morphogenetic protein 4 | Prostate stem cell antigen | Cerebellin-1 | GLLV3061 |
| Biotinidase | Protein patched homolog 2 | Carboxypeptidase O | GWSI6489 |
| Scavenger receptor cysteine-rich type 1 protein M130 | Chitobiosyldiphosphodolichol beta-mannosyltransferase | Myelin protein zero-like protein 2 (Epithelial V-like antigen 1) | cDNA FLJ53955, highly similar to Secreted frizzled-related protein 4 |
| Carboxypeptidase B2 | Protein sel-1 homolog 1 | Serine protease 1-like protein 1 | PPIF |
| Carboxypeptidase Z | ProSAAS | Coiled-coil domain-containing protein 70 | VSSW1971 |
| C-C motif chemokine 5 | Sialic acid-binding Ig-like lectin 9 | C-C motif chemokine 28 | KLIA6249 |
| C-C motif chemokine 7 | SLIT and NTRK-like protein 1 | Uncharacterized protein C4orf29 | ALLW1950 |
| C-C motif chemokine 8 | Statherin | CUB domain-containing protein 2 | GVEI466 |
| CD59 glycoprotein | Testisin | Trem-like transcript 4 protein | ESFI5812 |
| Complement factor I | Transmembrane channel-like protein 5 | Uncharacterized protein C6orf58 | GNNC2999 |
| Clusterin | Transmembrane protease, serine 4 | Chondroadherin | AAGG6488 |
| Collagen alpha-2(I) chain | Metastasis-suppressor KiSS-1 | Cartilage intermediate layer protein 2 | HHSL751 |
| Collagen alpha-1(III) chain | Islet amyloid polypeptide | Uncharacterized protein C10orf25 | Beta-defensin 108B |
| Collagen alpha-1(IV) chain | Trem-like transcript 2 protein | Isthmin-1 | Beta-defensin 118 |
| Collagen alpha-3(IV) chain | Thioredoxin domain-containing protein 12 | Cystatin-8 | Beta-defensin 124 |
| Collagen alpha-5(IV) chain | Vascular endothelial growth factor B | Cardiotrophin-1 (CT-1) | Beta-defensin 125 |
| Collagen alpha-3(VI) chain | Vascular endothelial growth factor C | Chymotrypsinogen B | Beta-defensin 126 |
| Complement component C6 | Reticulocalbin-3 | C-X-C motif chemokine 9 | Deoxyribonuclease-1-like 2 |
| Collagen alpha-1(IX) chain | Fibrillin-1 | C-X-C motif chemokine 13 | Stanniocalcin-2 |
| Collagen alpha-1(X) chain | Protein FAM3A | EMILIN-3 | Endothelial cell-specific molecule 1 |
| Collagen alpha-1(XVII) chain | Protein G7c | Secretagogin | Carboxylesterase 7 |
| Collagen alpha-1(XXI) chain | Neuropilin and tolloid-like protein 1 | Epididymal secretory protein E3-alpha | Protein NOV homolog |
| Coatomer subunit alpha | Pregnancy-specific beta-1-glycoprotein 11 | Epiphycan | UPF0528 protein FAM172A |
| Complement receptor type 1 | Serpin B4 | Protein FAM5C | Interleukin-27 subunit beta |
| Cystatin-SN | ADAM DEC1 | Fibroblast growth factor 20 | Protein FAM3C |
| Deoxyribonuclease-1 | ADP-dependent glucokinase | Fibroblast growth factor-binding protein 3 | Stromal cell-derived factor 2-like protein 1 |
| Extracellular matrix protein 1 | Alpha-amylase 2B | Transmembrane protein 204 | Butyrophilin subfamily 1 member A1 |
| Low affinity immunoglobulin gamma Fc region receptor III-A | UDP-GlcNAc: betaGal beta-1,3-N-acetylglucosaminyltransferase 3 | Phosphatidylethanolamine-binding protein 4 | Keratinocyte-associated transmembrane protein 2 |
| Alpha-fetoprotein | Calcitonin gene-related peptide 2 | Coagulation factor V | Immunoglobulin alpha Fc receptor |
| Heparin-binding growth factor 2 | Carboxypeptidase E | Coagulation factor VII | EMILIN-2 |
| Fibrinogen gamma chain | Cardiotrophin-like cytokine factor 1 | Pro-MCH | Ephrin type-A receptor 10 |
| Growth/differentiation factor 5 | Collagen alpha-2(VIII) chain | Folate receptor gamma | Exostosin-like 2 |
| Glial cell line-derived neurotrophic factor | Crumbs homolog 2 | Mucin-7 | Follistatin-related protein 4 |
| Insulin-like growth factor-binding protein 3 | Dentin matrix acidic phosphoprotein 1 | Galanin-like peptide | Follistatin-related protein 5 |
| Insulin-like growth factor IA | Down syndrome cell adhesion molecule | Hemicentin-1 | Transmembrane protein 66 |
| Ig gamma-1 chain C region | Immunoglobulin superfamily member 1 | Interleukin-6 | Growth/differentiation factor 2 |
| Ig gamma-2 chain C region | Interleukin-4 | Embryonic growth/differentiation factor 1 | GDNF family receptor alpha-4 |
| Ig gamma-3 chain C region | Interleukin-6 receptor subunit alpha | Interleukin-8 | Ig gamma-4 chain C region |

TABLE 1-continued

| | | | |
|---|---|---|---|
| Insulin-like 3 | Interleukin-24 | Gremlin-2 | Lymphocyte antigen 86 |
| Inter-alpha-trypsin inhibitor heavy chain | Ladinin-1 | Stromelysin-2 | Inhibin beta E chain |
| UPF0378 protein KIAA0100 | Lipase member I | Probable G-protein coupled receptor 171 | GRAM domain-containing protein 1C |
| Kininogen-1 | Pancreatic lipase-related protein 1 | Pappalysin-2 | Interferon alpha-10 |
| Laminin subunit alpha-2 | Leucine-rich alpha-2-glycoprotein | Microfibril-associated glycoprotein 4 | Interferon alpha-16 |
| Laminin subunit alpha-4 | Matrix-remodeling-associated protein 5 | Neuromedin-B | Interferon alpha-6 |
| Laminin subunit beta-1 | Netrin-4 | Mimecan | Immunoglobulin superfamily member 21 |
| Protein-lysine 6-oxidase | Hepatocyte growth factor receptor | Matrix metalloproteinase-19 | Agrin |
| Multimerin-1 | C-C motif chemokine 22 | Interleukin-11 | Prolactin |
| Vasopressin-neurophysin 2-copeptin | Nyctalopin | Interleukin-17A | Kelch-like protein 11 |
| Nidogen-1 | Osteocalcin | Interleukin-18 | Protein Wnt-16 |
| Phospholipase A2, | Basic salivary proline-rich protein 3 | Interleukin-26 | Properdin |
| Perforin-1 | Pregnancy-specific beta-1-glycoprotein 10 | Interleukin-28A | Kallikrein-13 |
| Phosphatidylinositol-glycan-specific phospholipase D | Leucine-rich repeat transmembrane protein FLRT2 | Transmembrane emp24 domain-containing protein 3 | 1-acyl-sn-glycerol-3-phosphate acyltransferase delta |
| Fibrocystin | R-spondin-3 | Interleukin-29 | Kallikrein-9 |
| Phospholipid transfer protein | Sialoadhesin | Insulin-like peptide INSL6 | Vitamin K-dependent protein S |
| Prostatic acid phosphatase | Trypsin-3 | Protein Wnt-2b | Butyrophilin-like protein 8 |
| Vitamin K-dependent protein Z | Dipeptidase 2 | Pregnancy-specific beta-1-glycoprotein 1 | Laminin subunit beta-4 |
| Salivary acidic proline-rich phosphoprotein 1/2 | Collagen and calcium-binding EGF domain-containing protein 1 | Sperm acrosome membrane-associated protein 4 | Lymphatic vessel endothelial hyaluronic acid receptor 1 |
| Pregnancy zone protein | Germ cell-specific gene 1-like protein | Laminin subunit gamma-3 | Cystatin-SA |
| Prorelaxin H2 | Leucine-rich repeat-containing protein 31 | Lysyl oxidase homolog 3 | Transmembrane protein 59 |
| Semaphorin-4D | Apolipoprotein O | Neurotensin/neuromedin N | Apolipoprotein(a)-like protein 2 |
| Slit homolog 2 protein | Dystroglycan | MAM domain-containing protein 2 | Lysozyme-like protein 2 |
| Alpha-tectorin | Neutrophil defensin 4 | Microfibrillar-associated protein 2 | Lysozyme-like protein 4 |
| Tenascin-X | Amphoterin-induced protein 3 | Melanoma inhibitory activity protein 2 | Reelin |
| Trefoil factor 3 | Gamma-secretase subunit APH-1B | Matrix metalloproteinase-24 | Retinol-binding protein 4 |
| Transferrin receptor protein 1 | Apolipoprotein C-IV | Matrix metalloproteinase-25 | Carbonic anhydrase 14 |
| Protransforming growth factor alpha | Arylsulfatase G | Netrin-1 | Tubulointerstitial nephritis antigen |
| Transforming growth factor beta-2 | Glia-activating factor | Netrin-3 | Neuropeptide W |
| Tumor necrosis factor ligand superfamily member 6 | Caspase recruitment domain-containing protein 18 | Alpha-N-acetylgalactosaminide alpha-2,6-sialyltransferase 1 | Alpha-1,3-mannosyl-glycoprotein 4-beta-N-acetylglucosaminyltransferase B |
| Tumor necrosis factor receptor superfamily member 1B | Heparan sulfate glucosamine 3-O-sulfotransferase 3A1 | Alpha-N-acetylgalactosaminide alpha-2,6-sialyltransferase 3 | Transmembrane emp24 domain-containing protein 5 |
| Tumor necrosis factor receptor superfamily member 5 | Thyrotropin-releasing hormone-degrading ectoenzyme | Melanoma-derived growth regulatory protein | Complement C1q tumor necrosis factor-related protein 3 |
| Thrombopoietin | Guanylin | FMRFamide-related peptides | Podocan-like protein 1 |
| VIP peptides | Choline transporter-like protein 3 | Otoconin-90 | Pregnancy-specific beta-1-glycoprotein 5 |
| Acidic mammalian chitinase | 17-beta-hydroxysteroid dehydrogenase 14 | Neurturin | Keratocan |
| Cysteine-rich secretory protein 2 | Immunoglobulin lambda-like polypeptide 1 | Neurexophilin-1 | Group IIE secretory phospholipase A2 |
| Haptoglobin-related protein | DnaJ homolog subfamily B member 14 | Neurexophilin-2 | Left-right determination factor 2 |
| C-C motif chemokine 26 | F-box only protein 8 | Platelet factor 4 variant | NKG2D ligand 2 |
| Collectin-11 | Fibroleukin | Nociceptin | Macrophage metalloelastase |
| Cysteine-rich with EGF-like domain protein 2 | Methionine-R-sulfoxide reductase B3, mitochondrial | V-set and transmembrane domain-containing protein 1 | Triggering receptor expressed on myeloid cells 1 |
| C-X-C motif chemokine 16 | Leucine-rich repeat LGI family member 2 | Proline-rich protein 4 | Cytokine receptor-like factor 1 |
| Fibroblast growth factor-binding protein 1 | Vesicle transport protein GOT1B | Prolactin-releasing peptide | Secretin |
| Interleukin-1 family member 5 | Integral membrane protein GPR177 | Serine protease 33 | Stromal cell-derived factor 2 |
| Interleukin-1 family member 9 | Probable G-protein coupled receptor 78 | Pregnancy-specific beta-1-glycoprotein 8 | Lysozyme-like protein 6 |
| Kallikrein-5 | HEPACAM family member 2 | Retbindin | Serpin A9 |
| Matrilin-2 | Interleukin-27 receptor subunit alpha | FMRFamide-related peptides | Sclerostin domain-containing protein 1 |
| Cell surface glycoprotein CD200 receptor 1 | Proenkephalin-A | Ribonuclease K6 | Lysocardiolipin acyltransferase 1 |

TABLE 1-continued

| | | | |
|---|---|---|---|
| Lysophosphatidic acid phosphatase type 6 | Integrin alpha-10 | Ribonuclease T2 | Plasma glutamate carboxypeptidase |
| Nucleotide exchange factor SIL1 | KIEL motif-containing protein 1 | Repetin | Slit homolog 3 protein |
| Thrombospondin type-1 domain-containing protein 4 | Leukocyte immunoglobulin-like receptor subfamily A member 5 | Complement C1r subcomponent-like protein | C3 and PZP-like alpha-2-macroglobulin domain-containing protein 8 |
| WNT1-inducible-signaling pathway protein 2 | Leucine-rich repeat and fibronectin type-III domain-containing protein 3 | Uncharacterized glycosyltransferase AER61 | Retinoic acid receptor responder protein 2 |
| Bromodomain-containing protein 9 | Uteroglobin | Semaphorin-3G | Cartilage acidic protein 1 |
| CD99 antigen-like protein 2 | Netrin-G1 ligand | Secretoglobin family 1C member 1 | Stanniocalcin-1 |
| Uncharacterized protein C1orf159 | Pannexin-1 | Secretoglobin family 1D member 1 | Beta-tectorin |
| Carbohydrate sulfotransferase 12 | Protocadherin-12 | Secretoglobin family 1D member 2 | Post-GPI attachment to proteins factor 3 |
| Probable serine carboxypeptidase CPVL | Protocadherin alpha-10 | Serpin A12 | Germ cell-specific gene 1 protein |
| Mucin-3A | Protocadherin beta-10 | Serpin I2 | Interleukin-21 receptor |
| CUB and zona pellucida-like domain-containing protein 1 | Osteopetrosis-associated transmembrane protein 1 | von Willebrand factor C and EGF domain-containing protein | V-set and immunoglobulin domain-containing protein 4 |
| Polypeptide N-acetylgalactosaminyltransferase 14 | Beta-galactoside alpha-2,6-sialyltransferase 1 | A disintegrin and metalloproteinase with thrombospondin motifs 15 | Scavenger receptor cysteine-rich domain-containing group B protein |
| Galectin-9 | GPI transamidase component PIG-S | Sodium channel subunit beta-2 | Prothyroliberin |
| Leucine-rich repeat-containing protein 17 | Proline-rich transmembrane protein 3 | Metalloproteinase inhibitor 4 | Semaphorin-4A |
| Leucine-rich repeat neuronal protein 2 | Sulfhydryl oxidase 2 | T-cell immunomodulatory protein | |
| Bifunctional heparan sulfate N-deacetylase/N-sulfotransferase 3 | A disintegrin and metalloproteinase with thrombospondin motifs 16 | A disintegrin and metalloproteinase with thrombospondin motifs 10 | Tumor necrosis factor receptor superfamily member 27 |
| Tuftelin | SH2 domain-containing protein 3A | Thymic stromal lymphopoietin | Toll-like receptor 7 |
| Brain mitochondrial carrier protein | SHC-transforming protein 4 | Transmembrane protein 130 | |
| Signal peptide, CUB and EGF-like domain-containing protein 3 | Disintegrin and metalloproteinase domain-containing protein 23 | Unique cartilage matrix-associated protein | Thioredoxin domain-containing protein 16 |
| 14-3-3 protein sigma | Transducin beta-like protein 2 | Urocortin-2 | Alpha-2-antiplasmin |
| Alpha-1-acid glycoprotein 1 | Tudor domain-containing protein 10 | Urocortin-3 ( | WAP four-disulfide core domain protein 3 |
| Alpha-1-acid glycoprotein 2 | Transmembrane 9 superfamily member 3 | Protein AMBP | Protein WFDC9 |
| von Willebrand factor A domain-containing protein 1 | Von Willebrand factor D and EGF domain-containing protein | Complement C1q tumor necrosis factor-related protein 9-like | A disintegrin and metalloproteinase with thrombospondin motifs 14 |
| Disintegrin and metalloproteinase domain-containing protein 9 | A disintegrin and metalloproteinase with thrombospondin motifs 17 | Growth inhibition and differentiation-related protein 88 | Adipocyte plasma membrane-associated protein |
| Angiotensinogen | Transmembrane channel-like protein 2 | Protein Wnt-10a | Peroxidasin homolog |
| Apolipoprotein A-II (Apo-AII) (ApoA-II) | Pregnancy-specific beta-1-glycoprotein 3 | Protein Wnt-3a | Progressive ankylosis protein homolog |
| Apolipoprotein A-IV (Apo-AIV) (ApoA-IV) | Tenomodulin | Proto-oncogene protein Wnt-3 | Chitinase-3-like protein 1 |
| Apolipoprotein C-II (Apo-CII) (ApoC-II) | Tetraspanin-6 | Protein Wnt-6 | UPF0672 protein CXorf36 |
| Beta-2-glycoprotein 1 | Thioredoxin domain-containing protein 5 | Protein Wnt-9a | Arylsulfatase J |
| Apoptosis-related protein 3 | Vascular endothelial growth factor D | Cytokine SCM-1 beta | Cortistatin |
| Beta-secretase 2 | Pregnancy-specific beta-1-glycoprotein 9 | Zymogen granule membrane protein 16 | Ceruloplasmin |
| Histo-blood group ABO system transferase | Semaphorin-3F | Zona pellucida-binding protein 1 | Angiopoietin-related protein 5 |
| Cathepsin L2 | Acid phosphatase-like protein 2 | Anterior gradient protein 3 homolog | Coiled-coil domain-containing protein 126 |
| C-C motif chemokine 3 | Apolipoprotein O-like | Amelotin | CD177 antigen |
| C-type lectin domain family 1 member B | Beta-defensin 119 | Uncharacterized protein C5orf46 | Protein canopy homolog 4 |
| Calcium-activated chloride channel regulator 1 | A disintegrin and metalloproteinase with thrombospondin motifs 12 | Uncharacterized aarF domain-containing protein kinase 1 | Fibronectin type-III domain-containing protein C4orf31 |
| Chymase | Protein FAM131A | Draxin | Protein FAM180A |
| Collagen alpha-1(VI) chain | Protein FAM3B | Fibroblast growth factor 18 | Platelet basic protein |
| Complement component C8 alpha chain | Beta-galactosidase-1-like protein | C-X-C motif chemokine 11 | Interferon epsilon |
| Complement component C9 | Lysozyme g-like protein 1 | Ly6/PLAUR domain-containing protein 6 | Intelectin-2 |
| Glucose-fructose oxidoreductase domain-containing protein 2 | Inter-alpha-trypsin inhibitor heavy chain H5-like protein | Chymotrypsin-like elastase family member 1 | Alpha-1,3-mannosyl-glycoprotein 4-beta-N-acetylglucosaminyltransferase A |
| DnaJ homolog subfamily B member 11 | Sperm acrosome-associated protein 5 | Erythropoietin receptor | Matrix extracellular phosphoglycoprotein |
| Ectonucleotide | Leucine-rich repeat and immunoglobulin- | MAM domain-containing | cDNA FLJ77863, highly similar to *Homo* |

TABLE 1-continued pyrophosphatase/phosphodiesterase family member 7
Endoplasmic reticulum aminopeptidase 1
Receptor tyrosine-protein kinase erbB-3
Endoplasmic reticulum resident protein ERp44
IgGFc-binding protein
Complement factor H-related protein 1
Polypeptide N-acetylgalactosaminyltransferase 2
Hemopexin
Hepatocyte growth factor activator
Major histocompatibility complex class I-related gene protein
Insulin-like growth factor-binding protein 6
Ig delta chain C region
Interleukin-1 beta
Low-density lipoprotein receptor-related protein 10
Junctional adhesion molecule C
Uncharacterized protein KIAA0319
Laminin subunit alpha-5
Fibronectin type III domain-containing protein 4
Lipoprotein lipase
Interstitial collagenase
Matrix metalloproteinase-9
Mucin-16
Mucin-2
Mucin-5B
Myocilin
Oxidized low-density lipoprotein receptor 1
Prostate tumor overexpressed gene 1 protein
Receptor-interacting serine/threonine-protein kinase 2
Equilibrative nucleoside transporter 3
Selenoprotein P
Pulmonary surfactant-associated protein D
Stimulated by retinoic acid gene 6 protein homolog
Trefoil factor 1
Tissue factor pathway inhibitor 2
Prothrombin
Toll-like receptor 9
Intercellular adhesion molecule 4
Interleukin-19
lsthmin-2
Kin of IRRE-like protein 1
Kallikrein-10
Latent-transforming growth factor beta-binding protein 4
Paired immunoglobulin-like type 2 receptor like domain-containing nogo receptor-interacting protein 2
Surfactant-associated protein 2
Adiponectin receptor protein 1
Multiple epidermal growth factor-like domains 6
Neuroendocrine protein 7B2
Alpha-1B-glycoprotein
WAP, kazal, immunoglobulin, kunitz and NTR domain-containing protein 2
Arylacetamide deacetylase-like 1
Histatin-3
Pro-neuregulin-3, membrane-bound isoform
Agouti-signaling protein
Claudin-8
UPF0454 protein C12orf49
von Willebrand factor A domain-containing protein 5B1
Cadherin-6
Cathelicidin antimicrobial peptide
Laminin subunit gamma-1
Dehydrogenase/reductase SDR family member 7B
C-C motif chemokine 16
C-C motif chemokine 24
HEAT repeat-containing protein C7orf27
Collagen alpha-2(IX) chain
Collagen alpha-3(IX) chain
Colipase
Collagen alpha-1(XXVII) chain
Carboxypeptidase N subunit 2
Leucine-rich repeat transmembrane neuronal protein 4
Collagen triple helix repeat-containing protein 1
Endothelin-2
Fibromodulin
Fc receptor-like B
Zinc finger RAD18 domain-containing protein C1orf124
Growth/differentiation factor 15
Glia-derived nexin
Progonadoliberin-1
Granzyme K
Interferon alpha-17
Interferon alpha-21
Interferon alpha-8
Interferon omega-1
Early placenta insulin-like peptide
EGF, latrophilin and seven transmembrane domain-containing protein 1
Fibronectin type 3 and ankyrin repeat glycosylphosphatidylinositol anchor protein 2
Matrix metalloproteinase-27
Inactive serine protease 35
Coiled-coil domain-containing protein 134
Suprabasin
Secretoglobin family 1D member 4
V-set and transmembrane domain-containing protein 2A
ADM
Uncharacterized protein C2orf82
Insulin growth factor-like family member 1
Cadherin-like protein 29
Bone morphogenetic protein 15
Plasma serine protease inhibitor
Carcinoembryonic antigen-related cell adhesion molecule 21
Alpha-lactalbumin
Sister chromatid cohesion protein DCC1
Galectin-3-binding protein
Dynein heavy chain domain-containing protein 1
C-C motif chemokine 17
Fatty acyl-CoA reductase 1
Fin bud initiation factor homolog
Polymeric immunoglobulin receptor
Prion-like protein doppel
C-X-C motif chemokine 6
C-X-C motif chemokine 10
Beta-defensin 1
Hyaluronan and proteoglycan link protein 2
Disintegrin and metalloproteinase domain-containing protein 30
Suppressor of fused homolog
Folate receptor beta
Extracellular sulfatase Sulf-2
Tumor necrosis factor receptor superfamily member 14
Artemin
Collagen alpha-1(XII) chain
Collagen alpha-1(XIV) chain
Beta-defensin 2
Interleukin-21
Interleukin-3
Interleukin-7
Inhibin alpha chain
Laminin subunit alpha-3
Dehydrogenase/reductase SDR family member on chromosome X
FXYD domain-containing ion transport

*sapiens* secreted and transmembrane 1 (SECTM1), mRNA
Epididymal-specific lipocalin-6
Afamin
Probable cation-transporting ATPase 13A5
Glutathione peroxidase 3
Claudin-18
Putative killer cell immunoglobulin-like receptor like protein KIR3DP1
Secretory phospholipase A2 receptor
Haptoglobin
Carcinoembryonic antigen-related cell adhesion molecule 20
Bone morphogenetic protein 3
Bone marrow stromal antigen 2
Cytochrome P450 20A1
Bactericidal/permeability-increasing protein-like 3
Protein dpy-19 homolog 2
Group IIF secretory phospholipase A2
Carboxypeptidase B
Glycosyltransferase 8 domain-containing protein 2
Protein FAM19A1
GDNF family receptor alpha-like
Probable glutathione peroxidase 8
Cystatin-D
Cystatin-F
Platelet-activating factor acetylhydrolase
Pappalysin-1
Solute carrier family 22 member 12
Chorionic somatomammotropin hormone-like 1
Regulator of microtubule dynamics protein 3
Retinol dehydrogenase 14
Galanin
Transcobalamin-2
Catechol-O-methyltransferase domain-containing protein 1
Tripeptidyl-peptidase 1
Trem-like transcript 1 protein
Guanylate cyclase activator 2B
Inducible T-cell costimulator Notch homolog 2 N-terminal-like protein
Laminin subunit beta-2
Neuropilin-2
EGF-containing fibulin-like extracellular matrix protein 1
Receptor-type tyrosine-protein TABLE 1-continued

| | | | |
|---|---|---|---|
| alpha | domains protein 1 | regulator 6 | phosphatase kappa |
| Regenerating islet-derived protein 3 alpha | Lysyl oxidase homolog 4 | Serine incorporator 2 | Regenerating islet-derived protein 4 |
| E3 ubiquitin-protein ligase RNF5 | Lumican | Stromelysin-3 | Tachykinin-4 |
| Protachykinin-1 | Adropin | Secreted phosphoprotein 1 | Matrix metalloproteinase-23 |
| Secreted frizzled-related protein 1, isoform | Leucine-rich repeat transmembrane protein | Serine beta-lactamase-like protein | Complement C1q tumor necrosis factor- |
| CRA__a | FLRT1 | LACTB, mitochondrial | related protein 5 |
| Plasminogen-related protein B | Nucleobindin-2 | Galectin-3 | Opticin |
| Probable palmitoyltransferase ZDHHC16 | Phospholipase A2 | Pancreatic prohormone | Pre-small/secreted glycoprotein |
| Angiopoietin-related protein 1 | Proenkephalin-B | Pregnancy-specific beta-1-glycoprotein 6 | Pentraxin-related protein PTX3 |
| UPF0510 protein C19orf63 | Peptidoglycan recognition protein I-beta | Dickkopf-related protein 3 | Carboxylesterase 8 |
| Scavenger receptor cysteine-rich type 1 | Immunoglobulin superfamily containing | Dehydrogenase/reductase SDR family | Thioredoxin-related transmembrane |
| protein M160 | leucine-rich repeat protein 2 | member 11 | protein 4 |
| ER degradation-enhancing alpha- | V-set and immunoglobulin domain- | Regenerating islet-derived protein 3 | Major facilitator superfamily domain- |
| mannosidase-like 2 | containing protein 2 | gamma | containing protein 2 |
| Beta-galactosidase-1-like protein 2 | Peptide YY | RING finger protein 43 | Kallikrein-12 |
| Interleukin-17 receptor E | Retinol-binding protein 3 | Semenogelin-2 | Brevican core protein |
| Interleukin-20 | Atherin | Mucin-15 | Porimin |
| Interleukin-25 | Translocation protein SEC63 homolog | Bone sialoprotein 2 | Torsin-1A |
| PDZ domain-containing protein 11 | Transforming growth factor beta-3 | Lymphotactin | C-C motif chemokine 23 |
| Relaxin-3 | Protein Wnt-10b | Growth-regulated alpha protein | Testican-3 |
| Retinoid-inducible serine carboxypeptidase | Renalase | R-spondin-2 | Basic salivary proline-rich protein 4 |
| Short palate, lung and nasal epithelium | Proprotein convertase subtilisin/kexin | Transmembrane and coiled-coil domain- | Tumor necrosis factor receptor |
| carcinoma-associated protein 2 | type 4 | containing protein 3 | superfamily member 18 |
| WAP four-disulfide core domain protein 5 | Carboxypeptidase A4 | VEGF co-regulated chemokine 1 | Brother of CDO |
| Platelet-derived growth factor C | Olfactomedin-4 | ADM2 | Beta-1,4-galactosyltransferase 4 |
| Disintegrin and metalloproteinase domain- | Insulin-like growth factor-binding protein | Hydroxysteroid 11-beta-dehydrogenase | Dehydrogenase/reductase SDR family |
| containing protein 33 | complex acid labile chain | 1-like protein | member 9 |
| BSD domain-containing protein 1 | Amelogenin, Y isoform | Delta-like protein 1 | Eppin |
| Cell adhesion molecule 3 | Arylsulfatase F | Ephrin-A1 | Otoancorin |
| CDC45-related protein | Choriogonadotropin subunit beta variant 2 | Fibroblast growth factor receptor-like 1 | Tenascin-R |
| Chondrolectin | Beta-defensin 104 | GDNF family receptor alpha-3 | Growth factor |
| Diacylglycerol O-acyltransferase 2 | Beta-defensin 105 | Platelet receptor Gi24 | Protein TSPEAR |
| 3-keto-steroid reductase | Beta-defensin 107 | Progonadoliberin-2 | Hephaestin |
| Interleukin-17 receptor C | Protein WFDC11 | Kallikrein-7 | Butyrophilin-like protein 3 |
| Interleukin-17 receptor D | WAP four-disulfide core domain protein 6 | Apolipoprotein F | Butyrophilin-like protein 9 |
| Integrator complex subunit 1 | Epigen | Protein CASC4 | Laminin subunit gamma-2 |
| Junctional adhesion molecule-like | Protein FAM19A5 | VIP36-like protein | Protein LMBR1L |
| E3 ubiquitin-protein ligase LNX | Claudin-6 | Magnesium transporter protein 1 | Mucin-21 |
| Leucine-rich repeat transmembrane | Carcinoembryonic antigen-related cell | Amiloride-sensitive amine oxidase | Endoplasmic reticulum mannosyl- |
| neuronal protein 3 | adhesion molecule 19 | [copper-containing] | oligosaccharide 1,2-alpha-mannosidase |
| Methionine adenosyltransferase 2 | A disintegrin and metalloproteinase with | DNA damage-regulated autophagy | Pancreatic secretory granule membrane |
| subunit beta | thrombospondin motifs 1 | modulator protein 2 | major glycoprotein GP2 |
| Podocalyxin-like protein 2 | Protein COQ10 A, mitochondrial | Transmembrane protein C17orf87 | Semaphorin-4B |
| Prominin-2 | Uncharacterized protein C19orf41 | Complement factor H-related protein 5 | Semaphorin-5B |
| Plexin domain-containing protein 2 | Uncharacterized protein C21orf63 | FK506-binding protein 7 | Epsilon-sarcoglycan |
| Roundabout homolog 4 | Protein delta homolog 2 | Serine incorporator 1 | Guanylate-binding protein 5 |

TABLE 1-continued

| | | | |
|---|---|---|---|
| Lactosylceramide alpha-2,3-sialyltransferase | Cocaine- and amphetamine-regulated transcript protein | Transmembrane and ubiquitin-like domain-containing protein 1 | Ectonucleoside triphosphate diphosphohydrolase 6 |
| SID1 transmembrane family member 2 | Lipoma HMGIC fusion partner-like 1 protein | Protein ERGIC-53-like | Serpin B3 |
| Sushi domain-containing protein 1 | Leucine-rich repeat-containing protein 18 | Toll-like receptor 10 | Protein RMD5 homolog B |
| Serine/threonine-protein kinase TAO2 | Leucine-rich repeat-containing protein 25 | Toll-like receptor 8 | Scavenger receptor class A member 5 |
| Transmembrane protease, serine 2 | Leucine-rich repeat-containing protein 3B | Selenoprotein T | Semaphorin-6B |
| UDP-glucuronic acid decarboxylase 1 | Leucine-rich repeat-containing protein 3 | Sialic acid-binding Ig-like lectin 11 | Transmembrane protein 108 |
| Uncharacterized protein C10orf58 | Ly6/PLAUR domain-containing protein 4 | Sorting nexin-24 | Sushi domain-containing protein 3 |
| Thioredoxin-related transmembrane protein 2 | Vitamin K epoxide reductase complex subunit 1 | Complement C1q tumor necrosis factor-related protein 1 | Latent-transforming growth factor beta-binding protein 2 |
| CMP-N-acetylneuraminate-beta-galactosamide-alpha-2,3-sialyltransferase | A disintegrin and metalloproteinase with thrombospondin motifs 20 | Putative uncharacterized protein UNQ6494/PRO21346 | Putative uncharacterized protein UNQ6190/PRO20217 |
| Putative uncharacterized protein ENSP00000380674 | Putative uncharacterized protein ENSP00000381830 | Secreted and transmembrane 1 precusor variant | Secreted and transmembrane 1 precusor variant |
| Transmembrane protein 119 | Cat eye syndrome critical region protein 1 | C-type lectin domain family 18 member A | Collagen alpha-1(XX) chain |
| Transmembrane protein 98 | Testis-expressed protein 101 | Cysteine-rich secretory protein 3 | Netrin receptor UNC5D |
| Pre-B lymphocyte protein 3 | Xylosyltransferase 2 | Complement C4-A | Mucin-13 |
| Putative uncharacterized protein C14orf144 | Protein FAM20A | Putative uncharacterized protein PRO2829 | ATP-dependent metalloprotease YME1L1 |
| Membrane-bound transcription factor site-1 protease | Transmembrane and immunoglobulin domain-containing protein 1 | Calcium-activated chloride channel regulator 2 | Proprotein convertase subtilisin/kexin type 5 |
| Ficolin (Collagen/fibrinogen domain containing) 3 (Hakata antigen) (NL3) (Ficolin (Collagen/fibrinogen domain containing) 3 (Hakata antigen), isoform CRA_b) | Putative killer cell immunoglobulin-like receptor-like protein KIR3DX1 (Leukocyte receptor cluster member 12) | Neuroblastoma suppressor of tumorigenicity 1 | |

The therapeutic proteins provided herein should not be considered to be exclusive. Rather, as is apparent from the disclosure provided herein, the methods of the invention are applicable to any protein wherein attachment of a water soluble polymer is desired according to the invention. For example, therapeutic proteins are described in US 2007/0026485, incorporated herein by reference in its entirety.

Blood Coagulation Proteins

In one aspect, the starting material of the present invention is a blood coagulation protein, which can be derived from human plasma, or produced by recombinant engineering techniques, as described in U.S. Pat. No. 4,757,006; U.S. Pat. No. 5,733,873; U.S. Pat. No. 5,198,349; U.S. Pat. No. 5,250,421; U.S. Pat. No. 5,919,766; and EP 306 968.

Therapeutic polypeptides such as blood coagulation proteins including Factor IX (FIX), Factor VIII (FVIII), Factor VIIa (FVIIa), Von Willebrand Factor (VWF), Factor FV (FV), Factor X (FX), Factor XI (FXI), Factor XII (FXII), thrombin (FII), protein C, protein S, tPA, PAI-1, tissue factor (TF) and ADAMTS 13 protease are rapidly degraded by proteolytic enzymes and neutralized by antibodies. This reduces their half-life and circulation time, thereby limiting their therapeutic effectiveness. Relatively high doses and frequent administration are necessary to reach and sustain the desired therapeutic or prophylactic effect of these coagulation proteins. As a consequence, adequate dose regulation is difficult to obtain and the need of frequent intravenous administrations imposes restrictions on the patient's way of living.

As described herein, blood coagulation proteins including, but not limited to, Factor IX (FIX), Factor VIII (FVIII), Factor VIIa (FVIIa), Von Willebrand Factor (VWF), Factor FV (FV), Factor X (FX), Factor XI, Factor XII (FXII), thrombin (FII), protein C, protein S, tPA, PAI-1, tissue factor (TF) and ADAMTS 13 protease are contemplated by the invention. As used herein, the term "blood coagulation protein" refers to any Factor IX (FIX), Factor VIII (FVIII), Factor VIIa (FVIIa), Von Willebrand Factor (VWF), Factor FV (FV), Factor X (FX), Factor XII (FXII), thrombin (FII), protein C, protein S, tPA, PAI-1, tissue factor (TF) and ADAMTS 13 protease which exhibits biological activity that is associated with that particular native blood coagulation protein.

The blood coagulation cascade is divided into three distinct segments: the intrinsic, extrinsic, and common pathways (Schenone et al., Curr Opin Hematol. 2004; 11:272-7). The cascade involves a series of serine protease enzymes (zymogens) and protein cofactors. When required, an inactive zymogen precursor is converted into the active form, which consequently converts the next enzyme in the cascade.

The intrinsic pathway requires the clotting factors VIII, IX, X, XI, and XII. Initiation of the intrinsic pathway occurs when prekallikrein, high-molecular-weight kininogen, factor XI (FXI) and factor XII (FXII) are exposed to a negatively charged surface. Also required are calcium ions and phospholipids secreted from platelets.

The extrinsic pathway is initiated when the vascular lumen of blood vessels is damaged. The membrane glycoprotein tissue factor is exposed and then binds to circulating factor VII (FVII) and to small preexisting amounts of its activated form FVIIa. This binding facilitates full conversion of FVII to FVIIa and subsequently, in the presence of calcium and phospholipids, the conversion of factor IX (FIX) to factor IXa (FIXa) and factor X (FX) to factor Xa (FXa). The association of FVIIa with tissue factor enhances the proteolytic activity by bringing the binding sites of FVII for the substrate (FIX and FX) into closer proximity and by inducing a conformational change, which enhances the enzymatic activity of FVIIa.

The activation of FX is the common point of the two pathways. Along with phospholipid and calcium, factors Va (FVa) and Xa convert prothrombin to thrombin (prothrombinase complex), which then cleaves fibrinogen to form fibrin monomers. The monomers polymerize to form fibrin strands. Factor XIIIa (FXIIIa) covalently bonds these strands to one another to form a rigid mesh.

Conversion of FVII to FVIIa is also catalyzed by a number of proteases, including thrombin, FIXa, FXa, factor XIa (FXIa), and factor XIIa (FXIIa). For inhibition of the early phase of the cascade, tissue factor pathway inhibitor targets FVIIa/tissue factor/FXa product complex.

Factor VIIa

FVII (also known as stable factor or proconvertin) is a vitamin K-dependent serine protease glycoprotein with a pivotal role in hemostasis and coagulation (Eigenbrot, Curr Protein Pept Sci. 2002; 3:287-99).

FVII is synthesized in the liver and secreted as a single-chain glycoprotein of 48 kD. FVII shares with all vitamin K-dependent serine protease glycoproteins a similar protein domain structure consisting of an amino-terminal gamma-carboxyglutamic acid (Gla) domain with 9-12 residues responsible for the interaction of the protein with lipid membranes, a carboxy-terminal serine protease domain (catalytic domain), and two epidermal growth factor-like domains containing a calcium ion binding site that mediates interaction with tissue factor. Gamma-glutamyl carboxylase catalyzes carboxylation of Gla residues in the amino-terminal portion of the molecule. The carboxylase is dependent on a reduced form of vitamin K for its action, which is oxidized to the epoxide form. Vitamin K epoxide reductase is required to convert the epoxide form of vitamin K back to the reduced form.

The major proportion of FVII circulates in plasma in zymogen form, and activation of this form results in cleavage of the peptide bond between arginine 152 and isoleucine 153. The resulting activated FVIIa consists of a NH2-derived light chain (20 kD) and a COOH terminal-derived heavy chain (30 kD) linked via a single disulfide bond (Cys 135 to Cys 262). The light chain contains the membrane-binding Gla domain, while the heavy chain contains the catalytic domain.

The plasma concentration of FVII determined by genetic and environmental factors is about 0.5 mg/mL (Pinotti et al., Blood. 2000; 95:3423-8). Different FVII genotypes can result in several-fold differences in mean FVII levels. Plasma FVII levels are elevated during pregnancy in healthy females and also increase with age and are higher in females and in persons with hypertriglyceridemia. FVII has the shortest half-life of all procoagulant factors (3-6 h). The mean plasma concentration of FVIIa is 3.6 ng/mL in healthy individuals and the circulating half-life of FVIIa is relatively long (2.5 h) compared with other coagulation factors.

Hereditary FVII deficiency is a rare autosomal recessive bleeding disorder with a prevalence estimated to be 1 case per 500,000 persons in the general population (Acharya et al., J Thromb Haemost. 2004; 2248-56). Acquired FVII deficiency from inhibitors is also very rare. Cases have also been reported with the deficiency occurring in association with drugs such as cephalosporins, penicillins, and oral anticoagulants. Furthermore, acquired FVII deficiency has been reported to occur spontaneously or with other conditions, such as myeloma, sepsis, aplastic anemia, with interleukin-2 and antithymocyte globulin therapy.

Reference polynucleotide and polypeptide sequences include, e.g., GenBank Accession Nos. J02933 for the genomic sequence, M13232 for the cDNA (Hagen et al. PNAS 1986; 83: 2412-6), and P08709 for the polypeptide sequence (references incorporated herein in their entireties). A variety of polymorphisms of FVII have been described, for example see Sabater-Lleal et al. (Hum Genet. 2006; 118:741-51) (reference incorporated herein in its entirety).

Factor IX

FIX is a vitamin K-dependent plasma protein that participates in the intrinsic pathway of blood coagulation by converting FX to its active form in the presence of calcium ions, phospholipids and FVIIIa. The predominant catalytic capability of FIX is as a serine protease with specificity for a particular arginine-isoleucine bond within FX. Activation of FIX occurs by FXIa which causes excision of the activation peptide from FIX to produce an activated FIX molecule comprising two chains held by one or more disulphide bonds. Defects in FIX are the cause of recessive X-linked hemophilia B.

Hemophilia A and B are inherited diseases characterized by deficiencies in FVIII and FIX polypeptides, respectively. The underlying cause of the deficiencies is frequently the result of mutations in FVIII and FIX genes, both of which are located on the X chromosome. Traditional therapy for hemophilias often involves intravenous administration of pooled plasma or semi-purified coagulation proteins from normal individuals. These preparations can be contaminated by pathogenic agents or viruses, such as infectious prions, HIV, parvovirus, hepatitis A, and hepatitis C. Hence, there is an urgent need for therapeutic agents that do not require the use of human serum.

The level of the decrease in FIX activity is directly proportional to the severity of hemophilia B. The current treatment of hemophilia B consists of the replacement of the missing protein by plasma-derived or recombinant FIX (so-called FIX substitution or replacement treatment or therapy).

Polynucleotide and polypeptide sequences of FIX can be found for example in the UniProtKB/Swiss-Prot Accession No. P00740, U.S. Pat. No. 6,531,298 and in FIG. 1 (SEQ ID NO: 1).

Factor VIII

Coagulation factor VIII (FVIII) circulates in plasma at a very low concentration and is bound non-covalently to Von Willebrand factor (VWF). During hemostasis, FVIII is separated from VWF and acts as a cofactor for activated factor IX (FIXa)-mediated FX activation by enhancing the rate of activation in the presence of calcium and phospholipids or cellular membranes.

FVIII is synthesized as a single-chain precursor of approximately 270-330 kD with the domain structure A1-A2-B-A3-C1-C2. When purified from plasma (e.g., "plasma-derived" or "plasmatic"), FVIII is composed of a heavy chain (A1-A2-B) and a light chain (A3-C1-C2). The molecular mass of the light chain is 80 kD whereas, due to proteolysis within the B domain, the heavy chain is in the range of 90-220 kD.

FVIII is also synthesized as a recombinant protein for therapeutic use in bleeding disorders. Various in vitro assays have been devised to determine the potential efficacy of recombinant FVIII (rFVIII) as a therapeutic medicine. These assays mimic the in vivo effects of endogenous FVIII. In vitro thrombin treatment of FVIII results in a rapid increase and subsequent decrease in its procoagulant activity, as measured by in vitro assays. This activation and inactivation coincides with specific limited proteolysis both in the heavy and the light chains, which alter the availability of different binding epitopes in FVIII, e.g. allowing FVIII to dissociate from VWF and bind to a phospholipid surface or altering the binding ability to certain monoclonal antibodies.

The lack or dysfunction of FVIII is associated with the most frequent bleeding disorder, hemophilia A. The treatment of choice for the management of hemophilia A is replacement therapy with plasma derived or rFVIII concentrates. Patients with severe hemophilia A with FVIII levels below 1%, are generally on prophylactic therapy with the aim of keeping FVIII above 1% between doses. Taking into account the average half-lives of the various FVIII products in the circulation, this result can usually be achieved by giving FVIII two to three times a week.

Reference polynucleotide and polypeptide sequences include, e.g., UniProtKB/Swiss-Prot P00451 (FA8_HUMAN); Gitschier J et al., Characterization of the human Factor VIII gene, Nature, 312(5992): 326-30 (1984); Vehar G H et al., Structure of human Factor VIII, Nature, 312(5992):337-42 (1984); Thompson A R. Structure and Function of the Factor VIII gene and protein, Semin Thromb Hemost, 2003:29; 11-29 (2002).

Von Willebrand Factor

Von Willebrand factor (VWF) is a glycoprotein circulating in plasma as a series of multimers ranging in size from about 500 to 20,000 kD. Multimeric forms of VWF are composed of 250 kD polypeptide subunits linked together by disulfide bonds. VWF mediates initial platelet adhesion to the sub-endothelium of the damaged vessel wall. Only the larger multimers exhibit hemostatic activity. It is assumed that endothelial cells secrete large polymeric forms of VWF and those forms of VWF which have a low molecular weight (low molecular weight VWF) arise from proteolytic cleavage. The multimers having large molecular masses are stored in the Weibel-Pallade bodies of endothelial cells and liberated upon stimulation.

VWF is synthesized by endothelial cells and megakaryocytes as prepro-VWF that consists to a large extent of repeated domains. Upon cleavage of the signal peptide, pro-VWF dimerizes through disulfide linkages at its C-terminal region. The dimers serve as protomers for multimerization, which is governed by disulfide linkages between the free end termini. The assembly to multimers is followed by the proteolytic removal of the propeptide sequence (Leyte et al., Biochem. J. 274 (1991), 257-261).

The primary translation product predicted from the cloned cDNA of VWF is a 2813-residue precursor polypeptide (prepro-VWF). The prepro-VWF consists of a 22 amino acid signal peptide and a 741 amino acid propeptide, with the mature VWF comprising 2050 amino acids (Ruggeri Z. A., and Ware, J., FASEB J., 308-316 (1993).

Defects in VWF are causal to Von Willebrand disease (VWD), which is characterized by a more or less pronounced bleeding phenotype. VWD type 3 is the most severe form, in which VWF is completely missing, and VWD type 1 relates to a quantitative loss of VWF and its phenotype can be very mild. VWD type 2 relates to qualitative defects of VWF and can be as severe as VWD type 3. VWD type 2 has many sub forms, some being associated with the loss or the decrease of high molecular weight multimers. Von Willebrand disease type 2a (VWD-2A) is characterized by a loss of both intermediate and large multimers. VWD-2B is characterized by a loss of highest-molecular-weight multimers. Other diseases and disorders related to VWF are known in the art.

The polynucleotide and amino acid sequences of prepro-VWF are available at GenBank Accession Nos. NM_000552 and NP_000543, respectively.

Other blood coagulation proteins according to the present invention are described in the art, e.g. Mann K G, Thromb Haemost, 1999; 82:165-74.

A. Polypeptides

In one aspect, the starting material of the present invention is a protein or polypeptide. As described herein, the term therapeutic protein refers to any therapeutic protein molecule which exhibits biological activity that is associated with the therapeutic protein. In one embodiment of the invention, the therapeutic protein molecule is a full-length protein.

Therapeutic protein molecules contemplated include full-length proteins, precursors of full length proteins, biologically active subunits or fragments of full length proteins, as well as biologically active derivatives and variants of any of these forms of therapeutic proteins. Thus, therapeutic protein include those that (1) have an amino acid sequence that has greater than about 60%, about 65%, about 70%, about 75%, about 80%, about 85%, about 90%, about 91%, about 92%, about 93%, about 94%, about 95%, about 96%, about 97%, about 98% or about 99% or greater amino acid sequence identity, over a region of at least about 25, about 50, about 100, about 200, about 300, about 400, or more amino acids, to a polypeptide encoded by a referenced nucleic acid or an amino acid sequence described herein; and/or (2) specifically bind to antibodies, e.g., polyclonal or monoclonal antibodies, generated against an immunogen comprising a referenced amino acid sequence as described herein, an immunogenic fragment thereof, and/or a conservatively modified variant thereof.

According to the present invention, the term "recombinant therapeutic protein" includes any therapeutic protein obtained via recombinant DNA technology. In certain embodiments, the term encompasses proteins as described herein.

As used herein, "endogenous therapeutic protein" includes a therapeutic protein which originates from the mammal intended to receive treatment. The term also includes therapeutic protein transcribed from a transgene or any other foreign DNA present in said mammal. As used herein, "exogenous therapeutic protein" includes a blood coagulation protein which does not originate from the mammal intended to receive treatment.

As used herein, "plasma-derived blood coagulation protein" or "plasmatic" includes all forms of the protein found in blood obtained from a mammal having the property participating in the coagulation pathway.

As used herein "biologically active derivative" or "biologically active variant" includes any derivative or variant of a molecule having substantially the same functional and/or biological properties of said molecule, such as binding properties, and/or the same structural basis, such as a peptidic backbone or a basic polymeric unit.

An "analog," such as a "variant" or a "derivative," is a compound substantially similar in structure and having the same biological activity, albeit in certain instances to a differing degree, to a naturally-occurring molecule. For example, a polypeptide variant refers to a polypeptide sharing substantially similar structure and having the same biological activity as a reference polypeptide. Variants or analogs differ in the composition of their amino acid sequences compared to the naturally-occurring polypeptide from which the analog is derived, based on one or more mutations involving (i) deletion of one or more amino acid residues at one or more termini of the polypeptide and/or one or more internal regions of the naturally-occurring polypeptide sequence (e.g., fragments), (ii) insertion or addition of one or more amino acids at one or more termini (typically an "addition" or "fusion") of the polypeptide and/or one or more internal regions (typically an "insertion") of the naturally-occurring polypeptide sequence or (iii) substitution of one or more amino acids for other amino acids in the naturally-occurring polypeptide sequence. By way of example, a "derivative" is a type of analog and refers to a polypeptide sharing the same or substantially similar structure as a reference polypeptide that has been modified, e.g., chemically.

A variant polypeptide is a type of analog polypeptide and includes insertion variants, wherein one or more amino acid residues are added to a therapeutic protein amino acid sequence of the invention. Insertions may be located at either or both termini of the protein, and/or may be positioned within internal regions of the therapeutic protein amino acid sequence. Insertion variants, with additional residues at either or both termini, include for example, fusion proteins and proteins including amino acid tags or other amino acid labels. In one aspect, the blood coagulation protein molecule optionally contains an N-terminal Met, especially when the molecule is expressed recombinantly in a bacterial cell such as *E. coli*.

In deletion variants, one or more amino acid residues in a therapeutic protein polypeptide as described herein are removed. Deletions can be effected at one or both termini of the therapeutic protein polypeptide, and/or with removal of one or more residues within the therapeutic protein amino acid sequence. Deletion variants, therefore, include fragments of a therapeutic protein polypeptide sequence.

In substitution variants, one or more amino acid residues of a therapeutic protein polypeptide are removed and replaced with alternative residues. In one aspect, the substitutions are conservative in nature and conservative substitutions of this type are well known in the art. Alternatively, the invention embraces substitutions that are also non-conservative. Exemplary conservative substitutions are described in Lehninger, [Biochemistry, 2nd Edition; Worth Publishers, Inc., New York (1975), pp. 71-77] and are set out immediately below.

Conservative Substitutions

| SIDE CHAIN CHARACTERISTIC | AMINO ACID |
|---|---|
| Non-polar (hydrophobic): | |
| A. Aliphatic | A L I V P |
| B. Aromatic | F W |
| C. Sulfur-containing | M |
| D. Borderline | G |
| Uncharged-polar: | |
| A. Hydroxyl | S T Y |
| B. Amides | N Q |
| C. Sulfhydryl | C |
| D. Borderline | G |
| Positively charged (basic) | K R H |
| Negatively charged (acidic) | D E |

Alternatively, exemplary conservative substitutions are set out immediately below.

Conservative Substitutions II

| ORIGINAL RESIDUE | EXEMPLARY SUBSTITUTION |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |

-continued

| ORIGINAL RESIDUE | EXEMPLARY SUBSTITUTION |
|---|---|
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

B. Polynucleotides

Nucleic acids encoding a therapeutic protein of the invention include, for example and without limitation, genes, pre-mRNAs, mRNAs, cDNAs, polymorphic variants, alleles, synthetic and naturally-occurring mutants.

Polynucleotides encoding a therapeutic protein of the invention also include, without limitation, those that (1) specifically hybridize under stringent hybridization conditions to a nucleic acid encoding a referenced amino acid sequence as described herein, and conservatively modified variants thereof; (2) have a nucleic acid sequence that has greater than about 95%, about 96%, about 97%, about 98%, about 99%, or higher nucleotide sequence identity, over a region of at least about 25, about 50, about 100, about 150, about 200, about 250, about 500, about 1000, or more nucleotides (up to the full length sequence of 1218 nucleotides of the mature protein), to a reference nucleic acid sequence as described herein. Exemplary "stringent hybridization" conditions include hybridization at 42° C. in 50% formamide, 5×SSC, 20 mM $Na.PO_4$, pH 6.8; and washing in 1×SSC at 55° C. for 30 minutes. It is understood that variation in these exemplary conditions can be made based on the length and GC nucleotide content of the sequences to be hybridized. Formulas standard in the art are appropriate for determining appropriate hybridization conditions. See Sambrook et al., Molecular Cloning: A Laboratory Manual (Second ed., Cold Spring Harbor Laboratory Press, 1989) §§9.47-9.51.

A "naturally-occurring" polynucleotide or polypeptide sequence is typically derived from a mammal including, but not limited to, primate, e.g., human; rodent, e.g., rat, mouse, hamster; cow, pig, horse, sheep, or any mammal. The nucleic acids and proteins of the invention can be recombinant molecules (e.g., heterologous and encoding the wild type sequence or a variant thereof, or non-naturally occurring).

C. Production of Therapeutic Proteins

Production of a therapeutic protein includes any method known in the art for (i) the production of recombinant DNA by genetic engineering, (ii) introducing recombinant DNA into prokaryotic or eukaryotic cells by, for example and without limitation, transfection, electroporation or microinjection, (iii) cultivating said transformed cells, (iv) expressing therapeutic protein, e.g. constitutively or upon induction, and (v) isolating said blood coagulation protein, e.g. from the culture medium or by harvesting the transformed cells, in order to obtain purified therapeutic protein.

In other aspects, the therapeutic protein is produced by expression in a suitable prokaryotic or eukaryotic host system characterized by producing a pharmacologically acceptable blood coagulation protein molecule. Examples of eukaryotic cells are mammalian cells, such as CHO, COS, HEK 293, BHK, SK-Hep, and HepG2.

A wide variety of vectors are used for the preparation of the therapeutic protein and are selected from eukaryotic and prokaryotic expression vectors. Examples of vectors for prokaryotic expression include plasmids such as, and without limitation, pRSET, pET, and pBAD, wherein the promoters used in prokaryotic expression vectors include one or more of, and without limitation, lac, trc, trp, recA, or araBAD. Examples of vectors for eukaryotic expression include: (i) for expression in yeast, vectors such as, and without limitation, pAO, pPIC, pYES, or pMET, using promoters such as, and without limitation, AOX1, GAP, GAL1, or AUG1; (ii) for expression in insect cells, vectors such as and without limitation, pMT, pAc5, pIB, pMIB, or pBAC, using promoters such as and without limitation PH, p10, MT, Ac5, OpIE2, gp64, or polh, and (iii) for expression in mammalian cells, vectors such as and without limitation pSVL, pCMV, pRc/RSV, pcDNA3, or pBPV, and vectors derived from, in one aspect, viral systems such as and without limitation vaccinia virus, adeno-associated viruses, herpes viruses, or retroviruses, using promoters such as and without limitation CMV, SV40, EF-1, UbC, RSV, ADV, BPV, and β-actin.

D. Administration

In one embodiment a conjugated therapeutic protein of the present invention may be administered by injection, such as intravenous, intramuscular, or intraperitoneal injection.

To administer compositions comprising a conjugated therapeutic protein of the present invention to human or test animals, in one aspect, the compositions comprise one or more pharmaceutically acceptable carriers. The terms "pharmaceutically" or "pharmacologically acceptable" refer to molecular entities and compositions that are stable, inhibit protein degradation such as aggregation and cleavage products, and in addition do not produce allergic, or other adverse reactions when administered using routes well-known in the art, as described below. "Pharmaceutically acceptable carriers" include any and all clinically useful solvents, dispersion media, coatings, antibacterial and antifungal agents, isotonic and absorption delaying agents and the like, including those agents disclosed above.

As used herein, "effective amount" includes a dose suitable for treating a disease or disorder or ameliorating a symptom of a disease or disorder. In one embodiment, "effective amount" includes a dose suitable for treating a mammal having a bleeding disorder as described herein.

The compositions may be administered orally, topically, transdermally, parenterally, by inhalation spray, vaginally, rectally, or by intracranial injection. The term parenteral as used herein includes subcutaneous injections, intravenous, intramuscular, intracisternal injection, or infusion techniques. Administration by intravenous, intradermal, intramuscular, intramammary, intraperitoneal, intrathecal, retrobulbar, intrapulmonary injection and or surgical implantation at a particular site is contemplated as well. Generally, compositions are essentially free of pyrogens, as well as other impurities that could be harmful to the recipient.

Single or multiple administrations of the compositions can be carried out with the dose levels and pattern being selected by the treating physician. For the prevention or treatment of disease, the appropriate dosage will depend on the type of disease to be treated, as described above, the severity and course of the disease, whether drug is administered for preventive or therapeutic purposes, previous therapy, the patient's clinical history and response to the drug, and the discretion of the attending physician.

The present invention also relates to a pharmaceutical composition comprising an effective amount of a conjugated therapeutic protein as defined herein. The pharmaceutical composition may further comprise a pharmaceutically acceptable carrier, diluent, salt, buffer, or excipient. The pharmaceutical composition can be used for treating the above-defined bleeding disorders. The pharmaceutical composition of the invention may be a solution or a lyophilized product. Solutions of the pharmaceutical composition may be subjected to any suitable lyophilization process.

As an additional aspect, the invention includes kits which comprise a composition of the invention packaged in a manner which facilitates its use for administration to subjects. In one embodiment, such a kit includes a compound or composition described herein (e.g., a composition comprising a conjugated therapeutic protein), packaged in a container such as a sealed bottle or vessel, with a label affixed to the container or included in the package that describes use of the compound or composition in practicing the method. In one embodiment, the kit contains a first container having a composition comprising a conjugated therapeutic protein and a second container having a physiologically acceptable reconstitution solution for the composition in the first container. In one aspect, the compound or composition is packaged in a unit dosage form. The kit may further include a device suitable for administering the composition according to a specific route of administration. Preferably, the kit contains a label that describes use of the therapeutic protein or peptide composition.

Water Soluble Polymers

In one aspect, a therapeutic protein derivative (i.e., a conjugated therapeutic protein) molecule provided is bound to a water-soluble polymer including, but not limited to, polyethylene glycol (PEG), branched PEG, polysialic acid (PSA), hydroxyalkyl starch (HAS), hydroxylethyl starch (HES), carbohydrate, polysaccharides, pullulane, chitosan, hyaluronic acid, chondroitin sulfate, dermatan sulfate, starch, dextran, carboxymethyl-dextran, polyalkylene oxide (PAO), polyalkylene glycol (PAG), polypropylene glycol (PPG) polyoxazoline, poly acryloylmorpholine, polyvinyl alcohol (PVA), polycarboxylate, polyvinylpyrrolidone, polyphosphazene, polyoxazoline, polyethylene-co-maleic acid anhydride, polystyrene-co-maleic acid anhydride, poly(1-hydroxymethylethylene hydroxymethylformal) (PHF), 2-methacryloyloxy-2'-ethyltrimethylammoniumphosphate (MPC). In one embodiment of the invention, the water soluble polymer is consisting of sialic acid molecule having a molecular weight range of 350 to 120,000, 500 to 100,000, 1000 to 80,000, 1500 to 60,000, 2,000 to 45,000 Da, 3,000 to 35,000 Da, and 5,000 to 25,000 Da. The coupling of the water soluble polymer can be carried out by direct coupling to the protein or via linker molecules. One example of a chemical linker is MBPH (4-[4-N-Maleimidophenyl]butyric acid hydrazide) containing a carbohydrate-selective hydrazide and a sulfhydryl-reactive maleimide group (Chamow et al., J Biol Chem 1992; 267:15916-22). Other exemplary and preferred linkers are described below.

In one embodiment, the derivative retains the full functional activity of native therapeutic protein products, and provides an extended half-life in vivo, as compared to native therapeutic protein products. In another embodiment, the derivative retains at least 20, 21, 22, 23, 24, 25, 26, 27, 28, 29, 30, 31, 32, 34, 35, 36, 37, 38, 39, 40, 41, 42, 43, 44. 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, or 150 percent (%) biological activity relative to native blood coagulation protein. In a related aspect, the biological activities of the derivative and native blood coagulation protein are determined by the ratios of chromogenic activity to blood coagulation factor antigen value (blood coagulation factor:Chr:blood coagulation factor:Ag). In still another embodiment of the invention, the half-life of the construct is decreased or increased 0.5, 0.6, 0.7, 0.8, 0.9, 1.0, 1.1, 1.2, 1.3, 1.4, 1.5, 2, 3, 4, 5, 6, 7, 8, 9, or 10-fold relative to the in vivo half-life of native therapeutic protein.

A. Sialic Acid and PSA

PSAs consist of polymers (generally homopolymers) of N-acetylneuraminic acid. The secondary amino group normally bears an acetyl group, but it may instead bear a glycolyl group. Possible substituents on the hydroxyl groups include acetyl, lactyl, ethyl, sulfate, and phosphate groups.

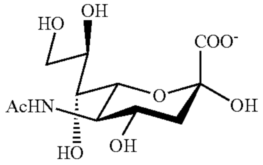

N-Acetylneuraminic acid
Neu5Ac

Structure of Sialic Acid (N-Acetylneuraminic Acid)

PSAs and mPSAs generally comprise linear polymers consisting essentially of N-acetylneuraminic acid moieties linked by 2,8- or 2,9-glycosidic linkages or combinations of these (e.g. alternating 2,8- and 2,9-linkages). In particularly preferred PSAs and mPSAs, the glycosidic linkages are α-2,8. Such PSAs and mPSAs are conveniently derived from colominic acids, and are referred to herein as "CAs" and "mCAs". Typical PSAs and mPSAs comprise at least 2, preferably at least 5, more preferably at least 10 and most preferably at least 20 N-acetylneuraminic acid moieties. Thus, they may comprise from 2 to 300 N-acetylneuraminic acid moieties, preferably from 5 to 200 N-acetylneuraminic acid moieties, or most preferably from 10 to 100 N-acetylneuraminic acid moieties. PSAs and CAs preferably are essentially free of sugar moieties other than N-acetylneuraminic acid. Thus PSAs and CAs preferably comprise at least 90%, more preferably at least 95% and most preferably at least 98% N-acetylneuraminic acid moieties.

Where PSAs and CAs comprise moieties other than N-acetylneuraminic acid (as, for example in mPSAS and mCAs) these are preferably located at one or both of the ends of the polymer chain. Such "other" moieties may, for example, be moieties derived from terminal N-acetylneuraminic acid moieties by oxidation or reduction.

For example, WO-A-0187922 describes such mPSAs and mCAs in which the non-reducing terminal N-acetylneuraminic acid unit is converted to an aldehyde group by reaction with sodium periodate. Additionally, WO 2005/016974 describes such mPSAs and mCAs in which the reducing terminal N-acetylneuraminic acid unit is subjected to reduction to reductively open the ring at the reducing terminal N-acetylneuraminic acid unit, whereby a vicinal diol group is formed, followed by oxidation to convert the vicinal diol group to an aldehyde group.

Sialic acid rich glycoproteins bind selectin in humans and other organisms. They play an important role in human influenza infections. E.g., sialic acid can hide mannose antigens on the surface of host cells or bacteria from mannose-binding lectin. This prevents activation of complement. Sialic acids also hide the penultimate galactose residue thus preventing rapid clearance of the glycoprotein by the galactose receptor on the hepatic parenchymal cells.

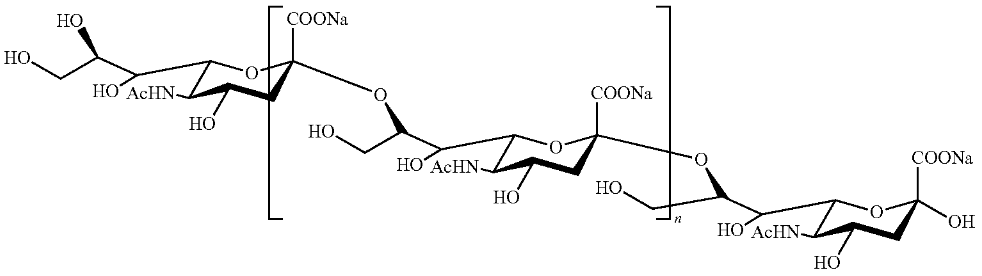

Structure of Colominic Acid (Homopolymer of N-Acetylneuraminic Acid)

Colominic acids (a sub-class of PSAs) are homopolymers of N-acetylneuraminic acid (NANA) with α (2→8) ketosidic linkage, and are produced, inter alia, by particular strains of *Escherichia coli* possessing K1 antigen. Colominic acids have many physiological functions. They are important as a raw material for drugs and cosmetics.

Comparative studies in vivo with polysialylated and unmodified asparaginase revealed that polysialylation increased the half-life of the enzyme (Fernandes and Gregoriadis, Biochimica Biophysica Acta 1341: 26-34, 1997).

As used herein, "sialic acid moieties" includes sialic acid monomers or polymers ("polysaccharides") which are soluble in an aqueous solution or suspension and have little or no negative impact, such as side effects, to mammals upon administration of the PSA-blood coagulation protein conjugate in a pharmaceutically effective amount. The polymers are characterized, in one aspect, as having 1, 2, 3, 4, 5, 10, 20, 30, 40, 50, 60, 70, 80, 90, 100, 200, 300, 400, or 500 sialic acid units. In certain aspects, different sialic acid units are combined in a chain.

In one embodiment of the invention, the sialic acid portion of the polysaccharide compound is highly hydrophilic, and in another embodiment the entire compound is highly hydrophilic. Hydrophilicity is conferred primarily by the pendant carboxyl groups of the sialic acid units, as well as the hydroxyl groups. The saccharide unit may contain other functional groups, such as, amine, hydroxyl or sulphate groups, or combinations thereof. These groups may be present on naturally-occurring saccharide compounds, or introduced into derivative polysaccharide compounds.

The naturally occurring polymer PSA is available as a polydisperse preparation showing a broad size distribution (e.g. Sigma C-5762) and high polydispersity (PD). Because the polysaccharides are usually produced in bacteria carrying the inherent risk of copurifying endotoxins, the purification of long sialic acid polymer chains may raise the probability of increased endotoxin content. Short PSA molecules with 1-4 sialic acid units can also be synthetically prepared (Kang S H et al., Chem. Commun. 2000; 227-8; Ress D K and Linhardt R J, Current Organic Synthesis. 2004; 1:31-46), thus minimizing the risk of high endotoxin levels. However PSA preparations with a narrow size distribution and low polydispersity, which are also endotoxin-free, can now be manufactured. Polysaccharide compounds of particular use for the invention are, in one aspect, those produced by bacteria. Some of these naturally-occurring polysaccharides are known as glycolipids. In one embodiment, the polysaccharide compounds are substantially free of terminal galactose units.

B. Polyethylene Glycol (PEG) and Pegylation

In certain aspects, therapeutic proteins are conjugated to a water soluble polymer by any of a variety of chemical methods (Roberts J M et al., Advan Drug Delivery Rev 2002; 54:459-76). For example, in one embodiment a therapeutic protein is modified by the conjugation of PEG to free amino groups of the protein using N-hydroxysuccinimide (NHS) esters. In another embodiment the water soluble polymer, for example PEG, is coupled to free SH groups using maleimide chemistry or the coupling of PEG hydrazides or PEG amines to carbohydrate moieties of the therapeutic protein after prior oxidation.

The conjugation is in one aspect performed by direct coupling (or coupling via linker systems) of the water soluble polymer to a therapeutic protein under formation of stable bonds. In addition degradable, releasable or hydrolysable linker systems are used in certain aspects the present invention (Tsubery et al. J Biol Chem 2004; 279:38118-24/Greenwald et al., J Med Chem 1999; 42:3657-67/Zhao et al., Bioconj Chem 2006; 17:341-51/WO2006/138572A2/U.S. Pat. No. 7,259,224B2/U.S. Pat. No. 7,060,259B2).

In one embodiment of the invention, a therapeutic protein is modified via lysine residues by use of polyethylene glycol derivatives containing an active N-hydroxysuccinimide ester (NHS) such as succinimidyl succinate, succinimidyl glutarate or succinimidyl propionate. These derivatives react with the lysine residues of the therapeutic protein under mild conditions by forming a stable amide bond. In one embodiment of the invention, the chain length of the PEG derivative is 5,000 Da. Other PEG derivatives with chain lengths of 500 to 2,000 Da, 2,000 to 5,000 Da, greater than 5,000 up to 10,000 Da or greater than 10,000 up to 20,000 Da, or greater than 20,000 up to 150,000 Da are used in various embodiments, including linear and branched structures.

Alternative methods for the PEGylation of amino groups are, without limitation, the chemical conjugation with PEG carbonates by forming urethane bonds, or the reaction with aldehydes or ketones by reductive amination forming secondary amide bonds.

In one embodiment of the present invention a therapeutic protein molecule is chemically modified using PEG derivatives that are commercially available. These PEG derivatives in alternative aspects have linear or branched structures. Examples of PEG-derivatives containing NHS groups are listed below.

The following PEG derivatives are non-limiting examples of those commercially available from Nektar Therapeutics (Huntsville, Ala.; see www.nektar.com/PEG reagent catalog; Nektar Advanced PEGylation, price list 2005-2006):

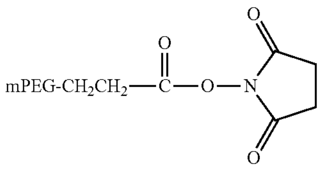

mPEG-Succinimidyl propionate (mPEG-SPA)

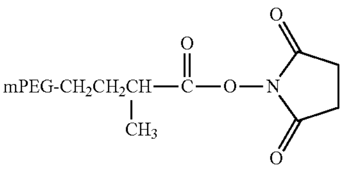

mPEG-Succinimidyl α-methylbutanoate (mPEG-SMB)

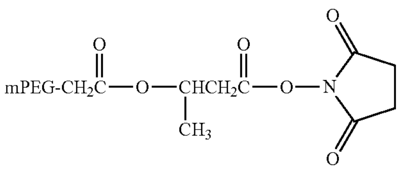

mPEG-CM-HBA-NHS (CM = carboxymethyl; HBA = Hydroxy butyric acid)

Structure of a Branched PEG-Derivative (Nektar Therapeutics)

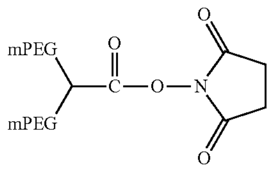

Branched PEG N-Hydroxysuccinimide (mPEG2-NHS)

This reagent with branched structure is described in more detail by Kozlowski et al. (BioDrugs 2001; 5:419-29).

Other non-limiting examples of PEG derivatives are commercially available from NOF Corporation (Tokyo, Japan; see www.nof.co.jp/english: Catalogue 2005)

General Structure of Linear PEG-Derivatives (NOF Corp.)

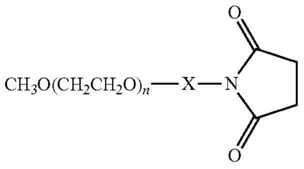

X = carboxymethyl

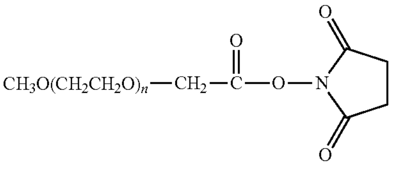

X = carboxypentyl

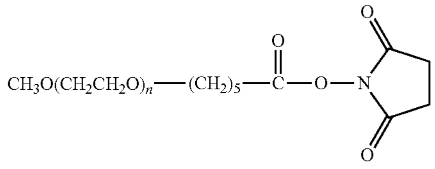

x = succinate

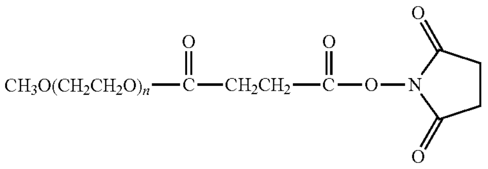

mPEG Succinimidyl succinate x = glutarate

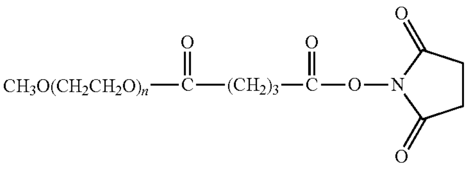

mPEG Succinimidyl glutarate

Structures of Branched PEG-Derivatives (NOF Corp.): 2,3-Bis(methylpolyoxyethylene-oxy)-1-(1,5-dioxo-5-succinimidyloxy, pentyloxy)propane

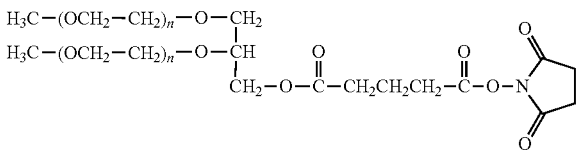

2,3-Bis(methylpolyoxyethylene-oxy)-1-(succinimidyl carboxypentyloxy)propane

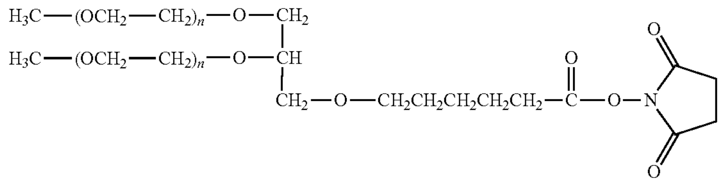

These propane derivatives show a glycerol backbone with a 1,2 substitution pattern. In the present invention branched PEG derivatives based on glycerol structures with 1,3 substitution or other branched structures described in US2003/0143596A1 are also contemplated.

PEG derivatives with degradable (for example, hydrolysable) linkers as described by Tsubery et al. (J Biol Chem 2004; 279:38118-24) and Shechter et al. (WO04089280A3) are also contemplated.

Surprisingly, the PEGylated therapeutic protein of this invention exhibits functional activity, combined with an extended half-life in vivo. In addition the PEGylated rFVIII, FVIIa, FIX, or other blood coagulation factor seems to be more resistant against thrombin inactivation.

C. Hydroxyalkyl Starch (HAS) and Hydroxylethyl Starch (HES)

In various embodiments of the present invention, a therapeutic protein molecule is chemically modified using hydroxyalkyl starch (HAS) or hydroxylethyl starch (HES) or derivatives thereof.

HES is a derivative of naturally occurring amylopectin and is degraded by alpha-amylase in the body. HES is a substituted derivative of the carbohydrate polymer amylopectin, which is present in corn starch at a concentration of up to 95% by weight. HES exhibits advantageous biological properties and is used as a blood volume replacement agent and in hemodilution therapy in the clinics (Sommermeyer et al., 1987, Krankenhauspharmazie, 8 (8), 271-278; and Weidler et al., 1991, Arzneim.-Forschung/Drug Res. g 419 494-498).

Amylopectin consists of glucose moieties, wherein in the main chain alpha-1,4-glycosidic bonds are present and at the branching sites alpha-1,6-glycosidic bonds are found. The physical-chemical properties of this molecule are mainly determined by the type of glycosidic bonds. Due to the nicked alpha-1,4-glycosidic bond, helical structures with about six glucose-monomers per turn are produced. The physico-chemical as well as the biochemical properties of the polymer can be modified via substitution. The introduction of a hydroxyethyl group can be achieved via alkaline hydroxyethylation. By adapting the reaction conditions it is possible to exploit the different reactivity of the respective hydroxy group in the unsubstituted glucose monomer with respect to a hydroxyethylation. Owing to this fact, the skilled person is able to influence the substitution pattern to a limited extent.

HAS refers to a starch derivative which has been substituted by at least one hydroxyalkyl group. Therefore, the term hydroxyalkyl starch is not limited to compounds where the terminal carbohydrate moiety comprises hydroxyalkyl groups R1, R2, and/or R3, but also refers to compounds in which at least one hydroxy group present anywhere, either in the terminal carbohydrate moiety and/or in the remaining part of the starch molecule, HAS', is substituted by a hydroxyalkyl group R1, R2, or R3.

(I)

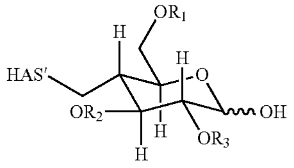

The alkyl group may be a linear or branched alkyl group which may be suitably substituted. Preferably, the hydroxyalkyl group contains 1 to 10 carbon atoms, more preferably from 1 to 6 carbon atoms, more preferably from 1 to 4 carbon atoms, and even more preferably 2-4 carbon atoms. "Hydroxyalkyl starch" therefore preferably comprises hydroxyethyl starch, hydroxypropyl starch and hydroxybutyl starch, wherein hydroxyethyl starch and hydroxypropyl starch are particularly preferred.

Hydroxyalkyl starch comprising two or more different hydroxyalkyl groups is also comprised in the present invention. The at least one hydroxyalkyl group comprised in HAS may contain two or more hydroxy groups. According to one embodiment, the at least one hydroxyalkyl group comprised HAS contains one hydroxy group.

The term HAS also includes derivatives wherein the alkyl group is mono- or polysubstituted. In one embodiment, the alkyl group is substituted with a halogen, especially fluorine, or with an aryl group, provided that the HAS remains soluble in water. Furthermore, the terminal hydroxy group a of hydroxyalkyl group may be esterified or etherified. HAS derivatives are described in WO/2004/024776, which is incorporated by reference in its entirety.

D. Methods of Attachment

A therapeutic protein may be covalently linked to the polysaccharide compounds by any of various techniques known to those of skill in the art. In various aspects of the invention, sialic acid moieties are bound to a therapeutic protein, e.g., FIX, FVIII, FVIIa or VWF, for example by the method described in U.S. Pat. No. 4,356,170, which is herein incorporated by reference.

Other techniques for coupling PSA to polypeptides are also known and contemplated by the invention. For example, US Publication No. 2007/0282096 describes conjugating an amine or hydrazide derivative of, e.g., PSA, to proteins. In addition, US Publication No. 2007/0191597 describes PSA derivatives containing an aldehyde group for reaction with substrates (e.g., proteins) at the reducing end. These references are incorporated by reference in their entireties.

Various methods are disclosed at column 7, line 15, through column 8, line 5 of U.S. Pat. No. 5,846,951 (incorporated by reference in its entirety). Exemplary techniques include linkage through a peptide bond between a carboxyl group on one of either the blood coagulation protein or polysaccharide and an amine group of the blood coagulation protein or polysaccharide, or an ester linkage between a carboxyl group of the blood coagulation protein or polysaccharide and a hydroxyl group of the therapeutic protein or polysaccharide. Another linkage by which the therapeutic protein is covalently bonded to the polysaccharide compound is via a Schiff base, between a free amino group on the blood coagulation protein being reacted with an aldehyde group formed at the non-reducing end of the polysaccharide by periodate oxidation (Jennings H J and Lugowski C, J. Immunol. 1981; 127:1011-8; Fernandes A I and Gregoriadis G, Biochim Biophys Acta. 1997; 1341; 26-34). The generated Schiff base is in one aspect stabilized by specific reduction with $NaCNBH_3$ to form a secondary amine. An alternative approach is the generation of terminal free amino groups in the PSA by reductive amination with $NH_4Cl$ after prior oxidation. Bifunctional reagents can be used for linking two amino or two hydroxyl groups. For example, PSA containing an amino group is coupled to amino groups of the protein with reagents like BS3 (Bis(sulfosuccinimidyl)suberate/Pierce, Rockford, Ill.). In addition heterobifunctional cross linking reagents like Sulfo-EMCS (N-ε-Maleimidocaproyloxy) sulfosuccinimide ester/Pierce) is used for instance to link amine and thiol groups.

In another approach, a PSA hydrazide is prepared and coupled to the carbohydrate moiety of the protein after prior oxidation and generation of aldehyde functions.

As described above, a free amine group of the therapeutic protein reacts with the 1-carboxyl group of the sialic acid residue to form a peptidyl bond or an ester linkage is formed between the 1-carboxylic acid group and a hydroxyl or other suitable active group on a blood coagulation protein. Alternatively, a carboxyl group forms a peptide linkage with deacetylated 5-amino group, or an aldehyde group of a molecule of a therapeutic protein forms a Schiff base with the N-deacetylated 5-amino group of a sialic acid residue.

Alternatively, the polysaccharide compound is associated in a non-covalent manner with a therapeutic protein. For example, the polysaccharide compound and the pharmaceutically active compound are in one aspect linked via hydrophobic interactions. Other non-covalent associations include electrostatic interactions, with oppositely charged ions attracting each other.

In various embodiments, the therapeutic protein is linked to or associated with the polysaccharide compound in stoichiometric amounts (e.g., 1:1, 1:2, 1:3, 1:4, 1:5, 1:6, 1:7, 1:7, 1:8, 1:9, or 1:10, etc.). In various embodiments, 1-6, 7-12 or 13-20 polysaccharides are linked to the blood coagulation protein. In still other embodiments, 1, 2, 3, 4, 5, 6, 7, 8, 9, 10, 11, 12, 13, 14, 15, 16, 17, 18, 19, 20 or more polysaccharides are linked to the blood coagulation protein.

In various embodiments, the therapeutic protein is modified to introduce glycosylation sites (i.e., sites other than the native glycosylation sites). Such modification may be accomplished using standard molecular biological techniques known in the art. Moreover, the therapeutic protein, prior to conjugation to a water soluble polymer via one or more carbohydrate moieties, may be glycosylated in vivo or in vitro. These glycosylated sites can serve as targets for conjugation of the proteins with water soluble polymers (US Patent Application No. 20090028822, US Patent Application No. 2009/0093399, US Patent Application No. 2009/0081188, US Patent Application No. 2007/0254836, US Patent Application No. 2006/0111279, and DeFrees S. et al., Glycobiology, 2006, 16, 9, 833-43). For example, a protein that is not naturally glycoslyated in vivo (e.g., a protein that is not a glycoprotein) may be modified as described above.

E. Aminooxy Linkage

In one embodiment of the invention, the reaction of hydroxylamine or hydroxylamine derivatives with aldehydes (e.g., on a carbohydrate moiety following oxidation by sodium periodate) to form an oxime group is applied to the preparation of conjugates of blood coagulation protein. For example, a glycoprotein (e.g., a therapeutic protein according to the present invention) is first oxidized with a oxidizing agent such as sodium periodate ($NaIO_4$) (Rothfus J A et Smith E L., J Biol Chem 1963, 238, 1402-10; and Van Lenten L and Ashwell G., J Biol Chem 1971, 246, 1889-94). The periodate oxidation of glycoproteins is based on the classical Malaprade reaction described in 1928, the oxidation of vicinal diols with periodate to form an active aldehyde group (Malaprade L., Analytical application, Bull Soc Chim France, 1928, 43, 683-96). Additional examples for such an oxidizing agent are lead tetraacetate (Pb(OAc)4), manganese acetate (MnO(Ac)3), cobalt acetate (Co(OAc)2), thallium acetate (TlOAc), cerium sulfate (Ce(SO4)2) (U.S. Pat. No. 4,367,309) or potassium perruthenate (KRuO4) (Marko et al., J Am Chem Soc 1997, 119, 12661-2). By "oxidizing agent" a mild oxidizing compound which is capable of oxidizing vicinal diols in carbohydrates, thereby generating active aldehyde groups under physiological reaction conditions is meant.

Figure 2:
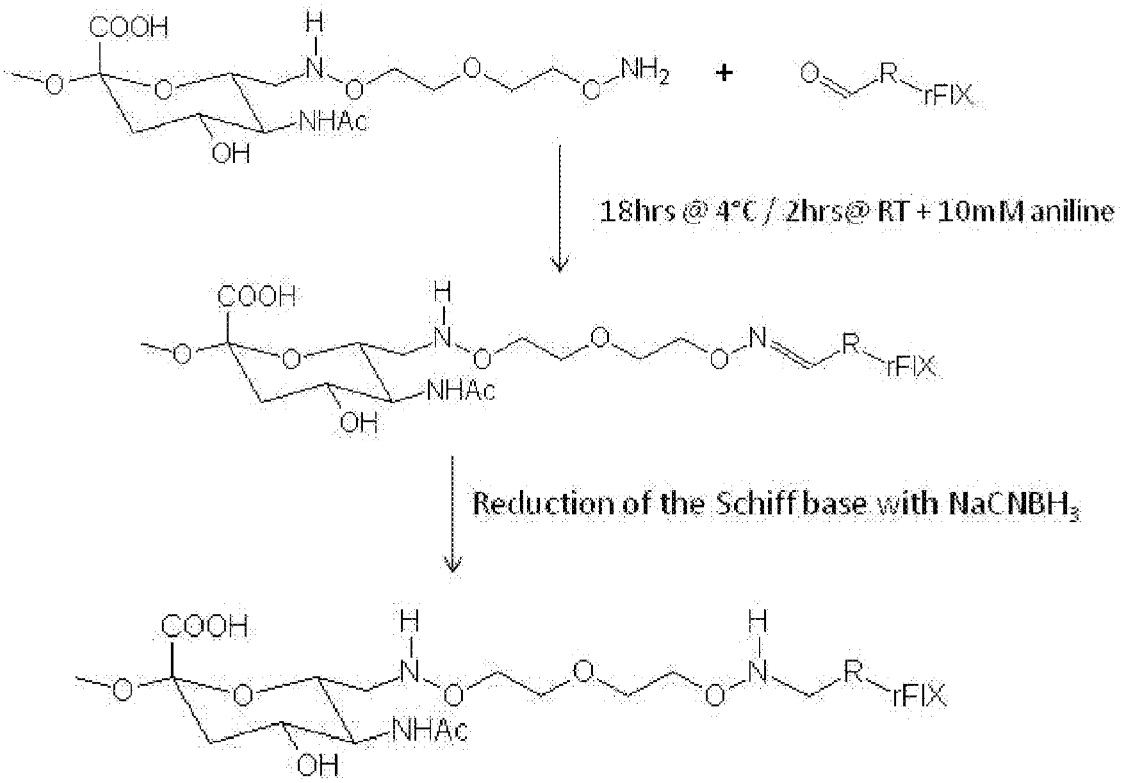
FIG. 2 shows the coupling of oxidized rFIX to aminooxy-PSA.

The second step is the coupling of the polymer containing an aminooxy group to the oxidized carbohydrate moiety to form an oxime linkage. In one embodiment of the invention, this step can be carried out in the presence of catalytic amounts of the nucleophilic catalyst aniline or aniline derivatives (Dirksen A et Dawson P E, Bioconjugate Chem. 2008; Zeng Y et al., Nature Methods 2009; 6:207-9). The aniline catalysis dramatically accelerates the oxime ligation allowing the use of very low concentrations of the reagents. In another embodiment of the invention the oxime linkage is stabilized by reduction with $NaCNBH_3$ to form an alkoxyamine linkage (FIG. 2). Additional catalysts are described below.

Additional information on aminooxy technology can be found in the following references, each of which is incorporated in their entireties: EP 1681303A1 (HASylated erythropoietin); WO 2005/014024 (conjugates of a polymer and a protein linked by an oxime linking group); WO96/40662 (aminooxy-containing linker compounds and their application in conjugates); WO 2008/025856 (Modified proteins); Peri F et al., Tetrahedron 1998, 54, 12269-78; Kubler-Kielb J et. Pozsgay V., J Org Chem 2005, 70, 6887-90; Lees A et al., Vaccine 2006, 24(6), 716-29; and Heredia K L et al., Macromolecules 2007, 40(14), 4772-9.

Numerous methods of coupling a water-soluble polymer to an aminooxy linker are contemplated by the present disclosure. For example, coupling of a linker to either the reducing or non-reducing end of a water-soluble polymer such as PSA is described herein. The coupling site (e.g., reducing end versus non-reducing end) is determined by one or more conditions (e.g., time and temperature) of the coupling process as well as the state (e.g., native versus oxidized) of the water-soluble polymer. In one embodiment, an oxidized water-soluble polymer such as PSA is coupled at it's non-reducing end to an aminooxy linker by performing the coupling reaction at a reduced temperature (e.g., between 2-8° C.). In another embodiment, a native (e.g., non-oxidized) water-soluble polymer such as PSA is coupled at it's reducing end to an aminooxy linker by performing the coupling reaction at a higher temperature (e.g., between 22-37° C.). The aforementioned embodiments are described in more detail below and in the Examples.

As described herein, the reaction of oxidized PSA with a diaminooxy linker shows two reactions: a "quick reaction" of the aldehyde group at the non-reducing end, and a "slow reaction" at the reducing end. If native PSA (which is not oxidized and does not contain an active aldehyde group) is reacted with the reducing end at room temperature, a derivatized PSA can be observed. Thus, in various embodiments, in order to minimize an unwanted side reaction at the reducing end of a water-soluble polymer such as PSA, the PSA-aminooxy linker reagent preparation is performed at a temperature between 2-8° C.

In still another embodiment of the present disclosure, the derivatization of native PSA at the reducing end is provided. As described herein, native PSA (which is not oxidized by $NaIO_4$ and thus does not contain a free aldehyde group at its non-reducing end) is reacted with a diaminooxy linker at room temperature, a derivatization of the PSA at its reducing end can be observed. This coupling occurs through ring opening at the reducing end and subsequent oxime formation (the actual side reaction described above and the cause for the presence of by-product in the aminooxy-PSA reagent). This reaction can be performed with native PSA yielding in a degree of modification up to approximately 70%.

As a main product the following structure was determined by 13C NMR spectroscopy

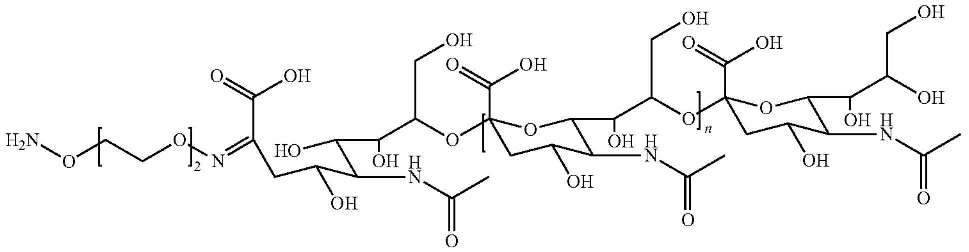

The reaction can be transferred to other carbohydrates like dextran and starch or other polysaccharides containing reducing end groups. The use of a nucleophilic catalyst like m-toluidine or aniline is also contemplated. Thus, preparation of aminooxy-PSA reagents using native PSA (i.e. without prior oxidation), which can then be used for chemical modification of therapeutic proteins, is provided herein.

Thus, in various embodiments of the present disclosure, methods are provided wherein the conditions of coupling, (e.g., 2-8° C. incubation temperature) a diaminooxy linker to a water soluble polymer such as oxidized PSA, favor the coupling to either the non-reducing end or, in one alternative, wherein the conditions of coupling (e.g., room temperature incubation) a diaminooxy linker to a water soluble polymer such as native, non-oxidized PSA, favor the coupling to either the reducing end.

In various embodiments of the invention, the water soluble polymer which is linked according to the aminooxy technology described herein to an oxidized carbohydrate moiety of a therapeutic protein (e.g., FVIII, FVIIa, or FIX) include, but are not limited to polyethylene glycol (PEG), branched PEG, polysialic acid (PSA), carbohydrate, polysaccharides, pullulane, chitosan, hyaluronic acid, chondroitin sulfate, dermatan sulfate, starch, dextran, carboxymethyl-dextran, polyalkylene oxide (PAO), polyalkylene glycol (PAG), polypropylene glycol (PPG) polyoxazoline, poly acryloylmorpholine, polyvinyl alcohol (PVA), polycarboxylate, polyvinylpyrrolidone, polyphosphazene, polyoxazoline, polyethylene-co-maleic acid anhydride, polystyrene-co-maleic acid anhydride, poly (1-hydroxymethylethylene hydroxymethylformal) (PHF), 2-methacryloyloxy-2'-ethyltrimethylammoniumphosphate (MPC).

Nucleophilic Catalysts

As described herein, the conjugation of water soluble polymers to therapeutic proteins can be catalyzed by aniline. Aniline strongly catalyzes aqueous reactions of aldehydes and ketones with amines to form stable imines such as hydrazones and oximes. The following diagram compares an uncatalyzed versus the aniline-catalyzed oxime ligation reaction (Kohler J J, ChemBioChem 2009; 10:2147-50):

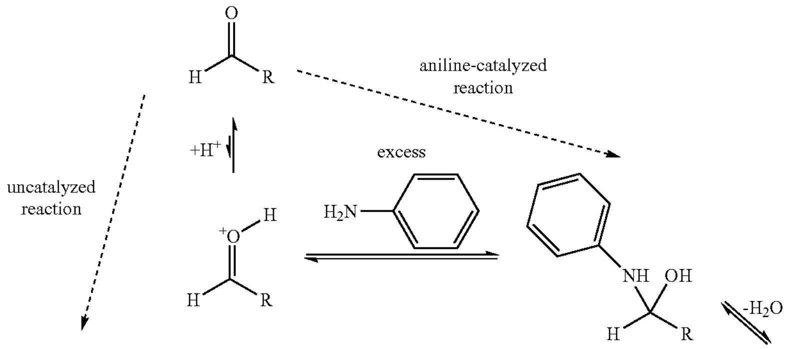

-continued

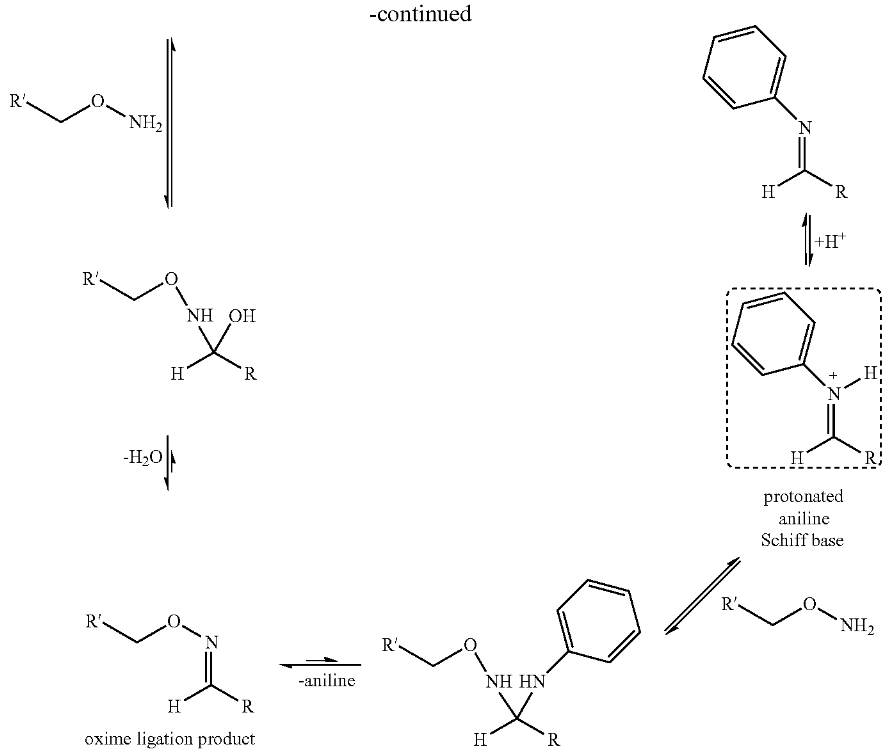

However, considering the numerous health risks associated with aniline, alternative catalysts are desirable. The present invention provides aniline derivatives as alternative oxime ligation catalysts. Such aniline derivatives include, but are not limited to, o-amino benzoic acid, m-amino benzoic acid, p-amino benzoic acid, sulfanilic acid, o-aminobenzamide, o-toluidine, m-toluidine, p-toluidine, o-anisidine, m-anisidine, and p-anisidine.

In one embodiment of the invention, m-toluidine (aka meta-toluidine, m-methylaniline, 3-methylaniline, or 3-amino-1-methylbenzene) is used to catalyze the conjugation reactions described herein. M-toluidine and aniline have similar physical properties and essentially the same pKa value (m-toluidine: pKa 4.73, aniline: pKa 4.63).

The nucleophilic catalysts of the invention are useful for oxime ligation (e.g., using aminooxy linkage) or hydrazone formation (e.g., using hydrazide chemistry). In various embodiments of the invention, the nucleophilic catalyst is provided in the conjugation reaction at a concentration of 0.1, 0.2, 0.3, 0.5, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 11, 12, 13, 14, 15, 16, 17, 18, 19, 20, 25, 30, 35, 40, 45, or 50 mM. In one embodiment, the nucleophilic catalyst is provided between 1 to 10 mM. In various embodiments of the invention, the pH range of conjugation reaction is 4.5, 5.0, 5.5, 6.0, 6.5, 7.0 and 7.5. In one embodiment, the pH is between 5.5 to 6.5.

Purification of Conjugated Proteins

In various embodiments, purification of a protein that has been incubated with an oxidizing agent and/or a therapeutic protein that has been conjugated with a water soluble polymer according to the present disclosure, is desired. Numerous purification techniques are known in the art and include, without limitation, chromatographic methods such as ion-exchange chromatography, hydrophobic interaction chromatography, size exclusion chromatography and affinity chromatography or combinations thereof, filtration methods (e.g., UF/DF), and precipitation methods as well as dialysis procedures and any combinations of the aforementioned techniques (Guide to Protein Purification, Meth. Enzymology Vol 463 (edited by Burgess R R and Deutscher M P), 2nd edition, Academic Press 2009).

The following examples are not intended to be limiting but only exemplary of specific embodiments of the invention.

EXAMPLES

Example 1

Preparation of the Homobifunctional Linker $NH_2[OCH_2CH_2]_2ONH_2$

The homobifunctional linker $NH_2[OCH_2CH_2]_2ONH_2$

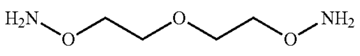

Figure 3:
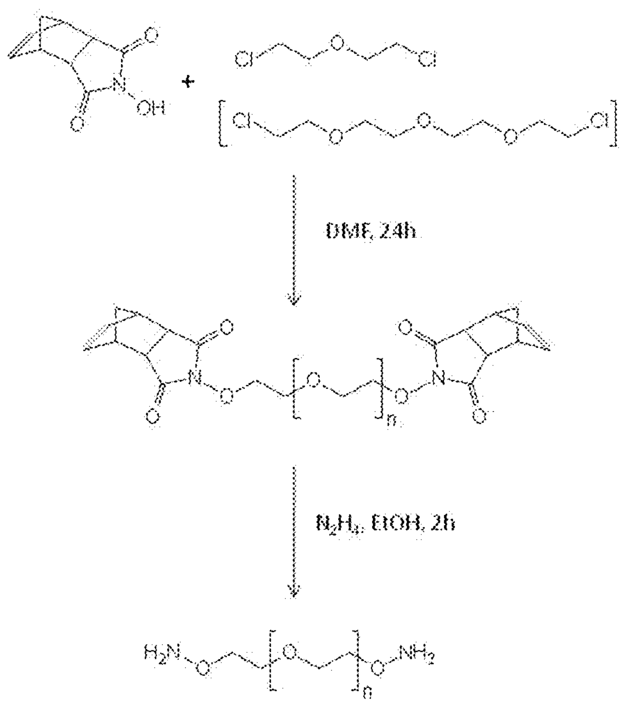
FIG. 3 shows the synthesis of the water soluble di-aminoxy linkers 3-oxa-pentane-1,5-dioxyamine and 3,6,9-trioxa-undecane-1,1'-dioxyamine.
Figure 4:
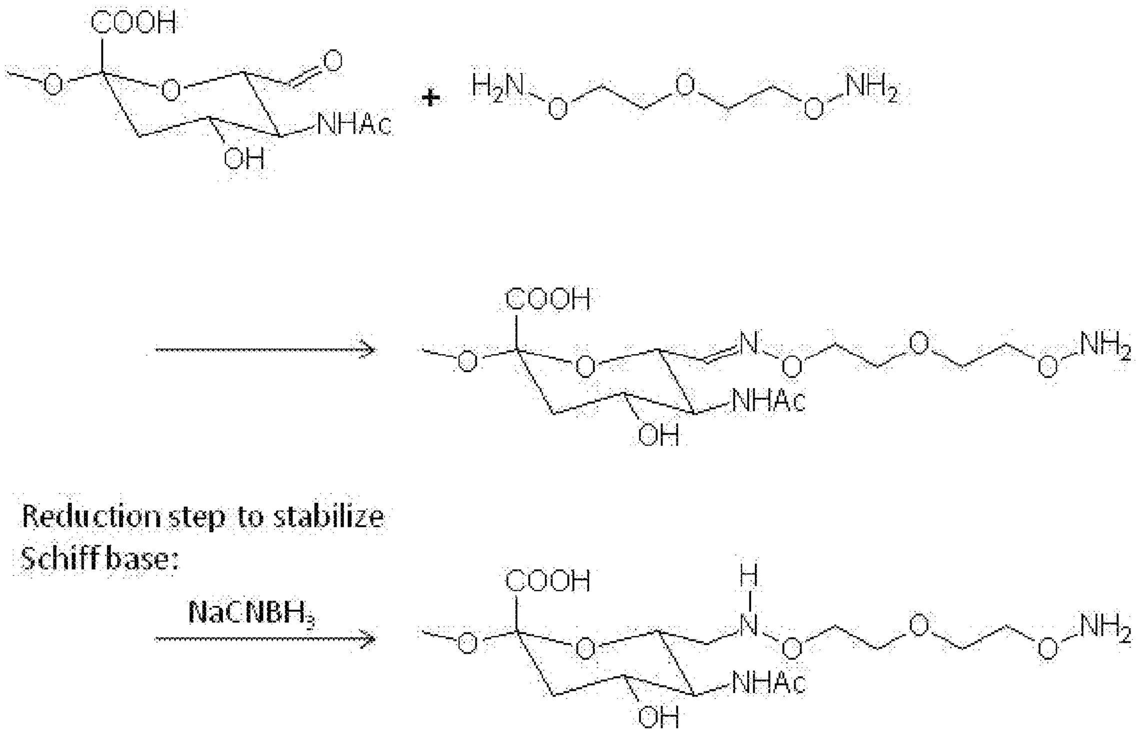
FIG. 4 shows the preparation of aminooxy-PSA.
Figure 6:
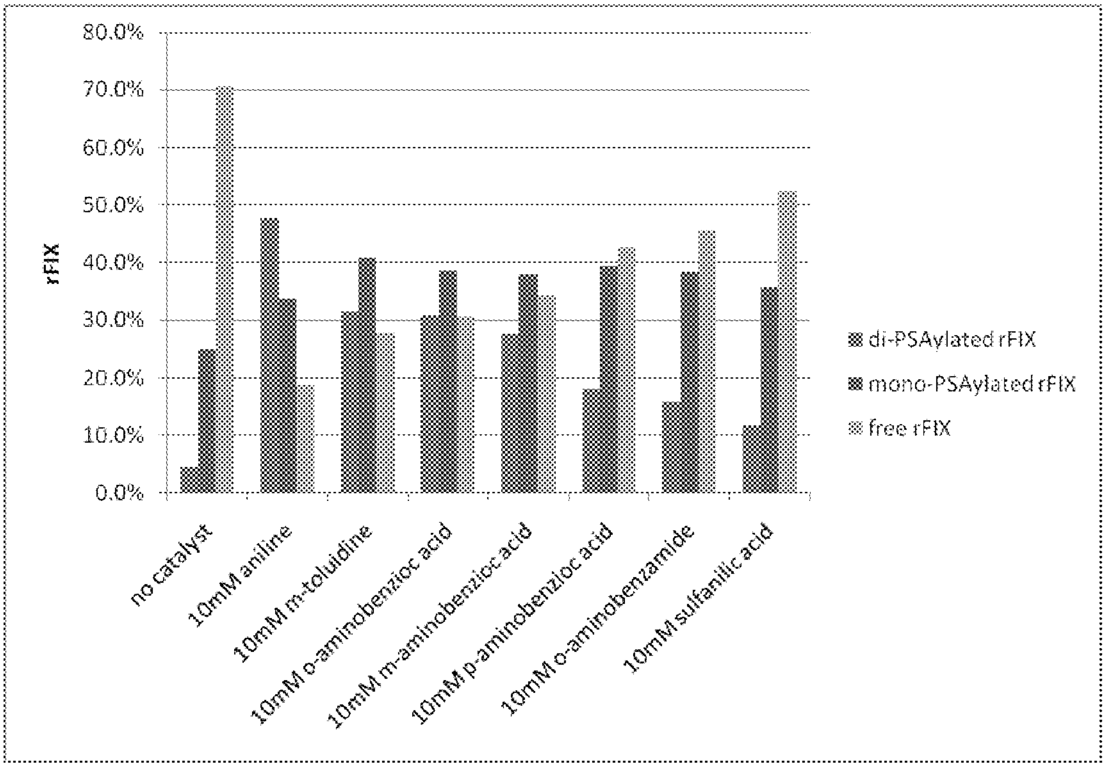
FIG. 6 shows percent of polysialylation with various nucleophilic catalysts.

(3-oxa-pentane-1,5-dioxyamine) containing two active aminooxy groups was synthesized according to Boturyn et al. (Tetrahedron 1997; 53:5485-92) in a two step organic reaction employing a modified Gabriel-Synthesis of primary amines (FIG. 3). In the first step, one molecule of 2,2-chlorodiethylether was reacted with two molecules of Endo-N-hydroxy-5-norbornene-2,3-dicarboximide in dimethylformamide (DMF). The desired homobifunctional product was prepared from the resulting intermediate by hydrazinolysis in ethanol.

Example 2

Preparation of the Homobifunctional Linker $NH_2[OCH_2CH_2]_4ONH_2$

The homobifunctional linker $NH_2[OCH_2CH_2]_4ONH_2$

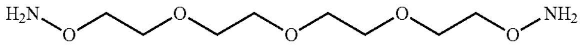 [SMILES: NOCCOCCOCCOCCON]

(3,6,9-trioxa-undecane-1,11-dioxyamine) containing two active aminooxy groups was synthesized according to Boturyn et al. (Tetrahedron 1997; 53:5485-92) in a two step organic reaction employing a modified Gabriel-Synthesis of primary amines (FIG. 3). In the first step one molecule of Bis-(2-(2-chlorethoxy)-ethyl)-ether was reacted with two molecules of Endo-N-hydroxy-5-norbornene-2,3-dicarboximide in DMF. The desired homobifunctional product was prepared from the resulting intermediate by hydrazinolysis in ethanol.

Example 3

Preparation of the Homobifunctional Linker $NH_2[OCH_2CH_2]_6ONH_2$

The homobifunctional linker $NH_2[OCH_2CH_2]_6ONH_2$

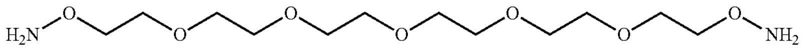 [SMILES: NOCCOCCOCCOCCOCCOCCON]

(3,6,9,12,15-penatoxa-heptadecane-1,17-dioxyamine) containing two active aminooxy groups was synthesized according to Boturyn et al. (Tetrahedron 1997; 53:5485-92) in a two step organic reaction employing a modified Gabriel-Synthesis of primary amines. In the first step one molecule of hexaethylene glycol dichloride was reacted with two molecules of Endo-N-hydroxy-5-norbornene-2,3-dicarboximide in DMF. The desired homobifunctional product was prepared from the resulting intermediate by hydrazinolysis in ethanol.

Example 4

Detailed Synthesis of the Aminooxy-PSA Reagent 3-oxa-pentane-1,5 dioxyamine was synthesized according to Botyryn et al (Tetrahedron 1997; 53:5485-92) in a two step organic synthesis as outlined in Example 1.

Step 1:

To a solution of Endo-N-hydroxy-5-norbornene-2,3-dicarboxiimide (59.0 g; 1.00 eq) in 700 ml anhydrous N,N-dimethylformamide anhydrous $K_2CO_3$ (45.51 g; 1.00 eq) and 2,2-dichlorodiethylether (15.84 ml; 0.41 eq) were added. The reaction mixture was stirred for 22 h at 50° C. The mixture was evaporated to dryness under reduced pressure. The residue was suspended in 2 L dichloromethane and extracted two times with saturated aqueous NaCl-solution (each 1 L). The Dichloromethane layer was dried over $Na_2SO_4$ and then evaporated to dryness under reduced pressure and dried in high vacuum to give 64.5 g of 3-oxapentane-1,5-dioxy-endo-2',3'-dicarboxydiimidenorbornene as a white-yellow solid (intermediate 1).

Step 2:

To a solution of intermediate 1 (64.25 g; 1.00 eq) in 800 ml anhydrous Ethanol, 31.0 ml Hydrazine hydrate (4.26 eq) were added. The reaction mixture was then refluxed for 2 hrs. The mixture was concentrated to the half of the starting volume by evaporating the solvent under reduced pressure. The occurring precipitate was filtered off. The remaining ethanol layer was evaporated to dryness under reduced pressure. The residue containing the crude product 3-oxa-pentane-1,5-dioxyamine was dried in vacuum to yield 46.3 g. The crude product was further purified by column chromatography (Silicagel 60; isocratic elution with Dichloromethane/Methanol mixture, 9/1) to yield 11.7 g of the pure final product 3-oxa-pentane-1,5-dioxyamine.

Example 5

Preparation of Aminooxy-PSA 1000 mg of oxidized PSA (MW=20 kD) obtained from the Serum Institute of India (Pune, India) was dissolved in 16 ml 50 mM phosphate buffer pH 6.0. Then 170 mg 3-oxa-pentane-1,5-dioxyamine was given to the reaction mixture. After shaking for 2 hrs at RT 78.5 mg sodium cyanoborohydride was added and the reaction was performed for 18 hours over night. The reaction mixture was then subjected to an ultrafiltration/diafiltration procedure (UF/DF) using a membrane with a 5 kD cut-off made of regenerated cellulose (50 $cm^2$, Millipore).

Example 6

Preparation of Aminooxy-PSA Employing a Chromatographic Purification Step 1290 mg of oxidized PSA (MW=20 kD) obtained from the Serum Institute of India (Pune, India) was dissolved in 25 ml 50 mM phosphate buffer pH 6.0 (Buffer A). Then 209 mg 3-oxa-pentane-1,5-dioxyamine was given to the reaction mixture. After shaking for 1 h at RT 101 mg sodium cyanoborohydride was added and the reaction was performed for 3 hours. Then the mixture was then subjected to a weak anion exchange chromatography step employing a Fractogel EMD DEAE 650-M chromatography gel (column dimension: XK26/135). The reaction mixture was diluted with 110 ml Buffer A and loaded onto the DEAE column pre-equilibrated with Buffer A at a flow rate of 1 cm/min. Then the column was washed with 20 CV Buffer B (20 mM Hepes, pH 6.0) to remove free 3-oxa-pentane-1,5-dioxyamine and cyanide at a flow rate of 2 cm/min. The aminooxy-PSA reagent was then eluted with a step gradient consisting of 67% Buffer B and 43% Buffer C (20 mM Hepes, 1M NaCl, pH 7.5). The eluate was concentrated by UF/DF using a 5 kD membrane made of polyether sulfone (50 $cm^2$, Millipore). The final diafiltration step was performed against Buffer D (20 mM Hepes, 90 mM NaCl, pH 7.4). The preparation was analytically characterized by measuring total PSA (Resorcinol assay) and total aminooxy groups (TNBS assay) to determine the degree of modification. Furthermore the polydispersity as well as free 3-oxa-pentane-1,5-dioxyamine and cyanide was determined.

Example 7

Preparation of Aminooxy-PSA without a Reduction Step 573 mg of oxidized PSA (MW=20 kD) obtained from the Serum Institute of India (Pune, India) was dissolved in 11.3 ml 50 mM phosphate buffer pH 6.0 (Buffer A). Then 94 mg 3-oxa-pentane-1,5-dioxyamine was given to the reaction mixture. After shaking for 5 h at RT the mixture was then subjected to a weak anion exchange chromatography step employing a Fractogel EMD DEAE 650-M chromatography gel (column dimension: XK16/105). The reaction mixture was diluted with 50 ml Buffer A and loaded onto the DEAE column pre-equilibrated with Buffer A at a flow rate of 1 cm/min. Then the column was washed with 20 CV Buffer B (20 mM Hepes, pH 6.0) to remove free 3-oxa-pentane-1,5-dioxyamine and cyanide at a flow rate of 2 cm/min. The aminooxy-PSA reagent was the eluted with a step gradient consisting of 67% Buffer B and 43% Buffer C (20 mM Hepes, 1 M NaCl, pH 7.5). The eluate was concentrated by UF/DF using a 5 kD membrane made of polyether sulfone (50 $cm^2$, Millipore). The final diafiltration step was performed against Buffer D (20 mM Hepes, 90 mM NaCl, pH 7.4). The preparation was analytically characterized by measuring total PSA (Resorcinol assay) and total aminooxy groups (TNBS assay) to determine the degree of modification. Furthermore the polydispersity as well as free 3-oxa-pentane-1,5-dioxyamine was determined.

Example 8

Preparation of Aminooxy-PSA without a Reduction Step in the Presence of the Nucleophilic Catalyst m-Toluidine 573 mg of oxidized PSA (MW=20 kD) obtained from the Serum Institute of India (Pune, India) is dissolved in 9 ml 50 mM phosphate buffer pH 6.0 (Buffer A). Then 94 mg 3-oxa-pentane-1,5-dioxyamine is given to this solution. Subsequently 2.3 ml of a 50 mM m-toluidine stock solution are added to this reaction mixture. After shaking for 2 h at RT the mixture is then subjected to a weak anion exchange chromatography step employing a Fractogel EMD DEAE 650-M chromatography gel (column dimension: XK16/105). The reaction mixture is diluted with 50 ml Buffer A and loaded onto the DEAE column pre-equilibrated with Buffer A at a flow rate of 1 cm/min. Then the column is washed with 20CV Buffer B (20 mM Hepes, pH 6.0) to remove free 3-oxa-pentane-1,5-dioxyamine and cyanide at a flow rate of 2 cm/min. The aminooxy-PSA reagent is the eluted with a step gradient consisting of 67% Buffer B and 43% Buffer C (20 mM Hepes, 1 M NaCl, pH 7.5). The eluate is concentrated by UF/DF using a 5 kD membrane made of polyether sulfone (50 $cm^2$, Millipore). The final diafiltration step is performed against Buffer D (20 mM Hepes, 90 mM NaCl, pH 7.4). The preparation is analytically characterized by measuring total PSA (Resorcinol assay) and total aminooxy groups (TNBS assay) to determine the degree of modification. Furthermore the polydispersity as well as free 3-oxa-pentane-1,5-dioxyamine is determined.

Example 9

Preparation of Aminooxy-PSA Reagent

An Aminooxy-PSA reagent was prepared according to the Examples 4-8. After diafiltration, the product was frozen at −80° C. and lyophilized. After lyophilization the reagent was dissolved in the appropriate volume of water and used for preparation of PSA-protein conjugates via carbohydrate modification.

Example 10

Evaluation of the Efficacy of Different Alternative Nucleophilic Catalysts rFIX was incubated with sodium periodate, aminooxy-PSA reagent under standardized conditions (1 mg/ml rFIX in 20 mM L-histidine, 150 mM NaCl, 5 mM $CaCl_2$, pH 6.0, 5-fold molar aminooxy-PSA reagent excess, 100 μM $NaIO_4$) using different nucleophilic catalysts (aniline, m-toluidine, o-anisidine, m-anisidine, o-aminobenzoic acid, m-aminobenzoic acid, p-aminobenzoic acid, p-aminobenzamide, sulfanilic acid/standard concentration: 10 mM) The reaction was carried out for 2 hrs in the dark at room temperature under gentle stirring and quenched for 15 min at room temperature by the addition of aqueous cysteine solution with a final concentration of 1 mM.

The coupling efficiency was determined by SDS-PAGE using an Invitrogen X-cell mini system. Samples were spiked with lithium dodecyl sulfate (LDS) buffer and denatured for 10 min at 70° C. Then the samples were applied on 3-8% TRIS-acetate gels and ran at 150 V for 60 min. Subsequently the gels were stained with Coomassie.

In addition the samples were characterized by use of a SEC-HPLC system using a Agilent 1200 HPLC system equipped with a Shodex KW 803 column under conditions as previously described (Kolarich et al, Transfusion 2006; 46:1959-77).

50 μl of samples were injected undiluted and eluted isocratically with a 0.22 μm filtered solution of 20 mM $NaH_2PO_4$, 50 mM $Na_2SO_4$, pH 6.1 at a flow rate of 0.5 ml/min. The elution pattern was recorded at 280 nm.

The results are summarized in FIGS. 5A-C and 6 (SDS PAGE) and Table 2 (SEC-HPLC results). The catalytic effect of the different preparations is demonstrated. It is shown that the use of m-toluidine leads to equivalent results as obtained with aniline.

TABLE 2

| nucleophilic catalysts | di-PSAylated rFIX | mono-PSAylated rFIX | free rFIX |
|---|---|---|---|
| no catalyst | 4.5% | 24.9% | 70.6% |
| 10 mM aniline | 47.7% | 33.6% | 18.7% |
| 10 mM m-toluidine | 31.4% | 40.8% | 27.8% |
| 10 mM o-aminobenzioc acid | 30.9% | 38.5% | 30.6% |
| 10 mM m-aminobenzioc acid | 27.6% | 38.0% | 34.4% |
| 10 mM p-aminobenzioc acid | 18.1% | 39.3% | 42.6% |
| 10 mM o-aminobenzamide | 15.9% | 38.4% | 45.7% |
| 10 mM sulfanilic acid | 11.8% | 35.8% | 52.4% |

Example 11

Polysialylation of rFIX Using Aminooxy-PSA and m-Toluidine as a Nucleophilic Catalyst Method 1:

12.3 mg rFIX was dissolved in 6.1 ml histidine buffer, pH 6.0 (20 mM L-histidine, 150 mM NaCl, 5 mM $CaCl_2$). 254 μl of an aqueous sodium periodate solution (5 mM) was then added and the reaction mixture is incubated for 1 h in the dark at 4° C. under gentle stirring and quenched for 15 min at room temperature by the addition of 6.5 μl of a 1 M aqueous cysteine solution. The mixture was subsequently subjected to UF/DF employing Vivaspin 15R 10 kD centrifugal filtrators to remove excess periodate, quencher and the byproducts thereof.

The retentate (8.8 ml), containing oxidized rFIX was mixed with 2.46 ml of an aqueous m-toluidine solution (50 mM) and incubated for 30 min at room temperature. Then aminooxy-PSA reagent with a MW of 20 kD (described above) was added to give a 5-fold molar reagent excess. This mixture was incubated for 2.5 h at RT in the dark under gentle stirring.

The free rFIX was removed by means of anion exchange chromatography (AEC). The reaction mixture was diluted with 15 ml Buffer A (50 mM Hepes, 5 mM $CaCl_2$, pH 7.5) and loaded onto a 20 ml HiPrep QFF 16/10 column (GE Healthcare, Fairfield, Conn.) pre-equilibrated with Buffer A. The column was then eluted with Buffer B (50 mM Hepes, 1 M NaCl, 5 mM $CaCl_2$, pH 7.5). Free rFIX elutes at a conductivity between 12-25 mS/cm and the conjugate between 27-45 mS/cm. The conductivity of the conjugate containing fractions was subsequently raised to 190 mS/cm with Buffer C (50 mM Hepes, 5M NaCl, 5 mM $CaCl_2$, pH 6.9) and loaded onto a 20 ml HiPrep Butyl FF 16/10 column (GE Healthcare, Fairfield, Conn.) pre-equilibrated with Buffer D (50 mM Hepes, 3 M NaCl, 5 mM $CaCl_2$, pH 6.9). Free aminooxy-PSA reagent was washed out within 5 CV Buffer D. Subsequently the conjugate is eluted with 100% Buffer E (50 mM Hepes, 5 mM $CaCl_2$, pH 7.4). The conjugate containing fractions were concentrated by UF/DF using Vivaspin 15R 10 kD centrifugal filtrator. The final diafiltration step was performed against histidine buffer, Ph 7.2 containing 150 mM NaCl and 5 mM $CaCl_2$. The preparation was analytically characterized by measuring total protein (Bradford) and FIX chromogenic activity. The PSA-rFIX conjugate showed a specific activity of >50% in comparison to native rFIX is determined.

Method 2:

12.3 mg rFIX is dissolved in L-histidine buffer, pH 6.0 (20 mM L-histidine, 150 mM NaCl, 5 mM $CaCl_2$) to get a final protein concentration of 1 mg rFIX/ml. A 5 mM aqueous sodium periodate solution is added to get a final concentration of 100 μM and the reaction mixture is incubated for 1 hour in the dark at 4° C. under gentle stirring at pH 6.0 and quenched for 15 min at room temperature by the addition of an 1 M aqueous L-cysteine solution (or other quenching reagents) to get a final concentration of 10 mM. The mixture is subsequently subjected to UF/DF employing Vivaspin 15R 10 kD centrifugal filtrators to remove excess periodate, quencher and the byproducts thereof.

The obtained retentate (8.8 ml), containing oxidized rFIX, is mixed with an aqueous m-toluidine solution (50 mM) to give a final concentration of 10 mM and incubated for 30 min at room temperature. Then aminooxy-PSA reagent with a MW of 20 kD (described above) is added to give a 5-fold molar reagent excess. This mixture was incubated at pH 6.0 for 2.5 hours at room temperature; 0.5 hours to 18 hours at +4° C.) in the dark under gentle stirring.

The free rFIX is removed by means of anion exchange chromatography (AEC). The reaction mixture is diluted with appropriate amounts of Buffer A (50 mM Hepes, 5 mM $CaCl_2$, pH 7.5) to correct the solutions conductivity and pH prior to load onto a 20 ml HiPrep QFF 16/10 column (GE Healthcare, Fairfield, Conn.) pre-equilibrated with buffer A. Then the column is eluted with Buffer B (50 mM Hepes, 1 M NaCl, 5 mM $CaCl_2$, pH 7.5). Free rFIX is eluted by a step gradient using 25% of Buffer B, which results in a conductivity between 12-25 mS/cm in the obtained fraction and the conjugate using a step gradient of 50% Buffer B, which results in a conductivity between 27-45 mS/cm in the conjugate fraction. The conductivity of the conjugate containing fraction is subsequently raised to 190 mS/cm with Buffer C (50 mM Hepes, 5 M NaCl, 5 mM $CaCl_2$, pH 6.9 or by use of anti-chaotropic salts e.g. ammonium sulphate, ammonium acetate etc.) and loaded onto a 20 ml HiPrep Butyl FF 16/10 column (GE Healthcare, Fairfield, Conn. or comparable HIC media) pre-equilibrated with Buffer D (50 mM Hepes, 3 M NaCl, 5 mM $CaCl_2$, pH 6.9). Free aminooxy-PSA reagent is washed out within 5 CV Buffer D. Subsequently, the conjugate is eluted with 100% Buffer E (50 mM Hepes, 5 mM $CaCl_2$, pH 7.4). The conjugate containing fractions are concentrated by UF/DF using a 10 kD membrane made of regenerated cellulose (88 cm2, cut-off 10 kD, Millipore). The final diafiltration step is performed against L-histidine buffer, pH 7.2 containing 150 mM NaCl and 5 mM CaCl2. The preparation is analytically characterized by measuring total protein (Bradford and BCA procedure) and FIX chromogenic- and clotting activity. For the PSA-rFIX conjugate a specific activity of >50% in comparison to native rFIX is determined.

Method 3:

25.4 mg rFIX was dissolved in 18.7 ml histidine buffer, pH 6.0 (20 mM L-histidine, 150 mM NaCl, 5 mM $CaCl_2$). 531 μl of an aqueous sodium periodate solution (5 mM) and 5.07 ml of an aqueous m-toluidine solution (50 mM) were then added. Subsequently, the aminooxy-PSA reagent with a MW of 20 kD (described above) was added to give a 5-fold molar reagent excess. The mixture was incubated for 2 h in the dark at room temperature under gentle stirring and quenched for 15 min at room temperature by the addition of 25 μl of 1 M aqueous cysteine solution.

The free rFIX was removed by means of anion exchange chromatography (AEC). The reaction mixture was diluted with 20 ml Buffer A (50 mM Hepes, 5 mM $CaCl_2$, pH 7.5) and loaded onto a 20 ml HiPrep QFF 16/10 column (GE Healthcare, Fairfield, Conn.) pre-equilibrated with Buffer A. Then the column was eluted with Buffer B (50 mM Hepes, 1 M NaCl, 5 mM $CaCl_2$, pH 7.5). Free rFIX eluted at a conductivity between 12-25 mS/cm and the conjugate between 27-45 mS/cm. The conductivity of the conjugate containing fractions was subsequently raised to 190 mS/cm with Buffer C (50 mM Hepes, 5 M NaCl, 5 mM $CaCl_2$, pH 6.9) and loaded onto a 20 ml HiPrep Butyl FF 16/10 column (GE Healthcare, Fairfield, Conn.) pre-equilibrated with Buffer D (50 mM Hepes, 3 M NaCl, 5 mM $CaCl_2$, pH 6.9). Free aminooxy-PSA reagent was washed out within 5 CV Buffer D. Subsequently, the conjugate was eluted with 100% Buffer E (50 mM Hepes, 5 mM $CaCl_2$, pH 7.4). The conjugate containing fractions were concentrated by UF/DF using a 10 kD membrane made of regenerated cellulose (88 cm2, cut-off 10 kD, Millipore). The final diafiltration step was performed against histidine buffer, pH 7.2 containing 150 mM NaCl and 5 mM $CaCl_2$. The preparation was analytically characterized by measuring total protein (Bradford) and FIX chromogenic activity. For the PSA-rFIX conjugate a specific activity of >50% in comparison to native rFIX was determined. The conjugate was additionally analytically characterized by Size Exclusion HPLC using a Agilent 1200 HPLC system equipped with a Shodex KW 803 column under conditions as previously described (Kolarich et al, Transfusion 2006; 46:1959-77). It was shown that the preparation contains no free FIX. The conjugate consisted of 57% mono-polysialylated and 31% di-polysialylated and 12% tri-polysialylated product.

Method 4:

25.4 mg rFIX was dissolved in L-histidine buffer, pH 6.0 (20 mM L-histidine, 150 mM NaCl, 5 mM $CaCl_2$) to get a final protein concentration of 2 mg rFIX/ml. Subsequently an 5 mM aqueous sodium periodate solution was added within 15 minutes to give a final concentration of 100 μM, followed by addition of an 50 mM aqueous m-toluidine solution to get a final concentration of 10 mM within a time period of 30 minutes. Then the aminooxy-PSA reagent with a MW of 20 kD (described above) was added to give a 5-fold molar reagent excess. After correction of the pH to 6.0 the mixture was incubated for 2 h in the dark at room temperature under gentle stirring and quenched for 15 min at room temperature by the addition of a 1 M aqueous L-cysteine solution to give a final concentration of 10 mM.

The free rFIX was removed by means of ion exchange chromatography (IEC). The reaction mixture was diluted with appropriate amounts of Buffer A (50 mM Hepes, 5 mM $CaCl_2$, pH 7.5) to correct the solutions conductivity and pH value prior to load onto a 20 ml HiPrep QFF 16/10 column (GE Healthcare, Fairfield, Conn.) pre-equilibrated with Buffer A. Then the column was eluted with Buffer B (50 mM Hepes, 1 M NaCl, 5 mM $CaCl_2$, pH 7.5). Free rFIX was eluted by a step gradient using 25% of Buffer B, which results in a conductivity between 12-25 mS/cm in the obtained fraction and the conjugate using a step gradient of 50% Buffer B, which results in a conductivity between 27-45 mS/cm in the conjugate fraction. The conductivity of the conjugate containing fraction was subsequently raised to 190 mS/cm with Buffer C (50 mM Hepes, 5 M NaCl, 5 mM $CaCl_2$, pH 6.9; by use of anti-chaotropic salts e.g. ammonium acetate) and loaded onto a 20 ml HiPrep Butyl FF 16/10 column (GE Healthcare, Fairfield, Conn.; or comparable HIC media) pre-equilibrated with Buffer D (50 mM Hepes, 3 M NaCl, 5 mM $CaCl_2$, pH 6.9). Free aminooxy-PSA reagent was washed out within 5 CV Buffer D. Subsequently the conjugate was eluted with 100% Buffer E (50 mM Hepes, 5 mM $CaCl_2$, pH 7.4). The conjugate containing fractions were concentrated by UF/DF using a 10 kD membrane made of regenerated cellulose (88 cm2, cut-off 10 kD, Millipore). The final diafiltration step was performed against L-histidine buffer, pH 7.2 containing 150 mM NaCl and 5 mM $CaCl_2$. The preparation was analytically characterized by measuring total protein (Bradford and BCA procedure) and FIX chromogenic- and clotting activity. For the PSA-rFIX conjugate a specific activity of >50% in comparison to native rFIX was determined. The conjugate was additionally analytically characterized by Size Exclusion HPLC using a Agilent 1200 HPLC system equipped with a Shodex KW 803 column under conditions as previously described (Kolarich et al, Transfusion 2006; 46:1959-77). It was shown that the preparation contains no free FIX. The conjugate consisted of 57% mono-polysialylated and 31% di-polysialylated and 12% tri-polysialylated product.

Example 12

Polysialylation of rFVIII Using Aminooxy-PSA and m-Toluidine as a Nucleophilic Catalyst Method 1:

50 mg rFVIII was transferred into reaction buffer (50 mM Hepes, 350 mM sodium chloride, 5 mM calcium chloride, pH 6.0) and diluted to obtain a protein concentration of 1 mg/ml. To this solution, $NaIO_4$ was added to give a final concentration of 200 μM. The oxidation was carried at RT for 30 min in the dark under gentle shaking. Then the reaction was quenched with cysteine (final concentration: 10 mM) for 60 min at RT. The solution was subjected to an IEX column with a volume of 20 ml (Merck EMD TMAE (M)) which was equilibrated with Buffer A (20 mM Hepes, 5 mM $CaCl_2$, pH 7.0). The column was equilibrated with 5 CV Buffer A. Then the oxidized rFVIII was eluted with Buffer B (20 mM Hepes, 5 mM $CaCl_2$, 1M NaCl, pH 7.0). The rFVIII containing fractions were collected. The protein content was determined (Coomassie, Bradford) and adjusted to 1 mg/ml with reaction buffer and adjusted to pH 6.0 by dropwise addition of 0.5 M HCl. Then a 50-fold molar excess of a aminooxy-PSA reagent with a MW of 20 kD (described above) was added followed by m-toluidine as a nucleophilic catalyst (final concentration: 10 mM). The coupling reaction was performed for 2 hours in the dark under gentle shaking at room temperature. The excess of aminooxy-PSA reagent was removed by means of HIC. The conductivity of the reaction mixture was raised to 130 mS/cm by adding a buffer containing ammonium acetate (50 mM Hepes, 350 mM sodium chloride, 5 mM calcium chloride, 8 M ammonium acetate, pH 6.9) and loaded onto a column filled with 80 ml Phenyl Sepharose FF (GE Healthcare, Fairfield, Conn.) pre-equilibrated with 50 mM Hepes, 2.5 M ammonium acetate, 350 mM sodium chloride, 5 mM calcium chloride, pH 6.9. Subsequently, the conjugate was eluted with 50 mM Hepes buffer pH 7.5 containing 5 mM $CaCl_2$. Finally, the PSA-rFVIII containing fractions were collected and subjected to UF/DF by use of a 30 kD membrane made of regenerated cellulose (88 $cm^2$, Millipore). The preparation was analytically characterized by measuring total protein (Coomassie, Bradford) and FVIII chromogenic activity. The PSA-rFVIII conjugate showed a specific activity of >70% in comparison to native rFVIII was determined.

Method 2:

58 mg of recombinant factor VIII (rFVIII) derived from the ADVATE process in Hepes buffer (50 mM HEPES, ~350 mM sodium chloride, 5 mM calcium chloride, 0.1% Polysorbate 80, pH 7.4) is dissolved in reaction buffer (50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5 N aqueous HCl solution. Subsequently, a 40 mM aqueous sodium periodate solution is added within 10 minutes to give a concentration of 200 μM. The oxidation reaction is carried out for 30+/−5 min at a temperature (T) of T=+22+/−2° C. Then the reaction is stopped by addition of an aqueous L-cysteine solution (1 M) within 15 minutes at T=+22+/−2° C. to give a final concentration of 10 mM in the reaction mixture and incubation for 60+/−5 min.

The oxidized rFVIII is further purified by anion exchange chromatography on EMD TMAE (M) (Merck). The mixture is diluted with Buffer A (20 mM Hepes, 5 mM $CaCl_2$, pH 6.5) to give a conductivity of 5 ms/cm. This solution is loaded onto the IEX column (bed height: 5.4 cm) with a column volume of 10 ml using a flow rate of 1.5 cm/min. This column is subsequently washed (flow rate: 1.5 cm/min) with 5 CV of a 92:8 mixture (w/w) of Buffer A and Buffer B (20 mM Hepes, 5 mM $CaCl_2$, 1.0 M NaCl, pH 7.0). Then the oxidized rFVIII is eluted with a 50:50 (w/w) mixture of Buffer A and Buffer B followed by a postelution step with 5 CV of Buffer B. The elution steps are carried out by use of a flow rate of 1.0 cm/min.

Subsequently, the aminooxy-polysialic acid ($PSA-ONH_2$) reagent is added in a 50-fold molar excess to the eluate containing the purified oxidized rFVIII within a maximum time period (t) of 15 minutes under gentle stirring. Then an aqueous m-toluidine solution (50 mM) is added within 15 minutes to get a final concentration of 10 mM. The reaction mixture is incubated for 120+/−10 min. in the dark at a temperature (T) of T=+22+/−2° C. under gentle shaking.

The obtained PSA-rFVIII conjugate is purified by Hydrophobic Interaction Chromatography (HIC) using a Phenyl Sepharose FF low sub resin (GE Healthcare) packed into a column manufactured by GE Healthcare with a bed height (h) of 15 cm and a resulting column volume (CV) of 81 ml.

The reaction mixture is spiked with ammonium acetate by addition of 50 mM Hepes buffer, containing 350 mM sodium chloride, 8 M ammonium acetate, 5 mM calcium chloride, pH 6.9. Two volumes of the reaction mixture are mixed with 1 volume of the ammonium acetate containing buffer system and the pH value is corrected to pH 6.9 by drop wise addition of a 0.5 N aqueous NaOH solution. This mixture is loaded onto the HIC column at flow rate of 1 cm/min followed by a washing step using >3 CV equilibration buffer (50 mM Hepes, 350 mM sodium chloride, 2.5 M ammonium acetate, 5 mM calcium chloride, pH 6.9).

For removal of reaction by-products and anti-chaotropic salt a second washing step is performed with >5 CV washing buffer 1 (50 mM Hepes, 3 M sodium chloride, 5 mM calcium chloride, pH 6.9) in upflow mode at a flow rate of 2 cm/min. Then elution of purified PSA-rFVIII conjugate is performed in down flow mode using a step gradient of 40% washing buffer 2 (50 mM Hepes, 1.5 M sodium chloride, 5 mM calcium chloride, pH 6.9) and 60% elution buffer (20 mM Hepes, 5 mM calcium chloride, pH 7.5) at a flow rate of 1 cm/min. The elution of the PSA-rFVIII conjugate is monitored at UV 280 nm and the eluate containing the conjugate is collected within <4 CV. The post elution step is performed with >3 CV elution buffer under the same conditions to separate minor and/or non modified rFVIII from the main product.

Finally the purified conjugate is concentrated by ultra-/diafiltration (UF/DF) using a membrane made of regenerated cellulose with a molecular weight cut off 30 kD (88 $cm^2$, Millipore).

The conjugate prepared by use of this procedure are analytically characterized by measuring total protein, FVIII chromogenic activity and determination of the polysialylation degree by measuring the PSA content (resorcinol assay). For the conjugate obtained a specific activity>50% and a PSA degree>5.0 is calculated.

Method 3:

50 mg rFVIII was transferred into reaction buffer (50 mM Hepes, 350 mM sodium chloride, 5 mM calcium chloride, pH 6.0) and diluted to obtain a protein concentration of 1 mg/ml. A 50-fold molar excess of aminooxy-PSA reagent with a MW of 20 kD (described above) was added followed by m-toluidine as a nucleophilic catalyst (final concentration: 10 mM) and $NaIO_4$ (final concentration: 400 μM). The coupling reaction was performed for 2 hours in the dark under gentle shaking at room temperature. Subsequently, the reaction was quenched with cysteine for 60 mM at RT (final concentration: 10 mM). Then the conductivity of the reaction mixture was raised to 130 mS/cm by adding a buffer containing ammonium acetate (50 mM Hepes, 350 mM sodium chloride, 5 mM calcium chloride, 8 M ammonium acetate, pH 6.9) and loaded onto a column filled with 80 ml Phenyl Sepharose FF (GE Healthcare, Fairfield, Conn.) pre-equilibrated with 50 mM Hepes, 2.5 M ammonium acetate, 350 mM sodium chloride, 5 mM calcium chloride, 0.01% Tween 80, pH 6.9. Subsequently, the conjugate was eluted with 50 mM Hepes, 5 mM calcium chloride, pH 7.5. Finally, the PSA-rFVIII containing fractions were collected and subjected to UF/DF by use of a 30 kD membrane made of regenerated cellulose (88 $cm^2$, Millipore). The preparation was analytically characterized by measuring total protein (Bradford) and FVIII chromogenic activity. For the PSA-rFVIII conjugate a specific activity of >70% in comparison to native rFVIII was determined.

Method 4:

50 mg recombinant factor VIII (rFVIII) derived from the ADVATE process in 50 mM Hepes buffer (50 mM HEPES, ~350 mM sodium chloride, 5 mM calcium chloride, 0.1% Polysorbate 80, pH 7.4) was dissolved in reaction buffer (50 mM Hepes, 350 mM sodium chloride, 5 mM calcium chloride, pH 6.0) to get a final protein concentration of 1.0+/−0.25 mg/ml. Then the pH of the solution was corrected to 6.0 by drop wise addition of a 0.5 N aqueous HCl solution.

Subsequently, the aminooxy-polysialic acid ($PSA-ONH_2$) reagent was added in a 50-fold molar excess to this rFVIII solution within a maximum time period (t) of 15 minutes under gentle stirring. Then an aqueous m-toluidine solution (50 mM) was added within 15 minutes to get a final concentration of 10 mM. Finally, a 40 mM aqueous sodium periodate solution was added to give a concentration of 400 μM.

The reaction mixture was incubated for 120+/−10 min. in the dark at a temperature (T) of T=+22+/−2° C. under gentle shaking. Then the reaction was stopped by the addition of an aqueous L-cysteine solution (1 M) to give a final concentration of 10 mM in the reaction mixture and incubation for 60+/−5 min.

The obtained PSA-rFVIII conjugate was purified by Hydrophobic Interaction Chromatography (HIC) using a Phenyl Sepharose FF low sub resin (GE Healthcare) packed into a column manufactured by GE Healthcare with a bed height (h) of 15 cm and a resulting column volume (CV) of 81 ml.

The reaction mixture was spiked with ammonium acetate by addition of 50 mM Hepes buffer, containing 350 mM sodium chloride, 8 M ammonium acetate, 5 mM calcium chloride, pH 6.9. Two volumes of the reaction mixture was mixed with 1 volume of the ammonium acetate containing buffer system and the pH value was corrected to pH 6.9 by drop wise addition of an 0.5 N aqueous NaOH solution. This mixture was loaded onto the HIC column using a flow rate of 1 cm/min followed by a washing step using >3 CV equilibration buffer (50 mM Hepes, 350 mM sodium chloride, 2.5 M ammonium acetate, 5 mM calcium chloride, pH 6.9).

For removal of reaction by-products and anti-chaotropic salt a second washing step was performed with >5CV washing buffer 1 (50 mM Hepes, 3 M sodium chloride, 5 mM calcium chloride, pH 6.9) in upflow mode at a flow rate of 2 cm/min. Then elution of purified rFVIII conjugate was performed in down flow mode using a step gradient of 40% washing buffer 2 (50 mM Hepes, 1.5 M sodium chloride, 5 mM calcium chloride, pH 6.9) and 60% elution buffer (20 mM Hepes, 5 mM calcium chloride, pH 7.5) at a flow rate of 1 cm/min. The elution of the PSA-rFVIII conjugate was monitored at UV 280 nm and the eluate containing the conjugate was collected within <4 CV. The post elution step was performed with >3 CV elution buffer under the same conditions to separate minor and/or non modified rFVIII from the main product.

Finally, the purified conjugate was concentrated by ultra-/diafiltration (UF/DF) using a membrane made of regenerated cellulose with a molecular weight cut off 30 kD (88 $cm^2$, Millipore).

The conjugates prepared by use of this procedure were analytically characterized by measuring total protein, FVIII chromogenic activity and determination of the polysialylation degree by measuring the PSA content (resorcinol assay).

Analytical data (mean of 6 consecutive batches):

Process yield (Bradford): 58.9%

Process yield (FVIII chrom.): 46.4%

Specific activity: (FVIII chrom./mg protein): 4148 IU/mg

Specific activity (% of starting material): 79.9%

PSA degree (mol/mol): 8.1

Example 13

PEGylation of rFVIII Using an Aminooxy-PEG Reagent and m-Toluidine as a Nucleophilic Catalyst Method 1:

rFVIII is PEGylated by use of a linear 20 kD PEGylation reagent containing an aminooxy group. An example of this type of reagent is the Sunbright® CA series from NOF (NOF Corp., Tokyo, Japan). 14.7 mg rFVIII is dissolved in 7.0 ml histidine buffer, pH 6.0 (20 mM L-histidine, 150 mM NaCl, 5 mM $CaCl_2$). Then 296 µl of an aqueous sodium periodate solution (5 mM) is added and the reaction mixture is incubated for 1 h in the dark at 4° C. under gentle stirring and quenched for 15 mM at room temperature by the addition of 7.5 µl of a 1 M aqueous cysteine solution. The mixture was subsequently subjected to UF/DF employing Vivaspin 15R 10 kD centrifugal filtrators to remove excess periodate, quencher and the byproducts thereof.

The retentate (10.9 ml), containing oxidized rFVIII, is mixed with 2.94 ml of an aqueous m-toluidine solution (50 mM) and incubated for 30 min at room temperature. Then aminooxy-PEG reagent with a MW of 20 kD is added to give a 5-fold molar reagent excess. This mixture was incubated for 2.5 h at room temperature in the dark under gentle stirring.

Finally, the PEG-rFVIII conjugate is purified by ion-exchange chromatography on Q Sepharose FF. 1.5 mg protein/ml gel is loaded on the column equilibrated with 50 mM Hepes buffer, pH 7.4 containing 5 mM $CaCl_2$. The conjugate is eluted with 50 mM Hepes buffer containing 5 mM $CaCl_2$ and 500 mM sodium chloride, pH 7.4 and is then subjected to UF/DF using a 30 kD membrane (50 cm2, Millipore). The preparation is analytically characterized by measuring total protein (Coomassie, Bradford) and FVIII chromogenic activity. It is expected that the PEG-rFVIII conjugate will demonstrate a specific activity of >70% in comparison to native rFVIII was determined.

Method 2:

rFVIII is PEGylated by use of a linear 20 kD PEGylation reagent containing an aminooxy group. An example of this type of reagent is the Sunbright® CA series from NOF (NOF Corp., Tokyo, Japan). A starting weight or concentration of rFVIII is dissolved in or transferred to a reaction buffer (50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5 N aqueous HCl solution. Subsequently a 40 mM aqueous sodium periodate solution is added within 10 minutes to give a concentration of 200 µM. The oxidation reaction is carried out for 30+/−5 min at a temperature (T) of T=+22+/−2° C. Then the reaction is stopped by addition of an aqueous L-cysteine solution (1 M) within 15 minutes at T=+22+/−2° C. to give a final concentration of 10 mM in the reaction mixture and incubation for 60+/−5 min.

The oxidized rFVIII is further purified by anion exchange chromatography on EMD TMAE (M) (Merck). The mixture is diluted with Buffer A (20 mM Hepes, 5 mM $CaCl_2$, pH 6.5) to give a conductivity of 5 ms/cm. This solution is loaded onto the IEX column (bed height: 5.4 cm) with a column volume of 10 ml using a flow rate of 1.5 cm/min. This column is subsequently washed (flow rate: 1.5 cm/min) with 5 CV of a 92:8 mixture (w/w) of Buffer A and Buffer B (20 mM Hepes, 5 mM $CaCl_2$, 1.0 M NaCl, pH 7.0). Then the oxidized rFVIII is eluted with a 50:50 (w/w) mixture of Buffer A and Buffer B followed by a postelution step with 5 CV of Buffer B. The elution steps are carried out by use of a flow rate of 1.0 cm/min.

Subsequently, the aminooxy-PEG reagent with a MW of 20 kD reagent is added in a 50-fold molar excess to the eluate containing the purified oxidized rFVIII within a maximum time period (t) of 15 minutes under gentle stirring. Then an aqueous m-toluidine solution (50 mM) is added within 15 minutes to get a final concentration of 10 mM. The reaction mixture is incubated for 120+/−10 min. in the dark at a temperature (T) of T=+22+/−2° C. under gentle shaking.

The obtained PEG-rFVIII conjugate is purified by Hydrophobic Interaction Chromatography (HIC) using a Phenyl Sepharose FF low sub resin (GE Healthcare) packed into a column manufactured by GE Healthcare with a bed height (h) of 15 cm and a resulting column volume (CV) of 81 ml.

The reaction mixture is spiked with ammonium acetate by addition of 50 mM Hepes buffer, containing 350 mM sodium chloride, 8 M ammonium acetate, 5 mM calcium chloride, pH 6.9. Two volumes of the reaction mixture are mixed with 1 volume of the ammonium acetate containing buffer system and the pH value is corrected to pH 6.9 by drop wise addition of a 0.5 N aqueous NaOH solution. This mixture is loaded onto the HIC column using a flow rate of 1 cm/min followed by a washing step using >3 CV equilibration buffer (50 mM Hepes, 350 mM sodium chloride, 2.5 M ammonium acetate, 5 mM calcium chloride, pH 6.9).

For removal of reaction by-products and anti-chaotropic salt a second washing step is performed with >5 CV washing buffer 1 (50 mM Hepes, 3 M sodium chloride, 5 mM calcium chloride, pH 6.9) in upflow mode at a flow rate of 2 cm/min. Then elution of purified rFVIII conjugate is performed in down flow mode using a step gradient of 40% washing buffer 2 (50 mM Hepes, 1.5 M sodium chloride, 5 mM calcium chloride, pH 6.9) and 60% elution buffer (20 mM Hepes, 5 mM calcium chloride, pH 7.5) at a flow rate of 1 cm/min. The elution of the PEG-rFVIII conjugate is monitored at UV 280 nm and the eluate containing the conjugate is collected within <4 CV. The post elution step is performed with >3 CV elution buffer under the same conditions to separate minor and/or non modified rFVIII from the main product.

Finally, the purified conjugate is concentrated by ultra-/diafiltration (UF/DF) using a membrane made of regenerated cellulose with a molecular weight cut off 30 kD (Millipore).

The conjugate prepared by use of this procedure are analytically characterized by measuring total protein and biological activity according to methods known in the art.

Method 3:

rFVIII is PEGylated by use of a linear 20 kD PEGylation reagent containing an aminooxy group. An example of this type of reagent is the Sunbright® CA series from NOF (NOF Corp., Tokyo, Japan). 7.84 mg rFVIII, dissolved in 6 ml Hepes buffer (50 mM Hepes, 150 mM sodium chloride, 5 mM calcium chloride, pH 6.0) are mixed with 314 µl of an aqueous sodium periodate solution (10 mM), and 1.57 ml of an aqueous m-toluidine solution (50 mM). Subsequently the aminooxy reagent is added to give a 20-fold molar reagent excess. The mixture is incubated for 2 h in the dark at room temperature under gentle stirring and quenched for 15 min at room temperature by the addition of 8 µl of aqueous cysteine solution (1 M).

Finally the PEG-rFVIII conjugate is purified by ion-exchange chromatography on Q-Sepharose FF. 1.5 mg protein/ml gel is loaded on the column pre equilibrated with 50 mM Hepes buffer, pH 7.4 containing 5 mM $CaCl_2$. The conjugate is eluted with 50 mM Hepes buffer containing 5 mM $CaCl_2$ and 500 mM sodium chloride, pH 7.4 and is then subjected to UF/DF using a 30 kD membrane (88 $cm^2$, Millipore). The analytical characterization of the conjugate by FVIII chromogenic assay and determination of total protein (Bradford) shows a specific activity of >60% compared to the rFVIII starting material.

Method 4:

rFVIII is PEGylated by use of a linear 20 kD PEGylation reagent containing an aminooxy group. An example of this type of reagent is the Sunbright® CA series from NOF (NOF Corp., Tokyo, Japan). An initial concentration or weight of rFVIII is transferred or dissolved in Hepes buffer (50 mM Hepes, 150 mM sodium chloride, 5 mM calcium chloride, pH 6.0) to get a final protein concentration of 2 mg rFVIII/ml. Subsequently, an 5 mM aqueous sodium periodate solution is added within 15 minutes to give a final concentration of 100 µM, followed by addition of an 50 mM aqueous m-toluidine solution to get a final concentration of 10 mM within a time period of 30 minutes. Then the aminooxy-PEG reagent with a MW of 20 kD (described above) is added to give a 20-fold molar excess. After correction of the pH to 6.0 the mixture is incubated for 2 h in the dark at room temperature under gentle stirring and quenched for 15 min at room temperature by the addition of a 1 M aqueous L-cysteine solution to give a final concentration of 10 mM.

The free rFVIII is removed by means of ion exchange chromatography (IEC). The reaction mixture was diluted with appropriate amounts of Buffer A (50 mM Hepes, 5 mM $CaCl_2$, pH 7.5) to correct the solutions conductivity and pH value prior to load onto a 20 ml HiPrep QFF 16/10 column (GE Healthcare, Fairfield, Conn.) pre-equilibrated with Buffer A. Then the column was eluted with Buffer B (50 mM Hepes, 1 M NaCl, 5 mM $CaCl_2$, pH 7.5). Free rFVIII was eluted by a step gradient using 25% of Buffer B, which results in a conductivity between 12-25 mS/cm in the obtained fraction and the conjugate using a step gradient of 50% Buffer B, which results in a conductivity between 27-45 mS/cm in the conjugate fraction. The conductivity of the conjugate containing fraction is subsequently raised with Buffer C (50 mM Hepes, 5 M NaCl, 5 mM $CaCl_2$, pH 6.9; by use of anti-chaotropic salts e.g. ammonium acetate, ammonium sulphate etc.) and loaded onto a 20 ml HiPrep Butyl FF 16/10 column (GE Healthcare, Fairfield, Conn.; or comparable HIC media) pre-equilibrated with Buffer D (50 mM Hepes, 3 M NaCl, 5 mM $CaCl_2$, pH 6.9). Free PEG-reagent was washed out within 5 CV Buffer D. Subsequently, the conjugate was eluted with 100% Buffer E (50 mM Hepes, 5 mM $CaCl_2$, pH 7.4). The conjugate containing fractions are concentrated by UF/DF using a 10 kD membrane made of regenerated cellulose (88 cm2, cut-off 10 kD, Millipore). The final diafiltration step is performed against Hepes buffer (50 mM Hepes, 5 mM $CaCl_2$, pH 7.5).

The preparation is analytically characterized by measuring total protein (Bradford and BCA procedure) and biological activity according to known methods.

Example 14

Polysialylation of rFVIIa Using Aminooxy-PSA and m-Toluidine as a Nucleophilic Catalyst Method 1:

A starting concentration or weight of recombinant factor VIIa (rFVIIa) is transferred or dissolved in reaction buffer (50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5 N aqueous NaOH solution. Subsequently, a 40 mM aqueous sodium periodate solution is added within 10 minutes to give a concentration of 50 µM. The oxidation reaction is carried out for 30+/−5 min at a temperature (T) of T=+22+/−2° C. Then the reaction is stopped by addition of an aqueous L-cysteine solution (1 M) within 15 minutes at T=+22+/−2° C. to give a final concentration of 10 mM in the reaction mixture and incubation for 60+/−5 min.

The oxidized rFVIIa is further purified by anion exchange chromatography on EMD TMAE (M) (Merck). The mixture is diluted with Buffer A (20 mM Hepes, 5 mM $CaCl_2$, pH 6.5) to give a conductivity of 5 ms/cm. This solution is loaded onto the IEX column (bed height: 5.4 cm) with a column volume of 10 ml using a flow rate of 1.5 cm/min. This column is subsequently washed (flow rate: 1.5 cm/min) with 5 CV of a 92:8 mixture (w/w) of Buffer A and Buffer B (20 mM Hepes, 5 mM $CaCl_2$, 1.0 M NaCl, pH 7.0). Then the oxidized rFVIIa is eluted with a 50:50 (w/w) mixture of Buffer A and Buffer B followed by a postelution step with 5 CV of Buffer B. The elution steps are carried out by use of a flow rate of 1.0 cm/min.

Subsequently, the aminooxy-polysialic acid (PSA-$ONH_2$) reagent is added in a 50-fold molar excess to the eluate containing the purified oxidized rFVIIa within a maximum time period (t) of 15 minutes under gentle stirring. Then an aqueous m-toluidine solution (50 mM) is added within 15 minutes to get a final concentration of 10 mM. The reaction mixture is incubated for 120+/−10 min. in the dark at a temperature (T) of T=+22+/−2° C. under gentle shaking.

The obtained PSA-rFVIIa conjugate is purified by Hydrophobic Interaction Chromatography (HIC) using a Phenyl Sepharose FF low sub resin (GE Healthcare) packed into a column manufactured by GE Healthcare with a bed height (h) of 15 cm and a resulting column volume (CV) of 81 ml.

The reaction mixture is spiked with ammonium acetate by addition of 50 mM Hepes buffer, containing 350 mM sodium chloride, 8 M ammonium acetate, 5 mM calcium chloride, pH 6.9. Two volumes of the reaction mixture are mixed with 1 volume of the ammonium acetate containing buffer system and the pH value is corrected to pH 6.9 by drop wise addition of a 0.5 N aqueous NaOH solution. This mixture is loaded onto the HIC column using a flow rate of 1 cm/min followed by a washing step using >3 CV equilibration buffer (50 mM Hepes, 350 mM sodium chloride, 2.5 M ammonium acetate, 5 mM calcium chloride, pH 6.9).

For removal of reaction by-products and anti-chaotropic salt a second washing step is performed with >5CV washing buffer 1 (50 mM Hepes, 3 M sodium chloride, 5 mM calcium chloride, pH 6.9) in upflow mode at a flow rate of 2 cm/min. Then elution of purified rFVIIa conjugate is performed in down flow mode using a step gradient of 40% washing buffer 2 (50 mM Hepes, 1.5 M sodium chloride, 5 mM calcium chloride, pH 6.9) and 60% elution buffer (20 mM Hepes, 5 mM calcium chloride, pH 7.5) at a flow rate of 1 cm/min. The elution of the PSA-rFVIIa conjugate is monitored at UV 280 nm and the eluate containing the conjugate is collected within <4 CV. The post elution step is performed with >3 CV elution buffer under the same conditions to separate minor and/or non modified rFVIIa from the main product.

Finally, the purified conjugate is concentrated by ultra-/diafiltration (UF/DF) using a membrane made of regenerated cellulose with an appropriate molecular weight cut off (e.g. 10 kD MWCO, 88 $cm^2$, Millipore).

The conjugate prepared by use of this procedure is analytically characterized by measuring total protein, biological activity, and determination of the polysialylation degree by measuring the PSA content (resorcinol assay).

Method 2:

A starting weight or concentration of rFVIIa is dissolved in or transferred to a reaction buffer (50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5 N aqueous NaOH solution.

Subsequently, the aminooxy-polysialic acid (PSA-$ONH_2$) reagent is added in a 50-fold molar excess to this rFVIIa solution within a maximum time period (t) of 15 minutes under gentle stirring. Then an aqueous m-toluidine solution (50 mM) is added within 15 minutes to get a final concentration of 10 mM. Finally a 40 mM aqueous sodium periodate solution is added to give a concentration of 150 μM.

The reaction mixture is incubated for 120+/−10 min. in the dark at a temperature (T) of T=+22+/−2° C. under gentle shaking. Then the reaction is stopped by the addition of an aqueous L-cysteine solution (1 M) to give a final concentration of 10 mM in the reaction mixture and incubation for 60+/−5 min.

The obtained PSA-rFVIIa conjugate is purified by Hydrophobic Interaction Chromatography (HIC) using a Phenyl Sepharose FF low sub resin (GE Healthcare) packed into a column manufactured by GE Healthcare with a bed height (h) of 15 cm and a resulting column volume (CV) of 81 ml.

The reaction mixture is spiked with ammonium acetate by addition of 50 mM Hepes buffer, containing 350 mM sodium chloride, 8 M ammonium acetate, 5 mM calcium chloride, pH 6.9. Two volumes of the reaction mixture is mixed with 1 volume of the ammonium acetate containing buffer system and the pH value is corrected to pH 6.9 by drop wise addition of an 0.5 N aqueous NaOH solution. This mixture is loaded onto the HIC column using a flow rate of 1 cm/min followed by a washing step using >3CV equilibration buffer (50 mM Hepes, 350 mM sodium chloride, 2.5 M ammonium acetate, 5 mM calcium chloride, pH 6.9).

For removal of reaction by-products and anti-chaotropic salt a second washing step is performed with >5CV washing buffer 1 (50 mM Hepes, 3 M sodium chloride, 5 mM calcium chloride, pH 6.9) in upflow mode at a flow rate of 2 cm/min. Then elution of purified rFVIIa conjugate is performed in down flow mode using a step gradient of 40% washing buffer 2 (50 mM Hepes, 1.5 M sodium chloride, 5 mM calcium chloride, pH 6.9) and 60% elution buffer (20 mM Hepes, 5 mM calcium chloride, pH 7.5) at a flow rate of 1 cm/min. The elution of the PSA-rFVIIa conjugate is monitored at UV 280 nm and the eluate containing the conjugate was collected within <4 CV. The post elution step is performed with >3 CV elution buffer under the same conditions to separate minor and/or non modified rFVIII from the main product.

Finally, the purified conjugate is concentrated by ultra-/diafiltration (UF/DF) using a membrane made of regenerated cellulose (Millipore).

The conjugates prepared by use of this procedure are analytically characterized by measuring total protein, biological activity according to methods known in the art, and determination of the polysialylation degree by measuring the PSA content (resorcinol assay).

Example 15

PEGylation of rFIX Using an Aminooxy-PEG Reagent and m-Toluidine as a Nucleophilic Catalyst Method 1:

rFIX is PEGylated by use of a linear 20 kD PEGylation reagent containing an aminooxy group. An example of this type of reagent is the Sunbright® CA series from NOF (NOF Corp., Tokyo, Japan). A starting weight or concentration of rFIX is dissolved in or transferred to a reaction buffer (50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5 N aqueous HCl solution. Subsequently, a 40 mM aqueous sodium periodate solution is added within 10 minutes to give a concentration of 200 μM. The oxidation reaction is carried out for 30+/−5 min at a temperature (T) of T=+22+/−2° C. Then the reaction is stopped by addition of an aqueous L-cysteine solution (1 M) within 15 minutes at T=+22+/−2° C. to give a final concentration of 10 mM in the reaction mixture and incubation for 60+/−5 min.

The oxidized rFVIII is further purified by anion exchange chromatography on EMD TMAE (M) (Merck). The mixture is diluted with Buffer A (20 mM Hepes, 5 mM CaCl2, pH 6.5) to give a conductivity of 5 mS/cm. This solution is loaded onto the IEX column (bed height: 5.4 cm) with a column volume of 10 ml using a flow rate of 1.5 cm/min. This column is subsequently washed (flow rate: 1.5 cm/min) with 5 CV of a 92:8 mixture (w/w) of Buffer A and Buffer B (20 mM Hepes, 5 mM $CaCl_2$, 1.0 M NaCl, pH 7.0). Then the oxidized rFIX is eluted with a 50:50 (w/w) mixture of Buffer A and Buffer B followed by a postelution step with 5 CV of Buffer B. The elution steps are carried out by use of a flow rate of 1.0 cm/min.

Subsequently, the aminooxy-PEG reagent with a MW of 20 kD reagent is added in a 50-fold molar excess to the eluate containing the purified oxidized rFIX within a maximum time period (t) of 15 minutes under gentle stirring. Then an aqueous m-toluidine solution (50 mM) is added within 15 minutes to get a final concentration of 10 mM. The reaction mixture is incubated for 120+/−10 min. in the dark at a temperature (T) of T=+22+/−2° C. under gentle shaking.

The obtained PEG-rFIX conjugate is purified by Hydrophobic Interaction Chromatography (HIC) using a Phenyl Sepharose FF low sub resin (GE Healthcare) packed into a column manufactured by GE Healthcare with a bed height (h) of 15 cm and a resulting column volume (CV) of 81 ml.

The reaction mixture is spiked with ammonium acetate by addition of 50 mM Hepes buffer, containing 350 mM sodium chloride, 8 M ammonium acetate, 5 mM calcium chloride, pH 6.9. Two volumes of the reaction mixture are mixed with 1 volume of the ammonium acetate containing buffer system and the pH value is corrected to pH 6.9 by drop wise addition of a 0.5 N aqueous NaOH solution. This mixture is loaded onto the HIC column using a flow rate of 1 cm/min followed by a washing step using >3 CV equilibration buffer (50 mM Hepes, 350 mM sodium chloride, 2.5 M ammonium acetate, 5 mM calcium chloride, pH 6.9).

For removal of reaction by-products and anti-chaotropic salt a second washing step is performed with >5CV washing buffer 1 (50 mM Hepes, 3 M sodium chloride, 5 mM calcium chloride, pH 6.9) in upflow mode at a flow rate of 2 cm/min. Then elution of purified rFIX conjugate is performed in down flow mode using a step gradient of 40% washing buffer 2 (50 mM Hepes, 1.5 M sodium chloride, 5 mM calcium chloride, pH 6.9) and 60% elution buffer (20 mM Hepes, 5 mM calcium chloride, pH 7.5) at a flow rate of 1 cm/min. The elution of the PEG-rFIX conjugate is monitored at UV 280 nm and the eluate containing the conjugate is collected within <4 CV. The post elution step is performed with >3 CV elution buffer under the same conditions to separate minor and/or non modified rFIX from the main product.

Finally, the purified conjugate is concentrated by ultra-/diafiltration (UF/DF) using a membrane made of regenerated cellulose with a molecular weight cut off 10 kD (88 cm2, Millipore).

The conjugate prepared by use of this procedure are analytically characterized by measuring total protein and biological activity according to methods known in the art.

Method 2:

rFIX is PEGylated by use of a linear 20 kD PEGylation reagent containing an aminooxy group. An example of this type of reagent is the Sunbright® CA series from NOF (NOF Corp., Tokyo, Japan). An initial concentration or weight of rFIX is transferred or dissolved in Hepes buffer (50 mM Hepes, 150 mM sodium chloride, 5 mM calcium chloride, pH 6.0) to get a final protein concentration of 2 mg rFIX/ml. Subsequently, an 5 mM aqueous sodium periodate solution is added within 15 minutes to give a final concentration of 100 µM, followed by addition of an 50 mM aqueous m-toluidine solution to get a final concentration of 10 mM within a time period of 30 minutes. Then the aminooxy-PEG reagent with a MW of 20 kD (described above) is added to give a 20-fold molar reagent excess. After correction of the pH to 6.0 the mixture is incubated for 2 h in the dark at room temperature under gentle stirring and quenched for 15 min at room temperature by the addition of a 1 M aqueous L-cysteine solution to give a final concentration of 10 mM.

The free rFIX is removed by means of ion exchange chromatography (IEC). The reaction mixture was diluted with appropriate amounts of Buffer A (50 mM Hepes, 5 mM $CaCl_2$, pH 7.5) to correct the solutions conductivity and pH value prior to load onto a 20 ml HiPrep QFF 16/10 column (GE Healthcare, Fairfield, Conn.) pre-equilibrated with Buffer A. Then the column was eluted with Buffer B (50 mM Hepes, 1 M NaCl, 5 mM $CaCl_2$, pH 7.5). Free rFIX was eluted by a step gradient using 25% of Buffer B, which results in a conductivity between 12-25 mS/cm in the obtained fraction and the conjugate using a step gradient of 50% Buffer B, which results in a conductivity between 27-45 mS/cm in the conjugate fraction. The conductivity of the conjugate containing fraction is subsequently raised with Buffer C (50 mM Hepes, 5 M NaCl, 5 mM $CaCl_2$, pH 6.9; by use of anti-chaotropic salts e.g. ammonium acetate, etc) and loaded onto a 20 ml HiPrep Butyl FF 16/10 column (GE Healthcare, Fairfield, Conn.; or comparable HIC media) pre-equilibrated with Buffer D (50 mM Hepes, 3 M NaCl, 5 mM $CaCl_2$, pH 6.9). Free aminooxy-PEG reagent was washed out within 5 CV Buffer D. Subsequently, the conjugate was eluted with 100% Buffer E (50 mM Hepes, 5 mM $CaCl_2$, pH 7.4). The conjugate containing fractions are concentrated by UF/DF using a 10 kD membrane made of regenerated cellulose (88 cm2, cut-off 10 kD, Millipore). The final diafiltration step is performed against Hepes buffer (50 mM Hepes, 5 mM $CaCl_2$, pH 7.5).

The preparation is analytically characterized by measuring total protein (Bradford and BCA procedure) and biological activity according to known methods.

Example 16

PEGylation of rFVIIa Using an Aminooxy-PEG Reagent and m-Toluidine as a Nucleophilic Catalyst Method 1:

rFVIIa is PEGylated by use of a linear 20 kD PEGylation reagent containing an aminooxy group. An example of this type of reagent is the Sunbright® CA series from NOF (NOF Corp., Tokyo, Japan). A starting weight or concentration of rFVIIa is dissolved in or transferred to a reaction buffer (50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5 N aqueous NaOH solution. Subsequently, a 40 mM aqueous sodium periodate solution is added within 10 minutes to give a concentration of 50 µM. The oxidation reaction is carried out for 30+/−5 min at a temperature (T) of T=+22+/−2° C. Then the reaction is stopped by addition of an aqueous L-cysteine solution (1 M) within 15 minutes at T=+22+/−2° C. to give a final concentration of 10 mM in the reaction mixture and incubation for 60+/−5 min.

The oxidized rFVIIa is further purified by anion exchange chromatography on EMD TMAE (M) (Merck). The mixture is diluted with Buffer A (20 mM Hepes, 5 mM $CaCl_2$, pH 6.5) to give a conductivity of 5 mS/cm. This solution is loaded onto the IEX column (bed height: 5.4 cm) with a column volume of 10 ml using a flow rate of 1.5 cm/min. This column is subsequently washed (flow rate: 1.5 cm/min) with 5 CV of a 92:8 mixture (w/w) of Buffer A and Buffer B (20 mM Hepes, 5 mM $CaCl_2$, 1.0 M NaCl, pH 7.0). Then the oxidized rFVIIa is eluted with a 50:50 (w/w) mixture of Buffer A and Buffer B followed by a postelution step with 5 CV of Buffer B. The elution steps are carried out by use of a flow rate of 1.0 cm/min.

Subsequently, the aminooxy-PEG reagent with a MW of 20 kD reagent is added in a 50-fold molar excess to the eluate containing the purified oxidized rFVIIa within a maximum time period (t) of 15 minutes under gentle stirring. Then an aqueous m-toluidine solution (50 mM) is added within 15 minutes to get a final concentration of 10 mM. The reaction mixture is incubated for 120+/−10 min. in the dark at a temperature (T) of T=+22+/−2° C. under gentle shaking.

The obtained PEG-rFVIIa conjugate is purified by Hydrophobic Interaction Chromatography (HIC) using a Phenyl Sepharose FF low sub resin (GE Healthcare) packed into a column manufactured by GE Healthcare with a bed height (h) of 15 cm and a resulting column volume (CV) of 81 ml.

The reaction mixture is spiked with ammonium acetate by addition of 50 mM Hepes buffer, containing 350 mM sodium chloride, 8 M ammonium acetate, 5 mM calcium chloride, pH 6.9. Two volumes of the reaction mixture are mixed with 1 volume of the ammonium acetate containing buffer system and the pH value is corrected to pH 6.9 by drop wise addition of a 0.5 N aqueous NaOH solution. This mixture is loaded onto the HIC column using a flow rate of 1 cm/min followed by a washing step using >3 CV equilibration buffer (50 mM Hepes, 350 mM sodium chloride, 2.5 M ammonium acetate, 5 mM calcium chloride, pH 6.9).

For removal of reaction by-products and anti-chaotropic salt a second washing step is performed with >5CV washing buffer 1 (50 mM Hepes, 3 M sodium chloride, 5 mM calcium chloride, pH 6.9) in upflow mode at a flow rate of 2 cm/min. Then elution of purified rFVIIa conjugate is performed in down flow mode using a step gradient of 40% washing buffer 2 (50 mM Hepes, 1.5 M sodium chloride, 5 mM calcium chloride, pH 6.9) and 60% elution buffer (20 mM Hepes, 5 mM calcium chloride, pH 7.5) at a flow rate of 1 cm/min. The elution of the PEG-rFVIIa conjugate is monitored at UV 280 nm and the eluate containing the conjugate is collected within <4 CV. The post elution step is performed with >3 CV elution buffer under the same conditions to separate minor and/or non modified rFVIIa from the main product.

Finally, the purified conjugate is concentrated by ultra-/diafiltration (UF/DF) using a membrane made of regenerated cellulose with a molecular weight cut off 10 kD (Millipore).

The conjugate prepared by use of this procedure are analytically characterized by measuring total protein and biological activity according to methods known in the art.

Method 2:

rFVIIa is PEGylated by use of a linear 20 kD PEGylation reagent containing an aminooxy group. An example of this type of reagent is the Sunbright® CA series from NOF (NOF Corp., Tokyo, Japan). An initial concentration or weight of rFVIIa is transferred or dissolved in Hepes buffer (50 mM Hepes, 150 mM sodium chloride, 5 mM calcium chloride, pH 6.0) to get a final protein concentration of 2 mg rFVIIa/ml. Subsequently an 5 mM aqueous sodium periodate solution is added within 15 minutes to give a final concentration of 100 µM, followed by addition of an 50 mM aqueous m-toluidine solution to get a final concentration of 10 mM within a time period of 30 minutes. Then the aminooxy-PEG reagent with a MW of 20 kD (described above) is added to give a 20-fold molar reagent excess. After correction of the pH to 6.0 the mixture is incubated for 2 h in the dark at room temperature under gentle stirring and quenched for 15 min at room temperature by the addition of a 1 M aqueous L-cysteine solution to give a final concentration of 10 mM.

The free rFVIIa is removed by means of ion exchange chromatography (IEC). The reaction mixture was diluted with appropriate amounts of Buffer A (50 mM Hepes, 5 mM $CaCl_2$, pH 7.5) to correct the solutions conductivity and pH value prior to load onto a 20 ml HiPrep QFF 16/10 column (GE Healthcare, Fairfield, Conn.) pre-equilibrated with Buffer A. Then the column was eluted with Buffer B (50 mM Hepes, 1 M NaCl, 5 mM $CaCl_2$, pH 7.5). Free rFVIIa was eluted by a step gradient using 25% of Buffer B, which results in a conductivity between 12-25 mS/cm in the obtained fraction and the conjugate using a step gradient of 50% Buffer B, which results in a conductivity between 27-45 mS/cm in the conjugate fraction. The conductivity of the conjugate containing fraction is subsequently raised with Buffer C (50 mM Hepes, 5 M NaCl, 5 mM $CaCl_2$, pH 6.9; by use of anti-chaotropic salts e.g. ammonium acetate) and loaded onto a 20 ml HiPrep Butyl FF 16/10 column (GE Healthcare, Fairfield, Conn.; or comparable HIC media) pre-equilibrated with Buffer D (50 mM Hepes, 3 M NaCl, 5 mM $CaCl_2$, pH 6.9). Free PEG-reagent was washed out within 5 CV Buffer D. Subsequently the conjugate was eluted with 100% Buffer E (50 mM Hepes, 5 mM $CaCl_2$, pH 7.4). The conjugate containing fractions are concentrated by UF/DF using a 10 kD membrane made of regenerated cellulose (88 cm2, cut-off 10 kD, Millipore). The final diafiltration step is performed against Hepes buffer (50 mM Hepes, 5 mM $CaCl_2$, pH 7.5).

The preparation is analytically characterized by measuring total protein (Bradford and BCA procedure) and biological activity according to known methods.

Example 17

Polysialylation of rFIX in the Presence of o-Amino Benzoic Acid

Method 1:

8.2 mg rFIX is dissolved in 4.0 ml histidine buffer, pH 6.0 (20 mM L-histidine, 150 mM NaCl, 5 mM $CaCl_2$). Then 82 µl of an aqueous sodium periodate solution (5 mM) is added and the reaction mixture is incubated for 1 h in the dark at 4° C. under gentle stirring and quenched for 15 min at room temperature by the addition of 4 µl of a 1 M aqueous cysteine solution. The mixture is subsequently subjected to UF/DF employing Vivaspin 6 10 kD centrifugal filtrators to remove excess periodate, quencher and the byproducts thereof.

The retentate (6.5 ml), containing oxidized rFIX, is mixed with 1.64 ml of an aqueous o-amino benzoic acid (50 mM) and incubated for 30 min at room temperature. Then aminooxy-PSA reagent with a MW of 20 kD (described above) is added to give a 5-fold molar reagent excess. This mixture was incubated for 2.5 h at room temperature in the dark under gentle stirring.

The further purification of the conjugate is carried out as described herein.

Method 2:

A solution of 1 mg rFIX in 0.65 ml sodium phosphate buffer, pH 6.0 containing a 5-fold molar excess of aminooxy-PSA reagent with a MW of 20 kD (described above) was prepared. Then 333 µl of an aqueous o-amino benzoic acid solution (30 mM) was added as nucleophilic catalyst to give a final concentration of 10 mM. Subsequently 20 µl of an aqueous solution of $NaIO_4$ (5 mM) was added yielding in a final concentration of 100 µM. The coupling process was performed for 2 hours in the dark under gentle shaking at room temperature and quenched for 15 min at room temperature by the addition of 1 µl of aqueous cysteine solution (1 M). The further purification of the conjugate is carried out as described herein.

Example 18

Polysialylation of EPO Using Aminooxy-PSA and m-Toluidine as a Nucleophilic Catalyst Method 1:

A starting concentration of erythropoietin (EPO) is transferred into a reaction buffer (e.g. 50 mM Hepes, 350 mM sodium chloride, 5 mM calcium chloride, pH 6.0) and diluted to obtain a protein concentration of 1 mg/ml. To this solution, $NaIO_4$ is added to give a final concentration of 200 µM. The oxidation is carried at RT for 30 min in the dark under gentle shaking. The reaction is then quenched with cysteine (final concentration: 10 mM) for 60 min at RT.

The solution is next subjected to UF/DF employing Vivaspin centrifugal filtrators to remove excess periodate, quencher and the byproducts thereof or, in the alternative, to an IEX column with a volume of 20 ml (Merck EMD TMAE (M)) which is equilibrated with Buffer A (20 mM Hepes, 5 mM $CaCl_2$, pH 7.0). The column is equilibrated with 5 CV Buffer A. The oxidized EPO is eluted with Buffer B (20 mM Hepes, 5 mM $CaCl_2$, 1M NaCl, pH 7.0). The EPO containing fractions are collected. The protein content is determined (Coomassie, Bradford) and adjusted to 1 mg/ml with reaction buffer and adjusted to pH 6.0 by dropwise addition of 0.5M HCl.

A 50-fold molar excess of a aminooxy-PSA reagent with a MW of 20 kD (described above) is added followed by m-toluidine as a nucleophilic catalyst (final concentration: 10 mM). The coupling reaction is performed for 2 hours in the dark under gentle shaking at room temperature. The excess of aminooxy-PSA reagent is removed by means of HIC. The conductivity of the reaction mixture is adjusted by adding a buffer containing ammonium acetate (50 mM Hepes, 350 mM sodium chloride, 5 mM calcium chloride, 8 M ammonium acetate, pH 6.9) and loaded onto a column filled with 80 ml Phenyl Sepharose FF (GE Healthcare, Fairfield, Conn.) pre-equilibrated with 50 mM Hepes, 2.5 M ammonium acetate, 350 mM sodium chloride, 5 mM calcium chloride, pH 6.9. Subsequently, the conjugate is eluted with 50 mM Hepes buffer pH 7.5 containing 5 mM $CaCl_2$. Finally the PSA-EPO containing fractions are collected and subjected to UF/DF by use of a membrane made of regenerated cellulose (MWCO 10 kD, 50 $cm^2$, Millipore). The preparation is next analytically characterized by measuring total protein (Coomassie, Bradford) and biological activity according to methods known in the art.

In an alternative embodiment, Method 1 is carried out as follows.

10 mg EPO is dissolved in 5 ml histidine buffer, pH 6.0 (20 mM L-histidine, 150 mM NaCl). 100 μl of an aqueous sodium periodate solution (5 mM) is then added and the reaction mixture is incubated for 1 h in the dark at 4° C. under gentle stirring and quenched for 15 min at room temperature by the addition of 50 μl of a 1 M aqueous cysteine solution. The mixture is subsequently subjected to UF/DF employing Vivaspin 15R 10 kD centrifugal filtrators to remove excess periodate, quencher and the byproducts thereof.

The retentate (approx. 7 ml), containing oxidized EPO, is mixed with 2 ml of an aqueous m-toluidine solution (50 mM) and incubated for 30 min at room temperature. Then aminooxy-PSA reagent with a MW of 20 kD (described above) is added to give a 5-fold molar reagent excess. This mixture is incubated for 2.5 h at RT in the dark under gentle stirring.

The free EPO is removed by means of anion exchange chromatography (AEC). The reaction mixture is diluted with 20 ml Buffer A (50 mM Hepes, pH 7.5) and loaded onto a 20 ml HiPrep QFF 16/10 column (GE Healthcare, Fairfield, Conn.) pre-equilibrated with Buffer A. Then the column is eluted with Buffer B (50 mM Hepes, 1 M NaCl, pH 7.5). Free EPO is eluted by washing the column with 25% Buffer B and the conjugate at 50% Buffer B. The conductivity of the conjugate containing fractions is subsequently raised to ~190 mS/cm with Buffer C (50 mM Hepes, 5 M NaCl, pH 6.9) and loaded onto a 20 ml HiPrep Butyl FF 16/10 column (GE Healthcare, Fairfield, Conn.) pre-equilibrated with Buffer D (50 mM Hepes, 3 M NaCl, pH 6.9). Free PSA-reagent is washed out within 5 CV Buffer D. Subsequently, the conjugate is eluted with 100% Buffer E (50 mM Hepes, pH 7.4). The conjugate containing fractions are concentrated by UF/DF using a 10 kD membrane made of regenerated cellulose (88 cm2, cut-off 10 kD/Millipore). The final diafiltration step is performed against histidine buffer, pH 7.2 containing 150 mM NaCl. The preparation is analytically characterized by measuring total protein (Bradford) and biological activity according to methods known in the art. For the PSA-EPO conjugate a specific activity of >50% in comparison to native EPO is determined. The conjugate is additionally analytically characterized by Size Exclusion HPLC using a Agilent 1200 HPLC system equipped with a Shodex KW 803 column under conditions as previously described (Kolarich et al, Transfusion 2006; 46:1959-77). It is shown that the preparation contains no free EPO.

Method 2:

EPO is transferred or dissolved in reaction buffer (e.g. 50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5 N aqueous HCl solution. Subsequently, a 40 mM aqueous sodium periodate solution is added within 10 minutes to give a concentration of 200 μM. The oxidation reaction is carried out for 30+/−5 min at a temperature (T) of T=+22+/−2° C. Then the reaction is stopped by addition of an aqueous L-cysteine solution (1 M) within 15 minutes at T=+22+/−2° C. to give a final concentration of 10 mM in the reaction mixture and incubation for 60+/−5 min.

The oxidized EPO is further purified by ion exchange chromatography. The oxidized EPO containing fractions of the eluate are collected and used for the conjugation reaction.

The aminooxy-polysialic acid (PSA-$ONH_2$) reagent is added in a 50-fold molar excess to the eluate containing the purified oxidized EPO within a maximum time period (t) of 15 minutes under gentle stirring. Then an aqueous m-toluidine solution (50 mM) is added within 15 minutes to get a final concentration of 10 mM. The reaction mixture is incubated for 120+/−10 min. at pH 6.0 in the dark at a temperature (T) of T=+22+/−2° C. under gentle shaking (protein concentration: 1 mg/ml).

The obtained PSA-EPO conjugate is further purified by ion exchange chromatography. The PSA-EPO conjugate containing fractions are collected and concentrated by ultra-/diafiltration (UF/DF) using a membrane made of regenerated cellulose with an appropriate molecular weight cut off (Millipore).

The conjugate prepared by use of this procedure is analytically characterized by measuring total protein, biological activity, and determination of the polysialylation degree by measuring the PSA content (resorcinol assay).

Method 3:

Erythropoietin (EPO) is transferred into reaction buffer (50 mM Hepes, 350 mM sodium chloride, 5 mM calcium chloride, pH 6.0) and diluted to obtain a protein concentration of 1 mg/ml. A 50 fold molar excess of a aminooxy-PSA reagent with a MW of 20 kD (described above) is added followed by m-toluidine as a nucleophilic catalyst (10 mM final concentration) and NaIO4 (final concentration: 400 μM). The coupling reaction is performed for 2 hours in the dark under gentle shaking at room temperature. Subsequently, the reaction is quenched with cysteine for 60 min at RT (cysteine concentration: 10 mM). Then the conductivity of the reaction mixture is adjusted by adding a buffer containing ammonium acetate (50 mM Hepes, 350 mM sodium chloride, 5 mM calcium chloride, 8 M ammonium acetate, pH 6.9) and loaded onto a column filled with Phenyl Sepharose FF (GE Healthcare, Fairfield, Conn.) pre-equilibrated with 50 mM Hepes, 2.5 M ammonium acetate, 350 mM sodium chloride, 5 mM calcium chloride, 0.01% Tween 80, pH 6.9. Subsequently, the conjugate is eluted with 50 mM Hepes, 5 mM calcium chloride, pH 7.5. Finally, the PSA-EPO containing fractions are collected and subjected to UF/DF by use of a membrane made of regenerated cellulose (MWCO 10 kD, 88 $cm^2$, Millipore). The preparation is analytically characterized by measuring total protein (Bradford) and biological activity according to methods known in the art.

In an alternative embodiment, Method 3 is carried out as follows. 10 mg EPO is dissolved in 8 ml histidine buffer, pH 6.0 (20 mM L-histidine, 150 mM NaCl). 200 μl of an aqueous sodium periodate solution (5 mM) and 2 ml of an aqueous m-toluidine solution (50 mM) are then added. Subsequently, the aminooxy-PSA reagent with a MW of 20 kD (described above) is added to give a 5-fold molar reagent excess. The mixture is incubated for 2 h in the dark at room temperature under gentle stirring and quenched for 15 min at room temperature by the addition of 100 μl of 1 M aqueous cysteine solution.

The free EPO is removed by means of anion exchange chromatography (AEC). The reaction mixture is diluted with 20 ml Buffer A (50 mM Hepes, pH 7.5) and loaded onto a 20 ml HiPrep QFF 16/10 column (GE Healthcare, Fairfield, Conn.) pre-equilibrated with Buffer A. Then the column is eluted with Buffer B (50 mM Hepes, 1 M NaCl, pH 7.5). Free EPO is eluted by washing the column with 25% Buffer B and the conjugate at 50% Buffer B. The conductivity of the conjugate containing fractions is subsequently raised to ~190 mS/cm with Buffer C (50 mM Hepes, 5 M NaCl, pH 6.9) and loaded onto a 20 ml HiPrep Butyl FF 16/10 column (GE Healthcare, Fairfield, Conn.) pre-equilibrated with Buffer D (50 mM Hepes, 3 M NaCl, pH 6.9). Free PSA-reagent is washed out within 5 CV Buffer D. Subsequently, the conjugate is eluted with 100% Buffer E (50 mM Hepes, pH 7.4). The conjugate containing fractions are concentrated by UF/DF using a 10 kD membrane made of regenerated cellulose (88 cm2, cut-off 10 kD, Millipore). The final diafiltration step is performed against histidine buffer, pH 7.2 containing 150 mM NaCl. The preparation is analytically characterized by measuring total protein (Bradford) and biological activity according to methods known in the art. For the PSA-EPO conjugate a specific activity of >50% in comparison to native EPO is determined. The conjugate is additionally analytically characterized by Size Exclusion HPLC using a Agilent 1200 HPLC system equipped with a Shodex KW 803 column under conditions as previously described (Kolarich et al, Transfusion 2006; 46:1959-77). It is shown that the preparation contains no free EPO.

Method 4:

EPO is dissolved in or transferred to a reaction buffer (e.g. 50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5 N aqueous HCl solution.

Subsequently, the aminooxy-polysialic acid (PSA-$ONH_2$) reagent is added in a 50-fold molar excess to this EPO solution within a maximum time period (t) of 15 minutes under gentle stirring. Then an aqueous m-toluidine solution (50 mM) is added within 15 minutes to get a final concentration of 10 mM. Finally a 40 mM aqueous sodium periodate solution is added to give a concentration of 400 μM.

The reaction mixture is incubated for 120+/−10 min. in the dark at a temperature (T) of T=+22+/−2° C. under gentle shaking. Then the reaction is stopped by the addition of an aqueous L-cysteine solution (1 M) to give a final concentration of 10 mM in the reaction mixture and incubation for 60+/−5 min.

The obtained PSA-EPO conjugate is purified by ion-exchange chromatography. The PSA-EPO containing fractions of the eluate are collected and concentrated by ultra-/diafiltration (UF/DF) using a membrane made of regenerated cellulose (MWCO 10 kD, 88 $cm^2$, Millipore).

The conjugates prepared by use of this procedure are analytically characterized by measuring total protein, biological activity according to methods known in the art, and determination of the polysialylation degree by measuring the PSA content (resorcinol assay).

Example 19

Polysialylation of Ang-2 Using Aminooxy-PSA and m-Toluidine as a Nucleophilic Catalyst Method 1:

A starting concentration of angiopoietin-2 (Ang-2) is transferred into a reaction buffer (e.g. 50 mM Hepes, 350 mM sodium chloride, 5 mM calcium chloride, pH 6.0) and diluted to obtain a protein concentration of 1 mg/ml. To this solution, $NaIO_4$ is added to give a final concentration of 200 μM. The oxidation is carried at RT for 30 min in the dark under gentle shaking. The reaction is then quenched with cysteine (final concentration: 10 mM) for 60 min at RT.

The solution is next subjected to UF/DF employing Vivaspin centrifugal filtrators to remove excess periodate, quencher and the byproducts, or, in the alternative, subjected to an IEX column with a volume of 20 ml (Merck EMD TMAE (M)) which is equilibrated with Buffer A (20 mM Hepes, 5 mM $CaCl_2$, pH 7.0). The column is equilibrated with 5 CV Buffer A. The oxidized Ang-2 is eluted with Buffer B (20 mM Hepes, 5 mM $CaCl_2$, 1 M NaCl, pH 7.0). The Ang-2 containing fractions are collected. The protein content is determined (Coomassie, Bradford) and adjusted to 1 mg/ml with reaction buffer and adjusted to pH 6.0 by dropwise addition of 0.5 M HCl.

A 50-fold molar excess of aminooxy-PSA reagent with a MW of 20 kD (described above) is added followed by m-toluidine as a nucleophilic catalyst (final concentration: 10 mM). The coupling reaction is performed for 2 hours in the dark under gentle shaking at room temperature. The excess of aminooxy reagent is removed by means of HIC. The conductivity of the reaction mixture is adjusted by adding a buffer containing ammonium acetate (50 mM Hepes, 350 mM sodium chloride, 5 mM calcium chloride, 8 M ammonium acetate, pH 6.9) and loaded onto a column filled with 80 ml Phenyl Sepharose FF (GE Healthcare, Fairfield, Conn.) pre-equilibrated with 50 mM Hepes, 2.5 M ammonium acetate, 350 mM sodium chloride, 5 mM calcium chloride, pH 6.9. Subsequently, the conjugate is eluted with 50 mM Hepes buffer pH 7.5 containing 5 mM $CaCl_2$. Finally, the PSA-Ang-2-containing fractions are collected and subjected to UF/DF by use of a membrane made of regenerated cellulose (Millipore). The preparation is next analytically characterized by measuring total protein (Coomassie, Bradford) and biological activity according to methods known in the art.

In an alternative embodiment, Method 1 is carried out as follows. Angiopoietin-2 (Ang-2) is transferred into a reaction buffer (e.g., 50 mM Hepes, 350 mM sodium chloride, 5 mM calcium chloride, pH 6.0) and diluted to obtain a protein concentration of 1 mg/ml. To this solution, $NaIO_4$ is added to give a final concentration of 200 μM. The oxidation is carried at RT for 30 min in the dark under gentle shaking. The reaction is then quenched with cysteine (final concentration: 10 mM) for 60 min at R.T.

The solution is next subjected to UF/DF employing Vivaspin centrifugal filtrators to remove excess periodate, quencher and the byproducts thereof.

A 50-fold molar excess of aminooxy-PSA reagent with a MW of 20 kD (described above) is added followed by m-toluidine as a nucleophilic catalyst (final concentration: 10 mM). The coupling reaction is performed for 2 hours in the dark under gentle shaking at room temperature. The excess of aminooxy reagent is removed by means of ion exchange chromatography. The PSA-Ang-2 conjugate-containing fractions of the eluate are collected and subjected to UF/DF by use of a membrane made of regenerated cellulose (Millipore). The preparation is next analytically characterized by measuring total protein (Coomassie, Bradford) and biological activity according to methods known in the art.

Method 2:

Ang-2 is transferred or dissolved in reaction buffer (e.g. 50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5 N aqueous HCl solution. Subsequently, a 40 mM aqueous sodium periodate solution is added within 10 minutes to give a concentration of 200 μM. The oxidation reaction is carried out for 30+/−5 min at a temperature (T) of T=+22+/−2° C. Then the reaction is stopped by addition of an aqueous L-cysteine solution (1 M) within 15 minutes at T=+22+/−2° C. to give a final concentration of 10 mM in the reaction mixture and incubation for 60+/−5 min.

The oxidized Ang-2 is further purified by ion exchange chromatography. The oxidized Ang-2 containing fractions of the eluate are collected and used for the conjugation reaction.

The aminooxy-polysialic acid ($PSA-ONH_2$) reagent is added in a 50-fold molar excess to the eluate containing the purified oxidized Ang-2 within a maximum time period (t) of 15 minutes under gentle stirring. Then an aqueous m-toluidine solution (50 mM) is added within 15 minutes to get a final concentration of 10 mM. The reaction mixture is incubated for 120+/−10 min. at pH 6.0 in the dark at a temperature (T) of T=+22+/−2° C. under gentle shaking (protein concentration: 1 mg/ml).

The obtained PSA-Ang-2 conjugate is further purified by ion-exchange chromatography The PSA-Ang-2 conjugate containing fractions are collected and concentrated by ultra-/diafiltration (UF/DF) using a membrane made of regenerated cellulose with an appropriate molecular weight cut off (Millipore).

The conjugate prepared by use of this procedure is analytically characterized by measuring total protein, biological activity, and determination of the polysialylation degree by measuring the PSA content (resorcinol assay).

Method 3:

Angiopoietin-2 (Ang-2) is transferred into reaction buffer (50 mM Hepes, 350 mM sodium chloride, 5 mM calcium chloride, pH 6.0) and diluted to obtain a protein concentration of 1 mg/ml. A 50 fold molar excess of a PSA aminooxy reagent with a MW of 20 kD (described above) is added followed by m-toluidine as a nucleophilic catalyst (10 mM final concentration) and $NaIO_4$ (final concentration: 400 μM). The coupling reaction is performed for 2 hours in the dark under gentle shaking at room temperature. Subsequently, the reaction is quenched with cysteine for 60 min at RT (cysteine concentration: 10 mM). Then the conductivity of the reaction mixture is adjusted by adding a buffer containing ammonium acetate (50 mM Hepes, 350 mM sodium chloride, 5 mM calcium chloride, 8 M ammonium acetate, pH 6.9) and loaded onto a column filled with Phenyl Sepharose FF (GE Healthcare, Fairfield, Conn.) pre-equilibrated with 50 mM Hepes, 2.5 M ammonium acetate, 350 mM sodium chloride, 5 mM calcium chloride, 0.01% Tween 80, pH 6.9. Subsequently, the conjugate is eluted with 50 mM Hepes, 5 mM calcium chloride, pH 7.5. Finally, the PSA Ang-2-containing fractions are collected and subjected to UF/DF by use of a membrane made of regenerated cellulose (Millipore). The preparation is analytically characterized by measuring total protein (Bradford) and biological activity according to methods known in the art.

In an alternative embodiment, Method 3 is carried out as follows. Angiopoietin-2 (Ang-2) is transferred into reaction buffer (e.g. 50 mM Hepes, 350 mM sodium chloride, 5 mM calcium chloride, pH 6.0) and diluted to obtain a protein concentration of 1 mg/ml. A 50-fold molar excess of a PSA aminooxy reagent with a MW of 20 kD (described above) is added followed by m-toluidine as a nucleophilic catalyst (10 mM final concentration) and $NaIO_4$ (final concentration: 400 μM). The coupling reaction is performed for 2 hours in the dark under gentle shaking at room temperature. Subsequently, the reaction is quenched with cysteine for 60 min at RT (cysteine concentration: 10 mM) and the conjugate is purified by ion exchange chromatography. PSA Ang-2-containing fractions of the eluate are collected and subjected to UF/DF by use of a membrane made of regenerated cellulose (Millipore). The preparation is analytically characterized by measuring total protein (Bradford) and biological activity according to methods known in the art.

Method 4:

Ang-2 is dissolved in or transferred to a reaction buffer (e.g. 50 mM Hepes, 350 mM sodium chloride, 5 mM calcium chloride, pH 6.0) to get a final protein concentration of 1.0+/−

0.25 mg/ml. Then the pH of the solution is corrected to 6.0 by drop wise addition of a 0.5 N aqueous HCl solution.

Subsequently, the aminooxy-polysialic acid ($PSA-ONH_2$) reagent is added in a 50-fold molar excess to this Ang-2 solution within a maximum time period (t) of 15 minutes under gentle stirring. Then an aqueous m-toluidine solution (50 mM) is added within 15 minutes to get a final concentration of 10 mM. Finally a 40 mM aqueous sodium periodate solution is added to give a concentration of 400 μM.

The reaction mixture is incubated for 120+/−10 min. in the dark at a temperature (T) of T=+22+/−2° C. under gentle shaking. Then the reaction is stopped by the addition of an aqueous L-cysteine solution (1 M) to give a final concentration of 10 mM in the reaction mixture and incubation for 60+/−5 min.

The obtained PSA-Ang-2 conjugate is purified by ion-exchange chromatography. The PSA-Ang-2 containing fractions of the eluate are collected and concentrated by ultra-/diafiltration (UF/DF) using a membrane made of regenerated cellulose (Millipore).

The conjugates prepared by use of this procedure are analytically characterized by measuring total protein, biological activity according to methods known in the art, and determination of the polysialylation degree by measuring the PSA content (resorcinol assay).

Example 20

Polysialylation of VEGF Using Aminooxy-PSA and m-Toluidine as a Nucleophilic Catalyst Method 1:

A starting concentration of vascular endothelial growth factor (VEGF) is transferred into a reaction buffer (e.g., 50 mM Hepes, 350 mM sodium chloride, 5 mM calcium chloride, pH 6.0) and diluted to obtain a protein concentration of 1 mg/ml. To this solution, $NaIO_4$ is added to give a final concentration of 200 μM. The oxidation is carried at RT for 30 min in the dark under gentle shaking. The reaction is then quenched with cysteine (final concentration: 10 mM) for 60 min at RT.

The solution is next subjected to UF/DF employing Vivaspin centrifugal filtrators to remove excess periodate, quencher and the byproducts thereof or, in the alternative, to an IEX column with a volume of 20 ml (Merck EMD TMAE (M)) which is equilibrated with Buffer A (20 mM Hepes, 5 mM $CaCl_2$, pH 7.0). The column is equilibrated with 5 CV Buffer A. The oxidized VEGF is eluted with Buffer B (20 mM Hepes, 5 mM $CaCl_2$, 1 M NaCl, pH 7.0). The VEGF containing fractions are collected. The protein content is determined (Coomassie, Bradford) and adjusted to 1 mg/ml with reaction buffer and adjusted to pH 6.0 by dropwise addition of 0.5M NaOH.

A 50-fold molar excess of aminooxy-PSA reagent with a MW of 20 kD (described above) is added followed by m-toluidine as a nucleophilic catalyst (final concentration: 10 mM). The coupling reaction is performed for 2 hours in the dark under gentle shaking at room temperature. The excess of aminooxy reagent is removed by means of HIC. The conductivity of the reaction mixture is adjusted by adding a buffer containing ammonium acetate (50 mM Hepes, 350 mM sodium chloride, 5 mM calcium chloride, 8 M ammonium acetate, pH 6.9) and loaded onto a column filled with 80 ml Phenyl Sepharose FF (GE Healthcare, Fairfield, Conn.) pre-equilibrated with 50 mM Hepes, 2.5 M ammonium acetate, 350 mM sodium chloride, 5 mM calcium chloride, pH 6.9. Subsequently, the conjugate is eluted with 50 mM Hepes buffer pH 7.5 containing 5 mM $CaCl_2$. Finally the PSA-VEGF-containing fractions are collected and subjected to UF/DF by use of a membrane made of regenerated cellulose (Millipore). The preparation is next analytically characterized by measuring total protein (Coomassie, Bradford) and biological activity according to methods known in the art.

In an alternative embodiment, Method 1 is carried out as follows. Vascular endothelial growth factor (VEGF) is transferred into a reaction buffer (e.g., 50 mM Hepes, 350 mM sodium chloride, 5 mM calcium chloride, pH 6.0) and diluted to obtain a protein concentration of 1 mg/ml. To this solution, $NaIO_4$ is added to give a final concentration of 200 μM. The oxidation is carried at RT for 30 min in the dark under gentle shaking. The reaction is then quenched with cysteine (final concentration: 10 mM) for 60 min at RT.

The solution is next subjected to UF/DF employing Vivaspin centrifugal filtrators to remove excess periodate, quencher and the byproducts thereof.

A 50-fold molar excess of aminooxy-PSA reagent with a MW of 20 kD (described above) is added followed by m-toluidine as a nucleophilic catalyst (final concentration: 10 mM). The coupling reaction is performed for 2 hours in the dark under gentle shaking at room temperature. The excess of aminooxy reagent is removed by means of ion exchange chromatography. The PSA-VEGF-containing fractions of the eluate are collected and subjected to UF/DF by use of a membrane made of regenerated cellulose (Millipore). The preparation is next analytically characterized by measuring total protein (Coomassie, Bradford) and biological activity according to methods known in the art.

Method 2:

VEGF is transferred or dissolved in reaction buffer (e.g. 50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5 N aqueous HCl solution. Subsequently a 40 mM aqueous sodium periodate solution is added within 10 minutes to give a concentration of 200 μM. The oxidation reaction is carried out for 30+/−5 min at a temperature (T) of T=+22+/−2° C. Then the reaction is stopped by addition of an aqueous L-cysteine solution (1 M) within 15 minutes at T=+22+/−2° C. to give a final concentration of 10 mM in the reaction mixture and incubation for 60+/−5 min.

The oxidized VEGF is further purified by ion exchange chromatography. The oxidized VEGF containing fractions of the eluate are collected and used for the conjugation reaction.

The aminooxy-polysialic acid ($PSA-ONH_2$) reagent is added in a 50-fold molar excess to the eluate containing the purified oxidized VEGF within a maximum time period (t) of 15 minutes under gentle stirring. Then an aqueous m-toluidine solution (50 mM) is added within 15 minutes to get a final concentration of 10 mM. The reaction mixture is incubated for 120+/−10 min. at pH 6.0 in the dark at a temperature (T) of T=+22+/−2° C. under gentle shaking (protein concentration: 1 mg/ml).

The obtained PSA-VEGF conjugate is further purified by ion exchange chromatography. The PSA-VEGF conjugate containing fractions are collected and concentrated by ultra-/diafiltration (UF/DF) using a membrane made of regenerated cellulose with an appropriate molecular weight cut off (Millipore).

The conjugate prepared by use of this procedure is analytically characterized by measuring total protein, biological activity, and determination of the polysialylation degree by measuring the PSA content (resorcinol assay).

Method 3:

Vascular endothelial growth factor (VEGF) is transferred into reaction buffer (50 mM Hepes, 350 mM sodium chloride, 5 mM calcium chloride, pH 6.0) and diluted to obtain a protein concentration of 1 mg/ml. A 50-fold molar excess of a PSA aminooxy reagent with a MW of 20 kD (described above) is added followed by m-toluidine as a nucleophilic catalyst (10 mM final concentration) and $NaIO_4$ (final concentration: 400 μM). The coupling reaction is performed for 2 hours in the dark under gentle shaking at room temperature. Subsequently, the reaction is quenched with cysteine for 60 min at RT (cysteine concentration: 10 mM). Then the conductivity of the reaction mixture is adjusted by adding a buffer containing ammonium acetate (50 mM Hepes, 350 mM sodium chloride, 5 mM calcium chloride, 8 M ammonium acetate, pH 6.9) and loaded onto a column filled with Phenyl Sepharose FF (GE Healthcare, Fairfield, Conn.) pre-equilibrated with 50 mM Hepes, 2.5 M ammonium acetate, 350 mM sodium chloride, 5 mM calcium chloride, 0.01% Tween 80, pH 6.9. Subsequently the conjugate is eluted with 50 mM Hepes, 5 mM calcium chloride, pH 7.5. Finally, the PSA-VEGF containing fractions are collected and subjected to UF/DF by use of a membrane made of regenerated cellulose (Millipore). The preparation is analytically characterized by measuring total protein (Bradford) and biological activity according to methods known in the art.

In an alternative embodiment, Method 3 is carried out as follows. Vascular endothelial growth factor (VEGF) is transferred into reaction buffer (e.g. 50 mM Hepes, 350 mM sodium chloride, 5 mM calcium chloride, pH 6.0) and diluted to obtain a protein concentration of 1 mg/ml. A 50-fold molar excess of aminooxy-PSA reagent with a MW of 20 kD (described above) is added followed by m-toluidine as a nucleophilic catalyst (10 mM final concentration) and $NaIO_4$ (final concentration: 400 μM). The coupling reaction is performed for 2 hours in the dark under gentle shaking at room temperature. Subsequently, the reaction is quenched with cysteine for 60 min at RT (cysteine concentration: 10 mM) and the conjugate is purified by ion exchange chromatography. The PSA-VEGF containing fractions of the eluate are collected and subjected to UF/DF by use of a membrane made of regenerated cellulose (Millipore). The preparation is analytically characterized by measuring total protein (Bradford) and biological activity according to methods known in the art.

Method 4:

VEGF is dissolved in or transferred to a reaction buffer (e.g. 50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5 N aqueous HCl solution.

Subsequently, the aminooxy-polysialic acid ($PSA-ONH_2$) reagent is added in a 50-fold molar excess to this VEGF solution within a maximum time period (t) of 15 minutes under gentle stirring. Then an aqueous m-toluidine solution (50 mM) is added within 15 minutes to get a final concentration of 10 mM. Finally a 40 mM aqueous sodium periodate solution is added to give a concentration of 400 μM.

The reaction mixture is incubated for 120+/−10 min. in the dark at a temperature (T) of T=+22+/−2° C. under gentle shaking. Then the reaction is stopped by the addition of an aqueous L-cysteine solution (1 M) to give a final concentration of 10 mM in the reaction mixture and incubation for 60+/−5 min.

The obtained VEGF-conjugate is purified by ion-exchange chromatography. The PSA-VEGF containing fractions of the eluate are collected and concentrated by ultra-/diafiltration (UF/DF) using a membrane made of regenerated cellulose (Millipore).

The conjugates prepared by use of this procedure are analytically characterized by measuring total protein, biological activity according to methods known in the art, and determination of the polysialylation degree by measuring the PSA content (resorcinol assay).

Example 21

Polysialylation of EGF Using Aminooxy-PSA and m-Toluidine as a Nucleophilic Catalyst Method 1:

A starting concentration of epidermal growth factor (EGF) is transferred into a reaction buffer (e.g., 50 mM Hepes, 350 mM sodium chloride, 5 mM calcium chloride, pH 6.0) and diluted to obtain a protein concentration of 1 mg/ml. To this solution, $NaIO_4$ is added to give a final concentration of 200 μM. The oxidation is carried at RT for 30 min in the dark under gentle shaking. The reaction is then quenched with cysteine (final concentration: 10 mM) for 60 min at R.T.

The solution is next subjected to UF/DF employing Vivaspin centrifugal filtrators to remove excess periodate, quencher and the byproducts thereof or, in the alternative, to an IEX column with a volume of 20 ml (Merck EMD TMAE (M)) which is equilibrated with Buffer A (20 mM Hepes, 5 mM $CaCl_2$, pH 7.0). The column is equilibrated with 5 CV Buffer A. The oxidized EGF is eluted with Buffer B (20 mM Hepes, 5 mM $CaCl_2$, 1M NaCl, pH 7.0). The EGF containing fractions are collected. The protein content is determined (Coomassie, Bradford) and adjusted to 1 mg/ml with reaction buffer and adjusted to pH 6.0 by dropwise addition of 0.5M HCl.

A 50-fold molar excess of aminooxy-PSA reagent with a MW of 20 kD (described above) is added followed by m-toluidine as a nucleophilic catalyst (final concentration: 10 mM). The coupling reaction is performed for 2 hours in the dark under gentle shaking at room temperature. The excess of aminooxy reagent is removed by means of HIC. The conductivity of the reaction mixture is adjusted by adding a buffer containing ammonium acetate (50 mM Hepes, 350 mM sodium chloride, 5 mM calcium chloride, 8 M ammonium acetate, pH 6.9) and loaded onto a column filled with 80 ml Phenyl Sepharose FF (GE Healthcare, Fairfield, Conn.) pre-equilibrated with 50 mM Hepes, 2.5 M ammonium acetate, 350 mM sodium chloride, 5 mM calcium chloride, pH 6.9. Subsequently, the conjugate is eluted with 50 mM Hepes buffer pH 7.5 containing 5 mM $CaCl_2$. Finally, the PSA-EGF containing fractions are collected and subjected to UF/DF by use of a membrane made of regenerated cellulose (Millipore). The preparation is next analytically characterized by measuring total protein (Coomassie, Bradford) and biological activity according to methods known in the art.

In an alternative embodiment, Method 1 is carried out as follows. Epidermal growth factor (EGF) is transferred into a reaction buffer (e.g., 50 mM Hepes, 350 mM sodium chloride, 5 mM calcium chloride, pH 6.0) and diluted to obtain a protein concentration of 1 mg/ml. To this solution, $NaIO_4$ is added to give a final concentration of 200 μM. The oxidation is carried at RT for 30 min in the dark under gentle shaking. The reaction is then quenched with cysteine (final concentration: 10 mM) for 60 min at R.T.

The solution is next subjected to UF/DF employing Vivaspin centrifugal filtrators to remove excess periodate, quencher and the byproducts thereof.

A 50-fold molar excess of aminooxy-PSA reagent with a MW of 20 kD (described above) is added followed by m-toluidine as a nucleophilic catalyst (final concentration: 10 mM). The coupling reaction is performed for 2 hours in the dark under gentle shaking at room temperature. The excess of aminooxy reagent is removed by means of ion exchange chromatography. The PSA-EGF containing fractions of the eluate are collected and subjected to UF/DF by use of a membrane made of regenerated cellulose (Millipore). The preparation is next analytically characterized by measuring total protein (Coomassie, Bradford) and biological activity according to methods known in the art.

Method 2:

EGF is transferred or dissolved in reaction buffer (e.g. 50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5 N aqueous HCl solution. Subsequently, a 40 mM aqueous sodium periodate solution is added within 10 minutes to give a concentration of 200 μM. The oxidation reaction is carried out for 30+/−5 min at a temperature (T) of T=+22+/−2° C. Then the reaction is stopped by addition of an aqueous L-cysteine solution (1 M) within 15 minutes at T=+22+/−2° C. to give a final concentration of 10 mM in the reaction mixture and incubation for 60+/−5 min.

The oxidized EGF is further purified by ion exchange chromatography. The oxidized EGF containing fractions of the eluate are collected and used for the conjugation reaction.

The aminooxy-polysialic acid ($PSA-ONH_2$) reagent is added in a 50-fold molar excess to the eluate containing the purified oxidized EGF within a maximum time period (t) of 15 minutes under gentle stirring. Then an aqueous m-toluidine solution (50 mM) is added within 15 minutes to get a final concentration of 10 mM. The reaction mixture is incubated for 120+/−10 min. at pH 6.0 in the dark at a temperature (T) of T=+22+/−2° C. under gentle shaking (protein concentration: 1 mg/ml).

The obtained PSA-EGF conjugate is further purified by ion exchange chromatography. The PSA-EGF conjugate containing fractions are collected and concentrated by ultra-/diafiltration (UF/DF) using a membrane made of regenerated cellulose with an appropriate molecular weight cut off (Millipore).

The conjugate prepared by use of this procedure is analytically characterized by measuring total protein, biological activity, and determination of the polysialylation degree by measuring the PSA content (resorcinol assay).

Method 3:

Epidermal growth factor (EGF) is transferred into reaction buffer (50 mM Hepes, 350 mM sodium chloride, 5 mM calcium chloride, pH 6.0) and diluted to obtain a protein concentration of 1 mg/ml. A 50-fold molar excess of a PSA aminooxy reagent with a MW of 20 kD (described above) is added followed by m-toluidine as a nucleophilic catalyst (10 mM final concentration) and $NaIO_4$ (final concentration: 400 μM). The coupling reaction is performed for 2 hours in the dark under gentle shaking at room temperature. Subsequently, the reaction is quenched with cysteine for 60 min at RT (cysteine concentration: 10 mM). Then the conductivity of the reaction mixture is adjusted by adding a buffer containing ammonium acetate (50 mM Hepes, 350 mM sodium chloride, 5 mM calcium chloride, 8 M ammonium acetate, pH 6.9) and loaded onto a column filled with Phenyl Sepharose FF (GE Healthcare, Fairfield, Conn.) pre-equilibrated with 50 mM Hepes, 2.5 M ammonium acetate, 350 mM sodium chloride, 5 mM calcium chloride, 0.01% Tween 80, pH 6.9. Subsequently the conjugate is eluted with 50 mM Hepes, 5 mM calcium chloride, pH 7.5. Finally the PSA-EGF containing fractions are collected and subjected to UF/DF by use of a membrane made of regenerated cellulose (Millipore). The preparation is analytically characterized by measuring total protein (Bradford) and biological activity according to methods known in the art.

In an alternative embodiment, Method 3 is carried out as follows. Epidermal growth factor (EGF) is transferred into reaction buffer (e.g. 50 mM Hepes, 350 mM sodium chloride, 5 mM calcium chloride, pH 6.0) and diluted to obtain a protein concentration of 1 mg/ml. A 50-fold molar excess of a PSA aminooxy reagent with a MW of 20 kD (described above) is added followed by m-toluidine as a nucleophilic catalyst (10 mM final concentration) and $NaIO_4$ (final concentration: 400 μM). The coupling reaction is performed for 2 hours in the dark under gentle shaking at room temperature. Subsequently, the reaction is quenched with cysteine for 60 min at RT (cysteine concentration: 10 mM) and the conjugate is purified by ion exchange chromatography. The conjugate containing fractions of the eluate are collected and subjected to UF/DF by use of a membrane made of regenerated cellulose (Millipore). The preparation is analytically characterized by measuring total protein (Bradford) and biological activity according to methods known in the art.

Method 4:

EGF is dissolved in or transferred to a reaction buffer (e.g. 50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5 N aqueous HCl solution.

Subsequently the aminooxy-polysialic acid ($PSA-ONH_2$) reagent is added in a 50-fold molar excess to this EGF-solution within a maximum time period (t) of 15 minutes under gentle stirring. Then an aqueous m-toluidine solution (50 mM) is added within 15 minutes to get a final concentration of 10 mM. Finally a 40 mM aqueous sodium periodate solution is added to give a concentration of 400 μM.

The reaction mixture is incubated for 120+/−10 min. in the dark at a temperature (T) of T=+22+/−2° C. under gentle shaking. Then the reaction is stopped by the addition of an aqueous L-cysteine solution (1 M) to give a final concentration of 10 mM in the reaction mixture and incubation for 60+/−5 min.

The obtained EGF-conjugate is purified by ion-exchange chromatography. The PSA-EGF containing fractions of the eluate are collected and concentrated by ultra-/diafiltration (UF/DF) using a membrane made of regenerated cellulose (Millipore).

The conjugates prepared by use of this procedure are analytically characterized by measuring total protein, biological activity according to methods known in the art, and determination of the polysialylation degree by measuring the PSA content (resorcinol assay).

Example 22

Polysialylation of NGF Using Aminooxy-PSA and m-Toluidine as a Nucleophilic Catalyst Method 1:

A starting concentration of nerve growth factor (NGF) is transferred into a reaction buffer (e.g., 50 mM Hepes, 350 mM sodium chloride, 5 mM calcium chloride, pH 6.0) and diluted to obtain a protein concentration of 1 mg/ml. To this solution, $NaIO_4$ is added to give a final concentration of 200 μM. The oxidation is carried at RT for 30 min in the dark under gentle shaking. The reaction is then quenched with cysteine (final concentration: 10 mM) for 60 min at RT.

The solution is next subjected to UF/DF employing Vivaspin centrifugal filtrators to remove excess periodate, quencher and the byproducts thereof or, in the alternative, to an IEX column with a volume of 20 ml (Merck EMD TMAE (M)) which is equilibrated with Buffer A (20 mM Hepes, 5 mM $CaCl_2$, pH 7.0). The column is equilibrated with 5 CV Buffer A. The oxidized NGF is eluted with Buffer B (20 mM Hepes, 5 mM $CaCl_2$, 1M NaCl, pH 7.0). The NGF containing fractions are collected. The protein content is determined (Coomassie, Bradford) and adjusted to 1 mg/ml with reaction buffer and adjusted to pH 6.0 by dropwise addition of 0.5M HCl.

A 50-fold molar excess of aminooxy-PSA reagent with a MW of 20 kD (described above) is added followed by m-toluidine as a nucleophilic catalyst (final concentration: 10 mM). The coupling reaction is performed for 2 hours in the dark under gentle shaking at room temperature. The excess of aminooxy reagent is removed by means of HIC. The conductivity of the reaction mixture is adjusted by adding a buffer containing ammonium acetate (50 mM Hepes, 350 mM sodium chloride, 5 mM calcium chloride, 8 M ammonium acetate, pH 6.9) and loaded onto a column filled with 80 ml Phenyl Sepharose FF (GE Healthcare, Fairfield, Conn.) pre-equilibrated with 50 mM Hepes, 2.5 M ammonium acetate, 350 mM sodium chloride, 5 mM calcium chloride, pH 6.9. Subsequently, the conjugate is eluted with 50 mM Hepes buffer pH 7.5 containing 5 mM $CaCl_2$. Finally, the PSA-NGF containing fractions are collected and subjected to UF/DF by use of a membrane made of regenerated cellulose (Millipore). The preparation is next analytically characterized by measuring total protein (Coomassie, Bradford) and biological activity according to methods known in the art.

In an alternative embodiment, Method 1 is carried out as follows. Nerve growth factor (NGF) is transferred into a reaction buffer (e.g., 50 mM Hepes, 350 mM sodium chloride, 5 mM calcium chloride, pH 6.0) and diluted to obtain a protein concentration of 1 mg/ml. To this solution, $NaIO_4$ is added to give a final concentration of 200 μM. The oxidation is carried at RT for 30 min in the dark under gentle shaking. The reaction is then quenched with cysteine (final concentration: 10 mM) for 60 min at RT.

The solution is next subjected to UF/DF employing Vivaspin centrifugal filtrators to remove excess periodate, quencher and the byproducts thereof.

A 50-fold molar excess of aminooxy-PSA reagent with a MW of 20 kD (described above) is added followed by m-toluidine as a nucleophilic catalyst (final concentration: 10 mM). The coupling reaction is performed for 2 hours in the dark under gentle shaking at room temperature. The excess of aminooxy reagent is removed by means of ion exchange chromatography. The PSA-NGF containing fractions of the eluate are collected and subjected to UF/DF by use of a membrane made of regenerated cellulose (Millipore). The preparation is next analytically characterized by measuring total protein (Coomassie, Bradford) and biological activity according to methods known in the art.

Method 2:

NGF is transferred or dissolved in reaction buffer (e.g. 50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5 N aqueous HCl solution. Subsequently, a 40 mM aqueous sodium periodate solution is added within 10 minutes to give a concentration of 200 μM. The oxidation reaction is carried out for 30+/−5 min at a temperature (T) of T=+22+/−2° C. Then the reaction is stopped by addition of an aqueous L-cysteine solution (1 M) within 15 minutes at T=+22+/−2° C. to give a final concentration of 10 mM in the reaction mixture and incubation for 60+/−5 min.

The oxidized NGF is further purified by ion exchange chromatography. The oxidized NGF containing fractions of the eluate are collected and used for the conjugation reaction.

The aminooxy-polysialic acid (PSA-$ONH_2$) reagent is added in a 50-fold molar excess to the eluate containing the purified oxidized NGF within a maximum time period (t) of 15 minutes under gentle stirring. Then an aqueous m-toluidine solution (50 mM) is added within 15 minutes to get a final concentration of 10 mM. The reaction mixture is incubated for 120+/−10 min. at pH 6.0 in the dark at a temperature (T) of T=+22+/−2° C. under gentle shaking (protein concentration: 1 mg/ml).

The obtained PSA-NGF conjugate is further purified by ion exchange chromatography. The PSA-NGF conjugate containing fractions are collected and concentrated by ultra-/diafiltration (UF/DF) using a membrane made of regenerated cellulose with an appropriate molecular weight cut off (Millipore).

The conjugate prepared by use of this procedure is analytically characterized by measuring total protein, biological activity, and determination of the polysialylation degree by measuring the PSA content (resorcinol assay).

Method 3:

Nerve growth factor (NGF) is transferred into reaction buffer (50 mM Hepes, 350 mM sodium chloride, 5 mM calcium chloride, pH 6.0) and diluted to obtain a protein concentration of 1 mg/ml. A 50-fold molar excess of aminooxy-PSA reagent with a MW of 20 kD (described above) is added followed by m-toluidine as a nucleophilic catalyst (10 mM final concentration) and $NaIO_4$ (final concentration: 400 μM). The coupling reaction is performed for 2 hours in the dark under gentle shaking at room temperature. Subsequently, the reaction is quenched with cysteine for 60 min at RT (cysteine concentration: 10 mM). Then the conductivity of the reaction mixture is adjusted by adding a buffer containing ammonium acetate (50 mM Hepes, 350 mM sodium chloride, 5 mM calcium chloride, 8 M ammonium acetate, pH 6.9) and loaded onto a column filled with Phenyl Sepharose FF (GE Healthcare, Fairfield, Conn.) pre-equilibrated with 50 mM Hepes, 2.5 M ammonium acetate, 350 mM sodium chloride, 5 mM calcium chloride, 0.01% Tween 80, pH 6.9. Subsequently the conjugate is eluted with 50 mM Hepes, 5 mM calcium chloride, pH 7.5. Finally, the PSA NGF-containing fractions are collected and subjected to UF/DF by use of a membrane made of regenerated cellulose (Millipore). The preparation is analytically characterized by measuring total protein (Bradford) and biological activity according to methods known in the art.

In an alternative embodiment, Method 3 is carried out as follows. Nerve growth factor (NGF) is transferred into reaction buffer (e.g. 50 mM Hepes, 350 mM sodium chloride, 5 mM calcium chloride, pH 6.0) and diluted to obtain a protein concentration of 1 mg/ml. A 50-fold molar excess of aminooxy-PSA reagent with a MW of 20 kD (described above) is added followed by m-toluidine as a nucleophilic catalyst (10 mM final concentration) and $NaIO_4$ (final concentration: 400 μM). The coupling reaction is performed for 2 hours in the dark under gentle shaking at room temperature. Subsequently, the reaction is quenched with cysteine for 60 min at RT (cysteine concentration: 10 mM) and the conjugate is purified by ion exchange chromatography. Then the PSA-NGF containing fractions of the eluate are collected and subjected to UF/DF by use of a membrane made of regenerated cellulose (Millipore). The preparation is analytically characterized by measuring total protein (Bradford) and biological activity according to methods known in the art.

Method 4:

NGF is dissolved in or transferred to a reaction buffer (e.g. 50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5 N aqueous HCl solution.

Subsequently, the aminooxy-polysialic acid (PSA-$ONH_2$) reagent is added in a 50-fold molar excess to this NGF-solution within a maximum time period (t) of 15 minutes under gentle stirring. Then an aqueous m-toluidine solution (50 mM) is added within 15 minutes to get a final concentration of 10 mM. Finally a 40 mM aqueous sodium periodate solution is added to give a concentration of 400 μM.

The reaction mixture is incubated for 120+/−10 min. in the dark at a temperature (T) of T=+22+/−2° C. under gentle shaking. Then the reaction is stopped by the addition of an aqueous L-cysteine solution (1 M) to give a final concentration of 10 mM in the reaction mixture and incubation for 60+/−5 min.

The obtained NGF-conjugate is purified by ion-exchange chromatography. The PSA-NGF containing fractions of the eluate are collected and concentrated by ultra-/diafiltration (UF/DF) using a membrane made of regenerated cellulose (Millipore).

The conjugates prepared by use of this procedure are analytically characterized by measuring total protein, biological activity according to methods known in the art, and determination of the polysialylation degree by measuring the PSA content (resorcinol assay).

Example 23

Polysialylation of HGH Using Aminooxy-PSA and m-Toluidine as a Nucleophilic Catalyst Method 1:

As described herein, the amino acid sequence of human growth hormone (HGH) is first modified to incorporate at least one glycosylation site. Following purification, HGH is glycosylated in vitro according to methods known in the art.

A starting concentration of human growth hormone (HGH) is transferred into a reaction buffer (e.g., 50 mM Hepes, 350 mM sodium chloride, 5 mM calcium chloride, pH 6.0) and diluted to obtain a protein concentration of 1 mg/ml. To this solution, $NaIO_4$ is added to give a final concentration of 200 μM. The oxidation is carried at RT for 30 min in the dark under gentle shaking. The reaction is then quenched with cysteine (final concentration: 10 mM) for 60 min at RT.

The solution is next subjected to UF/DF employing Vivaspin centrifugal filtrators to remove excess periodate, quencher and the byproducts thereof or, in the alternative, to an IEX column with a volume of 20 ml (Merck EMD TMAE (M)) which is equilibrated with Buffer A (20 mM Hepes, 5 mM $CaCl_2$, pH 7.0). The column is equilibrated with 5 CV Buffer A. The oxidized HGH is eluted with Buffer B (20 mM Hepes, 5 mM $CaCl_2$, 1 M NaCl, pH 7.0). The HGH containing fractions are collected. The protein content is determined (Coomassie, Bradford) and adjusted to 1 mg/ml with reaction buffer and adjusted to pH 6.0 by dropwise addition of 0.5 M HCl.

A 50-fold molar excess of aminooxy-PSA reagent with a MW of 20 kD (described above) is added followed by m-toluidine as a nucleophilic catalyst (final concentration: 10 mM). The coupling reaction is performed for 2 hours in the dark under gentle shaking at room temperature. The excess of aminooxy reagent is removed by means of HIC. The conductivity of the reaction mixture is adjusted by adding a buffer containing ammonium acetate (50 mM Hepes, 350 mM sodium chloride, 5 mM calcium chloride, 8 M ammonium acetate, pH 6.9) and loaded onto a column filled with 80 ml Phenyl Sepharose FF (GE Healthcare, Fairfield, Conn.) pre-equilibrated with 50 mM Hepes, 2.5 M ammonium acetate, 350 mM sodium chloride, 5 mM calcium chloride, pH 6.9. Subsequently the conjugate is eluted with 50 mM Hepes buffer pH 7.5 containing 5 mM $CaCl_2$. Finally, the PSA-HGH containing fractions are collected and subjected to UF/DF by use of a membrane made of regenerated cellulose (Millipore). The preparation is next analytically characterized by measuring total protein (Coomassie, Bradford) and biological activity according to methods known in the art.

In an alternative embodiment, Method 1 is carried out as follows. As described herein, the amino acid sequence of human growth hormone (HGH) is first modified to incorporate at least one glycosylation site. Following purification, HGH is glycosylated in vitro according to methods known in the art. HGH is transferred into a reaction buffer (e.g., 50 mM Hepes, 350 mM sodium chloride, 5 mM calcium chloride, pH 6.0) and diluted to obtain a protein concentration of 1 mg/ml. To this solution, $NaIO_4$ is added to give a final concentration of 200 μM. The oxidation is carried at RT for 30 min in the dark under gentle shaking. The reaction is then quenched with cysteine (final concentration: 10 mM) for 60 min at RT.

The solution is next subjected to UF/DF employing Vivaspin centrifugal filtrators to remove excess periodate, quencher and the byproducts thereof.

A 50-fold molar excess of aminooxy-PSA reagent with a MW of 20 kD (described above) is added followed by m-toluidine as a nucleophilic catalyst (final concentration: 10 mM). The coupling reaction is performed for 2 hours in the dark under gentle shaking at room temperature. The excess of aminooxy reagent is removed by means of ion exchange chromatography. The PSA-HGH containing fractions of the eluate are collected and subjected to UF/DF by use of a membrane made of regenerated cellulose (Millipore). The preparation is next analytically characterized by measuring total protein (Coomassie, Bradford) and biological activity according to methods known in the art.

Method 2:

As described herein, the amino acid sequence of human growth hormone (HGH) is first modified to incorporate at least one glycosylation site. Following purification, HGH is glycosylated in vitro according to methods known in the art.

HGH is transferred or dissolved in reaction buffer (e.g. 50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5 N aqueous HCl solution. Subsequently, a 40 mM aqueous sodium periodate solution is added within 10 minutes to give a concentration of 200 μM. The oxidation reaction is carried out for 30+/−5 min at a temperature (T) of T=+22+/−2° C. Then the reaction is stopped by addition of an aqueous L-cysteine solution (1 M) within 15 minutes at T=+22+/−2° C. to give a final concentration of 10 mM in the reaction mixture and incubation for 60+/−5 min.

The oxidized HGH is further purified by ion exchange chromatography. The oxidized HGH containing fractions of the eluate are collected and used for the conjugation reaction.

The aminooxy-polysialic acid ($PSA-ONH_2$) reagent is added in a 50-fold molar excess to the eluate containing the purified oxidized HGH within a maximum time period (t) of 15 minutes under gentle stirring. Then an aqueous m-toluidine solution (50 mM) is added within 15 minutes to get a final concentration of 10 mM. The reaction mixture is incubated for 120+/−10 min. at pH 6.0 in the dark at a temperature (T) of T=+22+/−2° C. under gentle shaking (protein concentration: 1 mg/ml).

The obtained PSA-HGH conjugate is further purified by ion exchange chromatography. The PSA-HGH conjugate containing fractions are collected and concentrated by ultra-/diafiltration (UF/DF) using a membrane made of regenerated cellulose with an appropriate molecular weight cut off (Millipore).

The conjugate prepared by use of this procedure is analytically characterized by measuring total protein, biological activity, and determination of the polysialylation degree by measuring the PSA content (resorcinol assay).

Method 3:

As described herein, the amino acid sequence of human growth hormone (HGH) is first modified to incorporate at least one glycosylation site. Following purification, HGH is glycosylated in vitro according to methods known in the art.

Human growth hormone (HGH) is transferred into reaction buffer (50 mM Hepes, 350 mM sodium chloride, 5 mM calcium chloride, pH 6.0) and diluted to obtain a protein concentration of 1 mg/ml. A 50 fold molar excess of aminooxy-PSA reagent with a MW of 20 kD (described above) is added followed by m-toluidine as a nucleophilic catalyst (10 mM final concentration) and $NaIO_4$ (final concentration: 400 μM). The coupling reaction is performed for 2 hours in the dark under gentle shaking at room temperature. Subsequently, the reaction is quenched with cysteine for 60 min at RT (cysteine concentration: 10 mM). Then the conductivity of the reaction mixture is adjusted by adding a buffer containing ammonium acetate (50 mM Hepes, 350 mM sodium chloride, 5 mM calcium chloride, 8 M ammonium acetate, pH 6.9) and loaded onto a column filled with Phenyl Sepharose FF (GE Healthcare, Fairfield, Conn.) pre-equilibrated with 50 mM Hepes, 2.5 M ammonium acetate, 350 mM sodium chloride, 5 mM calcium chloride, 0.01% Tween 80, pH 6.9. Subsequently the conjugate is eluted with 50 mM Hepes, 5 mM calcium chloride, pH 7.5. Finally, the PSA HGH-containing fractions are collected and subjected to UF/DF by use of a membrane made of regenerated cellulose (Millipore). The preparation is analytically characterized by measuring total protein (Bradford) and biological activity according to methods known in the art.

In an alternative embodiment, Method 3 is carried out as follows. As described herein, the amino acid sequence of human growth hormone (HGH) is first modified to incorporate at least one glycosylation site. Following purification, HGH is glycosylated in vitro according to methods known in the art. HGH is transferred into reaction buffer (e.g. 50 mM Hepes, 350 mM sodium chloride, 5 mM calcium chloride, pH 6.0) and diluted to obtain a protein concentration of 1 mg/ml. A 50 fold molar excess of aminooxy-PSA reagent with a MW of 20 kD (described above) is added followed by m-toluidine as a nucleophilic catalyst (10 mM final concentration) and $NaIO_4$ (final concentration: 400 μM). The coupling reaction is performed for 2 hours in the dark under gentle shaking at room temperature. Subsequently, the reaction is quenched with cysteine for 60 min at RT (cysteine concentration: 10 mM) and the conjugate is purified by ion exchange chromatography. Then the PSA-HGH-containing fractions of the eluate are collected and subjected to UF/DF by use of a membrane made of regenerated cellulose (Millipore). The preparation is analytically characterized by measuring total protein (Bradford) and biological activity according to methods known in the art.

Method 4:

As described herein, the amino acid sequence of human growth hormone (HGH) is first modified to incorporate at least one glycosylation site. Following purification, HGH is glycosylated in vitro according to methods known in the art.

HGH is dissolved in or transferred to a reaction buffer (e.g. 50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5 N aqueous HCl solution.

Subsequently, the aminooxy-polysialic acid (PSA-$ONH_2$) reagent is added in a 50-fold molar excess to this HGH-solution within a maximum time period (t) of 15 minutes under gentle stirring. Then an aqueous m-toluidine solution (50 mM) is added within 15 minutes to get a final concentration of 10 mM. Finally a 40 mM aqueous sodium periodate solution is added to give a concentration of 400 μM.

The reaction mixture is incubated for 120+/−10 min. in the dark at a temperature (T) of T=+22+/−2° C. under gentle shaking. Then the reaction is stopped by the addition of an aqueous L-cysteine solution (1 M) to give a final concentration of 10 mM in the reaction mixture and incubation for 60+/−5 min.

The obtained HGH-conjugate is purified by ion-exchange chromatography. The PSA-HGH containing fractions of the eluate are collected and concentrated by ultra-/diafiltration (UF/DF) using a membrane made of regenerated cellulose (Millipore).

The conjugates prepared by use of this procedure are analytically characterized by measuring total protein, biological activity according to methods known in the art, and determination of the polysialylation degree by measuring the PSA content (resorcinol assay).

Example 24

Polysialylation of TNF-Alpha Using Aminooxy-PSA and m-Toluidine as a Nucleophilic Catalyst A starting concentration of tumor necrosis factor-alpha (TNF-alpha) is transferred into a reaction buffer (e.g., 50 mM Hepes, 350 mM sodium chloride, 5 mM calcium chloride, pH 6.0) and diluted to obtain a protein concentration of 1 mg/ml. To this solution, $NaIO_4$ is added to give a final concentration of 200 μM. The oxidation is carried at RT for 30 min in the dark under gentle shaking. The reaction is then quenched with cysteine (final concentration: 10 mM) for 60 min at RT.

The solution is next subjected to UF/DF employing Vivaspin centrifugal filtrators to remove excess periodate, quencher and the byproducts thereof or, in the alternative, to an IEX column with a volume of 20 ml (Merck EMD TMAE (M)) which is equilibrated with Buffer A (20 mM Hepes, 5 mM $CaCl_2$, pH 7.0). The column is equilibrated with 5 CV Buffer A. The oxidized TNF-alpha is eluted with Buffer B (20 mM Hepes, 5 mM $CaCl_2$, 1M NaCl, pH 7.0). The TNF-alpha containing fractions are collected. The protein content is determined (Coomassie, Bradford) and adjusted to 1 mg/ml with reaction buffer and adjusted to pH 6.0 by dropwise addition of 0.5 M HCl.

A 50-fold molar excess of aminooxy-PSA reagent with a MW of 20 kD (described above) is added followed by m-toluidine as a nucleophilic catalyst (final concentration: 10 mM). The coupling reaction is performed for 2 hours in the dark under gentle shaking at room temperature. The excess of aminooxy reagent is removed by means of HIC. The conductivity of the reaction mixture is adjusted by adding a buffer containing ammonium acetate (50 mM Hepes, 350 mM sodium chloride, 5 mM calcium chloride, 8 M ammonium acetate, pH 6.9) and loaded onto a column filled with 80 ml Phenyl Sepharose FF (GE Healthcare, Fairfield, Conn.) pre-equilibrated with 50 mM Hepes, 2.5 M ammonium acetate, 350 mM sodium chloride, 5 mM calcium chloride, pH 6.9. Subsequently, the conjugate is eluted with 50 mM Hepes buffer pH 7.5 containing 5 mM $CaCl_2$. Finally the PSA-TNF-alpha-containing fractions are collected and subjected to UF/DF by use of a membrane made of regenerated cellulose (Millipore). The preparation is next analytically characterized by measuring total protein (Coomassie, Bradford) and biological activity according to methods known in the art.

In an alternative embodiment, Method 1 is carried out as follows. Tumor necrosis factor-alpha (TNF-alpha) is transferred into a reaction buffer (e.g. 50 mM Hepes, 350 mM sodium chloride, 5 mM calcium chloride, pH 6.0) and diluted to obtain a protein concentration of 1 mg/ml. To this solution, $NaIO_4$ is added to give a final concentration of 200 μM. The oxidation is carried at RT for 30 min in the dark under gentle shaking. The reaction is then quenched with cysteine (final concentration: 10 mM) for 60 min at RT.

The solution is next subjected to UF/DF employing Vivaspin centrifugal filtrators to remove excess periodate, quencher and the byproducts thereof. A 50-fold molar excess of aminooxy-PSA reagent with a MW of 20 kD (described above) is added followed by m-toluidine as a nucleophilic catalyst (final concentration: 10 mM). The coupling reaction is performed for 2 hours in the dark under gentle shaking at room temperature. The excess of aminooxy reagent is removed by means of ion exchange chromatography. The PSA-TNF-alpha containing fractions of the eluate are collected and subjected to UF/DF by use of a membrane made of regenerated cellulose (Millipore). The preparation is next analytically characterized by measuring total protein (Coomassie, Bradford) and biological activity according to methods known in the art.

Method 2:

TNF-alpha is transferred or dissolved in reaction buffer (e.g. 50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5 N aqueous HCl solution. Subsequently, a 40 mM aqueous sodium periodate solution is added within 10 minutes to give a concentration of 200 μM. The oxidation reaction is carried out for 30+/−5 min at a temperature (T) of T=+22+/−2° C. Then the reaction is stopped by addition of an aqueous L-cysteine solution (1 M) within 15 minutes at T=+22+/−2° C. to give a final concentration of 10 mM in the reaction mixture and incubation for 60+/−5 min.

The oxidized TNF-alpha is further purified by ion exchange chromatography. The oxidized TNF-alpha containing fractions of the eluate are collected and used for the conjugation reaction.

The aminooxy-polysialic acid (PSA-$ONH_2$) reagent is added in a 50-fold molar excess to the eluate containing the purified oxidized TNF-alpha within a maximum time period (t) of 15 minutes under gentle stirring. Then an aqueous m-toluidine solution (50 mM) is added within 15 minutes to get a final concentration of 10 mM. The reaction mixture is incubated for 120+/−10 min. at pH 6.0 in the dark at a temperature (T) of T=+22+/−2° C. under gentle shaking (protein concentration: 1 mg/ml).

The obtained PSA-TNF-alpha conjugate is further purified by ion exchange chromatography. The PSA-TNF-alpha conjugate containing fractions are collected and concentrated by ultra-/diafiltration (UF/DF) using a membrane made of regenerated cellulose with an appropriate molecular weight cut off (Millipore).

The conjugate prepared by use of this procedure is analytically characterized by measuring total protein, biological activity, and determination of the polysialylation degree by measuring the PSA content (resorcinol assay).

Method 3:

Tumor necrosis factor-alpha (TNF-alpha) is transferred into reaction buffer (e.g. 50 mM Hepes, 350 mM sodium chloride, 5 mM calcium chloride, pH 6.0) and diluted to obtain a protein concentration of 1 mg/ml. A 50-fold molar excess of aminooxy-PSA reagent with a MW of 20 kD (described above) is added followed by m-toluidine as a nucleophilic catalyst (10 mM final concentration) and $NaIO_4$ (final concentration: 400 μM). The coupling reaction is performed for 2 hours in the dark under gentle shaking at room temperature. Subsequently, the reaction is quenched with cysteine for 60 min at RT (cysteine concentration: 10 mM). Then the conductivity of the reaction mixture is adjusted by adding a buffer containing ammonium acetate (50 mM Hepes, 350 mM sodium chloride, 5 mM calcium chloride, 8 M ammonium acetate, pH 6.9) and loaded onto a column filled with Phenyl Sepharose FF (GE Healthcare, Fairfield, Conn.) pre-equilibrated with 50 mM Hepes, 2.5 M ammonium acetate, 350 mM sodium chloride, 5 mM calcium chloride, 0.01% Tween 80, pH 6.9. Subsequently the conjugate is eluted with 50 mM Hepes, 5 mM calcium chloride, pH 7.5. Finally the PSA-TNF-alpha-containing fractions are collected and subjected to UF/DF by use of a membrane made of regenerated cellulose (Millipore). The preparation is analytically characterized by measuring total protein (Bradford) and biological activity according to methods known in the art.

In an alternative embodiment, Method 3 is carried out as follows. Tumor necrosis factor-alpha (TNF-alpha) is transferred into reaction buffer (e.g. 50 mM Hepes, 350 mM sodium chloride, 5 mM calcium chloride, pH 6.0) and diluted to obtain a protein concentration of 1 mg/ml. A 50-fold molar excess of aminooxy-PSA reagent with a MW of 20 kD (described above) is added followed by m-toluidine as a nucleophilic catalyst (10 mM final concentration) and $NaIO_4$ (final concentration: 400 μM). The coupling reaction is performed for 2 hours in the dark under gentle shaking at room temperature. Subsequently, the reaction is quenched with cysteine for 60 min at RT (cysteine concentration: 10 mM). and the conjugate is purified by ion exchange chromatography. The PSA-TNF-alpha containing fractions of the eluate are collected and subjected to UF/DF by use of a membrane made of regenerated cellulose (Millipore). The preparation is analytically characterized by measuring total protein (Bradford) and biological activity according to methods known in the art.

Method 4:

TNF-alpha is dissolved in or transferred to a reaction buffer (e.g. 50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5 N aqueous HCl solution.

Subsequently the aminooxy-polysialic acid ($PSA-ONH_2$) reagent is added in a 50-fold molar excess to this TNF-alpha-solution within a maximum time period (t) of 15 minutes under gentle stirring. Then an aqueous m-toluidine solution (50 mM) is added within 15 minutes to get a final concentration of 10 mM. Finally a 40 mM aqueous sodium periodate solution is added to give a concentration of 400 μM.

The reaction mixture is incubated for 120+/−10 min. in the dark at a temperature (T) of T=+22+/−2° C. under gentle shaking. Then the reaction is stopped by the addition of an aqueous L-cysteine solution (1 M) to give a final concentration of 10 mM in the reaction mixture and incubation for 60+/−5 min.

The obtained TNF-alpha conjugate is purified by ion-exchange chromatography. The PSA-TNF-alpha containing fractions of the eluate are collected and concentrated by ultra-/diafiltration (UF/DF) using a membrane made of regenerated cellulose (Millipore).

The conjugates prepared by use of this procedure are analytically characterized by measuring total protein, biological activity according to methods known in the art, and determination of the polysialylation degree by measuring the PSA content (resorcinol assay).

Example 25

Polysialylation of Insulin Using Aminooxy-PSA and m-Toluidine as a Nucleophilic Catalyst Method 1:

As described herein, the amino acid sequence of insulin is first modified to incorporate at least one glycosylation site. Following purification, insulin is glycosylated in vitro according to methods known in the art. A starting concentration of insulin is transferred into a reaction buffer (e.g., 50 mM Hepes, 350 mM sodium chloride, 5 mM calcium chloride, pH 6.0) and diluted to obtain a protein concentration of 1 mg/ml. To this solution, $NaIO_4$ is added to give a final concentration of 200 μM. The oxidation is carried at RT for 30 min in the dark under gentle shaking. The reaction is then quenched with cysteine (final concentration: 10 mM) for 60 min at RT.

The solution is next subjected to UF/DF employing Vivaspin centrifugal filtrators to remove excess periodate, quencher and the byproducts thereof or, in the alternative, to an IEX column with a volume of 20 ml (Merck EMD TMAE (M)) which is equilibrated with Buffer A (20 mM Hepes, 5 mM $CaCl_2$, pH 7.0). The column is equilibrated with 5 CV Buffer A. The oxidized insulin is eluted with Buffer B (20 mM Hepes, 5 mM $CaCl_2$, 1 M NaCl, pH 7.0). The insulin containing fractions are collected. The protein content is determined (Coomassie, Bradford) and adjusted to 1 mg/ml with reaction buffer and adjusted to pH 6.0 by dropwise addition of 0.5 M HCl.

A 50-fold molar excess of aminooxy-PSA reagent with a MW of 20 kD (described above) is added followed by m-toluidine as a nucleophilic catalyst (final concentration: 10 mM). The coupling reaction is performed for 2 hours in the dark under gentle shaking at room temperature. The excess of aminooxy reagent is removed by means of HIC. The conductivity of the reaction mixture is adjusted by adding a buffer containing ammonium acetate (50 mM Hepes, 350 mM sodium chloride, 5 mM calcium chloride, 8 M ammonium acetate, pH 6.9) and loaded onto a column filled with 80 ml Phenyl Sepharose FF (GE Healthcare, Fairfield, Conn.) pre-equilibrated with 50 mM Hepes, 2.5 M ammonium acetate, 350 mM sodium chloride, 5 mM calcium chloride, pH 6.9. Subsequently the conjugate is eluted with 50 mM Hepes buffer pH 7.5 containing 5 mM $CaCl_2$. Finally the PSA-insulin containing fractions are collected and subjected to UF/DF by use of a membrane made of regenerated cellulose (Millipore). The preparation is next analytically characterized by measuring total protein (Coomassie, Bradford) and biological activity according to methods known in the art.

In an alternative embodiment, Method 1 is carried out as follows. As described herein, the amino acid sequence of insulin is first modified to incorporate at least one glycosylation site. Following purification, insulin is glycosylated in vitro according to methods known in the art. Insulin is transferred into a reaction buffer (e.g., 50 mM Hepes, 350 mM sodium chloride, 5 mM calcium chloride, pH 6.0) and diluted to obtain a protein concentration of 1 mg/ml. To this solution, $NaIO_4$ is added to give a final concentration of 200 μM. The oxidation is carried at RT for 30 min in the dark under gentle shaking. The reaction is then quenched with cysteine (final concentration: 10 mM) for 60 min at RT.

The solution is next subjected to UF/DF employing Vivaspin centrifugal filtrators to remove excess periodate, quencher and the byproducts thereof.

A 50-fold molar excess of aminooxy-PSA reagent with a MW of 20 kD (described above) is added followed by m-toluidine as a nucleophilic catalyst (final concentration: 10 mM). The coupling reaction is performed for 2 hours in the dark under gentle shaking at room temperature. The excess of aminooxy reagent is removed by means of ion exchange chromatography. The PSA-insulin containing fractions of the eluate are collected and subjected to UF/DF by use of a membrane made of regenerated cellulose (Millipore). The preparation is next analytically characterized by measuring total protein (Coomassie, Bradford) and biological activity according to methods known in the art.

Method 2:

As described herein, the amino acid sequence of insulin is first modified to incorporate at least one glycosylation site. Following purification, insulin is glycosylated in vitro according to methods known in the art.

Insulin is transferred or dissolved in reaction buffer (e.g. 50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5 N aqueous HCl solution. Subsequently, a 40 mM aqueous sodium periodate solution is added within 10 minutes to give a concentration of 200 μM. The oxidation reaction is carried out for 30+/−5 min at a temperature (T) of T=+22+/−2° C. Then the reaction is stopped by addition of an aqueous L-cysteine solution (1 M) within 15 minutes at T=+22+/−2° C. to give a final concentration of 10 mM in the reaction mixture and incubation for 60+/−5 min.

The oxidized insulin is further purified by ion exchange chromatography. The oxidized insulin containing fractions of the eluate are collected and used for the conjugation reaction.

The aminooxy-polysialic acid ($PSA-ONH_2$) reagent is added in a 50-fold molar excess to the eluate containing the purified oxidized insulin within a maximum time period (t) of 15 minutes under gentle stirring. Then an aqueous m-toluidine solution (50 mM) is added within 15 minutes to get a final concentration of 10 mM. The reaction mixture is incubated for 120+/−10 min. at pH 6.0 in the dark at a temperature (T) of T=+22+/−2° C. under gentle shaking (protein concentration: 1 mg/ml).

The obtained PSA-insulin conjugate is further purified by ion exchange chromatography. The PSA-insulin conjugate containing fractions are collected and concentrated by ultra-/diafiltration (UF/DF) using a membrane made of regenerated cellulose with an appropriate molecular weight cut off (Millipore).

The conjugate prepared by use of this procedure is analytically characterized by measuring total protein, biological activity, and determination of the polysialylation degree by measuring the PSA content (resorcinol assay).

Method 3:

As described herein, the amino acid sequence of insulin is first modified to incorporate at least one glycosylation site. Following purification, insulin is glycosylated in vitro according to methods known in the art.

Insulin is transferred into reaction buffer (50 mM Hepes, 350 mM sodium chloride, 5 mM calcium chloride, pH 6.0) and diluted to obtain a protein concentration of 1 mg/ml. A 50-fold molar excess of aminooxy-PSA reagent with a MW of 20 kD (described above) is added followed by m-toluidine as a nucleophilic catalyst (10 mM final concentration) and $NaIO_4$ (final concentration: 400 μM). The coupling reaction is performed for 2 hours in the dark under gentle shaking at room temperature. Subsequently, the reaction is quenched with cysteine for 60 min at RT (cysteine concentration: 10 mM). Then the conductivity of the reaction mixture is adjusted by adding a buffer containing ammonium acetate (50 mM Hepes, 350 mM sodium chloride, 5 mM calcium chloride, 8 M ammonium acetate, pH 6.9) and loaded onto a column filled with Phenyl Sepharose FF (GE Healthcare, Fairfield, Conn.) pre-equilibrated with 50 mM Hepes, 2.5 M ammonium acetate, 350 mM sodium chloride, 5 mM calcium chloride, 0.01% Tween 80, pH 6.9. Subsequently the conjugate is eluted with 50 mM Hepes, 5 mM calcium chloride, pH 7.5. Finally, the PSA-insulin containing fractions are collected and subjected to UF/DF by use of a membrane made of regenerated cellulose (Millipore). The preparation is analytically characterized by measuring total protein (Bradford) and biological activity according to methods known in the art.

In an alternative embodiment, Method 3 is carried out as follows. As described herein, the amino acid sequence of insulin is first modified to incorporate at least one glycosylation site. Following purification, insulin is glycosylated in vitro according to methods known in the art.

Insulin is transferred into reaction buffer (e.g. 50 mM Hepes, 350 mM sodium chloride, 5 mM calcium chloride, pH 6.0) and diluted to obtain a protein concentration of 1 mg/ml. A 50-fold molar excess of aminooxy-PSA reagent with a MW of 20 kD (described above) is added followed by m-toluidine as a nucleophilic catalyst (10 mM final concentration) and $NaIO_4$ (final concentration: 400 μM). The coupling reaction is performed for 2 hours in the dark under gentle shaking at room temperature. Subsequently, the reaction is quenched with cysteine for 60 min at RT (cysteine concentration: 10 mM) and the conjugate is purified by ion exchange chromatography. PSA-insulin containing fractions of the eluate are collected and subjected to UF/DF by use of a membrane made of regenerated cellulose (Millipore). The preparation is analytically characterized by measuring total protein (Bradford) and biological activity according to methods known in the art.

Method 4:

As described herein, the amino acid sequence of insulin is first modified to incorporate at least one glycosylation site. Following purification, insulin is glycosylated in vitro according to methods known in the art.

Insulin is dissolved in or transferred to a reaction buffer (e.g. 50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5 N aqueous HCl solution.

Subsequently, the aminooxy-polysialic acid ($PSA-ONH_2$) reagent is added in a 50-fold molar excess to this insulin-solution within a maximum time period (t) of 15 minutes under gentle stirring. Then an aqueous m-toluidine solution (50 mM) is added within 15 minutes to get a final concentration of 10 mM. Finally a 40 mM aqueous sodium periodate solution is added to give a concentration of 400 μM.

The reaction mixture is incubated for 120+/−10 min. in the dark at a temperature (T) of T=+22+/−2° C. under gentle shaking. Then the reaction is stopped by the addition of an aqueous L-cysteine solution (1 M) to give a final concentration of 10 mM in the reaction mixture and incubation for 60+/−5 min.

The obtained insulin conjugate is purified by ion-exchange chromatography. The PSA-insulin containing fractions of the eluate are collected and concentrated by ultra-/diafiltration (UF/DF) using a membrane made of regenerated cellulose (Millipore).

The conjugates prepared by use of this procedure are analytically characterized by measuring total protein, biological activity according to methods known in the art, and determination of the polysialylation degree by measuring the PSA content (resorcinol assay).

Example 26

Polysialylation of Interferon-Alpha Using Aminooxy-PSA and m-Toluidine as a Nucleophilic Catalyst Method 1:

A starting concentration of interferon-alpha is transferred into a reaction buffer (e.g., 50 mM Hepes, 350 mM sodium chloride, 5 mM calcium chloride, pH 6.0) and diluted to obtain a protein concentration of 1 mg/ml. To this solution, $NaIO_4$ is added to give a final concentration of 200 μM. The oxidation is carried at RT for 30 min in the dark under gentle shaking. The reaction is then quenched with cysteine (final concentration: 10 mM) for 60 min at RT.

The solution is next subjected to UF/DF employing Vivaspin centrifugal filtrators to remove excess periodate, quencher and the byproducts thereof or, in the alternative, to an IEX column with a volume of 20 ml (Merck EMD TMAE (M)) which is equilibrated with Buffer A (20 mM Hepes, 5 mM $CaCl_2$, pH 7.0). The column is equilibrated with 5 CV Buffer A. The oxidized interferon-alpha is eluted with Buffer B (20 mM Hepes, 5 mM $CaCl_2$, 1M NaCl, pH 7.0). The interferon-alpha containing fractions are collected. The protein content is determined (Coomassie, Bradford) and adjusted to 1 mg/ml with reaction buffer and adjusted to pH 6.0 by dropwise addition of 0.5 M HCl.

A 50-fold molar excess of aminooxy-PSA reagent with a MW of 20 kD (described above) is added followed by m-toluidine as a nucleophilic catalyst (final concentration: 10 mM). The coupling reaction is performed for 2 hours in the dark under gentle shaking at room temperature. The excess of aminooxy reagent is removed by means of HIC. The conductivity of the reaction mixture is adjusted by adding a buffer containing ammonium acetate (50 mM Hepes, 350 mM sodium chloride, 5 mM calcium chloride, 8 M ammonium acetate, pH 6.9) and loaded onto a column filled with 80 ml Phenyl Sepharose FF (GE Healthcare, Fairfield, Conn.) pre-equilibrated with 50 mM Hepes, 2.5 M ammonium acetate, 350 mM sodium chloride, 5 mM calcium chloride, pH 6.9. Subsequently, the conjugate is eluted with 50 mM Hepes buffer pH 7.5 containing 5 mM $CaCl_2$. Finally the PSA-interferon-alpha containing fractions are collected and subjected to UF/DF by use of a membrane made of regenerated cellulose (Millipore). The preparation is next analytically characterized by measuring total protein (Coomassie, Bradford) and biological activity according to methods known in the art.

In an alternative embodiment, Method 1 is carried out as follows. Interferon-alpha is transferred into a reaction buffer (e.g. 50 mM Hepes, 350 mM sodium chloride, 5 mM calcium chloride, pH 6.0) and diluted to obtain a protein concentration of 1 mg/ml. To this solution, $NaIO_4$ is added to give a final concentration of 200 μM. The oxidation is carried at RT for 30 min in the dark under gentle shaking. The reaction is then quenched with cysteine (final concentration: 10 mM) for 60 min at RT.

The solution is next subjected to UF/DF employing Vivaspin centrifugal filtrators to remove excess periodate, quencher and the byproducts thereof.

A 50-fold molar excess of aminooxy-PSA reagent with a MW of 20 kD (described above) is added followed by m-toluidine as a nucleophilic catalyst (final concentration: 10 mM). The coupling reaction is performed for 2 hours in the dark under gentle shaking at room temperature. The excess of aminooxy reagent is removed by means of ion-exchange chromatography. The PSA-interferon-alpha containing fractions of the eluate are collected and subjected to UF/DF by use of a membrane made of regenerated cellulose (Millipore). The preparation is next analytically characterized by measuring total protein (Coomassie, Bradford) and biological activity according to methods known in the art.

Method 2:

Interferon-alpha is transferred or dissolved in reaction buffer (e.g. 50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5 N aqueous HCl solution. Subsequently, a 40 mM aqueous sodium periodate solution is added within 10 minutes to give a concentration of 200 μM. The oxidation reaction is carried out for 30+/−5 min at a temperature (T) of T=+22+/−2° C. Then the reaction is stopped by addition of an aqueous L-cysteine solution (1 M) within 15 minutes at T=+22+/−2° C. to give a final concentration of 10 mM in the reaction mixture and incubation for 60+/−5 min.

The oxidized interferon-alpha is further purified by ion exchange chromatography. The oxidized interferon-alpha containing fractions of the eluate are collected and used for the conjugation reaction.

The aminooxy-polysialic acid ($PSA-ONH_2$) reagent is added in a 50-fold molar excess to the eluate containing the purified oxidized interferon-gamma within a maximum time period (t) of 15 minutes under gentle stirring. Then an aqueous m-toluidine solution (50 mM) is added within 15 minutes to get a final concentration of 10 mM. The reaction mixture is incubated for 120+/−10 min. at pH 6.0 in the dark at a temperature (T) of T=+22+/−2° C. under gentle shaking (protein concentration: 1 mg/ml).

The obtained PSA-interferon-alpha conjugate is further purified by ion exchange chromatography. The PSA-interferon-alpha conjugate containing fractions are collected and concentrated by ultra-/diafiltration (UF/DF) using a membrane made of regenerated cellulose with an appropriate molecular weight cut off (Millipore).

Method 3:

Interferon-alpha is transferred into reaction buffer (50 mM Hepes, 350 mM sodium chloride, 5 mM calcium chloride, pH 6.0) and diluted to obtain a protein concentration of 1 mg/ml. A 50-fold molar excess of a PSA aminooxy reagent with a MW of 20 kD (described above) is added followed by m-toluidine as a nucleophilic catalyst (10 mM final concentration) and $NaIO_4$ (final concentration: 400 μM). The coupling reaction is performed for 2 hours in the dark under gentle shaking at room temperature. Subsequently, the reaction is quenched with cysteine for 60 min at RT (cysteine concentration: 10 mM). Then the conductivity of the reaction mixture is adjusted by adding a buffer containing ammonium acetate (50 mM Hepes, 350 mM sodium chloride, 5 mM calcium chloride, 8 M ammonium acetate, pH 6.9) and loaded onto a column filled with Phenyl Sepharose FF (GE Healthcare, Fairfield, Conn.) pre-equilibrated with 50 mM Hepes, 2.5 M ammonium acetate, 350 mM sodium chloride, 5 mM calcium chloride, 0.01% Tween 80, pH 6.9. Subsequently the conjugate is eluted with 50 mM Hepes, 5 mM calcium chloride, pH 7.5. Finally, the PSA-interferon-alpha containing fractions are collected and subjected to UF/DF by use of a membrane made of regenerated cellulose (Millipore). The preparation is analytically characterized by measuring total protein (Bradford) and biological activity according to methods known in the art.

In an alternative embodiment, Method 3 is carried out as follows. Interferon-alpha is transferred into reaction buffer (e.g. 50 mM Hepes, 350 mM sodium chloride, 5 mM calcium chloride, pH 6.0) and diluted to obtain a protein concentration of 1 mg/ml. A 50-fold molar excess of aminooxy-PSA reagent with a MW of 20 kD (described above) is added followed by m-toluidine as a nucleophilic catalyst (10 mM final concentration) and $NaIO_4$ (final concentration: 400 μM). The coupling reaction is performed for 2 hours in the dark under gentle shaking at room temperature. Subsequently, the reaction is quenched with cysteine for 60 min at RT (cysteine concentration: 10 mM) and the conjugate is purified by ion exchange chromatography. The PSA-interferon-alpha containing fractions of the eluate are collected and subjected to UF/DF by use of a membrane made of regenerated cellulose (Millipore). The preparation is analytically characterized by measuring total protein (Bradford) and biological activity according to methods known in the art.

Method 4:

Interferon-alpha is dissolved in or transferred to a reaction buffer (e.g. 50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5 N aqueous HCl solution.

Subsequently, the aminooxy-polysialic acid ($PSA-ONH_2$) reagent is added in a 50-fold molar excess to this interferon-alpha solution within a maximum time period (t) of 15 minutes under gentle stirring. Then an aqueous m-toluidine solution (50 mM) is added within 15 minutes to get a final concentration of 10 mM. Finally, a 40 mM aqueous sodium periodate solution is added to give a concentration of 400 μM.

The reaction mixture is incubated for 120+/−10 min. in the dark at a temperature (T) of T=+22+/−2° C. under gentle shaking. Then the reaction is stopped by the addition of an aqueous L-cysteine solution (1 M) to give a final concentration of 10 mM in the reaction mixture and incubation for 60+/−5 min.

The obtained interferon-alpha conjugate is purified by ion-exchange chromatography. The PSA-interferon-alpha containing fractions of the eluate are collected and concentrated by ultra-/diafiltration (UF/DF) using a membrane made of regenerated cellulose (Millipore).

The conjugates prepared by use of this procedure are analytically characterized by measuring total protein, biological activity according to methods known in the art, and determination of the polysialylation degree by measuring the PSA content (resorcinol assay).

Example 27

Polysialylation of Interferon-Gamma Using Aminooxy-PSA and m-Toluidine as a Nucleophilic Catalyst Method 1:

10 mg interferon-gamma is dissolved in 5 ml histidine buffer, pH 6.0 (20 mM L-histidine, 150 mM NaCl). 100 μl of an aqueous sodium periodate solution (5 mM) is then added and the reaction mixture is incubated for 1 h in the dark at 4° C. under gentle stirring and quenched for 15 min at room temperature by the addition of 50 μl of a 1 M aqueous cysteine solution. The mixture is subsequently subjected to UF/DF employing Vivaspin 15R 10 kD centrifugal filtrators to remove excess periodate, quencher and the byproducts thereof.

The retentate (approx. 7 ml), containing oxidized interferon-gamma, is mixed with 2 ml of an aqueous m-toluidine solution (50 mM) and incubated for 30 min at room temperature. Then aminooxy-PSA reagent with a MW of 20 kD (described above) is added to give a 5-fold molar reagent excess. This mixture is incubated for 2.5 h at RT in the dark under gentle stirring.

The free Interferon-gamma is removed by means of cation exchange chromatography (CEC). The reaction mixture is diluted with 20 ml Buffer A (50 mM Hepes, pH 6.5) and loaded onto a 20 ml HiPrep SPFF 16/10 column (GE Healthcare, Fairfield, Conn.) pre-equilibrated with Buffer A. Then the column is eluted with Buffer B (50 mM Hepes, 1 M NaCl, pH 6.5). Free interferon-gamma is eluted by washing the column with 25% Buffer B and the conjugate at 50% Buffer B. The conductivity of the conjugate containing fractions is subsequently raised to ~190 mS/cm with Buffer C (50 mM Hepes, 5 M NaCl, pH 6.9) and loaded onto a 20 ml HiPrep Butyl FF 16/10 column (GE Healthcare, Fairfield, Conn.) pre-equilibrated with Buffer D (50 mM Hepes, 3 M NaCl, pH 6.9). Free PSA-reagent is washed out within 5 CV Buffer D. Subsequently, the conjugate is eluted with 100% Buffer E (50 mM Hepes, pH 6.9). The conjugate containing fractions are concentrated by UF/DF using a 10 kD membrane made of regenerated cellulose (88 cm2, cut-off 10 kD, Millipore). The final diafiltration step is performed against histidine buffer, pH 6.9 containing 150 mM NaCl. The preparation is analytically characterized by measuring total protein (Bradford) and biological activity according to methods known in the art. For the PSA-Interferon-gamma conjugate a specific activity of >50% in comparison to native Interferon-gamma is determined. The conjugate is additionally analytically characterized by Size Exclusion HPLC using a Agilent 1200 HPLC system equipped with a Shodex KW 803 column under conditions as previously described (Kolarich et al, Transfusion 2006; 46:1959-77). It is shown that the preparation contains no free Interferon gamma.

Method 2:

10 mg interferon-gamma is dissolved in 8 ml histidine buffer, pH 6.0 (20 mM L-histidine, 150 mM NaCl). 200 μl of an aqueous sodium periodate solution (5 mM) and 2 ml of an aqueous m-toluidine solution (50 mM) are then added. Subsequently the aminooxy-PSA reagent with a MW of 20 kD (described above) is added to give a 5-fold molar reagent excess. The mixture is incubated for 2 h in the dark at room temperature under gentle stirring and quenched for 15 min at room temperature by the addition of 100 μl of 1 M aqueous cysteine solution.

The free interferon gamma is removed by means of cation exchange chromatography (CEC). The reaction mixture is diluted with 20 ml Buffer A (50 mM Hepes, pH 6.5) and loaded onto a 20 ml HiPrep SPFF 16/10 column (GE Healthcare, Fairfield, Conn.) pre-equilibrated with Buffer A. Then the column is eluted with Buffer B (50 mM Hepes, 1 M NaCl, pH 6.5). Free interferon-gamma is eluted by washing the column with 25% Buffer B and the conjugate at 50% Buffer B. The conductivity of the conjugate containing fractions is subsequently raised to ~190 mS/cm with Buffer C (50 mM Hepes, 5 M NaCl, pH 6.9) and loaded onto a 20 ml HiPrep Butyl FF 16/10 column (GE Healthcare, Fairfield, Conn.) pre-equilibrated with Buffer D (50 mM Hepes, 3 M NaCl, pH 6.9). Free PSA-reagent is washed out within 5 CV Buffer D. Subsequently, the conjugate is eluted with 100% Buffer E (50 mM Hepes, pH 6.9). The conjugate containing fractions are concentrated by UF/DF using a 10 kD membrane made of regenerated cellulose (88 cm2, cut-off 10 kD/Millipore). The final diafiltration step is performed against histidine buffer, pH 6.9 containing 150 mM NaCl. The preparation is analytically characterized by measuring total protein (Bradford) and biological activity according to methods known in the art. For the PSAinterferon-gamma conjugate a specific activity of >50% in comparison to native interferon-gamma is determined. The conjugate is additionally analytically characterized by Size Exclusion HPLC using a Agilent 1200 HPLC system equipped with a Shodex KW 803 column under conditions as previously described (Kolarich et al, Transfusion 2006; 46:1959-77). It is shown that the preparation contains no free interferon-gamma.

Method 3:

10 mg interferon-gamma is dissolved in 8 ml histidine buffer, pH 6.0 (20 mM L-histidine, 150 mM NaCl). 200 μl of an aqueous sodium periodate solution (5 mM) and 2 ml of an aqueous m-toluidine solution (50 mM) are then added. Subsequently the aminooxy-PSA reagent with a MW of 20 kD (described above) is added to give a 5-fold molar reagent excess. The mixture is incubated for 2 h in the dark at room temperature under gentle stirring and quenched for 15 min at room temperature by the addition of 100 μl of 1 M aqueous cysteine solution.

The free interferon gamma is removed by means of cation exchange chromatography (CEC). The reaction mixture is diluted with 20 ml Buffer A (50 mM Hepes, pH 6.5) and loaded onto a 20 ml HiPrep SPFF 16/10 column (GE Healthcare, Fairfield, Conn.) pre-equilibrated with Buffer A. Then the column is eluted with Buffer B (50 mM Hepes, 1 M NaCl, pH 6.5). Free interferon-gamma is eluted by washing the column with 25% Buffer B and the conjugate at 50% Buffer B. The conductivity of the conjugate containing fractions is subsequently raised to ~190 mS/cm with Buffer C (50 mM Hepes, 5 M NaCl, pH 6.9) and loaded onto a 20 ml HiPrep Butyl FF 16/10 column (GE Healthcare, Fairfield, Conn.) pre-equilibrated with Buffer D (50 mM Hepes, 3 M NaCl, pH 6.9). Free PSA-reagent is washed out within 5 CV Buffer D. Subsequently the conjugate is eluted with 100% Buffer E (50 mM Hepes, pH 6.9). The conjugate containing fractions are concentrated by UF/DF using a 10 kD membrane made of regenerated cellulose (88 cm2, cut-off 10 kD/Millipore). The final diafiltration step is performed against histidine buffer, pH 6.9 containing 150 mM NaCl. The preparation is analytically characterized by measuring total protein (Bradford) and biological activity according to methods known in the art. For the PSAinterferon-gamma conjugate a specific activity of >50% in comparison to native interferon-gamma is determined. The conjugate is additionally analytically characterized by Size Exclusion HPLC using a Agilent 1200 HPLC system equipped with a Shodex KW 803 column under conditions as previously described (Kolarich et al, Transfusion 2006; 46:1959-77). It is shown that the preparation contains no free interferon-gamma.

Method 4:

Interferon-gamma is dissolved in or transferred to a reaction buffer (e.g. 50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5 N aqueous HCl solution.

Subsequently, the aminooxy-polysialic acid ($PSA-ONH_2$) reagent is added in a 50-fold molar excess to this interferon-gamma solution within a maximum time period (t) of 15 minutes under gentle stirring. Then an aqueous m-toluidine solution (50 mM) is added within 15 minutes to get a final concentration of 10 mM. Finally, a 40 mM aqueous sodium periodate solution is added to give a concentration of 400 μM.

The reaction mixture is incubated for 120+/−10 min. in the dark at a temperature (T) of T=+22+/−2° C. under gentle shaking. Then the reaction is stopped by the addition of an aqueous L-cysteine solution (1 M) to give a final concentration of 10 mM in the reaction mixture and incubation for 60+/−5 min.

The obtained interferon-gamma conjugate is purified by ion-exchange chromatography. The PSA-interferon-gamma containing fractions of the eluate are collected and concentrated by ultra-/diafiltration (UF/DF) using a membrane made of regenerated cellulose (Millipore).

The conjugates prepared by use of this procedure are analytically characterized by measuring total protein, biological activity according to methods known in the art, and determination of the polysialylation degree by measuring the PSA content (resorcinol assay).

Example 28

Polysialylation of G-CSF Using Aminooxy-PSA and m-Toluidine as a Nucleophilic Catalyst Method 1:

A starting concentration of granulocyte-colony stimulating factor (G-CSF) is transferred into a reaction buffer (e.g., 50 mM Hepes, 350 mM sodium chloride, 5 mM calcium chloride, pH 6.0) and diluted to obtain a protein concentration of 1 mg/ml. To this solution, $NaIO_4$ is added to give a final concentration of 200 μM. The oxidation is carried at RT for 30 min in the dark under gentle shaking. The reaction is then quenched with cysteine (final concentration: 10 mM) for 60 min at RT.

The solution is next subjected to UF/DF employing Vivaspin centrifugal filtrators to remove excess periodate, quencher and the byproducts thereof or, in the alternative, to an IEX column with a volume of 20 ml (Merck EMD TMAE (M)) which is equilibrated with Buffer A (20 mM Hepes, 5 mM $CaCl_2$, pH 7.0). The column is equilibrated with 5 CV Buffer A. The oxidized G-CSF is eluted with Buffer B (20 mM Hepes, 5 mM $CaCl_2$, 1 M NaCl, pH 7.0). The G-CSF containing fractions are collected. The protein content is determined (Coomassie, Bradford) and adjusted to 1 mg/ml with reaction buffer and adjusted to pH 6.0 by dropwise addition of 0.5 M HCl.

A 50-fold molar excess of aminooxy-PSA reagent with a MW of 20 kD (described above) is added followed by m-toluidine as a nucleophilic catalyst (final concentration: 10 mM). The coupling reaction is performed for 2 hours in the dark under gentle shaking at room temperature. The excess of aminooxy reagent is removed by means of HIC. The conductivity of the reaction mixture is adjusted by adding a buffer containing ammonium acetate (50 mM Hepes, 350 mM sodium chloride, 5 mM calcium chloride, 8 M ammonium acetate, pH 6.9) and loaded onto a column filled with 80 ml Phenyl Sepharose FF (GE Healthcare, Fairfield, Conn.) pre-equilibrated with 50 mM Hepes, 2.5 M ammonium acetate, 350 mM sodium chloride, 5 mM calcium chloride, pH 6.9. Subsequently, the conjugate is eluted with 50 mM Hepes buffer pH 7.5 containing 5 mM $CaCl_2$. Finally the PSA-G-CSF-containing fractions are collected and subjected to UF/DF by use of a membrane made of regenerated cellulose (Millipore). The preparation is next analytically characterized by measuring total protein (Coomassie, Bradford) and biological activity according to methods known in the art.

In an alternative embodiment, Method 1 is carried out as follows. Granulocyte-colony stimulating factor (G-CSF) is transferred into a reaction buffer (e.g., 50 mM Hepes, 350 mM sodium chloride, 5 mM calcium chloride, pH 6.0) and diluted to obtain a protein concentration of 1 mg/ml. To this solution, $NaIO_4$ is added to give a final concentration of 200 µM. The oxidation is carried at RT for 30 min in the dark under gentle shaking. The reaction is then quenched with cysteine (final concentration: 10 mM) for 60 min at RT.

The solution is next subjected to UF/DF employing Vivaspin centrifugal filtrators to remove excess periodate, quencher and the byproducts thereof. A 50-fold molar excess of aminooxy-PSA reagent with a MW of 20 kD (described above) is added followed by m-toluidine as a nucleophilic catalyst (final concentration: 10 mM). The coupling reaction is performed for 2 hours in the dark under gentle shaking at room temperature. The excess of aminooxy reagent is removed by means of ion exchange chromatography. The PSA-G-CSF containing fractions of the eluate are collected and subjected to UF/DF by use of a membrane made of regenerated cellulose (Millipore). The preparation is next analytically characterized by measuring total protein (Coomassie, Bradford) and biological activity according to methods known in the art.

Method 2:

G-CSF is transferred or dissolved in reaction buffer (e.g. 50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5 N aqueous HCl solution. Subsequently, a 40 mM aqueous sodium periodate solution is added within 10 minutes to give a concentration of 200 µM. The oxidation reaction is carried out for 30+/−5 min at a temperature (T) of T=+22+/−2° C. Then the reaction is stopped by addition of an aqueous L-cysteine solution (1 M) within 15 minutes at T=+22+/−2° C. to give a final concentration of 10 mM in the reaction mixture and incubation for 60+/−5 min.

The oxidized G-CSF is further purified by ion exchange chromatography. The oxidized G-CSF containing fractions of the eluate are collected and used for the conjugation reaction.

The aminooxy-polysialic acid ($PSA-ONH_2$) reagent is added in a 50-fold molar excess to the eluate containing the purified oxidized G-CSF within a maximum time period (t) of 15 minutes under gentle stirring. Then an aqueous m-toluidine solution (50 mM) is added within 15 minutes to get a final concentration of 10 mM. The reaction mixture is incubated for 120+/−10 min. at pH 6.0 in the dark at a temperature (T) of T=+22+/−2° C. under gentle shaking (protein concentration: 1 mg/ml).

The obtained PSA-G-CSF conjugate is further purified by ion exchange chromatography. The PSA-G-CSF conjugate containing fractions are collected and concentrated by ultra-/diafiltration (UF/DF) using a membrane made of regenerated cellulose with an appropriate molecular weight cut off (Millipore).

The conjugate prepared by use of this procedure is analytically characterized by measuring total protein, biological activity, and determination of the polysialylation degree by measuring the PSA content (resorcinol assay).

Method 3:

Granulocyte-colony stimulating factor (G-CSF) is transferred into reaction buffer (50 mM Hepes, 350 mM sodium chloride, 5 mM calcium chloride, pH 6.0) and diluted to obtain a protein concentration of 1 mg/ml. A 50-fold molar excess of aminooxy-PSA reagent with a MW of 20 kD (described above) is added followed by m-toluidine as a nucleophilic catalyst (10 mM final concentration) and $NaIO_4$ (final concentration: 400 µM). The coupling reaction is performed for 2 hours in the dark under gentle shaking at room temperature. Subsequently, the reaction is quenched with cysteine for 60 min at RT (cysteine concentration: 10 mM). Then the conductivity of the reaction mixture is adjusted by adding a buffer containing ammonium acetate (50 mM Hepes, 350 mM sodium chloride, 5 mM calcium chloride, 8 M ammonium acetate, pH 6.9) and loaded onto a column filled with Phenyl Sepharose FF (GE Healthcare, Fairfield, Conn.) pre-equilibrated with 50 mM Hepes, 2.5 M ammonium acetate, 350 mM sodium chloride, 5 mM calcium chloride, 0.01% Tween 80, pH 6.9. Subsequently the conjugate is eluted with 50 mM Hepes, 5 mM calcium chloride, pH 7.5. Finally, the PSA-G-CSF-containing fractions are collected and subjected to UF/DF by use of a membrane made of regenerated cellulose (Millipore). The preparation is analytically characterized by measuring total protein (Bradford) and biological activity according to methods known in the art.

In an alternative embodiment, Method 3 is carried out as follows. Granulocyte-colony stimulating factor (G-CSF) is transferred into reaction buffer (e.g. 50 mM Hepes, 350 mM sodium chloride, 5 mM calcium chloride, pH 6.0) and diluted to obtain a protein concentration of 1 mg/ml. A 50-fold molar excess of aminooxy-PSA reagent with a MW of 20 kD (described above) is added followed by m-toluidine as a nucleophilic catalyst (10 mM final concentration) and $NaIO_4$ (final concentration: 400 µM). The coupling reaction is performed for 2 hours in the dark under gentle shaking at room temperature. Subsequently, the reaction is quenched with cysteine for 60 min at RT (cysteine concentration: 10 mM) and the conjugate is purified by ion exchange chromatography. The PSA-G-CSF containing fractions of the eluate are collected and subjected to UF/DF by use of a membrane made of regenerated cellulose (Millipore). The preparation is analytically characterized by measuring total protein (Bradford) and biological activity according to methods known in the art.

Method 4:

G-CSF is dissolved in or transferred to a reaction buffer (e.g. 50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5 N aqueous HCl solution.

Subsequently, the aminooxy-polysialic acid ($PSA-ONH_2$) reagent is added in a 50-fold molar excess to this G-CSF solution within a maximum time period (t) of 15 minutes under gentle stirring. Then an aqueous m-toluidine solution (50 mM) is added within 15 minutes to get a final concentration of 10 mM. Finally, a 40 mM aqueous sodium periodate solution is added to give a concentration of 400 µM.

The reaction mixture is incubated for 120+/−10 min. in the dark at a temperature (T) of T=+22+/−2° C. under gentle shaking. Then the reaction is stopped by the addition of an aqueous L-cysteine solution (1 M) to give a final concentration of 10 mM in the reaction mixture and incubation for 60+/−5 min.

The obtained G-CSF conjugate is purified by ion-exchange chromatography. The PSA-G-CSF containing fractions of the eluate are collected and concentrated by ultra-/diafiltration (UF/DF) using a membrane made of regenerated cellulose (Millipore).

The conjugates prepared by use of this procedure are analytically characterized by measuring total protein, biological activity according to methods known in the art, and determination of the polysialylation degree by measuring the PSA content (resorcinol assay).

Example 29

Polysialylation of Humira Using Aminooxy-PSA and m-Toluidine as a Nucleophilic Catalyst Method 1:

A starting concentration of Humira is transferred into a reaction buffer (e.g. 50 mM Hepes, 350 mM sodium chloride, 5 mM calcium chloride, pH 6.0) and diluted to obtain a protein concentration of 1 mg/ml. To this solution, $NaIO_4$ is added to give a final concentration of 200 μM. The oxidation is carried at RT for 30 min in the dark under gentle shaking. The reaction is then quenched with cysteine (final concentration: 10 mM) for 60 min at RT.

The solution is next subjected to UF/DF employing Vivaspin centrifugal filtrators to remove excess periodate, quencher and the byproducts thereof or, in the alternative, to an IEX column with a volume of 20 ml (Merck EMD TMAE (M)) which is equilibrated with Buffer A (20 mM Hepes, 5 mM $CaCl_2$, pH 7.0). The column is equilibrated with 5 CV Buffer A. The oxidized Humira is eluted with Buffer B (20 mM Hepes, 5 mM $CaCl_2$, 1M NaCl, pH 7.0). The Humira containing fractions are collected. The protein content is determined (Coomassie, Bradford) and adjusted to 1 mg/ml with reaction buffer and adjusted to pH 6.0 by dropwise addition of 0.5M HCl.

A 50-fold molar excess of aminooxy-PSA reagent with a MW of 20 kD (described above) is added followed by m-toluidine as a nucleophilic catalyst (final concentration: 10 mM). The coupling reaction is performed for 2 hours in the dark under gentle shaking at room temperature. The excess of aminooxy reagent is removed by means of HIC. The conductivity of the reaction mixture is adjusted by adding a buffer containing ammonium acetate (50 mM Hepes, 350 mM sodium chloride, 5 mM calcium chloride, 8 M ammonium acetate, pH 6.9) and loaded onto a column filled with 80 ml Phenyl Sepharose FF (GE Healthcare, Fairfield, Conn.) pre-equilibrated with 50 mM Hepes, 2.5 M ammonium acetate, 350 mM sodium chloride, 5 mM calcium chloride, pH 6.9. Subsequently the conjugate is eluted with 50 mM Hepes buffer pH 7.5 containing 5 mM $CaCl_2$. Finally, the PSA-Humira containing fractions are collected and subjected to UF/DF by use of a membrane made of regenerated cellulose (Millipore). The preparation is next analytically characterized by measuring total protein (Coomassie, Bradford) and biological activity according to methods known in the art.

In an alternative embodiment, Method 1 is carried out as follows. Humira is transferred into a reaction buffer (e.g. 50 mM Hepes, 350 mM sodium chloride, 5 mM calcium chloride, pH 6.0) and diluted to obtain a protein concentration of 1 mg/ml. To this solution, $NaIO_4$ is added to give a final concentration of 200 μM. The oxidation is carried at RT for 30 min in the dark under gentle shaking. The reaction is then quenched with cysteine (final concentration: 10 mM) for 60 min at RT.

The solution is next subjected to UF/DF employing Vivaspin centrifugal filtrators to remove excess periodate, quencher and the byproducts thereof. A 50-fold molar excess of aminooxy-PSA reagent with a MW of 20 kD (described above) is added followed by m-toluidine as a nucleophilic catalyst (final concentration: 10 mM). The coupling reaction is performed for 2 hours in the dark under gentle shaking at room temperature. The excess of aminooxy reagent is removed by means of ion exchange chromatography The PSA-Humira containing fractions of the eluate are collected and subjected to UF/DF by use of a membrane made of regenerated cellulose (Millipore). The preparation is next analytically characterized by measuring total protein (Coomassie, Bradford) and biological activity according to methods known in the art.

Method 2:

Humira is transferred or dissolved in reaction buffer (e.g. 50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5 N aqueous HCl solution. Subsequently, a 40 mM aqueous sodium periodate solution is added within 10 minutes to give a concentration of 200 μM. The oxidation reaction is carried out for 30+/−5 min at a temperature (T) of T=+22+/−2° C. Then the reaction is stopped by addition of an aqueous L-cysteine solution (1 M) within 15 minutes at T=+22+/−2° C. to give a final concentration of 10 mM in the reaction mixture and incubation for 60+/−5 min.

The oxidized Humira is further purified by ion exchange chromatography. The oxidized Humira containing fractions of the eluate are collected and used for the conjugation reaction.

The aminooxy-polysialic acid (PSA-$ONH_2$) reagent is added in a 50-fold molar excess to the eluate containing the purified oxidized Humira within a maximum time period (t) of 15 minutes under gentle stirring. Then an aqueous m-toluidine solution (50 mM) is added within 15 minutes to get a final concentration of 10 mM. The reaction mixture is incubated for 120+/−10 min. at pH 6.0 in the dark at a temperature (T) of T=+22+/−2° C. under gentle shaking (protein concentration: 1 mg/ml).

The obtained PSA-Humira conjugate is further purified by ion exchange chromatography. The PSA-Humira conjugate containing fractions are collected and concentrated by ultra-/diafiltration (UF/DF) using a membrane made of regenerated cellulose with an appropriate molecular weight cut off (Millipore).

The conjugate prepared by use of this procedure is analytically characterized by measuring total protein, biological activity, and determination of the polysialylation degree by measuring the PSA content (resorcinol assay).

Method 3:

Humira is transferred into reaction buffer (50 mM Hepes, 350 mM sodium chloride, 5 mM calcium chloride, pH 6.0) and diluted to obtain a protein concentration of 1 mg/ml. A 50-fold molar excess of aminooxy-PSA reagent with a MW of 20 kD (described above) is added followed by m-toluidine as a nucleophilic catalyst (10 mM final concentration) and $NaIO_4$ (final concentration: 400 μM). The coupling reaction is performed for 2 hours in the dark under gentle shaking at room temperature. Subsequently, the reaction is quenched with cysteine for 60 min at RT (cysteine concentration: 10 mM). Then the conductivity of the reaction mixture is adjusted by adding a buffer containing ammonium acetate (50 mM Hepes, 350 mM sodium chloride, 5 mM calcium chloride, 8 M ammonium acetate, pH 6.9) and loaded onto a column filled with Phenyl Sepharose FF (GE Healthcare, Fairfield, Conn.) pre-equilibrated with 50 mM Hepes, 2.5 M ammonium acetate, 350 mM sodium chloride, 5 mM calcium chloride, 0.01% Tween 80, pH 6.9. Subsequently the conjugate is eluted with 50 mM Hepes, 5 mM calcium chloride, pH 7.5. Finally the PSA-Humira containing fractions are collected and subjected to UF/DF by use of a membrane made of regenerated cellulose (Millipore). The preparation is analytically characterized by measuring total protein (Bradford) and biological activity according to methods known in the art.

In an alternative embodiment, Method 3 is carried out as follows. Humira is transferred into reaction buffer (e.g. 50 mM Hepes, 350 mM sodium chloride, 5 mM calcium chloride, pH 6.0) and diluted to obtain a protein concentration of 1 mg/ml. A 50-fold molar excess of aminooxy-PSA reagent with a MW of 20 kD (described above) is added followed by m-toluidine as a nucleophilic catalyst (10 mM final concentration) and $NaIO_4$ (final concentration: 400 μM). The coupling reaction is performed for 2 hours in the dark under gentle shaking at room temperature. Subsequently, the reaction is quenched with cysteine for 60 min at RT (cysteine concentration: 10 mM) and the conjugate is purified by ion exchange chromatography. The PSA-Humira containing fractions of the eluate are collected and subjected to UF/DF by use of a membrane made of regenerated cellulose (Millipore). The preparation is analytically characterized by measuring total protein (Bradford) and biological activity according to methods known in the art.

Method 4:

Humira is dissolved in or transferred to a reaction buffer (e.g. 50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5 N aqueous HCl solution.

Subsequently, the aminooxy-polysialic acid ($PSA-ONH_2$) reagent is added in a 50-fold molar excess to this Humira solution within a maximum time period (t) of 15 minutes under gentle stirring. Then an aqueous m-toluidine solution (50 mM) is added within 15 minutes to get a final concentration of 10 mM. Finally a 40 mM aqueous sodium periodate solution is added to give a concentration of 400 μM.

The reaction mixture is incubated for 120+/−10 min. in the dark at a temperature (T) of T=+22+/−2° C. under gentle shaking. Then the reaction is stopped by the addition of an aqueous L-cysteine solution (1 M) to give a final concentration of 10 mM in the reaction mixture and incubation for 60+/−5 min.

The obtained Humira-conjugate is purified by ion-exchange chromatography. The PSA-Humira containing fractions of the eluate are collected and concentrated by ultra-/diafiltration (UF/DF) using a membrane made of regenerated cellulose (Millipore).

The conjugates prepared by use of this procedure are analytically characterized by measuring total protein, biological activity according to methods known in the art, and determination of the polysialylation degree by measuring the PSA content (resorcinol assay).

Example 30

Polysialylation of Prolia Using Aminooxy-PSA and m-Toluidine as a Nucleophilic Catalyst Method 1:

A starting concentration of Prolia is transferred into a reaction buffer (e.g. 50 mM Hepes, 350 mM sodium chloride, 5 mM calcium chloride, pH 6.0) and diluted to obtain a protein concentration of 1 mg/ml. To this solution, $NaIO_4$ is added to give a final concentration of 200 μM. The oxidation is carried at RT for 30 min in the dark under gentle shaking. The reaction is then quenched with cysteine (final concentration: 10 mM) for 60 min at RT.

The solution is next subjected to UF/DF employing Vivaspin centrifugal filtrators to remove excess periodate, quencher and the byproducts thereof or, in the alternative, to an IEX column with a volume of 20 ml (Merck EMD TMAE (M)) which is equilibrated with Buffer A (20 mM Hepes, 5 mM $CaCl_2$, pH 7.0). The column is equilibrated with 5 CV Buffer A. The oxidized Prolia is eluted with Buffer B (20 mM Hepes, 5 mM $CaCl_2$, 1M NaCl, pH 7.0). The Prolia containing fractions are collected. The protein content is determined (Coomassie, Bradford) and adjusted to 1 mg/ml with reaction buffer and adjusted to pH 6.0 by dropwise addition of 0.5 M HCl.

A 50-fold molar excess of aminooxy-PSA reagent with a MW of 20 kD (described above) is added followed by m-toluidine as a nucleophilic catalyst (final concentration: 10 mM). The coupling reaction is performed for 2 hours in the dark under gentle shaking at room temperature. The excess of aminooxy reagent is removed by means of HIC. The conductivity of the reaction mixture is adjusted by adding a buffer containing ammonium acetate (50 mM Hepes, 350 mM sodium chloride, 5 mM calcium chloride, 8 M ammonium acetate, pH 6.9) and loaded onto a column filled with 80 ml Phenyl Sepharose FF (GE Healthcare, Fairfield, Conn.) pre-equilibrated with 50 mM Hepes, 2.5 M ammonium acetate, 350 mM sodium chloride, 5 mM calcium chloride, pH 6.9. Subsequently the conjugate is eluted with 50 mM Hepes buffer pH 7.5 containing 5 mM $CaCl_2$. Finally, the PSA-Prolia containing fractions are collected and subjected to UF/DF by use of a membrane made of regenerated cellulose (Millipore). The preparation is next analytically characterized by measuring total protein (Coomassie, Bradford) and biological activity according to methods known in the art.

In an alternative embodiment, Method 1 is carried out as follows. 10 mg Prolia is dissolved in 5 ml histidine buffer, pH 6.0 (20 mM L-histidine, 150 mM NaCl). 100 μl of an aqueous sodium periodate solution (5 mM) is then added and the reaction mixture is incubated for 1 h in the dark at 4° C. under gentle stirring and quenched for 15 min at room temperature by the addition of 50 μl of a 1 M aqueous cysteine solution. The mixture is subsequently subjected to UF/DF employing Vivaspin 15R 10 kD centrifugal filtrators to remove excess periodate, quencher and the byproducts thereof.

The retentate (approx. 7 ml), containing oxidized Prolia, is mixed with 2 ml of an aqueous m-toluidine solution (50 mM) and incubated for 30 min at room temperature. Then aminooxy-PSA reagent with a MW of 20 kD (described above) is added to give a 5-fold molar reagent excess. This mixture is incubated for 2.5 h at RT in the dark under gentle stirring.

The free Prolia is removed by means of cation exchange chromatography (CEC). The reaction mixture is diluted with 20 ml Buffer A (50 mM Hepes, pH 6.5) and loaded onto a 20 ml HiPrep SPFF 16/10 column (GE Healthcare, Fairfield, Conn.) pre-equilibrated with Buffer A. Then the column is eluted with Buffer B (50 mM Hepes, 1 M NaCl, pH 6.5). Free Prolia is eluted by washing the column with 25% Buffer B and the conjugate at 50% Buffer B. The conductivity of the conjugate containing fractions is subsequently raised to ~190 mS/cm with Buffer C (50 mM Hepes, 5 M NaCl, pH 6.9) and loaded onto a 20 ml HiPrep Butyl FF 16/10 column (GE Healthcare, Fairfield, Conn.) pre-equilibrated with Buffer D (50 mM Hepes, 3 M NaCl, pH 6.9). Free PSA-reagent is washed out within 5 CV Buffer D. Subsequently, the conjugate is eluted with 100% Buffer E (50 mM Hepes, pH 6.9). The conjugate containing fractions are concentrated by UF/DF using a 10 kD membrane made of regenerated cellulose (88 cm2, cut-off 10 kD, Millipore). The final diafiltration step is performed against histidine buffer, pH 6.9 containing 150 mM NaCl. The preparation is analytically characterized by measuring total protein (Bradford) and biological activity according to methods known in the art. For the PSA-Prolia conjugate a specific activity of >50% in comparison to native Prolia is determined. The conjugate is additionally analytically characterized by Size Exclusion HPLC using a Agilent 1200 HPLC system equipped with a Shodex KW 803 column under conditions as previously described (Kolarich et al, Transfusion 2006; 46:1959-77). It is shown that the preparation contains no free Prolia.

Method 2:

Prolia is transferred or dissolved in reaction buffer (e.g. 50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5 N aqueous HCl solution. Subsequently, a 40 mM aqueous sodium periodate solution is added within 10 minutes to give a concentration of 200 μM. The oxidation reaction is carried out for 30+/−5 min at a temperature (T) of T=+22+/−2° C. Then the reaction is stopped by addition of an aqueous L-cysteine solution (1 M) within 15 minutes at T=+22+/−2° C. to give a final concentration of 10 mM in the reaction mixture and incubation for 60+/−5 min.

The oxidized Prolia is further purified by ion exchange chromatography. The oxidized Prolia containing fractions of the eluate are collected and used for the conjugation reaction.

The aminooxy-polysialic acid (PSA-$ONH_2$) reagent is added in a 50-fold molar excess to the eluate containing the purified oxidized Prolia within a maximum time period (t) of 15 minutes under gentle stirring. Then an aqueous m-toluidine solution (50 mM) is added within 15 minutes to get a final concentration of 10 mM. The reaction mixture is incubated for 120+/−10 min. at pH 6.0 in the dark at a temperature (T) of T=+22+/−2° C. under gentle shaking (protein concentration: 1 mg/ml).

The obtained Prolia conjugate is further purified by ion exchange chromatography. The Prolia conjugate containing fractions are collected and concentrated by ultra-/diafiltration (UF/DF) using a membrane made of regenerated cellulose with an appropriate molecular weight cut off (Millipore).

The conjugate prepared by use of this procedure is analytically characterized by measuring total protein, biological activity, and determination of the polysialylation degree by measuring the PSA content (resorcinol assay).

Method 3:

Prolia is transferred into reaction buffer (50 mM Hepes, 350 mM sodium chloride, 5 mM calcium chloride, pH 6.0) and diluted to obtain a protein concentration of 1 mg/ml. A 50-fold molar excess of aminooxy-PSA reagent with a MW of 20 kD (described above) is added followed by m-toluidine as a nucleophilic catalyst (10 mM final concentration) and $NaIO_4$ (final concentration: 400 μM). The coupling reaction is performed for 2 hours in the dark under gentle shaking at room temperature. Subsequently, the reaction is quenched with cysteine for 60 min at RT (cysteine concentration: 10 mM). Then the conductivity of the reaction mixture is adjusted by adding a buffer containing ammonium acetate (50 mM Hepes, 350 mM sodium chloride, 5 mM calcium chloride, 8 M ammonium acetate, pH 6.9) and loaded onto a column filled with Phenyl Sepharose FF (GE Healthcare, Fairfield, Conn.) pre-equilibrated with 50 mM Hepes, 2.5 M ammonium acetate, 350 mM sodium chloride, 5 mM calcium chloride, 0.01% Tween 80, pH 6.9. Subsequently the conjugate is eluted with 50 mM Hepes, 5 mM calcium chloride, pH 7.5. Finally the PSA Prolia-containing fractions are collected and subjected to UF/DF by use of a membrane made of regenerated cellulose (Millipore). The preparation is analytically characterized by measuring total protein (Bradford) and biological activity according to methods known in the art.

In an alternative embodiment, Method 3 is carried out as follows. 10 mg Prolia is dissolved in 8 ml histidine buffer, pH 6.0 (20 mM L-histidine, 150 mM NaCl). 200 μl of an aqueous sodium periodate solution (5 mM) and 2 ml of an aqueous m-toluidine solution (50 mM) are then added. Subsequently the aminooxy-PSA reagent with a MW of 20 kD (described above) is added to give a 5 fold molar reagent excess. The mixture is incubated for 2 h in the dark at room temperature under gentle stirring and quenched for 15 min at room temperature by the addition of 100 μl of 1 M aqueous cysteine solution.

The free Prolia is removed by means of cation exchange chromatography (CEC). The reaction mixture is diluted with 20 ml Buffer A (50 mM Hepes, pH 6.5) and loaded onto a 20 ml HiPrep SPFF 16/10 column (GE Healthcare, Fairfield, Conn.) pre-equilibrated with Buffer A. Then the column is eluted with Buffer B (50 mM Hepes, 1 M NaCl, pH 6.5). Free Prolia is eluted by washing the column with 25% Buffer B and the conjugate at 5 0% Buffer B. The conductivity of the conjugate containing fractions is subsequently raised to ~190 mS/cm with Buffer C (50 mM Hepes, 5 M NaCl, pH 6.9) and loaded onto a 20 ml HiPrep Butyl FF 16/10 column (GE Healthcare, Fairfield, Conn.) pre-equilibrated with Buffer D (50 mM Hepes, 3 M NaCl, pH 6.9). Free PSA-reagent is washed out within 5 CV Buffer D. Subsequently the conjugate is eluted with 100% Buffer E (50 mM Hepes, pH 6.9). The conjugate containing fractions are concentrated by UF/DF using a 10 kD membrane made of regenerated cellulose (88 $cm^2$, cut-off 10 kD/Millipore). The final diafiltration step is performed against histidine buffer, pH 6.9 containing 150 mM NaCl. The preparation is analytically characterized by measuring total protein (Bradford) and biological activity according to methods known in the art. For the PSA-Prolia conjugate a specific activity of >50% in comparison to native Prolia is determined. The conjugate is additionally analytically characterized by Size Exclusion HPLC using a Agilent 1200 HPLC system equipped with a Shodex KW 803 column under conditions as previously described (Kolarich et al, Transfusion 2006; 46:1959-77). It is shown that the preparation contains no free Prolia.

Method 4:

Prolia is dissolved in or transferred to a reaction buffer (e.g. 50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5 N aqueous HCl solution.

Subsequently the aminooxy-polysialic acid (PSA-$ONH_2$) reagent is added in a 50-fold molar excess to this Prolia-solution within a maximum time period (t) of 15 minutes under gentle stirring. Then an aqueous m-toluidine solution (50 mM) is added within 15 minutes to get a final concentration of 10 mM. Finally a 40 mM aqueous sodium periodate solution is added to give a concentration of 400 μM.

The reaction mixture is incubated for 120+/−10 min. in the dark at a temperature (T) of T=+22+/−2° C. under gentle shaking. Then the reaction is stopped by the addition of an aqueous L-cysteine solution (1 M) to give a final concentration of 10 mM in the reaction mixture and incubation for 60+/−5 min.

The obtained Prolia conjugate is purified by ion-exchange chromatography. The PSA-Prolia containing fractions of the eluate are collected and concentrated by ultra-/diafiltration (UF/DF) using a membrane made of regenerated cellulose (Millipore).

The conjugates prepared by use of this procedure are analytically characterized by measuring total protein, biological activity according to methods known in the art, and determination of the polysialylation degree by measuring the PSA content (resorcinol assay).

Example 31

Polysialylation of Other Therapeutic Proteins

Polysialylation reactions performed in the presence of alternative nucleophilic catalysts like m-toluidine or o-aminobenzoic acid as described herein may be extended to other therapeutic proteins. For example, in various aspects of the invention, the above polysialylation or PEGylation reactions as described herein with PSA aminooxy or PEG aminooxy reagents is repeated with therapeutic proteins such as those proteins described herein.

Example 32

PEGylation of EPO Using an Aminooxy-PEG Reagent and m-Toluidine as a Nucleophilic Catalyst Method 1:

Erythropoietin (EPO) is PEGylated by use of a linear 20 kD PEGylation reagent containing an aminooxy group. An example of this type of reagent is the Sunbright® CA series from NOF (NOF Corp., Tokyo, Japan). EPO is dissolved in 7.0 ml histidine buffer, pH 6.0 (20 mM L-histidine, 150 mM NaCl, 5 mM $CaCl_2$). An aqueous sodium periodate solution (5 mM) is then added and the reaction mixture is incubated for 1 h in the dark at 4° C. under gentle stirring and quenched for 15 min at room temperature by the addition of 7.5 μl of a 1 M aqueous cysteine solution. The mixture is subsequently subjected to UF/DF employing Vivaspin centrifugal filtrators to remove excess periodate, quencher and the byproducts thereof.

The retentate containing oxidized EPO is next mixed with an aqueous m-toluidine solution (50 mM) and incubated for 30 min at room temperature. aminooxy-PEG reagent with a MW of 20 kD is then added to give a 5-fold molar reagent excess. This mixture is incubated for 2.5 h at room temperature in the dark under gentle stirring.

Finally, the PEG-EPO conjugate is purified by ion-exchange chromatography (e.g. on Q Sepharose FF). For example, 1.5 mg protein/ml gel is loaded on the column equilibrated with 50 mM Hepes buffer, pH 7.4 containing 5 mM $CaCl_2$. The conjugate is eluted with 50 mM Hepes buffer containing 5 mM $CaCl_2$ and 500 mM sodium chloride, pH 7.4 and is then subjected to UF/DF using an appropriate MW cutoff membrane. The preparation is next analytically characterized by measuring total protein (Coomassie, Bradford) and biological activity according to methods known in the art.

In an alternative embodiment, Method 1 is carried out as follows. EPO is PEGylated by use of a linear 20 kD PEGylation reagent containing an aminooxy group. An example of this type of reagent is the Sunbright® CA series from NOF (NOF Corp., Tokyo, Japan). 10 mg EPO is dissolved in 5 ml histidine buffer, pH 6.0 (20 mM L-histidine, 150 mM NaCl). 100 μl of an aqueous sodium periodate solution (5 mM) is then added and the reaction mixture is incubated for 1 h in the dark at 4° C. under gentle stirring and quenched for 15 min at room temperature by the addition of 50 μl of a 1 M aqueous cysteine solution. The mixture is subsequently subjected to UF/DF employing Vivaspin 15R 10 kD centrifugal filtrators to remove excess periodate, quencher and the byproducts thereof.

The retentate (approx. 7 ml), containing oxidized EPO, is mixed with 2 ml of an aqueous m-toluidine solution (50 mM) and incubated for 30 min at room temperature. Then aminooxy-PEG reagent with a MW of 20 kD (described above) is added to give a 5-fold molar reagent excess. This mixture is incubated for 2.5 h at RT in the dark under gentle stirring.

Finally, the PEG-EPO conjugate is purified by ion-exchange chromatography on Q Sepharose FF. The reaction mixture is diluted with 20 ml Buffer A (50 mM Hepes, pH 7.5) and loaded onto a 20 ml HiPrep QFF 16/10 column (GE Healthcare, Fairfield, Conn.) pre-equilibrated with Buffer A. Then the column is eluted with Buffer B (50 mM Hepes, 1 M NaCl, pH 7.5). Free EPO is eluted by washing the column with 25% Buffer B and the conjugate at 50% Buffer B. The conjugate containing fractions are concentrated by UF/DF using a 10 kD membrane made of regenerated cellulose (88 cm2, cut-off 10 kD/Millipore). The final diafiltration step is performed against histidine buffer, pH 7.2 containing 150 mM NaCl. The preparation is analytically characterized by measuring total protein (Bradford) and biological activity biological activity according to methods known in the art. For the PEG-EPO conjugate a specific activity of >50% in comparison to native EPO is determined. The conjugate is additionally analytically characterized by Size Exclusion HPLC using a Agilent 1200 HPLC system equipped with a Shodex KW 803 column under conditions as previously described (Kolarich et al, Transfusion 2006; 46:1959-77). It is shown that the preparation contains no free EPO.

Method 2:

EPO is PEGylated by use of a linear 20 kD PEGylation reagent containing an aminooxy group. An example of this type of reagent is the Sunbright® CA series from NOF (NOF Corp., Tokyo, Japan).

EPO is transferred or dissolved in reaction buffer (e.g. 50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5 N aqueous HCl solution. Subsequently a 40 mM aqueous sodium periodate solution is added within 10 minutes to give a concentration of 200 μM. The oxidation reaction is carried out for 30+/−5 min at a temperature (T) of T=+22+/−2° C. Then the reaction is stopped by addition of an aqueous L-cysteine solution (1 M) within 15 minutes at T=+22+/−2° C. to give a final concentration of 10 mM in the reaction mixture and incubation for 60+/−5 min.

The oxidized EPO is further purified by ion exchange chromatography. The oxidized EPO containing fractions of the eluate are collected and used for the conjugation reaction.

The aminooxy-PEG reagent with a MW of 20 kD reagent is added in a 50-fold molar excess to the eluate containing the purified oxidized EPO within a maximum time period (t) of 15 minutes under gentle stirring. Then an aqueous m-toluidine solution (50 mM) is added within 15 minutes to get a final concentration of 10 mM. The reaction mixture is incubated for 120+/−10 min. in the dark at a temperature (T) of T=+22+/−2° C. under gentle shaking.

The obtained PEG-EPO conjugate is further purified by ion exchange chromatography. The PEG-EPO conjugate containing fractions are collected and concentrated by ultra-/diafiltration (UF/DF) using a membrane made of regenerated cellulose with an appropriate molecular weight cut off (Millipore).

The conjugate prepared by use of this procedure are analytically characterized by measuring total protein and biological activity according to methods known in the art.

Method 3:

EPO is PEGylated by use of a linear 20 kD PEGylation reagent containing an aminooxy group. An example of this type of reagent is the Sunbright® CA series from NOF (NOF Corp., Tokyo, Japan). EPO is dissolved in Hepes buffer (50 mM Hepes, 150 mM sodium chloride, 5 mM calcium chloride, pH 6.0) and mixed with an aqueous sodium periodate solution (10 mM), and an aqueous m-toluidine solution (50 mM). Subsequently, the aminooxy reagent is added to give a 20-fold molar reagent excess. The mixture is incubated for 2 h in the dark at room temperature under gentle stirring and quenched for 15 min at room temperature by the addition of 8 µl of aqueous cysteine solution (1 M).

Finally, the PEG-EPO conjugate is purified by ion-exchange chromatography on Q Sepharose FF. 1.5 mg protein/ml gel is loaded on the column pre equilibrated with 50 mM Hepes buffer, pH 7.4 containing 5 mM $CaCl_2$. The conjugate is eluted with 50 mM Hepes buffer containing 5 mM $CaCl_2$ and 500 mM sodium chloride, pH 7.4 and is then subjected to UF/DF using a membrane. The preparation is analytically characterized by measuring total protein (Bradford) and biological activity according to methods known in the art.

In an alternative embodiment, Method 3 is carried out as follows. EPO is PEGylated by use of a linear 20 kD PEGylation reagent containing an aminooxy group. An example of this type of reagent is the Sunbright® CA series from NOF (NOF Corp., Tokyo, Japan). 10 mg EPO is dissolved in ~8 ml histidine buffer, pH 6.0 (20 mM L-histidine, 150 mM NaCl). 200 µl of an aqueous sodium periodate solution (5 mM) and 2 ml of an aqueous m-toluidine solution (50 mM) are then added. Subsequently, the aminooxy-PEG reagent with a MW of 20 kD (described above) is added to give a 5-fold molar reagent excess. The mixture is incubated for 2 h in the dark at room temperature under gentle stirring and quenched for 15 min at room temperature by the addition of 100 µl of 1 M aqueous cysteine solution.

Finally, the PEG-EPO conjugate is purified by ion-exchange chromatography on Q Sepharose FF. The reaction mixture is diluted with 20 ml Buffer A (50 mM Hepes, pH 7.5) and loaded onto a 20 ml HiPrep QFF 16/10 column (GE Healthcare, Fairfield, Conn.) pre-equilibrated with Buffer A. Then the column is eluted with Buffer B (50 mM Hepes, 1 M NaCl, pH 7.5). Free EPO is eluted by washing the column with 25% Buffer B and the conjugate at 50% Buffer B. The conjugate containing fractions are concentrated by UF/DF using a 10 kD membrane made of regenerated cellulose (88 cm2, cut-off 10 kD/Millipore). The final diafiltration step is performed against histidine buffer, pH 7.2 containing 150 mM NaCl. The preparation is analytically characterized by measuring total protein (Bradford) and biological activity according to methods known in the art. For the PEG-EPO conjugate a specific activity of >50% in comparison to native EPO is determined. The conjugate is additionally analytically characterized by Size Exclusion HPLC using a Agilent 1200 HPLC system equipped with a Shodex KW 803 column under conditions as previously described (Kolarich et al, Transfusion 2006; 46:1959-77). It is shown that the preparation contains no free EPO.

Method 4:

EPO is PEGylated by use of a linear 20 kD PEGylation reagent containing an aminooxy group. An example of this type of reagent is the Sunbright® CA series from NOF (NOF Corp., Tokyo, Japan). An initial concentration or weight of EPO is transferred or dissolved in Hepes buffer (50 mM Hepes, 150 mM sodium chloride, 5 mM calcium chloride, pH 6.0) to get a final protein concentration of 2 mg EPO/ml. Subsequently an 5 mM aqueous sodium periodate solution is added within 15 minutes to give a final concentration of 100 µM, followed by addition of an 50 mM aqueous m-toluidine solution to get a final concentration of 10 mM within a time period of 30 minutes. Then the aminooxy-PEG reagent with a MW of 20 kD (described above) is added to give a 20-fold molar reagent excess. After correction of the pH to 6.0 the mixture is incubated for 2 h in the dark at room temperature under gentle stirring and quenched for 15 min at room temperature by the addition of a 1 M aqueous L-cysteine solution to give a final concentration of 10 mM.

The PEG-EPO conjugate is purified by means of ion exchange chromatography (IEC). The conjugate containing fractions of the eluate are concentrated by UF/DF using a 10 kD membrane made of regenerated cellulose (88 $cm^2$, cut-off 10 kD/Millipore). The final diafiltration step is performed against Hepes buffer (50 mM Hepes, 5 mM $CaCl_2$, pH 7.5).

The preparation is analytically characterized by measuring total protein (Bradford and BCA procedure) and biological activity according to known methods.

Example 33

PEGylation of Ang-2 Using an Aminooxy-PEG Reagent and m-Toluidine as a Nucleophilic Catalyst Method 1:

Ang-2 is PEGylated by use of a linear 20 kD PEGylation reagent containing an aminooxy group. An example of this type of reagent is the Sunbright® CA series from NOF (NOF Corp., Tokyo, Japan). Ang-2 is dissolved in 7.0 ml histidine buffer, pH 6.0 (20 mM L-histidine, 150 mM NaCl, 5 mM $CaCl_2$). An aqueous sodium periodate solution (5 mM) is then added and the reaction mixture is incubated for 1 h in the dark at 4° C. under gentle stirring and quenched for 15 min at room temperature by the addition of 7.5 µl of a 1 M aqueous cysteine solution. The mixture is subsequently subjected to UF/DF employing Vivaspin centrifugal filtrators to remove excess periodate, quencher and the byproducts thereof.

The retentate containing oxidized Ang-2 is next mixed with an aqueous m-toluidine solution (50 mM) and incubated for 30 min at room temperature. Aminooxy-PEG reagent with a MW of 20 kD is then added to give a 5-fold molar reagent excess. This mixture is incubated for 2.5 h at room temperature in the dark under gentle stirring.

Finally, the PEG-Ang-2 conjugate is purified by ion-exchange chromatography (e.g. on Q Sepharose FF). For example, 1.5 mg protein/ml gel is loaded on the column equilibrated with 50 mM Hepes buffer, pH 7.4 containing 5 mM $CaCl_2$. The conjugate is eluted with 50 mM Hepes buffer containing 5 mM $CaCl_2$ and 500 mM sodium chloride, pH 7.4 and is then subjected to UF/DF using an appropriate MW cutoff membrane. The preparation is next analytically characterized by measuring total protein (Coomassie, Bradford) and biological activity according to methods known in the art.

In an alternative embodiment, Method 1 is carried out as follows. Ang-2 is PEGylated by use of a linear 20 kD PEGylation reagent containing an aminooxy group. An example of this type of reagent is the Sunbright® CA series from NOF (NOF Corp., Tokyo, Japan). Ang-2 is dissolved in 7.0 ml histidine buffer, pH 6.0 (20 mM L-histidine, 150 mM NaCl, 5 mM $CaCl_2$). An aqueous sodium periodate solution (5 mM) is then added and the reaction mixture is incubated for 1 h in the dark at 4° C. under gentle stirring and quenched for 15 min at room temperature by the addition of 7.5 µl of a 1 M aqueous cysteine solution. The mixture is subsequently subjected to UF/DF employing Vivaspin centrifugal filtrators to remove excess periodate, quencher and the byproducts thereof.

The retentate containing oxidized Ang-2 is next mixed with an aqueous m-toluidine solution (50 mM) and incubated for 30 min at room temperature. Aminooxy-PEG reagent with a MW of 20 kD is then added to give a 5-fold molar reagent excess. This mixture is incubated for 2.5 h at room temperature in the dark under gentle stirring.

Finally, the PEG-Ang-2 conjugate is purified by ion-exchange chromatography. The conjugate containing fraction of the eluate are collected and then subjected to UF/DF using an appropriate MW cutoff membrane. The preparation is next analytically characterized by measuring total protein (Coomassie, Bradford) and biological activity according to methods known in the art.

Method 2:

Ang-2 is PEGylated by use of a linear 20 kD PEGylation reagent containing an aminooxy group. An example of this type of reagent is the Sunbright® CA series from NOF (NOF Corp., Tokyo, Japan).

Ang-2 is transferred or dissolved in reaction buffer (e.g. 50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5N aqueous HCl solution. Subsequently a 40 mM aqueous sodium periodate solution is added within 10 minutes to give a concentration of 200 μM. The oxidation reaction is carried out for 30+/−5 min at a temperature (T) of T=+22+/−2° C. Then the reaction is stopped by addition of an aqueous L-cysteine solution (1 M) within 15 minutes at T=+22+/−2° C. to give a final concentration of 10 mM in the reaction mixture and incubation for 60+/−5 min.

The oxidized Ang-2 is further purified by ion exchange chromatography. The oxidized Ang-2 containing fractions of the eluate are collected and used for the conjugation reaction.

The aminooxy-PEG reagent with a MW of 20 kD reagent is added in a 50-fold molar excess to the eluate containing the purified oxidized Ang-2 within a maximum time period (t) of 15 minutes under gentle stirring. Then an aqueous m-toluidine solution (50 mM) is added within 15 minutes to get a final concentration of 10 mM. The reaction mixture is incubated for 120+/−10 min. in the dark at a temperature (T) of T=+22+/−2° C. under gentle shaking.

The obtained PEG-Ang-2 conjugate is further purified by ion exchange chromatography. The PEG-Ang-2 conjugate containing fractions are collected and concentrated by ultra-/diafiltration (UF/DF) using a membrane made of regenerated cellulose with an appropriate molecular weight cut off (Millipore).

The conjugate prepared by use of this procedure are analytically characterized by measuring total protein and biological activity according to methods known in the art.

Method 3:

Ang-2 is PEGylated by use of a linear 20 kD PEGylation reagent containing an aminooxy group. An example of this type of reagent is the Sunbright® CA series from NOF (NOF Corp., Tokyo, Japan). Ang-2 is dissolved in Hepes buffer (50 mM Hepes, 150 mM sodium chloride, 5 mM calcium chloride, pH 6.0) and mixed with an aqueous sodium periodate solution (10 mM), and an aqueous m-toluidine solution (50 mM). Subsequently the aminooxy reagent is added to give a 20-fold molar reagent excess. The mixture is incubated for 2 h in the dark at room temperature under gentle stirring and quenched for 15 min at room temperature by the addition of 8 μl of aqueous cysteine solution (1 M).

Finally, the PEG-Ang-2 conjugate is purified by ion-exchange chromatography on Q Sepharose FF. 1.5 mg protein/ml gel is loaded on the column pre equilibrated with 50 mM Hepes buffer, pH 7.4 containing 5 mM $CaCl_2$. The conjugate is eluted with 50 mM Hepes buffer containing 5 mM $CaCl_2$ and 500 mM sodium chloride, pH 7.4 and is then subjected to UF/DF using a membrane. The preparation is analytically characterized by measuring total protein (Bradford) and biological activity according to methods known in the art.

In an alternative embodiment, Method 3 is carried out as follows. Ang-2 is PEGylated by use of a linear 20 kD PEGylation reagent containing an aminooxy group. An example of this type of reagent is the Sunbright® CA series from NOF (NOF Corp., Tokyo, Japan). Ang-2 is dissolved in Hepes buffer (50 mM Hepes, 150 mM sodium chloride, 5 mM calcium chloride, pH 6.0) and mixed with an aqueous sodium periodate solution (10 mM), and an aqueous m-toluidine solution (50 mM). Subsequently the aminooxy reagent is added to give a 20-fold molar reagent excess. The mixture is incubated for 2 h in the dark at room temperature under gentle stirring and quenched for 15 min at room temperature by the addition of 8 μl of aqueous cysteine solution (1 M).

Finally the PEG-Ang-2 conjugate is purified by ion-exchange chromatography The conjugate containing fractions of the eluate are collected and then subjected to UF/DF. The preparation is analytically characterized by measuring total protein (Bradford) and biological activity according to methods known in the art.

Method 4:

Ang-2 is PEGylated by use of a linear 20 kD PEGylation reagent containing an aminooxy group. An example of this type of reagent is the Sunbright® CA series from NOF (NOF Corp., Tokyo, Japan). An initial concentration or weight of Ang-2 is transferred or dissolved in Hepes buffer (50 mM Hepes, 150 mM sodium chloride, 5 mM calcium chloride, pH 6.0) to get a final protein concentration of 2 mg Ang-2/ml. Subsequently an 5 mM aqueous sodium periodate solution is added within 15 minutes to give a final concentration of 100 μM, followed by addition of an 50 mM aqueous m-toluidine solution to get a final concentration of 10 mM within a time period of 30 minutes. Then the aminooxy-PEG reagent with a MW of 20 kD (described above) is added to give a 20-fold molar reagent excess. After correction of the pH to 6.0 the mixture is incubated for 2 h in the dark at room temperature under gentle stirring and quenched for 15 min at room temperature by the addition of an 1 M aqueous L-cysteine solution to give a final concentration of 10 mM.

The PEG-Ang-2 conjugate is purified by means of ion exchange chromatography (IEC). The conjugate containing fractions of the eluate are concentrated by UF/DF using a 10 kD membrane made of regenerated cellulose (88 cm2, cut-off 10 kD/Millipore). The final diafiltration step is performed against Hepes buffer (50 mM Hepes, 5 mM $CaCl_2$, pH 7.5).

The preparation is analytically characterized by measuring total protein (Bradford and BCA procedure) and biological activity according to known methods.

Subsequently, the free Ang-2 is removed by means of ion exchange chromatography (IEC). The conjugate containing fractions of the eluate are concentrated by UF/DF.

Example 34

PEGylation of VEGF Using an Aminooxy-PEG Reagent and m-Toluidine as a Nucleophilic Catalyst Method 1:

VEGF is PEGylated by use of a linear 20 kD PEGylation reagent containing an aminooxy group. An example of this type of reagent is the Sunbright® CA series from NOF (NOF Corp., Tokyo, Japan). VEGF is dissolved in 7.0 ml histidine buffer, pH 6.0 (20 mM L-histidine, 150 mM NaCl, 5 mM $CaCl_2$). An aqueous sodium periodate solution (5 mM) is then added and the reaction mixture is incubated for 1 h in the dark at 4° C. under gentle stirring and quenched for 15 min at room temperature by the addition of 7.5 μl of a 1 M aqueous cysteine solution. The mixture is subsequently subjected to UF/DF employing Vivaspin centrifugal filtrators to remove excess periodate, quencher and the byproducts thereof.

The retentate containing oxidized VEGF is next mixed with an aqueous m-toluidine solution (50 mM) and incubated for 30 min at room temperature. Aminooxy-PEG reagent with a MW of 20 kD is then added to give a 5-fold molar reagent excess. This mixture is incubated for 2.5 h at room temperature in the dark under gentle stirring.

Finally, the PEG-VEGF conjugate is purified by ion-exchange chromatography (e.g., on Q Sepharose FF). For example, 1.5 mg protein/ml gel is loaded on the column equilibrated with 50 mM Hepes buffer, pH 7.4 containing 5 mM $CaCl_2$. The conjugate is eluted with 50 mM Hepes buffer containing 5 mM $CaCl_2$ and 500 mM sodium chloride, pH 7.4 and is then subjected to UF/DF using an appropriate MW cutoff membrane. The preparation is next analytically characterized by measuring total protein (Coomassie, Bradford) and biological activity according to methods known in the art.

In an alternative embodiment, Method 1 is carried out as follows. VEGF is PEGylated by use of a linear 20 kD PEGylation reagent containing an aminooxy group. An example of this type of reagent is the Sunbright® CA series from NOF (NOF Corp., Tokyo, Japan). VEGF is dissolved in 7.0 ml histidine buffer, pH 6.0 (20 mM L-histidine, 150 mM NaCl, 5 mM $CaCl_2$). An aqueous sodium periodate solution (5 mM) is then added and the reaction mixture is incubated for 1 h in the dark at 4° C. under gentle stirring and quenched for 15 min at room temperature by the addition of 7.5 μl of a 1 M aqueous cysteine solution. The mixture is subsequently subjected to UF/DF employing Vivaspin centrifugal filtrators to remove excess periodate, quencher and the byproducts thereof.

The retentate containing oxidized VEGF is next mixed with an aqueous m-toluidine solution (50 mM) and incubated for 30 min at room temperature. Aminooxy-PEG reagent with a MW of 20 kD is then added to give a 5-fold molar reagent excess. This mixture is incubated for 2.5 h at room temperature in the dark under gentle stirring.

Finally, the PEG-VEGF conjugate is purified by ion-exchange chromatography The conjugate containing fractions of the eluate are collected and then subjected to UF/DF using an appropriate MW cutoff membrane. The preparation is next analytically characterized by measuring total protein (Coomassie, Bradford) and biological activity according to methods known in the art.

Method 2:

VEGF is PEGylated by use of a linear 20 kD PEGylation reagent containing an aminooxy group. An example of this type of reagent is the Sunbright® CA series from NOF (NOF Corp., Tokyo, Japan). VEGF is transferred or dissolved in reaction buffer (e.g. 50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5 N aqueous HCl solution. Subsequently, a 40 mM aqueous sodium periodate solution is added within 10 minutes to give a concentration of 200 μM. The oxidation reaction is carried out for 30+/−5 min at a temperature (T) of T=+22+/−2° C. Then the reaction is stopped by addition of an aqueous L-cysteine solution (1 M) within 15 minutes at T=+22+/−2° C. to give a final concentration of 10 mM in the reaction mixture and incubation for 60+/−5 min.

The oxidized VEGF is further purified by ion exchange chromatography. The oxidized VEGF containing fractions of the eluate are collected and used for the conjugation reaction.

The aminooxy-PEG reagent with a MW of 20 kD reagent is added in a 50-fold molar excess to the eluate containing the purified oxidized VEGF within a maximum time period (t) of 15 minutes under gentle stirring. Then an aqueous m-toluidine solution (50 mM) is added within 15 minutes to get a final concentration of 10 mM. The reaction mixture is incubated for 120+/−10 min. in the dark at a temperature (T) of T=+22+/−2° C. under gentle shaking.

The obtained PEG-VEGF conjugate is further purified by ion exchange chromatography. The PEG-VEGF conjugate containing fractions are collected and concentrated by ultra-/diafiltration (UF/DF) using a membrane made of regenerated cellulose with an appropriate molecular weight cut off (Millipore).

The conjugate prepared by use of this procedure are analytically characterized by measuring total protein and biological activity according to methods known in the art.

Method 3:

VEGF is PEGylated by use of a linear 20 kD PEGylation reagent containing an aminooxy group. An example of this type of reagent is the Sunbright® CA series from NOF (NOF Corp., Tokyo, Japan). VEGF is dissolved in Hepes buffer (50 mM Hepes, 150 mM sodium chloride, 5 mM calcium chloride, pH 6.0) and mixed with an aqueous sodium periodate solution (10 mM), and an aqueous m-toluidine solution (50 mM). Subsequently, the aminooxy reagent is added to give a 20-fold molar reagent excess. The mixture is incubated for 2 h in the dark at room temperature under gentle stirring and quenched for 15 min at room temperature by the addition of 8 μl of aqueous cysteine solution (1 M).

Finally, the PEG-VEGF conjugate is purified by ion-exchange chromatography on Q Sepharose FF. 1.5 mg protein/ml gel is loaded on the column pre equilibrated with 50 mM Hepes buffer, pH 7.4 containing 5 mM $CaCl_2$. The conjugate is eluted with 50 mM Hepes buffer containing 5 mM $CaCl_2$ and 500 mM sodium chloride, pH 7.4 and is then subjected to UF/DF using a membrane. The preparation is analytically characterized by measuring total protein (Bradford) and biological activity according to methods known in the art.

In an alternative embodiment, Method 3 is carried out as follows. VEGF is PEGylated by use of a linear 20 kD PEGylation reagent containing an aminooxy group. An example of this type of reagent is the Sunbright® CA series from NOF (NOF Corp., Tokyo, Japan). VEGF is dissolved in Hepes buffer (50 mM Hepes, 150 mM sodium chloride, 5 mM calcium chloride, pH 6.0) and mixed with an aqueous sodium periodate solution (10 mM), and an aqueous m-toluidine solution (50 mM). Subsequently, the aminooxy reagent is added to give a 20-fold molar reagent excess. The mixture is incubated for 2 h in the dark at room temperature under gentle stirring and quenched for 15 min at room temperature by the addition of 8 μl of aqueous cysteine solution (1 M).

Finally, the PEG-VEGF conjugate is purified by ion-exchange chromatography. The conjugate fractions of the eluate are collected and then subjected to UF/DF. The preparation is analytically characterized by measuring total protein (Bradford) and biological activity according to methods known in the art.

Method 4:

VEGF is PEGylated by use of a linear 20 kD PEGylation reagent containing an aminooxy group. An example of this type of reagent is the Sunbright® CA series from NOF (NOF Corp., Tokyo, Japan). An initial concentration or weight of VEGF is transferred or dissolved in Hepes buffer (50 mM Hepes, 150 mM sodium chloride, 5 mM calcium chloride, pH 6.0) to get a final protein concentration of 2 mg VEGF/ml. Subsequently, an 5 mM aqueous sodium periodate solution is added within 15 minutes to give a final concentration of 100 μM, followed by addition of an 50 mM aqueous m-toluidine solution to get a final concentration of 10 mM within a time period of 30 minutes. Then the aminooxy-PEG reagent with a MW of 20 kD (described above) is added to give a 20-fold molar reagent excess. After correction of the pH to 6.0 the mixture is incubated for 2 h in the dark at room temperature under gentle stirring and quenched for 15 min at room temperature by the addition of an 1 M aqueous L-cysteine solution to give a final concentration of 10 mM.

The PEG-VEGF conjugate is purified by means of ion exchange chromatography (IEC). The conjugate containing fractions of the eluate are concentrated by UF/DF using a 10 kD membrane made of regenerated cellulose (88 cm2, cut-off 10 kD/Millipore). The final diafiltration step is performed against Hepes buffer (50 mM Hepes, 5 mM $CaCl_2$, pH 7.5).

The preparation is analytically characterized by measuring total protein (Bradford and BCA procedure) and biological activity according to known methods.

Example 35

PEGylation of EGF Using an Aminooxy-PEG Reagent and m-Toluidine as a Nucleophilic Catalyst Method 1:

EGF is PEGylated by use of a linear 20 kD PEGylation reagent containing an aminooxy group. An example of this type of reagent is the Sunbright® CA series from NOF (NOF Corp., Tokyo, Japan). EGF is dissolved in 7.0 ml histidine buffer, pH 6.0 (20 mM L-histidine, 150 mM NaCl, 5 mM $CaCl_2$). An aqueous sodium periodate solution (5 mM) is then added and the reaction mixture is incubated for 1 h in the dark at 4° C. under gentle stirring and quenched for 15 min at room temperature by the addition of 7.5 µl of a 1 M aqueous cysteine solution. The mixture is subsequently subjected to UF/DF employing Vivaspin centrifugal filtrators to remove excess periodate, quencher and the byproducts thereof.

The retentate containing oxidized EGF is next mixed with an aqueous m-toluidine solution (50 mM) and incubated for 30 min at room temperature. Aminooxy-PEG reagent with a MW of 20 kD is then added to give a 5-fold molar reagent excess. This mixture is incubated for 2.5 h at room temperature in the dark under gentle stirring.

Finally, the PEG-EGF conjugate is purified by ion-exchange chromatography (e.g., on Q Sepharose FF). For example, 1.5 mg protein/ml gel is loaded on the column equilibrated with 50 mM Hepes buffer, pH 7.4 containing 5 mM $CaCl_2$. The conjugate is eluted with 50 mM Hepes buffer containing 5 mM $CaCl_2$ and 500 mM sodium chloride, pH 7.4 and is then subjected to UF/DF using an appropriate MW cutoff membrane. The preparation is next analytically characterized by measuring total protein (Coomassie, Bradford) and biological activity according to methods known in the art.

In an alternative embodiment, Method 1 is carried out as follows. EGF is PEGylated by use of a linear 20 kD PEGylation reagent containing an aminooxy group. An example of this type of reagent is the Sunbright® CA series from NOF (NOF Corp., Tokyo, Japan). EGF is dissolved in 7.0 ml histidine buffer, pH 6.0 (20 mM L-histidine, 150 mM NaCl, 5 mM $CaCl_2$). An aqueous sodium periodate solution (5 mM) is then added and the reaction mixture is incubated for 1 h in the dark at 4° C. under gentle stirring and quenched for 15 min at room temperature by the addition of 7.5 µl of a 1 M aqueous cysteine solution. The mixture is subsequently subjected to UF/DF employing Vivaspin centrifugal filtrators to remove excess periodate, quencher and the byproducts thereof.

The retentate containing oxidized EGF is next mixed with an aqueous m-toluidine solution (50 mM) and incubated for 30 min at room temperature. Aminooxy-PEG reagent with a MW of 20 kD is then added to give a 5-fold molar reagent excess. This mixture is incubated for 2.5 h at room temperature in the dark under gentle stirring.

Finally, the PEG-EGF conjugate is purified by ion-exchange chromatography. The conjugate containing fractions of the eluate are collected and then subjected to UF/DF using an appropriate MW cutoff membrane. The preparation is next analytically characterized by measuring total protein (Coomassie, Bradford) and biological activity according to methods known in the art.

Method 2:

EGF is PEGylated by use of a linear 20 kD PEGylation reagent containing an aminooxy group. An example of this type of reagent is the Sunbright® CA series from NOF (NOF Corp., Tokyo, Japan). EGF is transferred or dissolved in reaction buffer (e.g. 50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5 N aqueous HCl solution. Subsequently, a 40 mM aqueous sodium periodate solution is added within 10 minutes to give a concentration of 200 µM. The oxidation reaction is carried out for 30+/−5 min at a temperature (T) of T=+22+/−2° C. Then the reaction is stopped by addition of an aqueous L-cysteine solution (1 M) within 15 minutes at T=+22+/−2° C. to give a final concentration of 10 mM in the reaction mixture and incubation for 60+/−5 min.

The oxidized EGF is further purified by ion exchange chromatography. The oxidized EGF containing fractions of the eluate are collected and used for the conjugation reaction.

The aminooxy-PEG reagent with a MW of 20 kD reagent is added in a 50-fold molar excess to the eluate containing the purified oxidized NGF within a maximum time period (t) of 15 minutes under gentle stirring. Then an aqueous m-toluidine solution (50 mM) is added within 15 minutes to get a final concentration of 10 mM. The reaction mixture is incubated for 120+/−10 min. in the dark at a temperature (T) of T=+22+/−2° C. under gentle shaking.

The obtained PEG-EGF conjugate is further purified by ion exchange chromatography. The PEG-EGF conjugate containing fractions are collected and concentrated by ultra-/diafiltration (UF/DF) using a membrane made of regenerated cellulose with an appropriate molecular weight cut off (Millipore).

The conjugate prepared by use of this procedure are analytically characterized by measuring total protein and biological activity according to methods known in the art.

Method 3:

EGF is PEGylated by use of a linear 20 kD PEGylation reagent containing an aminooxy group. An example of this type of reagent is the Sunbright® CA series from NOF (NOF Corp., Tokyo, Japan). EGF is dissolved in Hepes buffer (50 mM Hepes, 150 mM sodium chloride, 5 mM calcium chloride, pH 6.0) and mixed with an aqueous sodium periodate solution (10 mM), and an aqueous m-toluidine solution (50 mM). Subsequently the aminooxy reagent is added to give a 20-fold molar reagent excess. The mixture is incubated for 2 h in the dark at room temperature under gentle stirring and quenched for 15 min at room temperature by the addition of 8 µl of aqueous cysteine solution (1 M).

Finally, the PEG-EGF conjugate is purified by ion-exchange chromatography on Q-Sepharose FF. 1.5 mg protein/ml gel is loaded on the column pre equilibrated with 50 mM Hepes buffer, pH 7.4 containing 5 mM $CaCl_2$. The conjugate is eluted with 50 mM Hepes buffer containing 5 mM $CaCl_2$ and 500 mM sodium chloride, pH 7.4 and is then subjected to UF/DF using a membrane. The preparation is analytically characterized by measuring total protein (Bradford) and biological activity according to methods known in the art.

In an alternative embodiment, Method 3 is carried out as follows. EGF is PEGylated by use of a linear 20 kD PEGylation reagent containing an aminooxy group. An example of this type of reagent is the Sunbright® CA series from NOF (NOF Corp., Tokyo, Japan). EGF is dissolved in Hepes buffer (50 mM Hepes, 150 mM sodium chloride, 5 mM calcium chloride, pH 6.0) and mixed with an aqueous sodium periodate solution (10 mM), and an aqueous m-toluidine solution (50 mM). Subsequently the aminooxy reagent is added to give a 20-fold molar reagent excess. The mixture is incubated for 2 h in the dark at room temperature under gentle stirring and quenched for 15 min at room temperature by the addition of 8 µl of aqueous cysteine solution (1 M).

Finally, the PEG-EGF conjugate is purified by ion-exchange chromatography. The conjugate containing fractions of the eluate are collected and then subjected to UF/DF. The preparation is analytically characterized by measuring total protein (Bradford) and biological activity according to methods known in the art.

Method 4:

EGF is PEGylated by use of a linear 20 kD PEGylation reagent containing an aminooxy group. An example of this type of reagent is the Sunbright® CA series from NOF (NOF Corp., Tokyo, Japan). An initial concentration or weight of EGF is transferred or dissolved in Hepes buffer (50 mM Hepes, 150 mM sodium chloride, 5 mM calcium chloride, pH 6.0) to get a final protein concentration of 2 mg EGF/ml. Subsequently an 5 mM aqueous sodium periodate solution is added within 15 minutes to give a final concentration of 100 µM, followed by addition of an 50 mM aqueous m-toluidine solution to get a final concentration of 10 mM within a time period of 30 minutes. Then the aminooxy-PEG reagent with a MW of 20 kD (described above) is added to give a 20-fold molar reagent excess. After correction of the pH to 6.0 the mixture is incubated for 2 h in the dark at room temperature under gentle stirring and quenched for 15 min at room temperature by the addition of an 1 M aqueous L-cysteine solution to give a final concentration of 10 mM.

The PEG-EGF conjugate is purified by means of ion exchange chromatography (IEC). The conjugate containing fractions of the eluate are concentrated by UF/DF using a 10 kD membrane made of regenerated cellulose (88 cm2, cut-off 10 kD/Millipore). The final diafiltration step is performed against Hepes buffer (50 mM Hepes, 5 mM $CaCl_2$, pH 7.5).

The preparation is analytically characterized by measuring total protein (Bradford and BCA procedure) and biological activity according to known methods.

Example 36

PEGylation of NGF Using an Aminooxy-PEG Reagent and m-Toluidine as a Nucleophilic Catalyst Method 1:

NGF is PEGylated by use of a linear 20 kD PEGylation reagent containing an aminooxy group. An example of this type of reagent is the Sunbright® CA series from NOF (NOF Corp., Tokyo, Japan). NGF is dissolved in 7.0 ml histidine buffer, pH 6.0 (20 mM L-histidine, 150 mM NaCl, 5 mM $CaCl_2$). An aqueous sodium periodate solution (5 mM) is then added and the reaction mixture is incubated for 1 h in the dark at 4° C. under gentle stirring and quenched for 15 min at room temperature by the addition of 7.5 µl of a 1 M aqueous cysteine solution. The mixture is subsequently subjected to UF/DF employing Vivaspin centrifugal filtrators to remove excess periodate, quencher and the byproducts thereof.

The retentate containing oxidized NGF is next mixed with an aqueous m-toluidine solution (50 mM) and incubated for 30 min at room temperature. Aminooxy-PEG reagent with a MW of 20 kD is then added to give a 5-fold molar reagent excess. This mixture is incubated for 2.5 h at room temperature in the dark under gentle stirring.

Finally, the PEG-NGF conjugate is purified by ion-exchange chromatography (e.g., on Q-Sepharose FF). For example, 1.5 mg protein/ml gel is loaded on the column equilibrated with 50 mM Hepes buffer, pH 7.4 containing 5 mM $CaCl_2$. The conjugate is eluted with 50 mM Hepes buffer containing 5 mM $CaCl_2$ and 500 mM sodium chloride, pH 7.4 and is then subjected to UF/DF using an appropriate MW cutoff membrane. The preparation is next analytically characterized by measuring total protein (Coomassie, Bradford) and biological activity according to methods known in the art.

In an alternative embodiment, Method 1 is carried out as follows. NGF is PEGylated by use of a linear 20 kD PEGylation reagent containing an aminooxy group. An example of this type of reagent is the Sunbright® CA series from NOF (NOF Corp., Tokyo, Japan). NGF is dissolved in 7.0 ml histidine buffer, pH 6.0 (20 mM L-histidine, 150 mM NaCl, 5 mM $CaCl_2$). An aqueous sodium periodate solution (5 mM) is then added and the reaction mixture is incubated for 1 h in the dark at 4° C. under gentle stirring and quenched for 15 min at room temperature by the addition of 7.5 µl of a 1 M aqueous cysteine solution. The mixture is subsequently subjected to UF/DF employing Vivaspin centrifugal filtrators to remove excess periodate, quencher and the byproducts thereof.

The retentate containing oxidized NGF is next mixed with an aqueous m-toluidine solution (50 mM) and incubated for 30 min at room temperature. Aminooxy-PEG reagent with a MW of 20 kD is then added to give a 5-fold molar reagent excess. This mixture is incubated for 2.5 h at room temperature in the dark under gentle stirring.

Finally, the PEG-NGF conjugate is purified by ion-exchange chromatography (The conjugate containing fractions of the eluate are collected and then subjected to UF/DF using an appropriate MW cutoff membrane. The preparation is next analytically characterized by measuring total protein (Coomassie, Bradford) and biological activity according to methods known in the art.

Method 2:

NGF is PEGylated by use of a linear 20 kD PEGylation reagent containing an aminooxy group. An example of this type of reagent is the Sunbright® CA series from NOF (NOF Corp., Tokyo, Japan). NGF is transferred or dissolved in reaction buffer (e.g. 50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5N aqueous HCl solution. Subsequently a 40 mM aqueous sodium periodate solution is added within 10 minutes to give a concentration of 200 µM. The oxidation reaction is carried out for 30+/−5 min at a temperature (T) of T=+22+/−2° C. Then the reaction is stopped by addition of an aqueous L-cysteine solution (1 M) within 15 minutes at T=+22+/−2° C. to give a final concentration of 10 mM in the reaction mixture and incubation for 60+/−5 min.

The oxidized NGF is further purified by ion exchange chromatography. The oxidized NGF containing fractions of the eluate are collected and used for the conjugation reaction.

The aminooxy-PEG reagent with a MW of 20 kD reagent is added in a 50-fold molar excess to the eluate containing the purified oxidized NGF within a maximum time period (t) of 15 minutes under gentle stirring. Then an aqueous m-toluidine solution (50 mM) is added within 15 minutes to get a final concentration of 10 mM. The reaction mixture is incubated for 120+/−10 min. in the dark at a temperature (T) of T=+22+/−2° C. under gentle shaking.

The obtained PEG-NGF conjugate is further purified by ion exchange chromatography. The PEG-NGF conjugate containing fractions are collected and concentrated by ultra-/diafiltration (UF/DF) using a membrane made of regenerated cellulose with an appropriate molecular weight cut off (Millipore).

The conjugate prepared by use of this procedure are analytically characterized by measuring total protein and biological activity according to methods known in the art.

Method 3:

NGF is PEGylated by use of a linear 20 kD PEGylation reagent containing an aminooxy group. An example of this type of reagent is the Sunbright® CA series from NOF (NOF Corp., Tokyo, Japan). NGF is dissolved in Hepes buffer (50 mM Hepes, 150 mM sodium chloride, 5 mM calcium chloride, pH 6.0) and mixed with an aqueous sodium periodate solution (10 mM), and an aqueous m-toluidine solution (50 mM). Subsequently the aminooxy reagent is added to give a 20-fold molar reagent excess. The mixture is incubated for 2 h in the dark at room temperature under gentle stirring and quenched for 15 min at room temperature by the addition of 8 µl of aqueous cysteine solution (1 M).

Finally, the PEG-NGF conjugate is purified by ion-exchange chromatography on Q Sepharose FF. 1.5 mg protein/ml gel is loaded on the column pre equilibrated with 50 mM Hepes buffer, pH 7.4 containing 5 mM $CaCl_2$. The conjugate is eluted with 50 mM Hepes buffer containing 5 mM $CaCl_2$ and 500 mM sodium chloride, pH 7.4 and is then subjected to UF/DF using a membrane. The preparation is analytically characterized by measuring total protein (Bradford) and biological activity according to methods known in the art.

In an alternative embodiment, Method 3 is carried out as follows. NGF is PEGylated by use of a linear 20 kD PEGylation reagent containing an aminooxy group. An example of this type of reagent is the Sunbright® CA series from NOF (NOF Corp., Tokyo, Japan). NGF is dissolved in Hepes buffer (50 mM Hepes, 150 mM sodium chloride, 5 mM calcium chloride, pH 6.0) and mixed with an aqueous sodium periodate solution (10 mM), and an aqueous m-toluidine solution (50 mM). Subsequently the aminooxy reagent is added to give a 20-fold molar reagent excess. The mixture is incubated for 2 h in the dark at room temperature under gentle stirring and quenched for 15 min at room temperature by the addition of 8 µl of aqueous cysteine solution (1 M).

Finally, the PEG-NGF conjugate is purified by ion-exchange chromatography. The conjugate containing fractions are collected and then subjected to UF/DF. The preparation is analytically characterized by measuring total protein (Bradford) and biological activity according to methods known in the art.

Method 4:

NGF is PEGylated by use of a linear 20 kD PEGylation reagent containing an aminooxy group. An example of this type of reagent is the Sunbright® CA series from NOF (NOF Corp., Tokyo, Japan). An initial concentration or weight of NGF is transferred or dissolved in Hepes buffer (50 mM Hepes, 150 mM sodium chloride, 5 mM calcium chloride, pH 6.0) to get a final protein concentration of 2 mg NGF/ml. Subsequently an 5 mM aqueous sodium periodate solution is added within 15 minutes to give a final concentration of 100 µM, followed by addition of an 50 mM aqueous m-toluidine solution to get a final concentration of 10 mM within a time period of 30 minutes. Then the aminooxy-PEG reagent with a MW of 20 kD (described above) is added to give a 20-fold molar reagent excess. After correction of the pH to 6.0 the mixture is incubated for 2 h in the dark at room temperature under gentle stirring and quenched for 15 min at room temperature by the addition of an 1 M aqueous L-cysteine solution to give a final concentration of 10 mM.

The PEG-NGF conjugate is purified by means of ion exchange chromatography (IEC). The conjugate containing fractions of the eluate are concentrated by UF/DF using a 10 kD membrane made of regenerated cellulose (88 cm2, cut-off 10 kD/Millipore). The final diafiltration step is performed against Hepes buffer (50 mM Hepes, 5 mM $CaCl_2$, pH 7.5).

The preparation is analytically characterized by measuring total protein (Bradford and BCA procedure) and biological activity according to known methods.

Example 37

PEGylation of HGH Using an Aminooxy-PEG Reagent and m-Toluidine as a Nucleophilic Catalyst Method 1:

As described herein, the amino acid sequence of human growth hormone (HGH) is first modified to incorporate at least one glycosylation site. Following purification, HGH is glycosylated in vitro according to methods known in the art.

HGH is PEGylated by use of a linear 20 kD PEGylation reagent containing an aminooxy group. An example of this type of reagent is the Sunbright® CA series from NOF (NOF Corp., Tokyo, Japan). HGH is dissolved in 7.0 ml histidine buffer, pH 6.0 (20 mM L-histidine, 150 mM NaCl, 5 mM $CaCl_2$). An aqueous sodium periodate solution (5 mM) is then added and the reaction mixture is incubated for 1 h in the dark at 4° C. under gentle stirring and quenched for 15 min at room temperature by the addition of 7.5 µl of a 1 M aqueous cysteine solution. The mixture is subsequently subjected to UF/DF employing Vivaspin centrifugal filtrators to remove excess periodate, quencher and the byproducts thereof.

The retentate containing oxidized HGH is next mixed with an aqueous m-toluidine solution (50 mM) and incubated for 30 min at room temperature. Aminooxy-PEG reagent with a MW of 20 kD is then added to give a 5-fold molar reagent excess. This mixture is incubated for 2.5 h at room temperature in the dark under gentle stirring.

Finally, the PEG-HGH conjugate is purified by ion-exchange chromatography (e.g., on Q Sepharose FF). For example, 1.5 mg protein/ml gel is loaded on the column equilibrated with 50 mM Hepes buffer, pH 7.4 containing 5 mM $CaCl_2$. The conjugate is eluted with 50 mM Hepes buffer containing 5 mM $CaCl_2$ and 500 mM sodium chloride, pH 7.4 and is then subjected to UF/DF using an appropriate MW cutoff membrane. The preparation is next analytically characterized by measuring total protein (Coomassie, Bradford) and biological activity according to methods known in the art.

In an alternative embodiment, Method 1 is carried out as follows. As described herein, the amino acid sequence of human growth hormone (HGH) is first modified to incorporate at least one glycosylation site. Following purification, HGH is glycosylated in vitro according to methods known in the art.

HGH is PEGylated by use of a linear 20 kD PEGylation reagent containing an aminooxy group. An example of this type of reagent is the Sunbright® CA series from NOF (NOF Corp., Tokyo, Japan). HGH is dissolved in 7.0 ml histidine buffer, pH 6.0 (20 mM L-histidine, 150 mM NaCl, 5 mM $CaCl_2$). An aqueous sodium periodate solution (5 mM) is then added and the reaction mixture is incubated for 1 h in the dark at 4° C. under gentle stirring and quenched for 15 min at room temperature by the addition of 7.5 μl of a 1 M aqueous cysteine solution. The mixture is subsequently subjected to UF/DF employing Vivaspin centrifugal filtrators to remove excess periodate, quencher and the byproducts thereof.

The retentate containing oxidized HGH is next mixed with an aqueous m-toluidine solution (50 mM) and incubated for 30 min at room temperature. Aminooxy-PEG reagent with a MW of 20 kD is then added to give a 5-fold molar reagent excess. This mixture is incubated for 2.5 h at room temperature in the dark under gentle stirring.

Finally, the PEG-HGH conjugate is purified by ion-exchange chromatography (The conjugate containing fractions of the eluate are collected and then subjected to UF/DF using an appropriate MW cutoff membrane. The preparation is next analytically characterized by measuring total protein (Coomassie, Bradford) and biological activity according to methods known in the art.

Method 2:

As described herein, the amino acid sequence of human growth hormone (HGH) is first modified to incorporate at least one glycosylation site. Following purification, HGH is glycosylated in vitro according to methods known in the art.

HGH is PEGylated by use of a linear 20 kD PEGylation reagent containing an aminooxy group. An example of this type of reagent is the Sunbright® CA series from NOF (NOF Corp., Tokyo, Japan). HGH is transferred or dissolved in reaction buffer (e.g. 50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5N aqueous HCl solution. Subsequently, a 40 mM aqueous sodium periodate solution is added within 10 minutes to give a concentration of 200 μM. The oxidation reaction is carried out for 30+/−5 min at a temperature (T) of T=+22+/−2° C. Then the reaction is stopped by addition of an aqueous L-cysteine solution (1 M) within 15 minutes at T=+22+/−2° C. to give a final concentration of 10 mM in the reaction mixture and incubation for 60+/−5 min.

The oxidized HGH is further purified by ion exchange chromatography. The oxidized HGH containing fractions of the eluate are collected and used for the conjugation reaction.

The aminooxy-PEG reagent with a MW of 20 kD reagent is added in a 50-fold molar excess to the eluate containing the purified oxidized HGH within a maximum time period (t) of 15 minutes under gentle stirring. Then an aqueous m-toluidine solution (50 mM) is added within 15 minutes to get a final concentration of 10 mM. The reaction mixture is incubated for 120+/−10 min. in the dark at a temperature (T) of T=+22+/−2° C. under gentle shaking.

The obtained PEG-HGH conjugate is further purified by ion exchange chromatography. The PEG-NGF conjugate containing fractions are collected and concentrated by ultra-/diafiltration (UF/DF) using a membrane made of regenerated cellulose with an appropriate molecular weight cut off (Millipore).

The conjugate prepared by use of this procedure are analytically characterized by measuring total protein and biological activity according to methods known in the art.

Method 3:

As described herein, the amino acid sequence of human growth hormone (HGH) is first modified to incorporate at least one glycosylation site. Following purification, HGH is glycosylated in vitro according to methods known in the art.

HGH is PEGylated by use of a linear 20 kD PEGylation reagent containing an aminooxy group. An example of this type of reagent is the Sunbright® CA series from NOF (NOF Corp., Tokyo, Japan). HGH is dissolved in Hepes buffer (50 mM Hepes, 150 mM sodium chloride, 5 mM calcium chloride, pH 6.0) and mixed with an aqueous sodium periodate solution (10 mM), and an aqueous m-toluidine solution (50 mM). Subsequently the aminooxy reagent is added to give a 20-fold molar reagent excess. The mixture is incubated for 2 h in the dark at room temperature under gentle stirring and quenched for 15 min at room temperature by the addition of 8 μl of aqueous cysteine solution (1 M).

Finally, the PEG-HGH conjugate is purified by ion-exchange chromatography on Q-Sepharose FF. 1.5 mg protein/ml gel is loaded on the column pre equilibrated with 50 mM Hepes buffer, pH 7.4 containing 5 mM $CaCl_2$. The conjugate is eluted with 50 mM Hepes buffer containing 5 mM $CaCl_2$ and 500 mM sodium chloride, pH 7.4 and is then subjected to UF/DF using a membrane. The preparation is analytically characterized by measuring total protein (Bradford) and biological activity according to methods known in the art.

In an alternative embodiment, Method 3 is carried out as follows. As described herein, the amino acid sequence of human growth hormone (HGH) is first modified to incorporate at least one glycosylation site. Following purification, HGH is glycosylated in vitro according to methods known in the art. HGH is PEGylated by use of a linear 20 kD PEGylation reagent containing an aminooxy group. An example of this type of reagent is the Sunbright® CA series from NOF (NOF Corp., Tokyo, Japan). HGH is dissolved in Hepes buffer (50 mM Hepes, 150 mM sodium chloride, 5 mM calcium chloride, pH 6.0) and mixed with an aqueous sodium periodate solution (10 mM), and an aqueous m-toluidine solution (50 mM). Subsequently the aminooxy reagent is added to give a 20-fold molar reagent excess. The mixture is incubated for 2 h in the dark at room temperature under gentle stirring and quenched for 15 min at room temperature by the addition of 8 μl of aqueous cysteine solution (1 M).

Finally, the PEG-HGH conjugate is purified by ion-exchange chromatography. The conjugate containing fractions are collected and then subjected to UF/DF. The preparation is analytically characterized by measuring total protein (Bradford) and biological activity according to methods known in the art.

Method 4:

As described herein, the amino acid sequence of human growth hormone (HGH) is first modified to incorporate at least one glycosylation site. Following purification, HGH is glycosylated in vitro according to methods known in the art.

HGH is PEGylated by use of a linear 20 kD PEGylation reagent containing an aminooxy group. An example of this type of reagent is the Sunbright® CA series from NOF (NOF Corp., Tokyo, Japan). An initial concentration or weight of HGH is transferred or dissolved in Hepes buffer (50 mM Hepes, 150 mM sodium chloride, 5 mM calcium chloride, pH 6.0) to get a final protein concentration of 2 mg HGH/ml. Subsequently an 5 mM aqueous sodium periodate solution is added within 15 minutes to give a final concentration of 100 μM, followed by addition of an 50 mM aqueous m-toluidine solution to get a final concentration of 10 mM within a time period of 30 minutes. Then the aminooxy-PEG reagent with a MW of 20 kD (described above) is added to give a 20-fold molar reagent excess. After correction of the pH to 6.0 the mixture is incubated for 2 h in the dark at room temperature under gentle stirring and quenched for 15 min at room temperature by the addition of a 1 M aqueous L-cysteine solution to give a final concentration of 10 mM.

The PEG-HGH conjugate is purified by means of ion exchange chromatography (IEC). The conjugate containing fractions of the eluate are concentrated by UF/DF using a 10 kD membrane made of regenerated cellulose (88 cm2, cut-off 10 kD/Millipore). The final diafiltration step is performed against Hepes buffer (50 mM Hepes, 5 mM $CaCl_2$, pH 7.5).

The preparation is analytically characterized by measuring total protein (Bradford and BCA procedure) and biological activity according to known methods.

Example 38

PEGylation of TNF-Alpha Using an Aminooxy-PEG Reagent and m-Toluidine as a Nucleophilic Catalyst Method 1:

TNF-alpha is PEGylated by use of a linear 20 kD PEGylation reagent containing an aminooxy group. An example of this type of reagent is the Sunbright® CA series from NOF (NOF Corp., Tokyo, Japan). TNF-alpha is dissolved in 7.0 ml histidine buffer, pH 6.0 (20 mM L-histidine, 150 mM NaCl, 5 mM $CaCl_2$). An aqueous sodium periodate solution (5 mM) is then added and the reaction mixture is incubated for 1 h in the dark at 4° C. under gentle stirring and quenched for 15 min at room temperature by the addition of 7.5 μl of a 1 M aqueous cysteine solution. The mixture is subsequently subjected to UF/DF employing Vivaspin centrifugal filtrators to remove excess periodate, quencher and the byproducts thereof.

The retentate containing oxidized TNF-alpha is next mixed with an aqueous m-toluidine solution (50 mM) and incubated for 30 min at room temperature. Aminooxy-PEG reagent with a MW of 20 kD is then added to give a 5-fold molar reagent excess. This mixture is incubated for 2.5 h at room temperature in the dark under gentle stirring.

Finally, the PEG-TNF-alpha conjugate is purified by ion-exchange chromatography (e.g., on Q-Sepharose FF). For example, 1.5 mg protein/ml gel is loaded on the column equilibrated with 50 mM Hepes buffer, pH 7.4 containing 5 mM $CaCl_2$. The conjugate is eluted with 50 mM Hepes buffer containing 5 mM $CaCl_2$ and 500 mM sodium chloride, pH 7.4 and is then subjected to UF/DF using an appropriate MW cutoff membrane. The preparation is next analytically characterized by measuring total protein (Coomassie, Bradford) and biological activity according to methods known in the art.

In an alternative embodiment, Method 1 is carried out as follows. TNF-alpha is PEGylated by use of a linear 20 kD PEGylation reagent containing an aminooxy group. An example of this type of reagent is the Sunbright® CA series from NOF (NOF Corp., Tokyo, Japan). TNF-alpha is dissolved in 7.0 ml histidine buffer, pH 6.0 (20 mM L-histidine, 150 mM NaCl, 5 mM $CaCl_2$). An aqueous sodium periodate solution (5 mM) is then added and the reaction mixture is incubated for 1 h in the dark at 4° C. under gentle stirring and quenched for 15 min at room temperature by the addition of 7.5 μl of a 1 M aqueous cysteine solution. The mixture is subsequently subjected to UF/DF employing Vivaspin centrifugal filtrators to remove excess periodate, quencher and the byproducts thereof.

The retentate containing oxidized TNF-alpha is next mixed with an aqueous m-toluidine solution (50 mM) and incubated for 30 min at room temperature. Aminooxy-PEG reagent with a MW of 20 kD is then added to give a 5-fold molar reagent excess. This mixture is incubated for 2.5 h at room temperature in the dark under gentle stirring.

Finally, the PEG-TNF-alpha conjugate is purified by ion-exchange chromatography. The conjugate containing fractions of the eluate are collected and then subjected to UF/DF using an appropriate MW cutoff membrane. The preparation is next analytically characterized by measuring total protein (Coomassie, Bradford) and biological activity according to methods known in the art.

Method 2:

TNF-alpha is PEGylated by use of a linear 20 kD PEGylation reagent containing an aminooxy group. An example of this type of reagent is the Sunbright® CA series from NOF (NOF Corp., Tokyo, Japan). TNF-alpha is transferred or dissolved in reaction buffer (e.g. 50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5N aqueous HCl solution. Subsequently a 40 mM aqueous sodium periodate solution is added within 10 minutes to give a concentration of 200 μM. The oxidation reaction is carried out for 30+/−5 min at a temperature (T) of T=+22+/−2° C. Then the reaction is stopped by addition of an aqueous L-cysteine solution (1 M) within 15 minutes at T=+22+/−2° C. to give a final concentration of 10 mM in the reaction mixture and incubation for 60+/−5 min.

The oxidized TNF-alpha is further purified by ion exchange chromatography. The oxidized TNF-alpha containing fractions of the eluate are collected and used for the conjugation reaction.

The aminooxy-PEG reagent with a MW of 20 kD reagent is added in a 50-fold molar excess to the eluate containing the purified oxidized TNF alpha within a maximum time period (t) of 15 minutes under gentle stirring. Then an aqueous m-toluidine solution (50 mM) is added within 15 minutes to get a final concentration of 10 mM. The reaction mixture is incubated for 120+/−10 min. in the dark at a temperature (T) of T=+22+/−2° C. under gentle shaking.

The obtained PEG-TNF-alpha conjugate is further purified by ion exchange chromatography. The PEG-TNF-alpha conjugate containing fractions are collected and concentrated by ultra-/diafiltration (UF/DF) using a membrane made of regenerated cellulose with an appropriate molecular weight cut off (Millipore).

The conjugate prepared by use of this procedure are analytically characterized by measuring total protein and biological activity according to methods known in the art.

Method 3:

TNF-alpha is PEGylated by use of a linear 20 kD PEGylation reagent containing an aminooxy group. An example of this type of reagent is the Sunbright® CA series from NOF (NOF Corp., Tokyo, Japan). TNF-alpha is dissolved in Hepes buffer (50 mM Hepes, 150 mM sodium chloride, 5 mM calcium chloride, pH 6.0) and mixed with an aqueous sodium periodate solution (10 mM), and an aqueous m-toluidine solution (50 mM). Subsequently the aminooxy reagent is added to give a 20-fold molar reagent excess. The mixture is incubated for 2 h in the dark at room temperature under gentle stirring and quenched for 15 min at room temperature by the addition of 8 μl of aqueous cysteine solution (1 M).

Finally, the PEG-TNF-alpha conjugate is purified by ion-exchange chromatography on Q-Sepharose FF. 1.5 mg protein/ml gel is loaded on the column pre equilibrated with 50 mM Hepes buffer, pH 7.4 containing 5 mM $CaCl_2$. The conjugate is eluted with 50 mM Hepes buffer containing 5 mM $CaCl_2$ and 500 mM sodium chloride, pH 7.4 and is then subjected to UF/DF using a membrane. The preparation is analytically characterized by measuring total protein (Bradford) and biological activity according to methods known in the art.

In an alternative embodiment, Method 3 is carried out as follows. TNF-alpha is PEGylated by use of a linear 20 kD PEGylation reagent containing an aminooxy group. An example of this type of reagent is the Sunbright® CA series from NOF (NOF Corp., Tokyo, Japan). TNF-alpha is dissolved in Hepes buffer (50 mM Hepes, 150 mM sodium chloride, 5 mM calcium chloride, pH 6.0) and mixed with an aqueous sodium periodate solution (10 mM), and an aqueous m-toluidine solution (50 mM). Subsequently, the aminooxy reagent is added to give a 20-fold molar reagent excess. The mixture is incubated for 2 h in the dark at room temperature under gentle stirring and quenched for 15 min at room temperature by the addition of 8 µl of aqueous cysteine solution (1 M).

Finally, the PEG-TNF-alpha conjugate is purified by ion-exchange chromatography. The conjugate containing fractions are collected and then subjected to UF/DF. The preparation is analytically characterized by measuring total protein (Bradford) and biological activity according to methods known in the art.

Method 4:

TNF-alpha is PEGylated by use of a linear 20 kD PEGylation reagent containing an aminooxy group. An example of this type of reagent is the Sunbright® CA series from NOF (NOF Corp., Tokyo, Japan). An initial concentration or weight of TNF-alpha is transferred or dissolved in Hepes buffer (50 mM Hepes, 150 mM sodium chloride, 5 mM calcium chloride, pH 6.0) to get a final protein concentration of 2 mg TNF-alpha/ml. Subsequently, an 5 mM aqueous sodium periodate solution is added within 15 minutes to give a final concentration of 100 µM, followed by addition of an 50 mM aqueous m-toluidine solution to get a final concentration of 10 mM within a time period of 30 minutes. Then the aminooxy-PEG reagent with a MW of 20 kD (described above) is added to give a 20-fold molar reagent excess. After correction of the pH to 6.0 the mixture is incubated for 2 h in the dark at room temperature under gentle stirring and quenched for 15 min at room temperature by the addition of an 1 M aqueous L-cysteine solution to give a final concentration of 10 mM.

The PEG-TNF-alpha conjugate is purified by means of ion exchange chromatography (IEC). The conjugate containing fractions of the eluate are concentrated by UF/DF using a 10 kD membrane made of regenerated cellulose (88 cm2, cut-off 10 kD/Millipore). The final diafiltration step is performed against Hepes buffer (50 mM Hepes, 5 mM $CaCl_2$, pH 7.5).

The preparation is analytically characterized by measuring total protein (Bradford and BCA procedure) and biological activity according to known methods.

Example 39

PEGylation of Insulin Using an Aminooxy-PEG Reagent and m-Toluidine as a Nucleophilic Catalyst Method 1:

As described herein, the amino acid sequence of insulin is first modified to incorporate at least one glycosylation site. Following purification, insulin is glycosylated in vitro according to methods known in the art. Insulin is PEGylated by use of a linear 20 kD PEGylation reagent containing an aminooxy group. An example of this type of reagent is the Sunbright® CA series from NOF (NOF Corp., Tokyo, Japan). Insulin is dissolved in 7.0 ml histidine buffer, pH 6.0 (20 mM L-histidine, 150 mM NaCl, 5 mM $CaCl_2$). An aqueous sodium periodate solution (5 mM) is then added and the reaction mixture is incubated for 1 h in the dark at 4° C. under gentle stirring and quenched for 15 min at room temperature by the addition of 7.5 µl of a 1 M aqueous cysteine solution. The mixture is subsequently subjected to UF/DF employing Vivaspin centrifugal filtrators to remove excess periodate, quencher and the byproducts thereof.

The retentate containing oxidized insulin is next mixed with an aqueous m-toluidine solution (50 mM) and incubated for 30 min at room temperature. Aminooxy-PEG reagent with a MW of 20 kD is then added to give a 5-fold molar reagent excess. This mixture is incubated for 2.5 h at room temperature in the dark under gentle stirring.

Finally, the PEG-insulin conjugate is purified by ion-exchange chromatography (e.g., on Q-Sepharose FF). For example, 1.5 mg protein/ml gel is loaded on the column equilibrated with 50 mM Hepes buffer, pH 7.4 containing 5 mM $CaCl_2$. The conjugate is eluted with 50 mM Hepes buffer containing 5 mM $CaCl_2$ and 500 mM sodium chloride, pH 7.4 and is then subjected to UF/DF using an appropriate MW cutoff membrane. The preparation is next analytically characterized by measuring total protein (Coomassie, Bradford) and biological activity according to methods known in the art.

In an alternative embodiment, Method 1 is carried out as follows. As described herein, the amino acid sequence of insulin is first modified to incorporate at least one glycosylation site. Following purification, insulin is glycosylated in vitro according to methods known in the art. Insulin is PEGylated by use of a linear 20 kD PEGylation reagent containing an aminooxy group. An example of this type of reagent is the Sunbright® CA series from NOF (NOF Corp., Tokyo, Japan). Insulin is dissolved in 7.0 ml histidine buffer, pH 6.0 (20 mM L-histidine, 150 mM NaCl, 5 mM $CaCl_2$). An aqueous sodium periodate solution (5 mM) is then added and the reaction mixture is incubated for 1 h in the dark at 4° C. under gentle stirring and quenched for 15 min at room temperature by the addition of 7.5 µl of a 1 M aqueous cysteine solution. The mixture is subsequently subjected to UF/DF employing Vivaspin centrifugal filtrators to remove excess periodate, quencher and the byproducts thereof.

The retentate containing oxidized insulin is next mixed with an aqueous m-toluidine solution (50 mM) and incubated for 30 min at room temperature. Aminooxy-PEG reagent with a MW of 20 kD is then added to give a 5-fold molar reagent excess. This mixture is incubated for 2.5 h at room temperature in the dark under gentle stirring.

Finally, the PEG-insulin conjugate is purified by ion-exchange chromatography. The conjugate containing fractions of the eluate are collected and then subjected to UF/DF using an appropriate MW cutoff membrane. The preparation is next analytically characterized by measuring total protein (Coomassie, Bradford) and biological activity according to methods known in the art.

Method 2:

As described herein, the amino acid sequence of insulin is first modified to incorporate at least one glycosylation site. Following purification, insulin is glycosylated in vitro according to methods known in the art.

Insulin is PEGylated by use of a linear 20 kD PEGylation reagent containing an aminooxy group. An example of this type of reagent is the Sunbright® CA series from NOF (NOF Corp., Tokyo, Japan). Insulin is transferred or dissolved in reaction buffer (e.g. 50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5 N aqueous HCl solution. Subsequently, a 40 mM aqueous sodium periodate solution is added within 10 minutes to give a concentration of 200 µM. The oxidation reaction is carried out for 30+/−5 min at a temperature (T) of T=+22+/−2° C. Then the reaction is stopped by addition of an aqueous L-cysteine solution (1 M)

within 15 minutes at T=+22+/−2° C. to give a final concentration of 10 mM in the reaction mixture and incubation for 60+/−5 min.

The oxidized insulin is further purified by ion exchange chromatography. The oxidized insulin containing fractions of the eluate are collected and used for the conjugation reaction.

The aminooxy-PEG reagent with a MW of 20 kD reagent is added in a 50-fold molar excess to the eluate containing the purified oxidized insulin within a maximum time period (t) of 15 minutes under gentle stirring. Then an aqueous m-toluidine solution (50 mM) is added within 15 minutes to get a final concentration of 10 mM. The reaction mixture is incubated for 120+/−10 min. in the dark at a temperature (T) of T=+22+/−2° C. under gentle shaking.

The obtained PEG-insulin conjugate is further purified by ion exchange chromatography. The PEG-insulin conjugate containing fractions are collected and concentrated by ultra-/diafiltration (UF/DF) using a membrane made of regenerated cellulose with an appropriate molecular weight cut off (Millipore).

The conjugate prepared by use of this procedure are analytically characterized by measuring total protein and biological activity according to methods known in the art.

Method 3:

As described herein, the amino acid sequence of insulin is first modified to incorporate at least one glycosylation site. Following purification, insulin is glycosylated in vitro according to methods known in the art.

Insulin is PEGylated by use of a linear 20 kD PEGylation reagent containing an aminooxy group. An example of this type of reagent is the Sunbright® CA series from NOF (NOF Corp., Tokyo, Japan). Insulin is dissolved in Hepes buffer (50 mM Hepes, 150 mM sodium chloride, 5 mM calcium chloride, pH 6.0) and mixed with an aqueous sodium periodate solution (10 mM), and an aqueous m-toluidine solution (50 mM). Subsequently, the aminooxy reagent is added to give a 20-fold molar reagent excess. The mixture is incubated for 2 h in the dark at room temperature under gentle stirring and quenched for 15 min at room temperature by the addition of 8 μl of aqueous cysteine solution (1 M).

Finally, the PEG-insulin conjugate is purified by ion-exchange chromatography on Q Sepharose FF. 1.5 mg protein/ml gel is loaded on the column pre equilibrated with 50 mM Hepes buffer, pH 7.4 containing 5 mM $CaCl_2$. The conjugate is eluted with 50 mM Hepes buffer containing 5 mM $CaCl_2$ and 500 mM sodium chloride, pH 7.4 and is then subjected to UF/DF using a membrane. The preparation is analytically characterized by measuring total protein (Bradford) and biological activity according to methods known in the art.

In an alternative embodiment, Method 3 is carried out as follows. As described herein, the amino acid sequence of insulin is first modified to incorporate at least one glycosylation site. Following purification, insulin is glycosylated in vitro according to methods known in the art. Insulin is PEGylated by use of a linear 20 kD PEGylation reagent containing an aminooxy group. An example of this type of reagent is the Sunbright® CA series from NOF (NOF Corp., Tokyo, Japan). Insulin is dissolved in Hepes buffer (50 mM Hepes, 150 mM sodium chloride, 5 mM calcium chloride, pH 6.0) and mixed with an aqueous sodium periodate solution (10 mM), and an aqueous m-toluidine solution (50 mM). Subsequently the aminooxy reagent is added to give a 20-fold molar reagent excess. The mixture is incubated for 2 h in the dark at room temperature under gentle stirring and quenched for 15 min at room temperature by the addition of 8 μl of aqueous cysteine solution (1 M).

Finally, the insulin-conjugate is purified by ion-exchange chromatography. The conjugate containing fractions are collected and then subjected to UF/DF. The preparation is analytically characterized by measuring total protein (Bradford) and biological activity according to methods known in the art.

Method 4:

As described herein, the amino acid sequence of insulin is first modified to incorporate at least one glycosylation site. Following purification, insulin is glycosylated in vitro according to methods known in the art.

Insulin is PEGylated by use of a linear 20 kD PEGylation reagent containing an aminooxy group. An example of this type of reagent is the Sunbright® CA series from NOF (NOF Corp., Tokyo, Japan). An initial concentration or weight of insulin is transferred or dissolved in Hepes buffer (50 mM Hepes, 150 mM sodium chloride, 5 mM calcium chloride, pH 6.0) to get a final protein concentration of 2 mg insulin/ml. Subsequently an 5 mM aqueous sodium periodate solution is added within 15 minutes to give a final concentration of 100 μM, followed by addition of an 50 mM aqueous m-toluidine solution to get a final concentration of 10 mM within a time period of 30 minutes. Then the aminooxy-PEG reagent with a MW of 20 kD (described above) is added to give a 20-fold molar reagent excess. After correction of the pH to 6.0 the mixture is incubated for 2 h in the dark at room temperature under gentle stirring and quenched for 15 min at room temperature by the addition of a 1 M aqueous L-cysteine solution to give a final concentration of 10 mM.

The PEG-insulin conjugate is purified by means of ion exchange chromatography (IEC). The conjugate containing fractions of the eluate are concentrated by UF/DF using a 10 kD membrane made of regenerated cellulose (88 cm2, cut-off 10 kD/Millipore). The final diafiltration step is performed against Hepes buffer (50 mM Hepes, 5 mM $CaCl_2$, pH 7.5).

The preparation is analytically characterized by measuring total protein (Bradford and BCA procedure) and biological activity according to known methods.

Example 40

PEGylation of Interferon-Alpha Using an Aminooxy-PEG Reagent and m-Toluidine as a Nucleophilic Catalyst Method 1:

Interferon-alpha is PEGylated by use of a linear 20 kD PEGylation reagent containing an aminooxy group. An example of this type of reagent is the Sunbright® CA series from NOF (NOF Corp., Tokyo, Japan). Interferon-alpha is dissolved in 7.0 ml histidine buffer, pH 6.0 (20 mM L-histidine, 150 mM NaCl, 5 mM $CaCl_2$). An aqueous sodium periodate solution (5 mM) is then added and the reaction mixture is incubated for 1 h in the dark at 4° C. under gentle stirring and quenched for 15 min at room temperature by the addition of 7.5 μl of a 1 M aqueous cysteine solution. The mixture is subsequently subjected to UF/DF employing Vivaspin centrifugal filtrators to remove excess periodate, quencher and the byproducts thereof.

The retentate containing oxidized interferon-alpha is next mixed with an aqueous m-toluidine solution (50 mM) and incubated for 30 min at room temperature. Aminooxy-PEG reagent with a MW of 20 kD is then added to give a 5-fold molar reagent excess. This mixture is incubated for 2.5 h at room temperature in the dark under gentle stirring.

Finally, the PEG-interferon-alpha conjugate is purified by ion-exchange chromatography (e.g., on Q-Sepharose FF). For example, 1.5 mg protein/ml gel is loaded on the column equilibrated with 50 mM Hepes buffer, pH 7.4 containing 5 mM $CaCl_2$. The conjugate is eluted with 50 mM Hepes buffer containing 5 mM $CaCl_2$ and 500 mM sodium chloride, pH 7.4 and is then subjected to UF/DF using an appropriate MW cutoff membrane. The preparation is next analytically characterized by measuring total protein (Coomassie, Bradford) and biological activity according to methods known in the art.

In an alternative embodiment, Method 1 is carried out as follows. Interferon-alpha is PEGylated by use of a linear 20 kD PEGylation reagent containing an aminooxy group. An example of this type of reagent is the Sunbright® CA series from NOF (NOF Corp., Tokyo, Japan). Interferon-alpha is dissolved in 7.0 ml histidine buffer, pH 6.0 (20 mM L-histidine, 150 mM NaCl, 5 mM $CaCl_2$). An aqueous sodium periodate solution (5 mM) is then added and the reaction mixture is incubated for 1 h in the dark at 4° C. under gentle stirring and quenched for 15 min at room temperature by the addition of 7.5 μl of a 1 M aqueous cysteine solution. The mixture is subsequently subjected to UF/DF employing Vivaspin centrifugal filtrators to remove excess periodate, quencher and the byproducts thereof.

The retentate containing oxidized interferon-alpha is next mixed with an aqueous m-toluidine solution (50 mM) and incubated for 30 min at room temperature. Aminooxy-PEG reagent with a MW of 20 kD is then added to give a 5-fold molar reagent excess. This mixture is incubated for 2.5 h at room temperature in the dark under gentle stirring.

Finally, the PEG-interferon-alpha conjugate is purified by ion-exchange chromatography. The conjugate containing fractions are collected and then subjected to UF/DF using an appropriate MW cutoff membrane. The preparation is next analytically characterized by measuring total protein (Coomassie, Bradford) and biological activity according to methods known in the art.

Method 2:

Interferon-alpha is PEGylated by use of a linear 20 kD PEGylation reagent containing an aminooxy group. An example of this type of reagent is the Sunbright® CA series from NOF (NOF Corp., Tokyo, Japan). Interferon-alpha is transferred or dissolved in reaction buffer (e.g. 50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5 N aqueous HCl solution. Subsequently, a 40 mM aqueous sodium periodate solution is added within 10 minutes to give a concentration of 200 μM. The oxidation reaction is carried out for 30+/−5 min at a temperature (T) of T=+22+/−2° C. Then the reaction is stopped by addition of an aqueous L-cysteine solution (1 M) within 15 minutes at T=+22+/−2° C. to give a final concentration of 10 mM in the reaction mixture and incubation for 60+/−5 min.

The oxidized interferon-alpha is further purified by ion exchange chromatography. The oxidized interferon-alpha containing fractions of the eluate are collected and used for the conjugation reaction.

The aminooxy-PEG reagent with a MW of 20 kD reagent is added in a 50-fold molar excess to the eluate containing the purified oxidized interferon-alpha within a maximum time period (t) of 15 minutes under gentle stirring. Then an aqueous m-toluidine solution (50 mM) is added within 15 minutes to get a final concentration of 10 mM. The reaction mixture is incubated for 120+/−10 min. in the dark at a temperature (T) of T=+22+/−2° C. under gentle shaking.

The obtained PEG-interferon-alpha conjugate is further purified by ion exchange chromatography. The PEG-interferon alpha conjugate containing fractions are collected and concentrated by ultra-/diafiltration (UF/DF) using a membrane made of regenerated cellulose with an appropriate molecular weight cut off (Millipore).

The conjugate prepared by use of this procedure are analytically characterized by measuring total protein and biological activity according to methods known in the art.

Method 3:

Interferon-alpha is PEGylated by use of a linear 20 kD PEGylation reagent containing an aminooxy group. An example of this type of reagent is the Sunbright® CA series from NOF (NOF Corp., Tokyo, Japan). Interferon-alpha is dissolved in Hepes buffer (50 mM Hepes, 150 mM sodium chloride, 5 mM calcium chloride, pH 6.0) and mixed with an aqueous sodium periodate solution (10 mM), and an aqueous m-toluidine solution (50 mM). Subsequently the aminooxy reagent is added to give a 20-fold molar reagent excess. The mixture is incubated for 2 h in the dark at room temperature under gentle stirring and quenched for 15 min at room temperature by the addition of 8 μl of aqueous cysteine solution (1 M).

Finally, the PEG-interferon-alpha conjugate is purified by ion-exchange chromatography on Q-Sepharose FF. 1.5 mg protein/ml gel is loaded on the column pre equilibrated with 50 mM Hepes buffer, pH 7.4 containing 5 mM $CaCl_2$. The conjugate is eluted with 50 mM Hepes buffer containing 5 mM $CaCl_2$ and 500 mM sodium chloride, pH 7.4 and is then subjected to UF/DF using a membrane. The preparation is analytically characterized by measuring total protein (Bradford) and biological activity according to methods known in the art.

In an alternative embodiment, Method 3 is carried out as follows. Interferon-alpha is PEGylated by use of a linear 20 kD PEGylation reagent containing an aminooxy group. An example of this type of reagent is the Sunbright® CA series from NOF (NOF Corp., Tokyo, Japan). Interferon-alpha is dissolved in Hepes buffer (50 mM Hepes, 150 mM sodium chloride, 5 mM calcium chloride, pH 6.0) and mixed with an aqueous sodium periodate solution (10 mM), and an aqueous m-toluidine solution (50 mM). Subsequently the aminooxy reagent is added to give a 20-fold molar reagent excess. The mixture is incubated for 2 h in the dark at room temperature under gentle stirring and quenched for 15 min at room temperature by the addition of 8 μl of aqueous cysteine solution (1 M).

Finally, the PEG-interferon-alpha conjugate is purified by ion-exchange chromatography. The conjugate containing fractions are collected and then subjected to UF/DF using a membrane. The preparation is analytically characterized by measuring total protein (Bradford) and biological activity according to methods known in the art.

Method 4:

Interferon-alpha is PEGylated by use of a linear 20 kD PEGylation reagent containing an aminooxy group. An example of this type of reagent is the Sunbright® CA series from NOF (NOF Corp., Tokyo, Japan). An initial concentration or weight of interferon-alpha is transferred or dissolved in Hepes buffer (50 mM Hepes, 150 mM sodium chloride, 5 mM calcium chloride, pH 6.0) to get a final protein concentration of 2 mg interferon-alpha/ml. Subsequently, an 5 mM aqueous sodium periodate solution is added within 15 minutes to give a final concentration of 100 μM, followed by addition of an 50 mM aqueous m-toluidine solution to get a final concentration of 10 mM within a time period of 30 minutes. Then the aminooxy-PEG reagent with a MW of 20 kD (described above) is added to give a 20-fold molar reagent excess. After correction of the pH to 6.0 the mixture is incubated for 2 h in the dark at room temperature under gentle stirring and quenched for 15 min at room temperature by the addition of an 1 M aqueous L-cysteine solution to give a final concentration of 10 mM.

The PEG-interferon-alpha conjugate is purified by means of ion exchange chromatography (IEC). The conjugate containing fractions of the eluate are concentrated by UF/DF using a 10 kD membrane made of regenerated cellulose (88 cm2, cut-off 10 kD/Millipore). The final diafiltration step is performed against Hepes buffer (50 mM Hepes, 5 mM $CaCl_2$, pH 7.5).

The preparation is analytically characterized by measuring total protein (Bradford and BCA procedure) and biological activity according to known methods.

Example 41

PEGylation of Interferon-Gamma Using an Aminooxy-PEG Reagent and m-Toluidine as a Nucleophilic Catalyst Method 1:

Interferon-gamma is PEGylated by use of a linear 20 kD PEGylation reagent containing an aminooxy group. An example of this type of reagent is the Sunbright® CA series from NOF (NOF Corp., Tokyo, Japan). 10 mg Interferon-gamma is dissolved in 5 ml histidine buffer, pH 6.0 (20 mM L-histidine, 150 mM NaCl). 100 µl of an aqueous sodium periodate solution (5 mM) is then added and the reaction mixture is incubated for 1 h in the dark at 4° C. under gentle stirring and quenched for 15 min at room temperature by the addition of 50 µl of a 1 M aqueous cysteine solution. The mixture is subsequently subjected to UF/DF employing Vivaspin 15R 10 kD centrifugal filtrators to remove excess periodate, quencher and the byproducts thereof.

The retentate (approx. 7 ml), containing oxidized interferon-gamma, is mixed with 2 ml of an aqueous m-toluidine solution (50 mM) and incubated for 30 min at room temperature. Then aminooxy-PEG reagent with a MW of 20 kD (described above) is added to give a 5-fold molar reagent excess. This mixture is incubated for 2.5 h at RT in the dark under gentle stirring.

Finally, the PEG-interferon-gamma conjugate is purified by ion-exchange chromatography on SP Sepharose FF. The reaction mixture is diluted with 20 ml Buffer A (50 mM Hepes, pH 6.5) and loaded onto a 20 ml HiPrep SPFF 16/10 column (GE Healthcare, Fairfield, Conn.) pre-equilibrated with Buffer A. Then the column is eluted with Buffer B (50 mM Hepes, 1 M NaCl, pH 6.5). Free interferon-gamma is eluted by washing the column with 25% Buffer B and the conjugate at 50% Buffer B. The conjugate containing fractions are concentrated by UF/DF using a 10 kD membrane made of regenerated cellulose (88 cm2, cut-off 10 kD/Millipore). The final diafiltration step is performed against histidine buffer, pH 6.9 containing 150 mM NaCl. The preparation is analytically characterized by measuring total protein (Bradford) and biological activity according to methods known in the art. For the PEG-interferon-gamma conjugate a specific activity of >50% in comparison to native Interferon gamma is determined. The conjugate is additionally analytically characterized by Size Exclusion HPLC using a Agilent 1200 HPLC system equipped with a Shodex KW 803 column under conditions as previously described (Kolarich et al, Transfusion 2006; 46:1959-77). It is shown that the preparation contains no free Interferon-gamma.

Method 2:

Interferon-gamma is PEGylated by use of a linear 20 kD PEGylation reagent containing an aminooxy group. An example of this type of reagent is the Sunbright® CA series from NOF (NOF Corp., Tokyo, Japan). Interferon-gamma is transferred or dissolved in reaction buffer (e.g. 50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5 N aqueous HCl solution. Subsequently a 40 mM aqueous sodium periodate solution is added within 10 minutes to give a concentration of 200 µM. The oxidation reaction is carried out for 30+/−5 min at a temperature (T) of T=+22+/−2° C. Then the reaction is stopped by addition of an aqueous L-cysteine solution (1 M) within 15 minutes at T=+22+/−2° C. to give a final concentration of 10 mM in the reaction mixture and incubation for 60+/−5 min.

The oxidized interferon-gamma is further purified by ion exchange chromatography. The oxidized interferon-gamma containing fractions of the eluate are collected and used for the conjugation reaction.

The aminooxy-PEG reagent with a MW of 20 kD reagent is added in a 50-fold molar excess to the eluate containing the purified oxidized interferon-gamma within a maximum time period (t) of 15 minutes under gentle stirring. Then an aqueous m-toluidine solution (50 mM) is added within 15 minutes to get a final concentration of 10 mM. The reaction mixture is incubated for 120+/−10 min. in the dark at a temperature (T) of T=+22+/−2° C. under gentle shaking.

The obtained PEG-interferon-gamma conjugate is further purified by ion exchange chromatography. The PEG-interferon-gamma conjugate containing fractions are collected and concentrated by ultra-/diafiltration (UF/DF) using a membrane made of regenerated cellulose with an appropriate molecular weight cut off (Millipore).

The conjugate prepared by use of this procedure are analytically characterized by measuring total protein and biological activity according to methods known in the art.

Method 3:

Interferon-gamma is PEGylated by use of a linear 20 kD PEGylation reagent containing an aminooxy group. An example of this type of reagent is the Sunbright® CA series from NOF (NOF Corp., Tokyo, Japan). 10 mg interferon-gamma is dissolved in ~8 ml histidine-buffer, pH 6.0 (20 mM L-histidine, 150 mM NaCl). 200 µl of an aqueous sodium periodate solution (5 mM) and 2 ml of an aqueous m-toluidine solution (50 mM) are then added. Subsequently the aminooxy-PEG reagent with a MW of 20 kD (described above) is added to give a 5-fold molar reagent excess. The mixture is incubated for 2 h in the dark at room temperature under gentle stirring and quenched for 15 min at room temperature by the addition of 100 µl of 1 M aqueous cysteine solution.

Finally the PEG-interferon-gamma conjugate is purified by ion-exchange chromatography on SP-Sepharose FF. The reaction mixture is diluted with 20 ml Buffer A (50 mM Hepes, pH 6.5) and loaded onto a 20 ml HiPrep SP FF 16/10 column (GE Healthcare, Fairfield, Conn.) pre-equilibrated with Buffer A. Then the column is eluted with Buffer B (50 mM Hepes, 1 M NaCl, pH 6.5). Free interferon-gamma is eluted by washing the column with 25% Buffer B and the conjugate at 50% Buffer B. The conjugate containing fractions are concentrated by UF/DF using a 10 kD membrane made of regenerated cellulose (88 cm2, cut-off 10 kD/Millipore). The final diafiltration step is performed against histidine buffer, pH 6.9 containing 150 mM NaCl. The preparation is analytically characterized by measuring total protein (Bradford) and biological activity according to methods known in the art. For the PEG-interferon-gamma conjugate a specific activity of >50% in comparison to native interferon-gamma is determined. The conjugate is additionally analytically characterized by Size Exclusion HPLC using a Agilent 1200 HPLC system equipped with a Shodex KW 803 column under conditions as previously described (Kolarich et al, Transfusion 2006; 46:1959-77). It is shown that the preparation contains no free interferon-gamma.

Method 4:

Interferon-gamma is PEGylated by use of a linear 20 kD PEGylation reagent containing an aminooxy group. An example of this type of reagent is the Sunbright® CA series from NOF (NOF Corp., Tokyo, Japan). An initial concentration or weight of interferon-gamma is transferred or dissolved in Hepes buffer (50 mM Hepes, 150 mM sodium chloride, 5 mM calcium chloride, pH 6.0) to get a final protein concentration of 2 mg interferon-gamma/ml. Subsequently an 5 mM aqueous sodium periodate solution is added within 15 minutes to give a final concentration of 100 μM, followed by addition of an 50 mM aqueous m-toluidine solution to get a final concentration of 10 mM within a time period of 30 minutes. Then the aminooxy-PEG reagent with a MW of 20 kD (described above) is added to give a 20-fold molar reagent excess. After correction of the pH to 6.0 the mixture is incubated for 2 h in the dark at room temperature under gentle stirring and quenched for 15 min at room temperature by the addition of an 1 M aqueous L-cysteine solution to give a final concentration of 10 mM.

The PEG-interferon-gamma conjugate is purified by means of ion exchange chromatography (IEC). The conjugate containing fractions of the eluate are concentrated by UF/DF using a 10 kD membrane made of regenerated cellulose (88 cm2, cut-off 10 kD/Millipore). The final diafiltration step is performed against Hepes buffer (50 mM Hepes, mM $CaCl_2$, pH 7.5).

The preparation is analytically characterized by measuring total protein (Bradford and BCA procedure) and biological activity according to known methods.

Example 42

PEGylation of G-CSF Using an Aminooxy-PEG Reagent and m-Toluidine as a Nucleophilic Catalyst Method 1:

G-CSF is PEGylated by use of a linear 20 kD PEGylation reagent containing an aminooxy group. An example of this type of reagent is the Sunbright® CA series from NOF (NOF Corp., Tokyo, Japan). G-CSF is dissolved in 7.0 ml histidine buffer, pH 6.0 (20 mM L-histidine, 150 mM NaCl, 5 mM $CaCl_2$). An aqueous sodium periodate solution (5 mM) is then added and the reaction mixture is incubated for 1 h in the dark at 4° C. under gentle stirring and quenched for 15 min at room temperature by the addition of 7.5 μl of a 1 M aqueous cysteine solution. The mixture is subsequently subjected to UF/DF employing Vivaspin centrifugal filtrators to remove excess periodate, quencher and the byproducts thereof.

The retentate containing oxidized G-CSF is next mixed with an aqueous m-toluidine solution (50 mM) and incubated for 30 min at room temperature. Aminooxy-PEG reagent with a MW of 20 kD is then added to give a 5-fold molar reagent excess. This mixture is incubated for 2.5 h at room temperature in the dark under gentle stirring.

Finally, the PEG-G-CSF conjugate is purified by ion-exchange chromatography (e.g., on Q-Sepharose FF). For example, 1.5 mg protein/ml gel is loaded on the column equilibrated with 50 mM Hepes buffer, pH 7.4 containing 5 mM $CaCl_2$. The conjugate is eluted with 50 mM Hepes buffer containing 5 mM $CaCl_2$ and 500 mM sodium chloride, pH 7.4 and is then subjected to UF/DF using an appropriate MW cutoff membrane. The preparation is next analytically characterized by measuring total protein (Coomassie, Bradford) and biological activity according to methods known in the art.

In an alternative embodiment, Method 1 is carried out as follows. G-CSF is PEGylated by use of a linear 20 kD PEGylation reagent containing an aminooxy group. An example of this type of reagent is the Sunbright® CA series from NOF (NOF Corp., Tokyo, Japan). G-CSF is dissolved in 7.0 ml histidine buffer, pH 6.0 (20 mM L-histidine, 150 mM NaCl, 5 mM $CaCl_2$). An aqueous sodium periodate solution (5 mM) is then added and the reaction mixture is incubated for 1 h in the dark at 4° C. under gentle stirring and quenched for 15 min at room temperature by the addition of 7.5 μl of a 1 M aqueous cysteine solution. The mixture is subsequently subjected to UF/DF employing Vivaspin centrifugal filtrators to remove excess periodate, quencher and the byproducts thereof.

The retentate containing oxidized G-CSF is next mixed with an aqueous m-toluidine solution (50 mM) and incubated for 30 min at room temperature. Aminooxy-PEG reagent with a MW of 20 kD is then added to give a 5-fold molar reagent excess. This mixture is incubated for 2.5 h at room temperature in the dark under gentle stirring.

Finally, the PEG-G-CSF conjugate is purified by ion-exchange chromatography (The conjugate containing fractions of the eluate are collected and then subjected to UF/DF using an appropriate MW cutoff membrane. The preparation is next analytically characterized by measuring total protein (Coomassie, Bradford) and biological activity according to methods known in the art.

Method 2:

G-CSF is PEGylated by use of a linear 20 kD PEGylation reagent containing an aminooxy group. An example of this type of reagent is the Sunbright® CA series from NOF (NOF Corp., Tokyo, Japan). G-CSF is transferred or dissolved in reaction buffer (e.g. 50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5N aqueous HCl solution. Subsequently a 40 mM aqueous sodium periodate solution is added within 10 minutes to give a concentration of 200 μM. The oxidation reaction is carried out for 30+/−5 min at a temperature (T) of T=+22+/−2° C. Then the reaction is stopped by addition of an aqueous L-cysteine solution (1 M) within 15 minutes at T=+22+/−2° C. to give a final concentration of 10 mM in the reaction mixture and incubation for 60+/−5 min.

The oxidized G-CSF is further purified by ion exchange chromatography. The oxidized G-CSF containing fractions of the eluate are collected and used for the conjugation reaction.

The aminooxy-PEG reagent with a MW of 20 kD reagent is added in a 50-fold molar excess to the eluate containing the purified oxidized G-CSF within a maximum time period (t) of 15 minutes under gentle stirring. Then an aqueous m-toluidine solution (50 mM) is added within 15 minutes to get a final concentration of 10 mM. The reaction mixture is incubated for 120+/−10 min. in the dark at a temperature (T) of T=+22+/−2° C. under gentle shaking.

The obtained PEG-G-CSF conjugate is further purified by ion exchange chromatography. The PEG-G-CSF conjugate containing fractions are collected and concentrated by ultra-/diafiltration (UF/DF) using a membrane made of regenerated cellulose with an appropriate molecular weight cut off (Millipore).

Method 3:

G-CSF is PEGylated by use of a linear 20 kD PEGylation reagent containing an aminooxy group. An example of this type of reagent is the Sunbright® CA series from NOF (NOF Corp., Tokyo, Japan). G-CSF is dissolved in Hepes buffer (50 mM Hepes, 150 mM sodium chloride, 5 mM calcium chloride, pH 6.0) and mixed with an aqueous sodium periodate solution (10 mM), and an aqueous m-toluidine solution (50 mM). Subsequently, the aminooxy reagent is added to give a 20-fold molar reagent excess. The mixture is incubated for 2 h in the dark at room temperature under gentle stirring and quenched for 15 min at room temperature by the addition of 8 μl of aqueous cysteine solution (1 M).

Finally, the PEG-G-CSF conjugate is purified by ion-exchange chromatography on Q-Sepharose FF. 1.5 mg protein/ml gel is loaded on the column pre equilibrated with 50 mM Hepes buffer, pH 7.4 containing 5 mM $CaCl_2$. The conjugate is eluted with 50 mM Hepes buffer containing 5 mM $CaCl_2$ and 500 mM sodium chloride, pH 7.4 and is then subjected to UF/DF using a membrane. The preparation is analytically characterized by measuring total protein (Bradford) and biological activity according to methods known in the art.

In an alternative embodiment, Method 3 is carried out as follows. G-CSF is PEGylated by use of a linear 20 kD PEGylation reagent containing an aminooxy group. An example of this type of reagent is the Sunbright® CA series from NOF (NOF Corp., Tokyo, Japan). G-CSF is dissolved in Hepes buffer (50 mM Hepes, 150 mM sodium chloride, 5 mM calcium chloride, pH 6.0) and mixed with an aqueous sodium periodate solution (10 mM), and an aqueous m-toluidine solution (50 mM). Subsequently, the aminooxy reagent is added to give a 20-fold molar reagent excess. The mixture is incubated for 2 h in the dark at room temperature under gentle stirring and quenched for 15 min at room temperature by the addition of 8 μl of aqueous cysteine solution (1 M).

Finally, the PEG-G-CSF conjugate is purified by ion-exchange chromatography. The conjugate containing fractions of the eluate are collected and then subjected to UF/DF using a membrane. The preparation is analytically characterized by measuring total protein (Bradford) and biological activity according to methods known in the art.

Method 4:

G-CSF is PEGylated by use of a linear 20 kD PEGylation reagent containing an aminooxy group. An example of this type of reagent is the Sunbright® CA series from NOF (NOF Corp., Tokyo, Japan). An initial concentration or weight of G-CSF is transferred or dissolved in Hepes buffer (50 mM Hepes, 150 mM sodium chloride, 5 mM calcium chloride, pH 6.0) to get a final protein concentration of 2 mg G-CSF/ml. Subsequently, an 5 mM aqueous sodium periodate solution is added within 15 minutes to give a final concentration of 100 μM, followed by addition of an 50 mM aqueous m-toluidine solution to get a final concentration of 10 mM within a time period of 30 minutes. Then the aminooxy-PEG reagent with a MW of 20 kD (described above) is added to give a 20-fold molar reagent excess. After correction of the pH to 6.0 the mixture is incubated for 2 h in the dark at room temperature under gentle stirring and quenched for 15 min at room temperature by the addition of an 1 M aqueous L-cysteine solution to give a final concentration of 10 mM.

The G-CSF conjugate is purified by means of ion exchange chromatography (IEC). The conjugate containing fractions of the eluate are concentrated by UF/DF using a 10 kD membrane made of regenerated cellulose (88 cm2, cut-off 10 kD/Millipore). The final diafiltration step is performed against Hepes buffer (50 mM Hepes, 5 mM $CaCl_2$, pH 7.5).

The preparation is analytically characterized by measuring total protein (Bradford and BCA procedure) and biological activity according to known methods.

Example 43

PEGylation of Humira Using an Aminooxy-PEG Reagent and m-Toluidine as a Nucleophilic Catalyst Method 1:

Humira is PEGylated by use of a linear 20 kD PEGylation reagent containing an aminooxy group. An example of this type of reagent is the Sunbright® CA series from NOF (NOF Corp., Tokyo, Japan). Humira is dissolved in 7.0 ml histidine buffer, pH 6.0 (20 mM L-histidine, 150 mM NaCl, 5 mM $CaCl_2$). An aqueous sodium periodate solution (5 mM) is then added and the reaction mixture is incubated for 1 h in the dark at 4° C. under gentle stirring and quenched for 15 min at room temperature by the addition of 7.5 μl of a 1 M aqueous cysteine solution. The mixture is subsequently subjected to UF/DF employing Vivaspin centrifugal filtrators to remove excess periodate, quencher and the byproducts thereof.

The retentate containing oxidized Humira is next mixed with an aqueous m-toluidine solution (50 mM) and incubated for 30 min at room temperature. Aminooxy-PEG reagent with a MW of 20 kD is then added to give a 5-fold molar reagent excess. This mixture is incubated for 2.5 h at room temperature in the dark under gentle stirring.

Finally, the PEG-Humira conjugate is purified by ion-exchange chromatography (e.g., on Q-Sepharose FF). For example, 1.5 mg protein/ml gel is loaded on the column equilibrated with 50 mM Hepes buffer, pH 7.4 containing 5 mM $CaCl_2$. The conjugate is eluted with 50 mM Hepes buffer containing 5 mM $CaCl_2$ and 500 mM sodium chloride, pH 7.4 and is then subjected to UF/DF using an appropriate MW cutoff membrane. The preparation is next analytically characterized by measuring total protein (Coomassie, Bradford) and biological activity according to methods known in the art.

In an alternative embodiment, Method 1 is carried out as follows. Humira is PEGylated by use of a linear 20 kD PEGylation reagent containing an aminooxy group. An example of this type of reagent is the Sunbright® CA series from NOF (NOF Corp., Tokyo, Japan). Humira is dissolved in 7.0 ml histidine buffer, pH 6.0 (20 mM L-histidine, 150 mM NaCl, 5 mM $CaCl_2$). An aqueous sodium periodate solution (5 mM) is then added and the reaction mixture is incubated for 1 h in the dark at 4° C. under gentle stirring and quenched for 15 min at room temperature by the addition of 7.5 μl of a 1 M aqueous cysteine solution. The mixture is subsequently subjected to UF/DF employing Vivaspin centrifugal filtrators to remove excess periodate, quencher and the byproducts thereof.

The retentate containing oxidized Humira is next mixed with an aqueous m-toluidine solution (50 mM) and incubated for 30 min at room temperature. Aminooxy-PEG reagent with a MW of 20 kD is then added to give a 5-fold molar reagent excess. This mixture is incubated for 2.5 h at room temperature in the dark under gentle stirring.

Finally, the PEG-Humira conjugate is purified by ion-exchange chromatography. The conjugate containing fractions of the eluate are collected and then subjected to UF/DF using an appropriate MW cutoff membrane. The preparation is next analytically characterized by measuring total protein (Coomassie, Bradford) and biological activity according to methods known in the art.

Method 2:

Humira is PEGylated by use of a linear 20 kD PEGylation reagent containing an aminooxy group. An example of this type of reagent is the Sunbright® CA series from NOF (NOF Corp., Tokyo, Japan). Humira is transferred or dissolved in reaction buffer (e.g. 50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5N aqueous HCl solution. Subsequently a 40 mM aqueous sodium periodate solution is added within 10 minutes to give a concentration of 200 μM. The oxidation reaction is carried out for 30+/−5 min at a temperature (T) of T=+22+/−2° C. Then the reaction is stopped by addition of an aqueous L-cysteine solution (1 M) within 15 minutes at T=+22+/−2° C. to give a final concentration of 10 mM in the reaction mixture and incubation for 60+/−5 min.

The oxidized Humira is further purified by ion exchange chromatography. The oxidized Humira containing fractions of the eluate are collected and used for the conjugation reaction.

The aminooxy-PEG reagent with a MW of 20 kD reagent is added in a 50-fold molar excess to the eluate containing the purified oxidized Humira within a maximum time period (t) of 15 minutes under gentle stirring. Then an aqueous m-toluidine solution (50 mM) is added within 15 minutes to get a final concentration of 10 mM. The reaction mixture is incubated for 120+/−10 min. in the dark at a temperature (T) of T=+22+/−2° C. under gentle shaking.

The obtained PEG-Humira conjugate is further purified by ion exchange chromatography. The PEG-Humira conjugate containing fractions are collected and concentrated by ultra-/diafiltration (UF/DF) using a membrane made of regenerated cellulose with an appropriate molecular weight cut off (Millipore).

Method 3:

Humira is PEGylated by use of a linear 20 kD PEGylation reagent containing an aminooxy group. An example of this type of reagent is the Sunbright® CA series from NOF (NOF Corp., Tokyo, Japan). Humira is dissolved in Hepes buffer (50 mM Hepes, 150 mM sodium chloride, 5 mM calcium chloride, pH 6.0) and mixed with an aqueous sodium periodate solution (10 mM), and an aqueous m-toluidine solution (50 mM). Subsequently, the aminooxy reagent is added to give a 20-fold molar reagent excess. The mixture is incubated for 2 h in the dark at room temperature under gentle stirring and quenched for 15 min at room temperature by the addition of 8 μl of aqueous cysteine solution (1 M).

Finally, the PEG-Humira conjugate is purified by ion-exchange chromatography on Q-Sepharose FF. 1.5 mg protein/ml gel is loaded on the column pre equilibrated with 50 mM Hepes buffer, pH 7.4 containing 5 mM $CaCl_2$. The conjugate is eluted with 50 mM Hepes buffer containing 5 mM $CaCl_2$ and 500 mM sodium chloride, pH 7.4 and is then subjected to UF/DF using a membrane. The preparation is analytically characterized by measuring total protein (Bradford) and biological activity according to methods known in the art.

In an alternative embodiment, Method 3 is carried out as follows. Humira is PEGylated by use of a linear 20 kD PEGylation reagent containing an aminooxy group. An example of this type of reagent is the Sunbright® CA series from NOF (NOF Corp., Tokyo, Japan). Humira is dissolved in Hepes buffer (50 mM Hepes, 150 mM sodium chloride, 5 mM calcium chloride, pH 6.0) and mixed with an aqueous sodium periodate solution (10 mM), and an aqueous m-toluidine solution (50 mM). Subsequently the aminooxy reagent is added to give a 20-fold molar reagent excess. The mixture is incubated for 2 h in the dark at room temperature under gentle stirring and quenched for 15 min at room temperature by the addition of 8 μl of aqueous cysteine solution (1 M).

Finally, the PEG-Humira conjugate is purified by ion-exchange chromatography. The conjugate containing fractions are collected and then subjected to UF/DF using a membrane. The preparation is analytically characterized by measuring total protein (Bradford) and biological activity according to methods known in the art.

Method 4:

Humira is PEGylated by use of a linear 20 kD PEGylation reagent containing an aminooxy group. An example of this type of reagent is the Sunbright® CA series from NOF (NOF Corp., Tokyo, Japan). An initial concentration or weight of Humira is transferred or dissolved in Hepes buffer (50 mM Hepes, 150 mM sodium chloride, 5 mM calcium chloride, pH 6.0) to get a final protein concentration of 2 mg Humira/ml. Subsequently an 5 mM aqueous sodium periodate solution is added within 15 minutes to give a final concentration of 100 μM, followed by addition of an 50 mM aqueous m-toluidine solution to get a final concentration of 10 mM within a time period of 30 minutes. Then the aminooxy-PEG reagent with a MW of 20 kD (described above) is added to give a 20-fold molar reagent excess. After correction of the pH to 6.0 the mixture is incubated for 2 h in the dark at room temperature under gentle stirring and quenched for 15 min at room temperature by the addition of a 1 M aqueous L-cysteine solution to give a final concentration of 10 mM.

The Humira conjugate is purified by means of ion exchange chromatography (IEC). The conjugate containing fractions of the eluate are concentrated by UF/DF using a 10 kD membrane made of regenerated cellulose (88 cm2, cut-off 10 kD/Millipore). The final diafiltration step is performed against Hepes buffer (50 mM Hepes, 5 mM $CaCl_2$, pH 7.5).

The preparation is analytically characterized by measuring total protein (Bradford and BCA procedure) and biological activity according to known methods.

Example 44

PEGylation of Prolia Using an Aminooxy-PEG Reagent and m-Toluidine as a Nucleophilic Catalyst Method 1:

Prolia is PEGylated by use of a linear 20 kD PEGylation reagent containing an aminooxy group. An example of this type of reagent is the Sunbright® CA series from NOF (NOF Corp., Tokyo, Japan). Prolia is dissolved in 7.0 ml histidine buffer, pH 6.0 (20 mM L-histidine, 150 mM NaCl, 5 mM $CaCl_2$). An aqueous sodium periodate solution (5 mM) is then added and the reaction mixture is incubated for 1 h in the dark at 4° C. under gentle stirring and quenched for 15 min at room temperature by the addition of 7.5 μl of a 1 M aqueous cysteine solution. The mixture is subsequently subjected to UF/DF employing Vivaspin centrifugal filtrators to remove excess periodate, quencher and the byproducts thereof.

The retentate containing oxidized Prolia is next mixed with an aqueous m-toluidine solution (50 mM) and incubated for 30 min at room temperature. Aminooxy-PEG reagent with a MW of 20 kD is then added to give a 5-fold molar reagent excess. This mixture is incubated for 2.5 h at room temperature in the dark under gentle stirring.

Finally, the PEG-Prolia conjugate is purified by ion-exchange chromatography (e.g., on Q-Sepharose FF). For example, 1.5 mg protein/ml gel is loaded on the column equilibrated with 50 mM Hepes buffer, pH 7.4 containing 5 mM $CaCl_2$. The conjugate is eluted with 50 mM Hepes buffer containing 5 mM $CaCl_2$ and 500 mM sodium chloride, pH 7.4 and is then subjected to UF/DF using an appropriate MW cutoff membrane. The preparation is next analytically characterized by measuring total protein (Coomassie, Bradford) and biological activity according to methods known in the art.

In an alternative embodiment, Method 1 is carried out as follows. Prolia is PEGylated by use of a linear 20 kD PEGylation reagent containing an aminooxy group. An example of this type of reagent is the Sunbright® CA series from NOF (NOF Corp., Tokyo, Japan). 10 mg rFIX is dissolved in 5 ml histidine-buffer, pH 6.0 (20 mM L-histidine, 150 mM NaCl). 100 µl of an aqueous sodium periodate solution (5 mM) is then added and the reaction mixture is incubated for 1 h in the dark at 4° C. under gentle stirring and quenched for 15 min at room temperature by the addition of 50 µl of a 1 M aqueous cysteine solution. The mixture is subsequently subjected to UF/DF employing Vivaspin 15R 10 kD centrifugal filtrators to remove excess periodate, quencher and the byproducts thereof.

The retentate (approx. 7 ml), containing oxidized Prolia, is mixed with 2 ml of an aqueous m-toluidine solution (50 mM) and incubated for 30 min at room temperature. Then aminooxy-PEG reagent with a MW of 20 kD (described above) is added to give a 5-fold molar reagent excess. This mixture is incubated for 2.5 h at RT in the dark under gentle stirring.

Finally the PEG-Prolia conjugate is purified by ion-exchange chromatography on SP Sepharose FF. The reaction mixture is diluted with 20 ml Buffer A (50 mM Hepes, pH 6.5) and loaded onto a 20 ml HiPrep SP FF 16/10 column (GE Healthcare, Fairfield, Conn.) pre-equilibrated with Buffer A. Then the column is eluted with Buffer B (50 mM Hepes, 1 M NaCl, pH 6.5). Free Prolia is eluted by washing the column with 25% Buffer B and the conjugate at 50% Buffer B. The conjugate containing fractions are concentrated by UF/DF using a 10 kD membrane made of regenerated cellulose (88 cm2, cut-off 10 kD/Millipore). The final diafiltration step is performed against histidine buffer, pH 6.9 containing 150 mM NaCl. The preparation is analytically characterized by measuring total protein (Bradford) and biological activity according to methods known in the art. For the PEG-Prolia conjugate a specific activity of >50% in comparison to native Prolia is determined. The conjugate is additionally analytically characterized by Size Exclusion HPLC using a Agilent 1200 HPLC system equipped with a Shodex KW 803 column under conditions as previously described (Kolarich et al, Transfusion 2006; 46:1959-77). It is shown that the preparation contains no free Prolia.

Method 2:

Prolia is PEGylated by use of a linear 20 kD PEGylation reagent containing an aminooxy group. An example of this type of reagent is the Sunbright® CA series from NOF (NOF Corp., Tokyo, Japan). Prolia is transferred or dissolved in reaction buffer (e.g. 50 mM Hepes, 350 mM sodium chloride, 5 mM calcium chloride, pH 6.0) to get a final protein concentration of 1.0+/−0.25 mg/ml. Then the pH of the solution is corrected to 6.0 by drop wise addition of a 0.5N aqueous HCl solution. Subsequently, a 40 mM aqueous sodium periodate solution is added within 10 minutes to give a concentration of 200 µM. The oxidation reaction is carried out for 30+/−5 min at a temperature (T) of T=+22+/−2° C. Then the reaction is stopped by addition of an aqueous L-cysteine solution (1 M) within 15 minutes at T=+22+/−2° C. to give a final concentration of 10 mM in the reaction mixture and incubation for 60+/−5 min.

The oxidized Prolia is further purified by ion exchange chromatography. The oxidized Humira containing fractions of the eluate are collected and used for the conjugation reaction.

The aminooxy-PEG reagent with a MW of 20 kD reagent is added in a 50-fold molar excess to the eluate containing the purified oxidized Prolia within a maximum time period (t) of 15 minutes under gentle stirring. Then an aqueous m-toluidine solution (50 mM) is added within 15 minutes to get a final concentration of 10 mM. The reaction mixture is incubated for 120+/−10 min. in the dark at a temperature (T) of T=+22+/−2° C. under gentle shaking.

The obtained PEG-Prolia conjugate is further purified by ion exchange chromatography. The PEG-Prolia conjugate containing fractions are collected and concentrated by ultra-/diafiltration (UF/DF) using a membrane made of regenerated cellulose with an appropriate molecular weight cut off (Millipore).

Method 3:

Prolia is PEGylated by use of a linear 20 kD PEGylation reagent containing an aminooxy group. An example of this type of reagent is the Sunbright® CA series from NOF (NOF Corp., Tokyo, Japan). EPO is dissolved in Hepes buffer (50 mM Hepes, 150 mM sodium chloride, 5 mM calcium chloride, pH 6.0) and mixed with an aqueous sodium periodate solution (10 mM), and an aqueous m-toluidine solution (50 mM). Subsequently the aminooxy reagent is added to give a 20-fold molar reagent excess. The mixture is incubated for 2 h in the dark at room temperature under gentle stirring and quenched for 15 min at room temperature by the addition of 8 µl of aqueous cysteine solution (1 M).

Finally, the PEG-Prolia conjugate is purified by ion-exchange chromatography on Q-Sepharose FF. 1.5 mg protein/ml gel is loaded on the column pre equilibrated with 50 mM Hepes buffer, pH 7.4 containing 5 mM $CaCl_2$. The conjugate is eluted with 50 mM Hepes buffer containing 5 mM $CaCl_2$ and 500 mM sodium chloride, pH 7.4 and is then subjected to UF/DF using a membrane. The preparation is analytically characterized by measuring total protein (Bradford) and biological activity according to methods known in the art.

In an alternative embodiment, Method 3 is carried out as follows.

Prolia is PEGylated by use of a linear 20 kD PEGylation reagent containing an aminooxy group. An example of this type of reagent is the Sunbright® CA series from NOF (NOF Corp., Tokyo, Japan). 10 mg Prolia is dissolved in ~8 ml histidine buffer, pH 6.0 (20 mM L-histidine, 150 mM NaCl). 200 µl of an aqueous sodium periodate solution (5 mM) and 2 ml of an aqueous m-toluidine solution (50 mM) are then added. Subsequently, the aminooxy-PEG reagent with a MW of 20 kD (described above) is added to give a 5-fold molar reagent excess. The mixture is incubated for 2 h in the dark at room temperature under gentle stirring and quenched for 15 min at room temperature by the addition of 100 µl of 1 M aqueous cysteine solution.

Finally the PEG-Prolia conjugate is purified by ion-exchange chromatography on SP-Sepharose FF. The reaction mixture is diluted with 20 ml Buffer A (50 mM Hepes, pH 6.5) and loaded onto a 20 ml HiPrep SPFF 16/10 column (GE Healthcare, Fairfield, Conn.) pre-equilibrated with Buffer A. Then the column is eluted with Buffer B (50 mM Hepes, 1 M NaCl, pH 6.5). Free Prolia is eluted by washing the column with 25% Buffer B and the conjugate at 50% Buffer B. The conjugate containing fractions are concentrated by UF/DF using a 10 kD membrane made of regenerated cellulose (88 cm2, cut-off 10 kD/Millipore). The final diafiltration step is performed against histidine buffer, pH 6.9 containing 150 mM NaCl. The preparation is analytically characterized by measuring total protein (Bradford) and biological activity according to methods known in the art. For the PEG-Prolia conjugate a specific activity of >50% in comparison to native Prolia is determined. The conjugate is additionally analytically characterized by Size Exclusion HPLC using a Agilent 1200 HPLC system equipped with a Shodex KW 803 column under conditions as previously described (Kolarich et al, Transfusion 2006; 46:1959-77). It is shown that the preparation contains no free Prolia.

Method 4:

Prolia is PEGylated by use of a linear 20 kD PEGylation reagent containing an aminooxy group. An example of this type of reagent is the Sunbright® CA series from NOF (NOF Corp., Tokyo, Japan). An initial concentration or weight of Humira is transferred or dissolved in Hepes buffer (50 mM Hepes, 150 mM sodium chloride, 5 mM calcium chloride, pH 6.0) to get a final protein concentration of 2 mg Prolia/ml. Subsequently an 5 mM aqueous sodium periodate solution is added within 15 minutes to give a final concentration of 100 μM, followed by addition of an 50 mM aqueous m-toluidine solution to get a final concentration of 10 mM within a time period of 30 minutes. Then the aminooxy-PEG reagent with a MW of 20 kD (described above) is added to give a 20-fold molar reagent excess. After correction of the pH to 6.0 the mixture is incubated for 2 h in the dark at room temperature under gentle stirring and quenched for 15 min at room temperature by the addition of an 1 M aqueous L-cysteine solution to give a final concentration of 10 mM.

The Prolia conjugate is purified by means of ion exchange chromatography (IEC). The conjugate containing fractions of the eluate are concentrated by UF/DF using a 10 kD membrane made of regenerated cellulose (88 cm2, cut-off 10 kD/Millipore). The final diafiltration step is performed against Hepes buffer (50 mM Hepes, 5 mM $CaCl_2$, pH 7.5).

The preparation is analytically characterized by measuring total protein (Bradford and BCA procedure) and biological activity according to known methods.

Example 45

PEGylation of a Therapeutic Protein Using Branched PEG

PEGylation of a therapeutic protein of the invention may be extended to a branched or linear PEGylation reagent, which is made of an aldehyde and a suitable linker containing an active aminooxy group.

Example 46

Coupling of a Diaminooxy Linker to Native PSA

This Example describes procedures to prepare aminooxy-PSA reagents using native PSA (i.e. without prior oxidation), which can be used for chemical modification of therapeutic proteins.

a) Coupling at Ambient Temperature 52.2 mg of native PSA (MW=20 kD) obtained from the Serum Institute of India (Pune, India) was dissolved in 1.05 ml 50 mM phosphate buffer pH 6.0. Then 10.3 mg 3-oxa-pentane-1,5-dioxyamine (linker molecule) was added drop wise to the reaction mixture. The reaction was incubated for 2 hrs at room temperature under gentle agitation in the dark.

b) Coupling at Increased Temperature 52.2 mg of native PSA (MW=20 kD) obtained from the Serum Institute of India (Pune, India) was dissolved in 1.05 ml 50 mM phosphate buffer pH 6.0. Then 10.3 mg 3-oxa-pentane-1,5-dioxyamine (linker molecule) was added drop wise to the reaction mixture. The reaction was incubated for 2 hrs at room temperature under gentle agitation in the dark. Then the temperature was increased to 32-37° C. and the reaction mixture was incubated for another 14 hrs.

c) Coupling at Increased Temperature and Increased Linker Excess 52.2 mg of native PSA (MW=20 kD) obtained from the Serum Institute of India (Pune, India) was dissolved in 1.05 ml 50 mM phosphate buffer pH 6.0. Then 10.3 mg 3-oxa-pentane-1,5-dioxyamine (linker molecule) was added drop wise to the reaction mixture. The reaction was incubated for 2 hrs at room temperature under gentle agitation in the dark. Then 26.3 mg 3-oxa-pentane-1,5-dioxyamine were added drop wise to the reaction, the temperature was increased to 32-37° C. and the reaction mixture was incubated for another 14 hrs.

d) Purification of PSA Derivatives

After the incubation was completed, the reaction mixtures generated under points a-c were purified by extensive dialysis. Therefore samples of the reaction mixtures were loaded into Slide-A-Lyzer dialysis cassettes (0-5-3 ml, MWCO 3.5 kD, reg. cellulose, Pierce) and dialyzed against 10 mM phosphate buffer pH 8.0 according to the following pattern:

2 hrs against 500 ml buffer at room temperature 2 hrs against 500 ml buffer at room temperature 12 hrs against 500 ml buffer at 4° C.

1 h against 50 ml 'Slide-A-Lyzer Concentrating Solution for Dialysis' at room temperature for concentration to initial sample volume.

The purified aminooxy-PSA is thus ready to be used in a protein conjugation reaction according to, for example, Examples 11, 12, 14, and 17-31, above. Likewise, any of the water-soluble polymers described herein can be coupled to an aminooxy linker as described in this Example and then conjugated to a protein as set out in the above Examples.

The preparation was analytically characterized by measuring total PSA (Resorcinol assay) and total aminooxy groups (TNBS assay) to determine the degree of modification. For preparation (a) a modification degree (MD) of 0.35, for (b) MD=0.54 and for (c) MD=0.58 was determined. Furthermore the polydispersity as well as free 3-oxa-pentane-1,5-dioxyamine was measured. The polydispersity was lower than 1.15 for all preparations and the content of free linker was lower than 0.15 mol % of the PSA concentration.

For the PSA modified at the reducing end the following structure was determined by $^{13}C$ NMR spectroscopy.

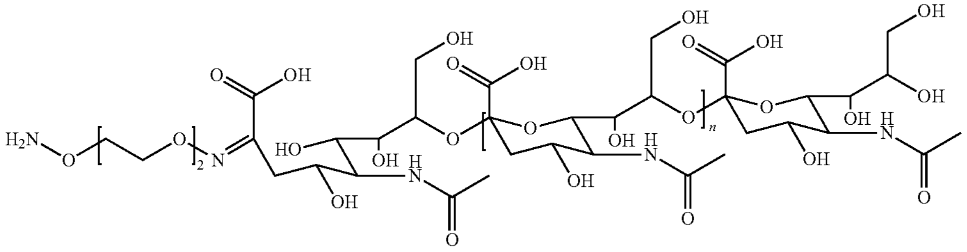

Example 47

Preparation of Aminooxy-PSA at 4° C. Employing a Chromatographic Purification Step During a detailed analytical characterization of the aminooxy-PSA reagent prepared at room temperature, NMR studies (See, e.g., U.S. Provisional Application No. 61/647,814, incorporated by reference in it's entirety) revealed that the derivatization of oxidized PSA with the diaminooxy linker consists of two distinct reactions: a quick reaction of the aldehyde group at the non-reducing end of PSA and a slow reaction of the aldehyde group (in the form of a hemiketal) at the reducing end of PSA. The latter reaction could be considered an unwanted side reaction that is to be avoided for reagent production.

Therefore, the process for the preparation of the aminooxy-PSA reagent has been optimized as described in the instant Example. The reducing end only occurs to a significant degree if the process is performed at room temperature. Hence, the process was adjusted and is conducted at 2-8° C. By performing the whole process (chemical reaction and purification of the PSA reagent by IEX) at 2-8° C., the side reaction at the reducing end of PSA was substantially reduced. This process change thus leads to a reagent of higher quality.

Procedure 1290 mg of oxidized PSA (MW=20 kD) obtained from the Serum Institute of India (Pune, India) was dissolved in 25 ml 50 mM phosphate buffer pH 6.0 (Buffer A). Then 209 mg 3-oxa-pentane-1,5-dioxyamine was added to the reaction mixture and incubated for 1 h at 2-8° C. under gentle agitation in the dark.

After incubation, the mixture was subjected to a weak anion exchange chromatography step employing a Fractogel EMD DEAE 650-M chromatography gel (column dimension: XK26/135) carried out in a cold room at temperature of 2-8° C. The reaction mixture was diluted with pre-cooled 110 ml Buffer A and loaded onto the DEAE column pre-equilibrated with Buffer A at a flow rate of 1 cm/min. Then the column was washed with 20 CV Buffer B (20 mM Hepes, pH 6.0) at a flow rate of 2 cm/min to remove free 3-oxa-pentane-1,5-dioxyamine. The aminooxy-PSA reagent was then eluted with a step gradient consisting of 67% Buffer B and 43% Buffer C (20 mM Hepes, 1M NaCl, pH 7.5). The eluate was concentrated by UF/DF using a 5 kD membrane made of polyether sulfone (50 cm2, Millipore). The preparation was analytically characterized by measuring total PSA (Resorcinol assay) and total aminooxy groups (TNBS assay) to determine the degree of modification. The PSA concentration in the final preparation was 46.0 mg/ml and the modification degree was 83.5%. Furthermore a polydispersity value of 1.131 was determined. In addition a concentration of 0.22 μg/ml (0.07 mol % of PSA) was measured for free 3-oxa-pentane-1,5-dioxyamine.

The purified aminooxy-PSA is thus ready to be used in a conjugation reaction according to Examples 11, 12, 14, and 17-31, above.

What is claimed:

1. A method of conjugating a water soluble polymer to an oxidized carbohydrate moiety of a therapeutic protein comprising contacting the oxidized carbohydrate moiety with an activated water soluble polymer under conditions that allow conjugation;

said water soluble polymer containing an active aminooxy group and is selected from the group consisting of polyethylene glycol (PEG), branched PEG, PolyPEG® (Warwick Effect Polymers; Coventry, UK), polysialic acid (PSA), carbohydrate, polysaccharides, pullulane, chitosan, hyaluronic acid, chondroitin sulfate, dermatan sulfate, dextran, carboxymethyl-dextran, polyalkylene oxide (PAO), polyalkylene glycol (PAG), polypropylene glycol (PPG), polyoxazoline, polyacryloylmorpholine, polyvinyl alcohol (PVA), polycarboxylate, polyvinylpyrrolidone, polyphosphazene, polyoxazoline, polyethylene-co-maleic acid anhydride, polystyrene-co-maleic acid anhydride, poly(1-hydroxymethylethylene hydroxymethylformal) (PHF), 2-methacryloyloxy-2'-ethyltrimethylammoniumphosphate (MPC);

wherein the water soluble polymer containing an active aminooxy group is prepared by a method comprising:

a) incubating a solution comprising an oxidized water-soluble polymer with an aminooxy linker comprising an active aminooxy group under conditions that allow the formation of a stable oxime linkage between the oxidized water-soluble polymer and the activated aminooxy linker, said conditions comprising a time period between about 1 minute and about 24 hours; a temperature between about 2° C. and about 8° C.; in the presence or absence of light, and with or without stirring; thereby forming a water-soluble polymer containing an active aminooxy group; and b) purifying the water soluble polymer containing an active aminooxy group by a method selected from the group consisting of chromatography, filtration, dialysis, and precipitation, at a temperature between about 2° C. and about 8° C.;

said carbohydrate moiety oxidized by incubation with a buffer comprising an oxidizing agent selected from the group consisting of sodium periodate ($NaIO_4$), lead tetraacetate ($Pb(OAc)_4$) and potassium perruthenate (KRuO4);

wherein an oxime linkage is formed between the oxidized carbohydrate moiety and the active aminooxy group on the water soluble polymer; and wherein said oxime linkage formation is catalyzed by the nucleophilic catalyst m-toluidine.

2. The method according to claim 1 wherein the solution comprising the oxidized water-soluble polymer and the aminooxy linker comprising an active aminooxy group is incubated at 4° C. for 1 h in the absence of light with stirring.

3. The method according to claim 1 wherein the water soluble polymer containing an active aminooxy group is purified by anion exchange chromatography at a temperature of 4° C.

4. The method according to claim 3 wherein the oxidized water soluble polymer is PSA and is oxidized by incubation with $NaIO_4$.

5. A method of conjugating a water soluble polymer to an oxidized carbohydrate moiety of a therapeutic protein comprising contacting the oxidized carbohydrate moiety with an activated water soluble polymer under conditions that allow conjugation;

said water soluble polymer containing an active aminooxy group and is selected from the group consisting of polyethylene glycol (PEG), branched PEG, PolyPEG® (Warwick Effect Polymers; Coventry, UK), polysialic acid (PSA), carbohydrate, polysaccharides, pullulane, chitosan, hyaluronic acid, chondroitin sulfate, dermatan sulfate, dextran, carboxymethyl-dextran, polyalkylene oxide (PAO), polyalkylene glycol (PAG), polypropylene glycol (PPG), polyoxazoline, polyacryloylmorpholine, polyvinyl alcohol (PVA), polycarboxylate, polyvinylpyrrolidone, polyphosphazene, polyoxazoline, polyethylene-co-maleic acid anhydride, polystyrene-co-maleic acid anhydride, poly(1-hydroxymethylethylene hydroxymethylformal) (PHF), 2-methacryloyloxy-2'-ethyltrimethylammoniumphosphate (MPC);

wherein the water soluble polymer containing an active aminooxy group is prepared by a method comprising:

a) incubating a solution comprising a water-soluble polymer with an aminooxy linker comprising an active aminooxy group under conditions that allow the formation of a stable oxime linkage between the water-soluble polymer and the activated aminooxy linker, said conditions comprising a time period between about 1 minute and about 24 hours; a temperature between about 22° C. and about 37° C.; in the presence or absence of light, and with or without stirring; thereby forming a water-soluble polymer containing an active aminooxy group; and b) purifying the water soluble polymer containing an active aminooxy group by a method selected from the group consisting of chromatography, filtration, dialysis, and precipitation;

said carbohydrate moiety oxidized by incubation with a buffer comprising an oxidizing agent selected from the group consisting of sodium periodate ($NaIO_4$), lead tetraacetate ($Pb(OAc)_4$) and potassium perruthenate (KRuO4);

wherein an oxime linkage is formed between the oxidized carbohydrate moiety and the active aminooxy group on the water soluble polymer; and wherein said oxime linkage formation is catalyzed by the nucleophilic catalyst m-toluidine.

6. The method according to claim 5 wherein the solution comprising the water-soluble polymer and the aminooxy linker comprising an active aminooxy group is incubated at 22° C. for 2 h in the absence of light with stirring.

7. The method according to claim 5 wherein the solution comprising the water-soluble polymer and the aminooxy linker comprising an active aminooxy group is incubated at 22° C. for 2 h in the absence of light with stirring; said method further comprising the step of increasing the temperature of the solution to a temperature between about 32° C. and about 37° C. and incubating for an additional 12-24 hours.

8. The method according to claim 7 comprising the additional step of adding an additional amount of aminooxy linker comprising an active aminooxy group immediately prior to increasing the temperature.

9. The method according to any one of claims 5-8 wherein the water soluble polymer containing an active aminooxy group is purified by a method selected from the group consisting of dialysis, ultrafiltration/diafiltration (UF/DF), and chromatography at a temperature of 22° C.

10. The method according to claim 9 further comprising the step of purifying the water soluble polymer containing an active aminooxy group by a method selected from the group consisting of dialysis, UF/DF or chromatography at 4° C.

11. The method according to any one of claim 1 or 5 wherein the therapeutic protein selected from the group consisting of Factor IX (FIX), Factor VIII (FVIII), Factor VIIa (FVIIa), Von Willebrand Factor (VWF), Factor FV (FV), Factor X (FX), Factor XI (FXI), Factor XII (FXII), thrombin (FII), protein C, protein S, tPA, PAI-1, tissue factor (TF), ADAMTS 13 protease, IL-1 alpha, IL-1 beta, IL-2, IL-3, IL-4, IL-5, IL-6, IL-11, colony stimulating factor-1 (CSF-1), M-CSF, SCF, GM-CSF, granulocyte colony stimulating factor (G-CSF), EPO, interferon-alpha (IFN-alpha), consensus interferon, IFN-beta, IFN-gamma, IFN-omega, IL-7, IL-8, IL-9, IL-10, IL-12, IL-13, IL-14, IL-15, IL-16, IL-17, IL-18, IL-19, IL-20, IL-21, IL-22, IL-23, IL-24, IL-31, IL-32 alpha, IL-33, thrombopoietin (TPO), Ang-1, Ang-2, Ang-4, Ang-Y, angiopoietin-like polypeptide 1 (ANGPTL1), angiopoietin-like polypeptide 2 (ANGPTL2), angiopoietin-like polypeptide 3 (ANGPTL3), angiopoietin-like polypeptide 4 (ANGPTL4), angiopoietin-like polypeptide 5 (ANGPTL5), angiopoietin-like polypeptide 6 (ANGPTL6), angiopoietin-like polypeptide 7 (ANGPTL7), vitronectin, vascular endothelial growth factor (VEGF), angiogenin, activin A, activin B, activin C, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, bone morphogenic protein receptor II, brain derived neurotrophic factor, cardiotrophin-1, ciliary neutrophic factor, ciliary neutrophic factor receptor, cripto, cryptic, cytokine-induced neutrophil chemotactic factor 1, cytokine-induced neutrophil, chemotactic factor 2α, cytokine-induced neutrophil chemotactic factor 2β, β endothelial cell growth factor, endothelin 1, epidermal growth factor, epigen, epiregulin, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor 11, fibroblast growth factor 12, fibroblast growth factor 13, fibroblast growth factor 16, fibroblast growth factor 17, fibroblast growth factor 19, fibroblast growth factor 20, fibroblast growth factor 21, fibroblast growth factor acidic, fibroblast growth factor basic, glial cell line-derived neutrophic factor receptor α1, glial cell line-derived neutrophic factor receptor α2, growth related protein, growth related protein α, growth related protein β, growth related protein γ, heparin binding epidermal growth factor, hepatocyte growth factor, hepatocyte growth factor receptor, hepatoma-derived growth factor, insulin-like growth factor I, insulin-like growth factor receptor, insulin-like growth factor II, insulin-like growth factor binding protein, keratinocyte growth factor, leukemia inhibitory factor, leukemia inhibitory factor receptor α, nerve growth factor nerve growth factor receptor, neuropoietin, neurotrophin-3, neurotrophin-4, oncostatin M (OSM), placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor a, platelet derived growth factor receptor β, pre-B cell growth stimulating factor, stem cell factor (SCF), stem cell factor receptor, TNF, TNF0, TNF1, TNF2, transforming growth factor α, transforming growth factor β, transforming growth factor β1, transforming growth factor β1.2, transforming growth factor β2, transforming growth factor β3, transforming growth factor β5, latent transforming growth factor β1, transforming growth factor β binding protein I, transforming growth factor β binding protein II, transforming growth factor β binding protein III, thymic stromal lymphopoietin (TSLP), tumor necrosis factor receptor type I, tumor necrosis factor receptor type II, urokinase-type plasminogen activator receptor, phospholipase-activating protein (PUP), insulin, lectin ricin, prolactin, chorionic gonadotropin, follicle-stimulating hormone, thyroid-stimulating hormone, tissue plasminogen activator, IgG, IgE, IgM, IgA, and IgD, α-galactosidase, β-galactosidase, DNAse, fetuin, leutinizing hormone, estrogen, insulin, albumin, lipoproteins, fetoprotein, transferrin, thrombopoietin, urokinase, integrin, thrombin, leptin, Humira (adalimumab), Prolia (denosumab), Enbrel (etanercept), and a protein in Table 1.

12. The method according to claim 11 wherein a solution comprising an initial concentration of the therapeutic protein between about 0.3 mg/ml and about 3.0 mg/ml is adjusted to a pH value between about 5.0 and about 8.0 prior to contacting with the activated water soluble polymer.

13. The method of claim 11 wherein the therapeutic protein is contacted by a desired excess concentration of activated water soluble polymer, wherein the excess concentration is between about 1-molar and about 300-molar excess.

14. The method according to claim 11 wherein the nucleophilic catalyst is added in an amount to result in a final concentration between about 1.0 mM and about 50 mM nucleophilic catalyst, under conditions comprising a time period between about 0.1 minutes and about 30 minutes; a temperature between about 2° C. and about 37° C.; in the presence or absence of light; and with or without stirring.

15. The method according to claim 11 wherein the oxidizing agent is added in an amount to result in a final concentration between about 50 μM and about 1000 μM oxidizing agent, under conditions comprising a time period between about 0.1 minutes and 120 minutes; a temperature between about 2° C. and about 37° C.; in the presence or absence of light; and with or without stirring.

16. The method of claim 11 wherein the conjugating the water soluble polymer to the oxidized carbohydrate moiety of the therapeutic protein is stopped by the addition of a quenching agent selected from the group consisting of L-cysteine, methionine, glutathione, glycerol, sodium meta bisulfite ($Na_2S_2O_5$), tryptophane, tyrosine, histidine or derivatives thereof, kresol, imidazol, and combinations thereof;

wherein the quenching agent is added in an amount to result in a final concentration between about 1 mM and about 100 mM quenching agent, under conditions comprising a time period between about 5 minutes and about 120 minutes; a temperature between about 2° C. and about 37° C.; in the presence or absence of light; and with or without stirring.

17. The method of claim 11 comprising:

a) a first step comprising adjusting the pH value of a solution comprising the therapeutic protein to a pH value between about 5.0 and about 8.0, wherein the therapeutic protein concentration is between about 0.3 mg/ml and about 3.0 mg/ml;

b) a second step comprising oxidizing one or more carbohydrates on the therapeutic protein, wherein the oxidizing agent is added to the solution in the first step to result in a final concentration between about 50 μM and about 1000 μM, under conditions comprising a time period between about 0.1 minutes and about 120 minutes; a temperature between about 2° C. and about 37° C.; in the presence or absence of light, and with or without stirring;

c) a third step comprising contacting the therapeutic protein with a desired excess concentration of activated water soluble polymer, wherein the excess concentration is between about 1-molar excess and about 300-molar excess, under conditions comprising a time period between about 0.5 hours and about 24 hours, a temperature between about 2° C. and about 37° C.; in the presence or absence of light; and with or without stirring;

d) a fourth step comprising adding a nucleophilic catalyst to the solution of the third step, wherein the nucleophilic catalyst is added to result in a final concentration between about 1 mM and about 50 mM, under conditions comprising a time period between about 0.1 minutes and about 30 minutes; a temperature between about 2° C. and about 37° C.; in the presence or absence of light, and with or without stirring;

e) a fifth step wherein the therapeutic protein is incubated with the activated water soluble polymer and nucleophilic catalyst under conditions that allow conjugation of the activated water-soluble polymer to one or more oxidized carbohydrates on the therapeutic protein, said conditions comprising a time period between about 0.5 hours and about 24 hours, a temperature between about 2° C. and about 37° C.; in the presence or absence of light, and with or without stirring; and f) a sixth step wherein the conjugating the water soluble polymer to the one or more oxidized carbohydrates of the therapeutic protein in the fifth step is stopped by the addition of a quenching agent selected from the group consisting of L-cysteine, methionine, glutathione, glycerol, $Na_2S_2O_5$ (sodium meta bisulfite), tryptophane, tyrosine, histidine or derivatives thereof, kresol, imidazol, and combinations thereof; wherein the quenching agent is added to result in a final concentration of about 1 mM and about 100 mM, under conditions comprising a time period between about 5 minutes and about 120 minutes; a temperature between about 2° C. and about 37° C.; in the presence or absence of light, and with or without stirring.

18. The method of claim 17 wherein the initial concentration of the therapeutic protein in the first step is about 1 mg/ml and the pH is about 6.0;

wherein the final concentration of oxidizing agent in the second step is about 400 μM, and the conditions in the fifth step comprise a time period of about 10 minutes, a temperature of about 22° C., the absence of light and with stirring;

wherein the excess concentration in the third step is about 50 molar excess; wherein the conditions in the third step comprise a time period of about 15 minutes, a temperature of about 22° C., the absence of light and with stirring;

wherein the final concentration of the nucleophilic catalyst in the fourth step is about 10 mM, and the conditions in the fourth step comprise a time period of about 15 minutes, a temperature of about 22° C., the absence of light and with stirring;

wherein the conditions of incubating the therapeutic protein with the activated water soluble polymer and nucleophilic catalyst in the fifth step comprise a time period of about 2 hours; a temperature of about 22° C.; the absence of light; and with stirring; and wherein the quenching agent in the sixth step is L-cysteine; and wherein the L-cysteine is added to result in a final concentration of about 10 mM and the conditions in the sixth step comprise a time period of about 60 minutes, a temperature of about 22° C., the absence of light and with stirring.

19. The method according to claim 11 wherein the water soluble polymer is PSA.

20. The method according to claim 11 wherein the water soluble polymer is PEG.

21. The method according to claim 19 wherein the PSA is comprised of about 10-300 sialic acid units.

22. The method according to claim 17 wherein the therapeutic protein is FIX.

23. The method according to claim 17 wherein the therapeutic protein is FVIIa.

24. The method according to claim 17 wherein the therapeutic protein is FVIII.

25. The method according to claim 17 wherein the oxidizing agent is sodium periodate ($NaIO_4$).

26. The method according to claim 19 wherein the PSA comprises an activated aminooxy linker selected from the group consisting of:

a) a 3-oxa-pentane-1,5-dioxyamine linker of the formula:

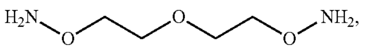

b) a 3,6,9-trioxa-undecane-1,1'-dioxyamine linker of the formula:

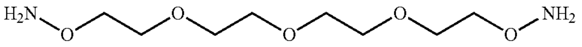 [SMILES: NOCCOCCOCCOCCON]

and c) a 3,6,9,12,15-penatoxa-heptadecane-1,17-dioxyamine linker of the formula:

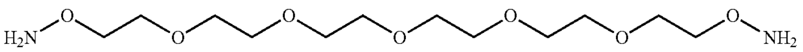

wherein the PSA is oxidized by incubation with an oxidizing agent to form a terminal aldehyde group at the non-reducing end of the PSA.

27. The method according to claim 26 wherein the aminooxy linker is 3-oxa-pentane-1,5-dioxyamine.

28. The method according to claim 17 wherein the nucleophilic catalyst is provided at a concentration between about 1 mM and about 50 mM.

29. The method according to claim 28 wherein the nucleophilic catalyst is present in the conjugation reaction at a concentration of about 10 mM.

30. The method according to claim 17 further comprising the step of purifying the conjugated therapeutic protein.

31. The method according to claim 30 wherein the conjugated therapeutic protein is purified by a method selected from the group consisting of chromatography, filtration and precipitation.

32. The method of claim 11 wherein the conjugated therapeutic protein is purified using chromatography; wherein an anti-chaotropic salt is used for a loading step and for a washing step; the method comprising one or more washing steps wherein flow direction is set to up-flow and wherein the flow rate is between about 0.2 cm/min and about 6.7 cm/min and one or more elution steps wherein flow direction is set to down-flow and wherein the flow rate is between about 0.2 cm/min and about 6.7 cm/min; further comprising concentrating the conjugated therapeutic protein by ultra-/diafiltration (UF/DF).

33. The method according to claim 19 wherein the PSA-aminooxy reagent with an aminooxy group is prepared by a method comprising:

a) incubating a solution comprising an oxidized PSA with an aminooxy linker comprising an active aminooxy group under conditions that allow the formation of a stable oxime linkage between the oxidized PSA and the activated aminooxy linker, said conditions comprising a time period 1 hour; a temperature of 4° C.; in the absence of light, and with stirring; thereby forming a PSA containing an active aminooxy group; and b) purifying the PSA containing an active aminooxy group by anion exchange chromatography, a temperature of 4° C.;

said activated aminooxy linker is 3-oxa-pentane-1,5-dioxyamine linker of the formula:

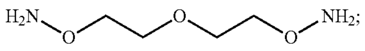

thereby forming an oxime linkage between the PSA and the aminooxy linker.

34. The method according to claim 19 wherein the PSA-aminooxy reagent with an aminooxy group is prepared by a method comprising:

a) incubating a solution comprising a non-oxidized PSA with an aminooxy linker comprising an active aminooxy group under conditions that allow the formation of a stable oxime linkage between the non-oxidized PSA and the activated aminooxy linker, said conditions comprising a time period 2 hours; a temperature of 22° C.; in the absence of light, and with stirring; thereby forming a PSA containing an active aminooxy group; and b) purifying the PSA containing an active aminooxy group by dialysis at a temperature of 22° C.;

said activated aminooxy linker is 3-oxa-pentane-1,5-dioxyamine linker of the formula:

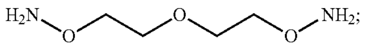

thereby forming an oxime linkage between the non-oxidized PSA and the aminooxy linker.

* * * * *